US011519036B2

(12) United States Patent
Noerholm et al.

(10) Patent No.: US 11,519,036 B2
(45) Date of Patent: *Dec. 6, 2022

(54) USE OF MICROVESICLES IN ANALYZING NUCLEIC ACID PROFILES

(71) Applicant: THE GENERAL HOSPITAL CORPORATION, Boston, MA (US)

(72) Inventors: Mikkel Noerholm, Gauting (DE); Johan Karl Olov Skog, Lincoln, MA (US); Xandra O. Breakefield, Newton, MA (US); Bob Carter, San Diego, CA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 767 days.

This patent is subject to a terminal disclaimer.

(21) Appl. No.: 16/520,130

(22) Filed: Jul. 23, 2019

(65) Prior Publication Data

US 2020/0017920 A1    Jan. 16, 2020

Related U.S. Application Data

(60) Division of application No. 14/792,212, filed on Jul. 6, 2015, now Pat. No. 10,407,728, which is a continuation of application No. 13/395,284, filed as application No. PCT/US2010/048293 on Sep. 9, 2010, now abandoned.

(60) Provisional application No. 61/241,014, filed on Sep. 9, 2009.

(51) Int. Cl.
*G01N 33/574* (2006.01)
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *G01N 33/57407* (2013.01); *C12Q 2600/158* (2013.01)

(58) Field of Classification Search
CPC .................. G01N 33/57407; C12Q 1/6886
USPC ...................................................... 435/6.14
See application file for complete search history.

(56) References Cited

U.S. PATENT DOCUMENTS

| | | |
|---|---|---|
| 5,219,727 A | 6/1993 | Wang |
| 5,538,871 A | 7/1996 | Nuovo |
| 5,547,859 A | 8/1996 | Goodman |
| 5,556,773 A | 9/1996 | Yourno |
| 5,582,981 A | 12/1996 | Toole |
| 5,639,606 A | 6/1997 | Willey |
| 5,639,611 A | 6/1997 | Wallace |
| 5,811,250 A | 9/1998 | Solum |
| 5,840,867 A | 11/1998 | Toole |
| 6,004,755 A | 12/1999 | Wang |
| 6,329,179 B1 | 12/2001 | Kopreski |
| 6,525,154 B1 | 2/2003 | Shea |
| 6,607,898 B1 | 8/2003 | Kopreski |
| 6,759,217 B2 | 7/2004 | Kopreski |
| 6,794,135 B1 | 9/2004 | Kopreski |
| 6,812,023 B1 | 11/2004 | Lamparski |
| 6,893,837 B2 | 5/2005 | Slamon |
| 6,899,863 B1 | 5/2005 | Dhellin |
| 6,913,879 B1 | 7/2005 | Schena |
| 6,916,634 B2 | 7/2005 | Kopreski |
| 6,939,671 B2 | 9/2005 | Kopreski |
| 6,994,960 B1 | 2/2006 | Foote |
| 7,074,563 B2 | 7/2006 | Koster |
| 7,186,512 B2 | 3/2007 | Martienssen |
| 7,198,893 B1 | 4/2007 | Koster |
| 7,198,923 B1 | 4/2007 | Abrignani |
| 7,332,533 B2 | 2/2008 | Kim |
| 7,332,552 B2 | 2/2008 | Benicewicz |
| 7,332,553 B2 | 2/2008 | Sellergen |
| 7,364,848 B2 | 4/2008 | Van Beuningen |
| 7,378,245 B2 | 5/2008 | Liu |
| 7,384,589 B2 | 6/2008 | Hart |
| 7,671,010 B2 | 3/2010 | Arap |
| 7,691,383 B2 | 4/2010 | Chakrabarty |
| 7,776,523 B2 | 8/2010 | Garcia |
| 7,807,183 B2 | 10/2010 | Hong |
| 7,897,356 B2 | 3/2011 | Klass |
| 10,174,361 B2 | 1/2019 | Skog et al. |
| 10,407,728 B2 * | 9/2019 | Noerholm ............ C12Q 1/6886 |
| 2002/0106684 A1 | 8/2002 | Kopreski |
| 2003/0077808 A1 | 4/2003 | Rosen et al. |
| 2005/0003426 A1 | 1/2005 | Ranum |

(Continued)

FOREIGN PATENT DOCUMENTS

CA    2453198 A1    7/2005
CA    2676113 A1    1/2009

(Continued)

OTHER PUBLICATIONS

Abravaya et al., "Detection of point mutations with a modified ligase chain reaction (Gap-LCR)", Nucleic Acids Res 23(4) 675-682 (1995).
Affymetriix, "Gene Chip Human Genome U133 set", Apr. 20, 2001 URL: http://www.affymetrix.com/products/arrays/specific/hgu133.asp.
Alessi et al., "New insights into mTOR signaling: mTORC2 and beyond", Sci Signal 2(67) pe27 (2009).
Allawi et al., Quantitation of microRNAs using a modified Invader assay, RNA 10(7) 1153-1161 (2004).

(Continued)

*Primary Examiner* — Raymond J Henley, III
(74) *Attorney, Agent, or Firm* — Nixon Peabody LLP; David S. Resnick; Shayne Y. Huff

(57) ABSTRACT

The invention concerns gene signatures obtained from microvesicles and a method of applying these gene signatures in helping to determine a biological condition. The determination of a biological condition may aid, for example, the diagnosis, prognosis, and therapy treatment selection for disease in a subject.

7 Claims, 41 Drawing Sheets

(56) References Cited

U.S. PATENT DOCUMENTS

| | | |
|---|---|---|
| 2005/0250100 A1 | 11/2005 | Hayashizaki |
| 2006/0081516 A1 | 4/2006 | Hendrickson |
| 2006/0116321 A1 | 6/2006 | Robbins |
| 2006/0160087 A1 | 7/2006 | McGrath et al. |
| 2006/0223072 A1 | 10/2006 | Boyes |
| 2007/0104738 A1 | 5/2007 | Tatischeff |
| 2007/0105105 A1 | 5/2007 | Clelland |
| 2007/0254351 A1 | 11/2007 | Abrignani |
| 2007/0298118 A1 | 12/2007 | Lotvall |
| 2008/0268429 A1 | 10/2008 | Pietrzkowski |
| 2008/0287669 A1 | 11/2008 | Braman |
| 2009/0169636 A1 | 7/2009 | O'Hagan |
| 2009/0220944 A1 | 9/2009 | Fais |
| 2009/0227533 A1 | 9/2009 | Bader |
| 2010/0008978 A1 | 1/2010 | Drummond |
| 2010/0075315 A1 | 3/2010 | Pietrzkowski |
| 2010/0184046 A1 | 7/2010 | Klass |
| 2010/0196426 A1 | 8/2010 | Skog |
| 2010/0209355 A1 | 8/2010 | Chakrabarty |
| 2010/0255514 A1 | 10/2010 | Rak |
| 2011/0081651 A1 | 4/2011 | Hillan |
| 2012/0142001 A1 | 6/2012 | Skog |
| 2012/0238467 A1 | 9/2012 | Taylor |
| 2013/0040833 A1 | 2/2013 | Noerholm |

FOREIGN PATENT DOCUMENTS

| | | |
|---|---|---|
| CA | 2699646 A1 | 3/2009 |
| CN | 101085349 A | 12/2007 |
| JP | H08-509806 A | 10/1996 |
| JP | 2002521071 A | 7/2002 |
| JP | 2002535665 A | 10/2002 |
| JP | 2003514523 A | 4/2003 |
| JP | 2003531864 A | 10/2003 |
| JP | 2008501336 A | 1/2008 |
| JP | 2008035779 A | 2/2008 |
| JP | 2008509806 A | 4/2008 |
| JP | 2008541699 A | 11/2008 |
| JP | 2010534480 A | 11/2010 |
| JP | 2011-510663 A | 4/2011 |
| JP | 5156829 B2 | 3/2013 |
| WO | 1994/011018 A1 | 5/1994 |
| WO | 1994/022018 A1 | 9/1994 |
| WO | 2000/004194 A1 | 1/2000 |
| WO | 2001/036601 A1 | 5/2001 |
| WO | 2001/082958 A2 | 11/2001 |
| WO | 2002/099064 A2 | 12/2002 |
| WO | 2003/023065 A1 | 3/2003 |
| WO | 2003/050290 A2 | 6/2003 |
| WO | 2003/076603 A2 | 9/2003 |
| WO | 2005/000098 A2 | 1/2005 |
| WO | 2005/000098 A3 | 1/2005 |
| WO | 2005/081867 A2 | 9/2005 |
| WO | 2005/081867 A3 | 9/2005 |
| WO | 2005/121359 A1 | 12/2005 |
| WO | 2005/121369 A2 | 12/2005 |
| WO | 2006/020707 A2 | 2/2006 |
| WO | 2006/048291 A2 | 5/2006 |
| WO | 2006/048291 A3 | 5/2006 |
| WO | 2006/113590 A2 | 10/2006 |
| WO | 2007/015174 A2 | 2/2007 |
| WO | 2007/103572 A1 | 9/2007 |
| WO | 2007/126386 A1 | 11/2007 |
| WO | 2007/127848 A1 | 11/2007 |
| WO | 2008/084331 A2 | 7/2008 |
| WO | 2008/104543 A2 | 9/2008 |
| WO | 2009/015357 A1 | 1/2009 |
| WO | 2009/021322 A1 | 2/2009 |
| WO | 2009/030029 A1 | 3/2009 |
| WO | 2009/036236 A1 | 3/2009 |
| WO | 2009/092386 A2 | 7/2009 |
| WO | 2009/100029 A1 | 8/2009 |
| WO | 2009/155505 A1 | 12/2009 |
| WO | 2010/028099 A1 | 3/2010 |
| WO | 2010/056337 A2 | 5/2010 |
| WO | 2010/065968 A1 | 6/2010 |
| WO | 2010/099184 A1 | 9/2010 |
| WO | 2010/141955 A2 | 12/2010 |
| WO | 2011/009104 A1 | 1/2011 |
| WO | 2011/031877 A1 | 3/2011 |
| WO | 2011/031892 A1 | 3/2011 |
| WO | 2011/088226 A2 | 7/2011 |
| WO | 2011/127219 A1 | 10/2011 |
| WO | 2012/031008 A2 | 3/2012 |

OTHER PUBLICATIONS

Al-Nedawi et al., "Intercellular transfer of the oncogenic receptor EGFRvIII by microvesicles derived from tumour cells", Nat Cell Biol 10(5) 619-624 (2008).

Ason et al., "Differences in vertebrate microRNA expression", Proc Natl Acad Sci USA 103(39) 14385-14389 (2006).

Baj-Krzyworzeka et al., "Tumour-derived microvesicles carry several surface determinants and mRNA of tumour cells and transfer some of these determinants to monocytes", Cancer Immunol Immunother 55(7) 808-818 (2006).

Balzar et al., "The biology of the 17-1A antigen (Ep-CAM)", J Mol Med (Berl) 77(10) 699-712 (1999).

Bamford et al., "The COSMIC (Catalogue of Somatic Mutations in Cancer) database and website", Br J Cancer 91 (2) 355-358 (2004).

Benner et al., "Evolution, language and analogy in functional genomics", Trends Genet 17(7) 414-418 (2001).

Bergsmedh et al., "Horizontal transfer of oncogenes by uptake of apoptotic bodies", Proc Natl Acad Sci USA 98(11) 6407-6411 (2001).

Booth et al., "Exosomes and HIV Gag bud from endosome-like domains of the T cell plasma membrane", J Cell Biol 172(6) 923-935 (2006).

Bossi et al., "Molecularly imprinted polymers for the recognition of proteins: the state of the art", Biosens Bioelectron 22(6) 1131-1137 (2007).

Bratthauer et al., "Expression of LINE-1 retrotransposons in human breast cancer", Cancer 73(9) 2333-2336 (1994).

Burghoff et al., "Horizontal gene transfer from human endothelial cells to rat cardiomyocytes after intracoronary transplantation", Cardiovasc Res 77(3) 534-543 (2008).

Cadieux et al., "Genome-wide hypomethylation in human glioblastomas associated with specific copy number alteration, methylenetetrahydrofolate reductase allele status, and increased proliferation", Cancer Res 66(17) 8469-8476 (2006).

Cancer Genome Altas Research Network, "Comprehensive genomic characterization defines human glioblastoma genes and core pathways", Nature 455(7216) 1061-1068 (2008).

Carr et al., "Circulating membrane vesicles in leukemic blood", Cancer Res 45(11 Pt 2) 5944-5951 (1985).

Cermelli et al., "Circulating microRNAs in patients with chronic hepatitis C and non-alcoholic fatty liver disease", PLoS One 6(8) e23937 (2011).

Chaput et al., "The potential of exosomes in immunotherapy", Expert Opin Biol Ther 5(6) 737-747 (2005).

Chen et al., "Characterization of microRNAs in serum: a novel class of biomarkers for diagnosis of cancer and other diseases", Cell Res 18(10 997-1006 (2008).

Chen et al., "Microfluidic isolation and transcriptome analysis of serum microvesicles", Lab Chip 10(4) 505-511 (2010).

Chen et al., "Real-time quantification of microRNAs by stem-loop RT-PCR", Nucleic Acids Res 33(20) e1779 (2005).

Cheng et al., "Advances of AKT pathway in human oncogenesis and as a target for anti-cancer drug discovery", Curr Cancer Drug Targets 8(1) 2-6 (2008).

Cheruvanky et al., "Rapid isolation of urinary exosomal biomarkers using a nanomembrane ultrafiltration concentrator", Am J Physciol Renal Physiol 292(5) F1657-F1661 (2007).

Cheung et al., "Natural variation in human gene expression assessed in lymphoblastoid cells", Nat Genet 33(3) 422-425 (2003).

(56) References Cited

OTHER PUBLICATIONS

Cho et al., "Hypermethylation of CpG island loci and hypomethylation of LINE-1 and Alu repeats in prostate adenocarcinoma and their relationship to clinicopathological features", J Pathol 211 (3) 269-277 (2007).
Ciafre et al., "Extensive modulation of a set of microRNAs in primary glioblastoma", Biochem Biophys Res Commun 334(4) 1351-1358 (2005).
Clayton et al., "Human tumor-derived exosomes selectively impair lymphocyte responses to interleukin-2", Cancer Res 67(15) 7458-7466 (2007).
Cocucci et al., "Shedding microvesicles: artefacts no more", Trends Cell Biol 19(2) 43-51 (2009).
Contreras-Galindo et al., "Human endogenous retrovirus K (HML-2) elements in the plasma of people with lymphoma and breast cancer", J Virol 82(19) 9329-9336 (2008).
Corsten et al., "Circulating MicroRNA-208b and MicroRNA-499 reflect myocardial damage in cardiovascular disease", Circ Cardiovasc Genet 3(6) 499-506 (2010).
Cortez et al., "MicroRNA identification in plasma and serum: a new tool to diagnose and monitor diseases", Expert Opin Biol Ther 9(6) 703-711 (2009).
Cotton et al., "Reactivity of cytosine and thymine in single-base-pair mismatches with hydroxylamine and osmium tetroxide and its application to the study of mutations", Proc Natl Acad Scie USA 85(12) 4397-4401 (1988).
Cowell et al., "Application of oligonucleotides arrays for coincident comparative genomic hybridization, ploidy status and loss of heterozygosity studies in human cancers", Methods Mol Biol 556: 47-65 (2009).
Daskalos et al., "Hypomethylation of retrotransposable elements correlates with genomic instability in non-small cell lung cancer", Int J Cancer 124(1) 81-87 (2009).
Day et al., "PCA3: from basic molecular science to the clinical lab", Cancer Lett 301(1) 1-6 (2011).
Deregibus et al., "Endothelial progenitor cell derived microvesicles activate an angiogenic program in endothelial cells by a horizontal transfer of mRNA", Blood 110(7) 2440-2448 (2007).
Diehl et al., "BEAMing: single-molecule PCR on microparticles in water-in-oil emulsions", Nat Methods 3(7) 551-559 (2006).
Diehl et al., "Circulating mutant DNA to assess tumor dynamics", Nat Med 14(9) 985-990 (2008).
Dowling et al., "mTORCI-mediated cell proliferation, but not cell growth, controlled by the 4E-BPs", Science 328 (5982) 1172-1176 (2010).
Dressman et al., "Transforming single DNA molecules into fluorescent magnetic particles for detection and enumeration of genetic variations", Proc Natl Acad Sci USA 100(15) 8817-8822 (2003).
Duijvesz et al., "Exosomes as biomarker treasure chests for prostate cancer", Eur Urol 59(5) 823-831 (2011).
El-Hefnawy et al., "Characterization of amplifiable, circulating RNA in plasma and its potential as a tool for cancer diagnostics", Clin Chem 50(3) 564-573 (2004).
Estecio et al., "LINE-1 hypomethylation in cancer is highly variable and inversely correlated with microsatellite instability", PLoS One 2(5) e399 (2007).
Fabbri et al., "MicroRNA-29 family reverts aberrant methylation in lung cancer by targeting DNA methyltransferases 3A and 3B", Proc Natl Acad Sci USA 104(4) 15805-15810 (2007).
Fiorentino et al., "The minisequencing method: an alternative strategy for preimplantation genetic diagnosis of single gene disorders", Mol Human Reprod 9(7) 399-410 (2003).
Fischer et al., "Length-independent separation of DNA restriction fragments in two-dimensional gel electrophoresis", Cell 16(1) 191-200 (1979).
Fischer et al., "Two-dimensional electrophoretic separation of restriction enzyme fragments of DNA", Methods Enzymol 68: 183-191 (1979).

Forbes et al., "COSMIC (the Catalogue of Somatic Mutations in Cancer): a resource to investigate acquired mutations in human cancer", Nucleic Acids Res 38(Database issue) D652-D657 (2010).
Lee et al., "MicroRNA expression and clinical outcome of small cell lung cancer", PLoS On3e 6(6) e21300 (2011).
Li et al., "Replacing PCR with COLD-PCR enriches variant DNA sequences and redefines the sensitivity of genetic testing", Nat Med 14(50 579-584 (2008).
Liu et al., "Murine mammary carcinoma exosomes promote tumor growth by suppression of NK cell function", J Immunol 1767(3) 1375-1385 (2006).
Liu et al., "Reconstitution, activities, and structure of the eukaryotic RNA exosome", Cell 127(6) 1223-1237 (2006).
Lo et al., "Automated gating of flow cytometry data via robust model-based clustering", Cytometry 73(4) 321-332 (2008).
Lo et al., "Plasma placental RNA allelic ratio permits noninvasive prenatal chromosomal aneuploidy detection", Nat Med 13(2) 218-223 (2007).
Lo et al., "Prenatal diagnosis: progress through plasma nucleic acids", Nat Rev Genet 8(1) 71-77 (2007).
Lower et al., "The viruses in all of us: characteristics and biological significance of human endogenous retrovirus sequences", Proc Natl Acad Sci USA 93(11) 5177-5184 (1996).
Mack et al., "Transfer of the chemokine receptor CCR5 between cells by membrane-derived microparticles: a mechanism for cellular human immunodeficiency virus 1 infection", Nat Med 6(7) 769-775 (2000).
Maheswaran et al., "Detection of mutations in EGFR in circulating lung-cancer cells", N Engl J Med 359(4) 366-377 (2008).
Mallardo et al., "Isolation and characterization of Staufen-containing ribonucleoprotein particles from rat brain", Proc Natl Acad Sci USA 100(4) 2100-2105 (2003).
Maron et al., "Gene expression analysis in pregnant women and their infants identifies unique fetal biomarkers that circulate in maternal blood", J Clin Invest 117(10) 3007-3019 (2007).
Miele et al., "Autocatalytic replication of a recombinant RNA", J Mol Biol 171(3) 281-295 (1983).
Millimaggi et al., "Tumor vesicle-associated CD147 modulates the angiogenic capability of endothelial cells", Neoplasia 9(4) 349-357 (2007).
Miranda et al., "Nucleic acids within urinary exosomes/microvesicles are potential biomarkers for renal disease", Kidney Int 78(2) 191-199 (2010).
Mitchell et al., "Can urinary exosomes act as treatment response markers in prostate cancer?", J Transl Med 7:4 (2009).
Myers et al., "Detection of single base substitutions by ribonuclease cleavage at mismatches in RNA:DNA duplexes", Science 230(4731) 1242-1246 (1985).
Nagrath et al., "Isolation of rare circulating tumour cells in cancer patients by microchip technology", Nature 450 (7173) 1235-1239 (2007).
Nakanishi et al., "PCA3 molecular urine assay correlates with prostate cancer tumor volume: implication in selecting candidates for active surveillance", J Urol 179(5) 1804-1809 (2008).
Nakazawa et al., "UV and skin cancer: specific p53 gene mutation in normal skin as a biologically relevant exposure measurement", Proc Natl Acad Sci USA 91 (1) 360-364 (1994).
Ng et al., "mRNA of placental origin is readily detectable in maternal plasma", Proc Natl Acad Sci USA 100(8) 4748-4753 (2003).
Ng et al., "The concentration of circulating corticotropin-releasing hormone mRNA in maternal plasma is increased in preeclampsia", Clin Chem 49(5) 727-731 (2003).
Nilsson et al., "Prostate cancer-derived urine exosomes: a novel approach to biomarkers for prostate cancer", Br J Cancer 100(10) 1603-1607 (2009).
Nishikawa et al., Immunohistochemical analysis of the mutant epidermal growth factor, deltaEGFR, in glioblastoma, Brain Tumor Pathol 21(2) 53-56 (2004).
Noerholm et al., "RNA expression patterns in serum microvesicles from patients with glioblastoma multiforme and controls", BMC Cancer 12: 22 (2012).

(56) References Cited

OTHER PUBLICATIONS

Novakova et al., "MicroRNA involvement in glioblastoma pathogenesis", Biochem Biophys Res Commun 386(1) 1-5 (2009).
Oliveira et al., "Distinct patterns of KRAS mutations in colorectal carcinomas according to germline mismatch repair defects and hMLH1 methylation status", Hum Mol Genet 13(19) 2303-2311 (2004).
Orita et al., "Detection of polymorphisms of human DNA by gel electrophoresis as single-strand conformation polymorphisms", Proc Natl Acad Sci USA 86*8) 3766-3770 (1989).
Ostrowski et al., "Rab27a and Rab27b control different steps of the exosome secretion pathway", Nat Cell Biol 12 (K1) 19-30 sup pp. 1-13 (2010).
Parsons et al., "An integrated genomic analysis of human glioblastoma multiforme", Science 321(5897) 1807-1813 (2008).
Pelloski et al., "Epidermal growth factor receptor variant III status defines clinically distinct subtypes of glioblastoma", J Clin Oncol 25(16) 2288-2294 (2007).
Pisitkun et al., "Discovery of urinary biomarkers", Mol Cell Proteomics 5(10) 1760-1771 (2006).
Pleasance et al., "A comprehensive catalogue of somatic mutations from a human cancer genome", Nature 463 (7278) 191-196 (2010).
Rak et al., "Genetic determinants of cancer coagulopathy, angiogenesis and disease progression", Vnitr Lek 52(Suppl 1) 135-138 (2006).
Raposo et al., "B lymphocytes secrete antigen-presenting vesicles", J Exp Med 183(3) 1161-1173 (1996).
Ratajczak et al., "Membrane-derived microvesicles: important and underappreciated mediators of cell-to-cell communication", Leukemia 20(9) 1487-1495 (2006).
Revenfeld et al., "Diagnostic and prognostic potential of extracellular vesicles in peripheral blood", Clin Ther 36(6) 830-846 (2014).
Roman-Gomez et al., "Repetitive DNA hypomethylation in the advanced phase of chronic myeloid leukemia", Leuk Res 32(3) 487-490 (2008).
Ruprecht et al., "Endogenous retroviruses and cancer", Cell Mol Life Sci 65(21) 3366-3382 (2008).
Ryan et al,. "A prospective study of circulating mutant KRAS2 in the serum of patients with colorectal neoplasia: strong prognostic indicator in postoperative follow up", Gut 52(1) 101-108 (2003).
Saal et al., "MicroRNAs and the kidney: coming of age", Curr Opin Nephrol Hypertens 18(4) 317-323 (2009).
Sarbassov et al., "Prolonged rapamycin treatment inhibits mTORC2 assembly and Akt/PKB", Mol Cell 22(2) 159-168 (2006).
Schetter et al., "MicroRNA expression profiles associated with prognosis and therapeutic outcome in colon adenocarcinoma", JAMA 299(4) 425-436 (2008).
Shinojima et al., "Prognostic value of epidermal growth factor receptor in patients with glioblastoma multiforme", Cancer Res 63(20) 6962-6970 (2003).
Silva et al., "Selective gene silencing by viral delivery of short hairpin RNA", Virol J 7: 248 (2010).
Simons et al., "Exosomes—vesicular carriers for intercellular communication", Curr Opin Cell Biol 21(4) 575-581 (2009).
Skog et al., "Glioblastoma microvesicles transport RNA and proteins that promote tumour growth and provide diagnostic biomarkers", Nat Cell Biol 10(12) 1470-1476 (2008).
Srikantan et al., "PCGEM1, a prostate-specific gene, is overexpressed in prostate cancer", Proc Natl Acad Sci USA 97(22) 12216-12221 (2000).
Steemers et al., "Whole-genome genotyping with the single-base extension assay", Nat Methods 3(1) 31-33 (2006).
Stoorvogel et al., "The biogenesis and functions of exosomes", Traffic 3(5) 321-330 (2002).
Forbes et al., "COSMIC: mining complete cancer genomes in the Catalogue of Somatic Mutations in Cancer", Nuclec Acids Res 39(Database issue) D945-D950 (2011).
Forbes et al., "The Catalogue of Somatic Mutations in Cancer (COSMIC)", Supplement 57:10.11.1-10.11.26 (2008).
Furnari et al., "Malignant astrocytic glioma: genetics, biology, and paths to treatment", Genes Dev 21(21) 2683-2710 (2007).

Gambim et al., "Platelet-derived exosomes induce endothelial cell apoptosis through peroxynitrite generation: experimental evidence for a novel mechanism of septic vascular dysfunction", Crit Care 11(5) R107 (2007).
Geiss et al., "Direct multiplexed measurement of gene expression with color-coded probe pairs", Nat Biotechnol 26(3) 317-325 (2008).
GenBank (Accession NM_005896) submitted Jan. 31, 2003.
Gene Annot, "Probes for MYC availible on Affymetrix arrays HG-U95, HG-U133, HG-U133 Plus 2.0", Weizmann Institue of Science found at URL http://genecards.weizmann.ac.il/cgi-bin/geneannot/ga_search.pl (Apr. 20, 2001, retrieved from the Internet on May 21, 2003).
Ginestra et al., "The amount and proteolytic content of vesicles shed by human cancer cell lines correlates with their in vitro invasiveness", Anticancer 18(5A) 3433-3437 (1998).
Golan et al., "Human endogenous retrovirus (HERV-K) reverse transcriptase as a breast cancer prognostic marker", Neoplasia 10(6) 521-533 (2008).
Gonzales et al., "Urinary exosomes: is there a future?", Nephrol Dial Transplant 23(6) 1799-1801 (2008).
Goodier et al., "Retrotransposons revisited: the restraint and rehabilitation of parasites", Cell 135(1) 23-35 (2008).
Gormally et al., "Circulating free DNA in plasma or serum as biomarker of carcinogenesis: practical aspects and biological significance", Mutat Res 635(2-3) 10-117 (2007).
Greco et al., "Argosomes: a potential vehicle for the spread of morphogens through epithelia", Cell 106(5) 633-645 (2001).
Green et al., "The prognostic significance of IDH1 mutations in younger adult patients with acute myeloid leukemia is dependent on FLT3/ITD status", Blood 116(15) 277-2782 (2010).
Groskopf et al., "Aptima PCA3 molecular urine test: development of a method to aid in the diagnosis of prostate cancer", Clin Chem 52(6) 1089-1095 (2006).
Guatelli et al., "Isothermal, in vitro amplification of nucleic acids by a multienzyme reaction modeled after retroviral replication", Proc Natl Acad Sci USA 87(19) 7797 (1990).
Guescini et al., "Astrocytes and Glioblastoma cells release exosomes carrying mtDNA", J Neural Transm (Vienna) 117(1) 1-4 (2010).
Hahn, "Molecular biology of double-minute chromosomes", Bioessays 15(7) 477-484 (1993).
Hanahan et al., "The hallmarks of cancer", Cell 100(1) 57-70 (2000).
Hartman et al., "Patients with IDH1 wild type anaplastic astrocytomas exhibit worse prognosis than IDH1-mutated glioblastomas, and IDH1 mutation status accounts for the unfavorable prognostic effect of higher age: implications for classification of gliomas", Acta Neuropathol 120(6) 707-718 (2010).
Heimberger et al., "The natural history of EGFR and EGFRvIII in glioblastoma patients", J Transl Med 3: 38 (2005).
Hessels et al., "DD3(PCA3)-based molecular urine analysis for the diagnosis of prostate cancer", Eur Urol 44(1) 8-15 (2003).
Hessels et al., "Detection of TMPRSS2-ERG fusion transcripts and prostate cancer antigen 3 in urinary sediments may improve diagnosis of prostate cancer", Clin Cancer Res 13(17) 5103-5108 (2007).
Hildebrant et al., "Genetic variations in the PI3K/PTEN/AKT/mTOR pathway are associated with clinical outcomes in esophageal cancer patients treated with chemoradiotherapy", J Clin Oncol 27(6) 857-871 (2009).
Holdhoff et al., Analysis of circulating tumor DNA to confirm somatic KRAS mutations, J Natl Cancer Inst 101(18) 1284-1285 (2009).
Hunter et al., "Detection of microRNA expression in human peripheral blood microvesicles", PLoS One 3(11) e3694 (2008).
Iero et al., "Tumour-released exosomes and their implications in cancer immunity", Cell Death Differ 15(1) 80/88 (2008).
Iorio et al., "MicroRNA signatures in human ovarian cancer", Cancer Res 67(18) 8699-8707 (2007).
Itadani et al., "Can systems biology understand pathway activation? Gene expression signatures as surrogate markers for understanding the complexity of pathway activation", Curr Genomics 9(5) 349-360 (2008).

(56) References Cited

OTHER PUBLICATIONS

Janowska-Wieczorek et al., "Microvesicles derived from activated platelets induce metastasis and angiogenesis in lung cancer", Int J Cancer 113(5) 752-760 (2005).
Ji et al., "MALAT-1, a novel noncoding RNA, and thymosin beta4 predict metastasis and survival in early-stage non-small cell lung cancer", Oncogene 22(39) 8031-8041 (2003).
Johnson et al., "Surface-immobilized peptide aptamers as probe molecules for protein detection", Anal Chem 80(4) 978-983 (2008).
Jones et al., "Core signaling pathways in human pancreatic cancers revealed by global genomic analyses", Science 321(5897) 1801-1806 (2008).
Kan et al., "Antenatal diagnosis of sickle-cell anaemia by D.N.A. analysis of amniotic-fluid cells", Lancet 2(8096) 910-912 (1978).
Kan et al., "Polymorphism of DNA sequence adjacent to human beta-globin structural gene: relationship to sickle mutation", Proc Natl Acad Sci 75(11) 5631-5635 (1978).
Kang et al., "Mutational analysis of IDH1 codon 132 in glioblastomas and other common cancers", Int J Cancer 125 (2) 353-355 (2009).
Kato et al., "A monoclonal antibody IMab-1 specifically recognizes IDH1R132H, the most common glioma-derived mutation", Biochem Biophys Res Commun 390(3) 547-551 (2009).
Katoh et al., "Association of endogenous retroviruses and long terminal repeats with human disorders", Front Oncol 3:234 (2013).
Keller et al., "CD24 is a marker of exosomes secreted into urine and amniotic fluid", Kidney Int 72(9) 1095-1102 (2007).
Kislauski et al., "Sequences responsible for intracellular localization of beta-actin messenger RNA also affect cell phenotype", J Cell Biol 127(2) 441-451 (1994).
Kleiman et al., "HERV-K(HML-2) GAG/ENV antibodies as indicator for therapy effect in patients with germ cell tumors", Int J Cancer 110(3) 459-461 (2004).
Klein et al., "Combined transcriptome and genome analysis of single micrometastatic cells", Nat Biotechnol 20(4) 387-392 (2002).
Klemke et al., "Regulation of cell motility by mitogen-activated protein kinase", J Cell Biol 137(2) 481-492 (1997).
Koga et al., "Purification, characterization and biological significance of tumor-derived exosomes", Anticancer Res 25 (6A) 3703-3707 (2005).
Kosaka et al., "Circulating microRNA in body fluid: a new potential biomarker for cancer diagnosis and prognosis", Cancer Sci 101 (10) 2087-2092 (2010).
Kristensen et al., "PCR-based methods for detecting single-locus DNA methylation biomarkers in cancer diagnostics, prognostics, and response to treatment", Clin Chem 55(8) 1471-1483 (2009).
Krupp, "Stringent RNA quality control using Agilent 2100 bioanalyzer", Applicant note, Agilent. (2005).
Kwoh et al., "Transcription-based amplification system and detection of amplified human immunodeficiency virus type 1 with a bead-based sandwich hybridization format", Proc Natl Acad Sci USA 86(4) 1173-1177 (1989).
Landegren et al., "A ligase-mediated gene detection technique", Science 241(4869) 1077-1080 (1988).
Laxman et al., "A first-generation multiplex biomarker analysis of urine for the early detection of prostate cancer", Cancer Res 68(3) 645-649 (2008).
Halatsch et al. "Epidermal growth factor receptor inhibition for the treatment of the glioblastoma multiforme and other malignant brain tumors." Cancer Treatment Reviews, 32: 74-89, (2006).
Schalken "Validation of molecular targets in prostate cancer." BJU International, 96: 23-29 (2005).
Smalheiser. "Exosomal transfer of proteins and RNAs at synapses in the nervous system." Biology Direct 2(1): 1-15 (2007).
Tam et al., "The emergent role of microRNAs in molecular diagnostics of cancer", J Mol Diagn 10(5) 411-414 (2008).
Taylor et al., "MicroRNA signatures of tumor-derived exosomes as diagnostic biomarkers of ovarian cancer", Gynecol Oncol 110(1) 13-21 (2008).
Taylor et al., "Tumour-derived exosomes and their role in cancer-associated T-cell signalling defects", Br J Cancer 92(2) 305-311 (2005).
Tewes et al., "Molecular profiling and predictive value of circulating tumor cells in patients with metastatic breast cancer: an option for monitoring response to breast cancer related therapies", Breast Cancer Res Treat 115(3) 581-590 (2009).
Thery et al., "Exosomes: composition, biogenesis and function", Nat Rev Immunol 2(8) 569-579 (2002).
Thery et al., "Isolation and characterization of exosomes from cell culture supernatants and biological fluids", Curr Protoc Cell Biol Chp3(Unit 3.22) (2006).
Ting et al., "Aberrant overexpression of satellite repeats in pancreatic and other epithelial cancers", Science 331 (6017) 593-596 (2011).
Tomlins et al., "Recurrent fusion of TMPRSS2 and ETS transcription factor genes in prostate cancer", Science 310 (5748) 644-648 (2005).
Valadi et al., "Exosome-mediated transfer of mRNAs and microRNAs is a novel mechanism of genetic exchange between cells", Nat Cell Biol 9(6) 654-659 (2007).
Van Dijk et al., "Human cell growth requires a functional cytoplasmic exosome, which is involved in various mRNA decay pathways", RNA 13(7) 1027-1035 (2007).
Velculescu et al., "Serial analysis of gene expression", Science 270(5235) 484-487 (1995).
Voisset et al., "Human RNA "rumor" viruses: the search for novel human retroviruses in chronic disease", Microbiol Mol Biol Rev 72(1) 157-196 (2008).
Wang-Johanning et al., "Human endogenous retrovirus K triggers an antigen-specific immune response in breast cancer patients", Cancer Res 68(14) 5869-5877 (2008).
Went et al., "Frequent EpCam protein expression in human carcinomas", Hum Pathol 35(1) 122-128 (2004).
Wieckowski et al.,. "Human tumor-derived vs dendritic cell-derived exosomes have distinct biologic roles and molecular profiles", Immunol Res 36(1-3) 247-254 (2006).
Wong et al., "Circulating placental RNA in maternal plasma is associated with a preponderance of 5' mRNA fragments: implications for noninvasive prenatal diagnosis and monitoring", Clin Chem 51 (10) 1786-1795 (2005).
Wood et al., "The genomic landscapes of human breast and colorectal cancers", Science 318(5853) 1108-1113 (2007).
Wright et al., "Newer potential biomarkers in prostate cancer", Rev Urol 9(4) 207-213 (2007).
Yan et al., "IDH1 and IDH2 mutations in gliomas", N Engl J Med 360(8) 765-773 (2009).
Yoshimoto et al., "Development of a real-time RT-PCR assay for detecting EGFRvIII in glioblastoma samples", Clin Cancer Res 14(2) 488-493 (2008).
Yu et al., "Oncogenic events regulating tissue factor expression", Hematology Meeting Reports 1(9) 18-20 (2005).
Yuan et al., "Transfer of microRNAs by embryonic stem cell microvesicles", PLoS One 4(3) e4772 (2009).
Bess et al., "Microvesicles are a source of contaminating cellular proteins found in purified HIV-1 preparations." Virology 230(1):134-144 (1997).
Biernat et al., "Predominant expression of mutant EGFR (EGFRvIII) is rare in primary glioblastomas", Brain Pathol 14(2) 131-136 (2004).
Chabert et al., "Cell culture of tumors alters endogenous poly(ADPR)polymerase expression and activity", Int J Cancer 53(5) 837-842 (1993).
Choi et al., "Proteomic analysis of microvesicles derived from human colorectal cancer ascites.", Proteomic 11(13) 2745-2751 (2011).
Cooperberg et al., "The changing face of low-risk prostate cancer: trends in clinical presentation and primary management", J Clin Oncol 22(11) 2141-9 (2004).
Dermer "Another anniversary for the war on cancer." Nature Biotechnology 12(3):320 (1994).

(56) References Cited

OTHER PUBLICATIONS

Diehl et al., "Detection and quantification of mutations in the plasma of patients with colorectal tumors." PNAS 102 (45) 16268-16373 (2005).

Eastham et al., "Relationship between clonogenic cell survival, DNA damage and chromosomal radiosensitivity in nine human cervix carcinoma cell lines" Int. Journal Radiat. Biol 77(3) 295-302 (2001).

Grant et al., "The proteins of normal urine." Journal of Clinical Pathology 10(4):360-367 (1957).

Huang et al. "Optimization of DNase I Removal of Contaminating DNA from RNA for Use in Quantitative RNA-PCR." Biotechniques 20(6): 1012-1020 (1996).

Johnstone. "Exosomes biological significance: A concise review." Blood Cells, Molecules, and Diseases 36(2): 315-321 (2006).

Keller et al., "Exosomes: from biogenesis and secretion to biological function", Immunol Lett 107(2) 102-8 (2006).

Lotvall at al. "Cell to Cell Signalling via Exosomes Through esRNA." Cell Adhesion & Migration 1(3): 156-158 (2007).

May "How Many Species are there on Earth?", Science 241(1) 1441-1449 (1998).

Moderk et al., "Genome-wide detection of alternatives splicing in expressed sequences of human genes", Nucleic Acids Research 29(13) 2850-2859 (2001).

Perkel. "Finding Points to Possible Blood Test for Brain Tumors." HealthDay News [retrieved Apr. 18, 2019] https://www.medicinenet.com/script/main/art.asp?articlekey=94287 1-3 (2008).

Ruprecht et al., "Human endogenous retrovirus family HERV-K(HML-2) RNA transcripts are selectively packaged into retroviral particles produced by the human germ cell tumor line Tera-1 and originate mainly from a provirus on chromosome 22q11.21" J Virol 82(20) 10008-10016 (2008).

Saito-Hisaminto et al., "Genome-Wide Profiling of Gene Expression in 29 Normal Human Tissues with cDNA Microarray", DNA Research 9 35-45 (2002).

Singh et al., "Gene Expression correlates of clinical prostate cancer behavior", Cancer Cell 1(2) 203-209 (2002).

The International SNP Map Working Group., "A map of human genome sequence variation containing 1.42 million single nucleotide polymorphisms" NATURE 409 928-933 (2001).

Tullis et al., "Calcium protects DNase I from proteinase K: a new method for the removal of contaminating RNase from DNase I." Analytical Biochemistry 107(1):260-264 (1980).

Yu et al., "Shedding of tissue factor (TF)-containing microparticles rather than alternatively spliced TF is the main source of TF activity released from human cancer cells", J Throm Haemost 2(11) 2065-2067 (2004).

Thery et al. "Isolation and Characterization of Exosomes from Cell Culture Supernatants and Biological Fluids" Curr Protoc Cell Biol Chapter 3 Unit 3.22 1-29 (2006).

Moscatello et al., "Frequent expression of a mutant epidermal growth factor receptor in multiple human tumors", Cancer Res 55(23) 5536-5539 (1995).

Schmidt et al., "Quantitative multi-gene expression profiling of primary prostate cancer", Prostate 66(14) 1521-34 (2006).

Mellinghoff et al., "Molecular determinants of the response of glioblastomas to EGFR kinase inhibitors", N Engl J Med 353(19) 2012-2024 (2005).

* cited by examiner

USE OF MICROVESICLES IN ANALYZING NUCLEIC ACID PROFILES

CROSS REFERENCE TO RELATED APPLICATIONS

This Application is a Divisional Application of U.S. Ser. No. 14/792,212, filed Jul. 6, 2015 which is a Continuation Application of U.S. Ser. No. 13/395,284, filed Oct. 26, 2012 which is a 35 U.S.C. 371 National Stage entry of International Application No. PCT/US2010/048293, filed Sep. 9, 2010, which designates the United States, and which claims the benefit under 35 U.S.C. § 119(e) of US Provisional Application No. 61/241,014, filed Sep. 9, 2009, the contents of each of which are incorporated herein by reference in their entirety.

FIELD OF INVENTION

The present invention relates to the general fields of nucleic acid analysis in human or other animal subjects, particularly the profiling of nucleic acids from a biological sample, and in particular, from microvesicles.

BACKGROUND

Cancer molecular diagnostics is becoming increasingly important with the accumulating knowledge of the molecular mechanisms underlying various types of cancers and the implications for diagnosis, treatment selection and prognosis.

Various molecular diagnostic tests like mutational analysis, methylation status of genomic DNA and gene expression analysis are currently being used to answer clinical questions. Differential gene expression analysis of cancer cells has so far primarily been done on cancer cells derived from surgically removed tumor tissue or from tissue obtained by biopsy. However, the ability to profile gene expression using a blood sample from a cancer patient rather than a tissue sample is desirable because a non-invasive approach such as this has wide ranging implications in terms of patient welfare, the ability to conduct longitudinal disease monitoring, and the ability to obtain expression profiles even when tissue cells are not easily accessible, e.g., in ovarian or brain cancer patients.

So far, gene expression profiling using a blood sample is confined to analyzing RNA extracted from Peripheral Blood Mononuclear Cells (PBMC) (Hakonarson et al., 2005) or Circulating Tumor Cells (CTC) (Cristofanilli and Mendelsohn, 2006). This invention discloses a novel method of profiling gene expressions and provides novel gene expression signatures associated with diseases by analyzing nucleic acids extracted from microvesicles from a bodily fluid, e.g., a blood sample.

BRIEF SUMMARY OF THE INVENTION

The present invention provides genetic profiles associated with biological conditions and methods of applying these profiles in evaluating the biological conditions. As such, in one aspect, the present invention is directed to a profile of one or more RNA transcripts obtained from microvesicles. The one or more RNA transcripts are selected from those listed in Tables 1-20. In one embodiment, the microvesicles from which the profile is obtained are isolated from a bodily fluid from a subject. The bodily fluid may be blood, serum, plasma or urine. In a further embodiment, the subject is a human subject. In an even further embodiment, the human subject is a brain cancer patient such as a glioblastoma patient.

In another embodiment, the profile is obtained through analyzing RNA transcripts obtained from microvesicles. The analysis of RNA transcripts is performed by a method such as microarray analysis, Reverse Transcription PCR, Quantitative PCR or a combination of these above methods. In a further embodiment, the analysis includes an additional step of data analysis. The data analysis can be accomplished with Clustering Analysis, Principle Component Analysis, Linear Discriminant Analysis, Receiver Operating Characteristic Curve Analysis, Binary Analysis, Cox Proportional Hazards Analysis, Support Vector Machines and Recursive Feature Elimination (SVM-RFE), Classification to Nearest Centroid, Evidence-based Analysis, or a combination of the above methods. In yet another embodiment, the profile obtained from microvesicles is a profile of the one or more RNA transcripts selected from any one of the Tables 1-20. In yet another embodiment, the profile from microvesicles is a profile of each of the RNA transcripts listed in any one of the Tables 1-20.

In another aspect, the present invention refers to a method of aiding diagnosis, prognosis or therapy treatment planning for a subject, comprising the steps of: a) isolating microvesicles from a subject; b) measuring the expression level of one or more RNA transcripts extracted from the isolated microvesicles; c) determining a profile of the one or more RNA transcripts based on the expression level; and d) comparing the profile to a reference profile to aid diagnosis, prognosis or therapy treatment planning for the subject. In one embodiment, the microvesicles used in the method are isolated from a bodily fluid from the subject. The bodily fluid may be blood, serum, plasma or urine. In a further embodiment, the subject is a human subject. In an even further embodiment, the human subject is a brain cancer patient such as a glioblastoma patient. The step (b) in the method is accomplished with a microarray analysis, Reverse Transcription PCR, Quantitative PCR or a combination of the above methods. In a further embodiment, the step (c) in the method includes an additional step of data analysis. The data analysis can be accomplished with Clustering Analysis, Principle Component Analysis, Linear Discriminant Analysis, Receiver Operating Characteristic Curve Analysis, Binary Analysis, Cox Proportional Hazards Analysis, Support Vector Machines and Recursive Feature Elimination (SVM-RFE), Classification to Nearest Centroid, Evidence-based Analysis, or a combination of the above methods. The RNA transcripts whose profiles are determined in are one or more RNA transcripts selected from those listed in Tables 1-20. In yet another embodiment, the RNA transcripts whose profiles are determined include one or more RNA transcripts selected from any one of the Tables 1-20. In a further embodiment, the RNA transcripts are all of the transcripts listed in any one of Tables 1-20.

In yet another aspect, the present invention refers to a method of preparing a personalized genetic profile report for a subject, comprising the steps of: (a) isolating microvesicles from a subject; (b) detecting or measuring one or more genetic aberrations within the isolated microvesicles; (c) determining one or more genetic profiles from the data obtained from steps (a) and (b); (d) optionally comparing the one or more genetic profiles to one or more reference profiles; and (e) creating a report summarizing the data obtained from steps (a) through (d) and optionally including diagnostic, prognostic or therapeutic treatment information. In one embodiment of the method, step (b) comprises the quantitative measurement of one or more nucleic acids within the isolated microvesicles and step (c) comprises the determination of one or more quantitative nucleic acid profiles. In another embodiment of the method, the one or more nucleic acids are RNA transcripts selected from Tables 1-20. In a further embodiment of the method, the one or more nucleic acids are RNA transcripts selected from any one of Tables 1-20. In another further embodiment of the method, one or more nucleic acids comprise each of the RNA transcripts in any one of the Tables 1-20.

In yet another aspect, the present invention is a kit for genetic analysis of an exosome preparation from a body fluid sample from a subject, comprising, in a suitable container, one or more reagents suitable for hybridizing to or amplifying one or more of the RNA transcripts selected from Tables 1-20. In one embodiment, the kit includes one or more reagents suitable for hybridizing to or amplifying one or more of the RNA transcripts selected from any one of Tables 1-20. In another embodiment, the kit includes one or more reagents suitable for hybridizing to or amplifying each of the RNA transcripts in any one of Tables 1-20.

In yet another aspect, the present invention is a custom-designed oligonucleotide microarray for genetic analysis of an exosome preparation from a body fluid sample from a subject, wherein the oligos on the array exclusively hybridize to one or more transcripts selected from any one of Tables 1-20.

In yet another aspect, the present invention is a method of identifying at least one potential biomarker for a disease or other medical condition, the method comprising: (a) isolating microvesicles from subjects having a disease or other medical condition of interest and from subjects who do not have the disease or other medical condition of interest; (b) measuring the expression level of a target RNA transcript extracted from the isolated microvesicles from each of the subjects; (c) comparing the measured levels of the target RNA transcript from each of the subjects; and (d) determining whether there is a statistically significant difference in the measured levels; wherein a determination resulting from step (d) of a statistically significant difference in the measured levels identifies the target RNA transcript and its corresponding gene as potential biomarkers for the disease or other medical condition. Preferably, the target RNA transcript is selected from Tables 1-20.

In yet another aspect, the present invention is a method of profiling genetic aberrations in a subject, comprising the steps of: (a) isolating microvesicles from a subject; (b) detecting or measuring one or more genetic aberrations within the isolated microvesicles; and (c) determining one or more genetic profiles from the data obtained from steps (a) and (b). In one embodiment of the method, step (b) comprises the quantitative measurement of one or more nucleic acids within the isolated microvesicles and step (c) comprises the determination of one or more quantitative nucleic acid profiles. In a further embodiment of the method, the one or more nucleic acids are RNA transcripts selected from Tables 1-20. In another embodiment, the one or more nucleic acids are RNA transcripts selected from any one of Tables 1-20. In yet another further embodiment, the one or more nucleic acids comprise each of the RNA transcripts in any one of Tables 1-20. In any of the inventive methods, a step of enriching the isolated microvesicles for microvesicles originating from a specific cell type may be optionally included.

The present invention may be as defined in any one of the following numbered paragraphs.

1. A profile of one or more RNA transcripts obtained from microvesicles, wherein the one or more RNA transcripts are selected from Tables 1-20.
2. The profile of paragraph 1, wherein the microvesicles are isolated from a bodily fluid from a subject.
3. The profile of paragraph 2, wherein the bodily fluid is blood, serum, plasma or urine.
4. The profile of paragraph 2, wherein the subject is a human subject.
5. The profile of paragraph 4, wherein the human subject is a brain cancer patient.
6. The profile of paragraph 5, wherein the brain cancer is glioblastoma.
7. The profile of paragraph 1, wherein the profile is obtained through analyzing RNA transcripts obtained from microvesicles.
8. The profile of paragraph 7, wherein the analysis of RNA transcripts is performed by a method comprising microarray analysis, Reverse Transcription PCR, Quantitative PCR or a combination thereof.
9. The profile of paragraph 8, wherein the analytic method further comprises data analysis.
10. The profile of paragraph 9, wherein the data analysis comprises Clustering Analysis, Principle Component Analysis, Linear Discriminant Analysis, Receiver Operating Characteristic Curve Analysis, Binary Analysis, Cox Proportional Hazards Analysis, Support Vector Machines and Recursive Feature Elimination (SVM-RFE), Classification to Nearest Centroid, Evidence-based Analysis, or a combination thereof.
11. The profile of paragraph 10, wherein the data analysis comprises Clustering Analysis, Principle Component Analysis, Linear Discriminant Analysis, or a combination thereof.
12. The profile of paragraph 1, wherein the one or more RNA transcripts are selected from Table 1.
13. The profile of paragraph 1, wherein the one or more RNA transcripts comprise each of the transcripts in Table 1.
14. The profile of paragraph 1, wherein the one or more RNA transcripts are selected from Table 2.
15. The profile of paragraph 1, wherein the one or more RNA transcripts comprise each of the transcripts in Table 2.
16. The profile of paragraph 1, wherein the one or more RNA transcripts are selected from Table 3.
17. The profile of paragraph 1, wherein the one or more RNA transcripts comprise each of the transcripts in Table 3.
18. The profile of paragraph 1, wherein the one or more RNA transcripts are selected from Table 4.
19. The profile of paragraph 1, wherein the one or more RNA transcripts comprise each of the transcripts in Table 4.
20. The profile of paragraph 1, wherein the one or more RNA transcripts are selected from Table 5.
21. The profile of paragraph 1, wherein the one or more RNA transcripts comprise each of the transcripts in Table 5.
22. The profile paragraph 1, wherein the one or more RNA transcripts are selected from Table 6.
23. The profile of paragraph 1, wherein the one or more RNAs transcripts comprise each of the transcripts in Table 6.
24. The profile of paragraph 1, wherein the one or more RNA transcripts are selected from Table 7.

25. The profile of paragraph 1, wherein the one or more RNA transcripts comprise each of the transcripts in Table 7.
26. The profile of paragraph 1, wherein the one or more RNA transcripts are selected from Table 8.
27. The profile of paragraph 1, wherein the one or more RNA transcripts comprise each of the transcripts in Table 8.
28. The profile of paragraph 1, wherein the one or more RNA transcripts are selected from Table 9.
29. The profile of paragraph 1, wherein the one or more RNA transcripts comprise each of the transcripts in Table 9.
30. The profile of paragraph 1, wherein the one or more RNA transcripts are selected from Table 10.
31. The profile of paragraph 1, wherein the one or more RNA transcripts comprise each of the transcripts in Table 10.
32. The profile of paragraph 1, wherein the one or more RNA transcripts are selected from Table 11.
33. The profile of paragraph 1, wherein the one or more RNA transcripts comprise each of the transcripts in Table 11.
34. The profile of paragraph 1, wherein the one or more RNA transcripts are selected from Table 12.
35. The profile of paragraph 1, wherein the one or more RNA transcripts comprise each of the transcripts in Table 12.
36. The profile of paragraph 1, wherein the one or more RNA transcripts are selected from Table 13.
37. The profile of paragraph 1, wherein the one or more RNA transcripts comprise each of the transcripts in Table 13.
38. The profile of paragraph 1, wherein the one or more RNA transcripts are selected from Table 14.
39. The profile of paragraph 1, wherein the one or more RNA transcript comprise each of the transcripts in Table 14.
40. The profile of paragraph 1, wherein the one or more RNA transcripts are selected from Table 15.
41. The profile of paragraph 1, wherein the one or more RNA transcripts comprise each of the transcripts in Table 15.
42. The profile of paragraph 1, wherein the one or more RNA transcripts are selected from Table 16.
43. The profile of paragraph 1, wherein the one or more RNA transcripts comprise each of the transcripts in Table 16.
44. The profile of paragraph 1, wherein the one or more RNA transcripts are selected from Table 17.
45. The profile of paragraph 1, wherein the one or more RNA transcripts comprise each of the transcripts in Table 17.
46. The profile of paragraph 1, wherein the one or more RNA transcripts are selected from Table 18.
47. The profile of paragraph 1, wherein the one or more RNA transcripts comprise each of the transcripts in Table 18.
48. The profile of paragraph 1, wherein the one or more RNA transcripts are selected from Table 19.
49. The profile of paragraph 1, wherein the one or more RNA transcripts comprise each of the transcripts in Table 19.
50. The profile of paragraph 1, wherein the one or more RNA transcripts are selected from Table 20.
51. The profile of paragraph 1, wherein the one or more RNA transcripts comprise each of the transcripts in Table 20.
52. A method of aiding diagnosis, prognosis or therapy treatment planning for a subject, comprising:
   a. isolating microvesicles from a subject;
   b. measuring the expression level of one or more RNA transcripts extracted from the isolated microvesicles;
   c. determining a profile of the one or more RNA transcripts based on the expression level; and
   d. comparing the profile to a reference profile to aid diagnosis, prognosis or therapy treatment planning for the subject.
53. The method of paragraph 52, wherein the microvesicles are isolated from a bodily fluid from the subject.
54. The method of paragraph 53, wherein the bodily fluid is blood, plasma, serum or urine.
55. The method of paragraph 53, wherein the subject is a human subject.
56. The method of paragraph 55, wherein the human subject is a brain cancer patient.
57. The method of paragraph 55, wherein the brain cancer is glioblastoma.
58. The method of paragraph 52, wherein step (b) is performed by a method comprising microarray analysis, Reverse Transcription PCR, Quantitative PCR or a combination thereof.
59. The method of paragraph 52, wherein step (c) performed by a method of data analysis.
60. The method of paragraph 59, wherein the data analysis comprises Clustering Analysis, Principle Component Analysis, Linear Discriminant Analysis, Receiver Operating Characteristic Curve Analysis, Binary Analysis, Cox Proportional Hazards Analysis, Support Vector Machines and Recursive Feature Elimination (SVM-RFE), Classification to Nearest Centroid, Evidence-based Analysis, or a combination thereof.
61. The method of paragraph 60, wherein the data analysis comprises Clustering Analysis, Principle Component Analysis, Linear Discriminant Analysis, or a combination thereof.
62. The method of paragraph 52, wherein the one or more RNA transcripts are selected from Tables 1-16.
63. The method of paragraph 52, wherein the one or more RNA transcripts are selected from Table 1.
64. The method of paragraph 52, wherein the one or more RNA transcripts comprise each of the transcripts in Table 1.
65. The method of paragraph 52, wherein the one or more RNA transcripts are selected from Table 2.
66. The method of paragraph 52, wherein the one or more RNA transcripts comprise each of the transcripts in Table 2.
67. The method of paragraph 52, wherein the one or more RNA transcripts are selected from Table 3.
68. The method of paragraph 52, wherein the one or more RNA transcripts comprise each of the transcripts in Table 3.
69. The method of paragraph 52, wherein the one or more RNA transcripts are selected from Table 4.
70. The method of paragraph 52, wherein the one or more RNA transcripts comprise each of the transcripts in Table 4.
71. The method of paragraph 52, wherein the one or more RNA transcripts are selected from Table 5.

72. The method of paragraph 52, wherein the one or more RNA transcripts comprise each of the transcripts in Table 5.
73. The method of paragraph 52, wherein the one or more RNA transcripts are selected from Table 6.
74. The method of paragraph 52, wherein the one or more RNA transcripts comprise each of the transcripts in Table 6.
75. The method of paragraph 52, wherein the one or more RNA transcripts are selected from Table 7.
76. The method of paragraph 52, wherein the one or more RNA transcripts comprise each of the transcripts in Table 7.
77. The method of paragraph 52, wherein the one or more RNA transcripts are selected from Table 8.
78. The method of paragraph 52, wherein the one or more RNA transcripts comprise each of the transcripts in Table 8.
79. The method of paragraph 52, wherein the one or more RNA transcripts are selected from Table 9.
80. The method of paragraph 52, wherein the one or more RNA transcripts comprise each of the transcripts in Table 9.
81. The method of paragraph 52, wherein the one or more RNA transcripts are selected from Table 10.
82. The method of paragraph 52, wherein the one or more RNA transcripts comprise each of the transcripts in Table 10.
83. The method of paragraph 52, wherein the one or more RNA transcripts are selected from Table 11.
84. The method of paragraph 52, wherein the one or more RNA transcripts comprise each of the transcripts in Table 11.
85. The method of paragraph 52, wherein the one or more RNA transcripts are selected from Table 12.
86. The method of paragraph 52, wherein the one or more RNA transcripts comprise each of the transcripts in Table 12.
87. The method of paragraph 52, wherein the one or more RNA transcripts are selected from Table 13.
88. The method of paragraph 52, wherein the one or more RNA transcripts comprise each of the transcripts in Table 13.
89. The method of paragraph 52, wherein the one or more RNA transcripts are selected from Table 14.
90. The method of paragraph 52, wherein the one or more RNA transcripts comprise each of the transcripts from Table 14.
91. The method of paragraph 52, wherein the one or more RNA transcripts are selected from Table 15.
92. The method in paragraph 52, wherein the one or more RNA transcripts comprise each of the transcripts from Table 15.
93. The method of paragraph 52, wherein the one or more RNA transcripts are selected from Table 16.
94. The method of paragraph 52, wherein the one or more RNA transcripts comprise each of the transcripts from Table 16.
95. The method of paragraph 52, wherein the one or more RNA transcripts are selected from Table 17.
96. The method of paragraph 52, wherein the one or more RNA transcripts comprise each of the transcripts from Table 17.
97. The method of paragraph 52, wherein the one or more RNA transcripts are selected from Table 18.
98. The method of paragraph 52, wherein the one or more RNA transcripts comprise each of the transcripts from Table 18.
99. The method of paragraph 52, wherein the one or more RNA transcripts are selected from Table 19.
100. The method of paragraph 52, wherein the one or more RNA transcripts comprise each of the transcripts from Table 19.
101. The method of paragraph 52, wherein the one or more RNA transcripts are selected from Table 20.
102. The method of paragraph 52, wherein the one or more RNA transcripts comprise each of the transcripts from Table 20.
103. A method of preparing a personalized genetic profile report for a subject, comprising the steps of:
    (a) isolating microvesicles from a subject;
    (b) detecting or measuring one or more genetic aberrations within the isolated microvesicles;
    (c) determining one or more genetic profiles from the data obtained from steps (a) and (b);
    (d) optionally comparing the one or more genetic profiles to one or more reference profiles; and
    (e) creating a report summarizing the data obtained from steps (a) through (d) and optionally including diagnostic, prognostic or therapeutic treatment information.
104. The method of paragraph 103, wherein step (b) comprises the quantitative measurement of one or more nucleic acids within the isolated microvesicles and step (c) comprises the determination of one or more quantitative nucleic acid profiles.
105. The method of paragraph 104, wherein the one or more nucleic acids are RNA transcripts selected from Tables 1-20.
106. The method of paragraph 104, wherein the one or more nucleic acids are RNA transcripts selected from any one of Tables 1-20.
107. The method of paragraph 104, wherein the one or more nucleic acids comprise each of the RNA transcripts in any one of Tables 1-20.
108. A kit for genetic analysis of an exosome preparation from a body fluid sample from a subject, comprising, in a suitable container, one or more reagents suitable for hybridizing to or amplifying one or more of the RNA transcripts selected from Tables 1-20.
109. The kit of paragraph 108, comprising one or more reagents suitable for hybridizing to or amplifying one or more of the RNA transcripts selected from any one of Tables 1-20.
110. The kit of paragraph 108, comprising one or more reagents suitable for hybridizing to or amplifying each of the RNA transcripts in any one of Tables 1-20.
111. An oligonucleotide microarray for genetic analysis of an exosome preparation from a body fluid sample from a subject, wherein the oligos on the array are custom-designed to hybridize exclusively to one or more transcripts selected from Tables 1-20.
112. A method of identifying at least one potential biomarker for a disease or other medical condition, the method comprising:
    (a) isolating microvesicles from subjects having a disease or other medical condition of interest and from subjects who do not have the disease or other medical condition of interest;
    (b) measuring the expression level of a target RNA transcript extracted from the isolated microvesicles from each of the subjects;

(c) comparing the measured levels of the target RNA transcript from each of the subjects; and
(d) determining whether there is a statistically significant difference in the measured levels;
113. The method of paragraph 112, wherein a determination resulting from step (d) of a statistically significant difference in the measured levels identifies the target RNA transcript and its corresponding gene as potential biomarkers for the disease or other medical condition, and wherein the target RNA transcript is selected from Tables 1-20.
114. A method of profiling genetic aberrations in a subject, comprising the steps of:
(a) isolating microvesicles from a subject;
(b) detecting or measuring one or more genetic aberrations within the isolated microvesicles;
(c) determining one or more genetic profiles from the data obtained from steps (a) and (b).
115. The method of paragraph 114, wherein step (b) comprises the quantitative measurement of one or more nucleic acids within the isolated microvesicles and step (c) comprises the determination of one or more quantitative nucleic acid profiles.
116. The method of paragraph 114, wherein the one or more nucleic acids are RNA transcripts selected from Tables 1-20.
117. The method of paragraph 114, wherein the one or more nucleic acids are RNA transcripts selected from any one of Tables 1-20.
118. The method of paragraph 114, wherein the one or more nucleic acids comprise each of the RNA transcripts in any one of Tables 1-20.
119. The method of any of paragraphs 52, 103, 112 or 114, further comprising the step of enriching the isolated microvesicles for microvesicles originating from a specific cell type.

DETAILED DESCRIPTION OF THE INVENTION

Figure 1A:
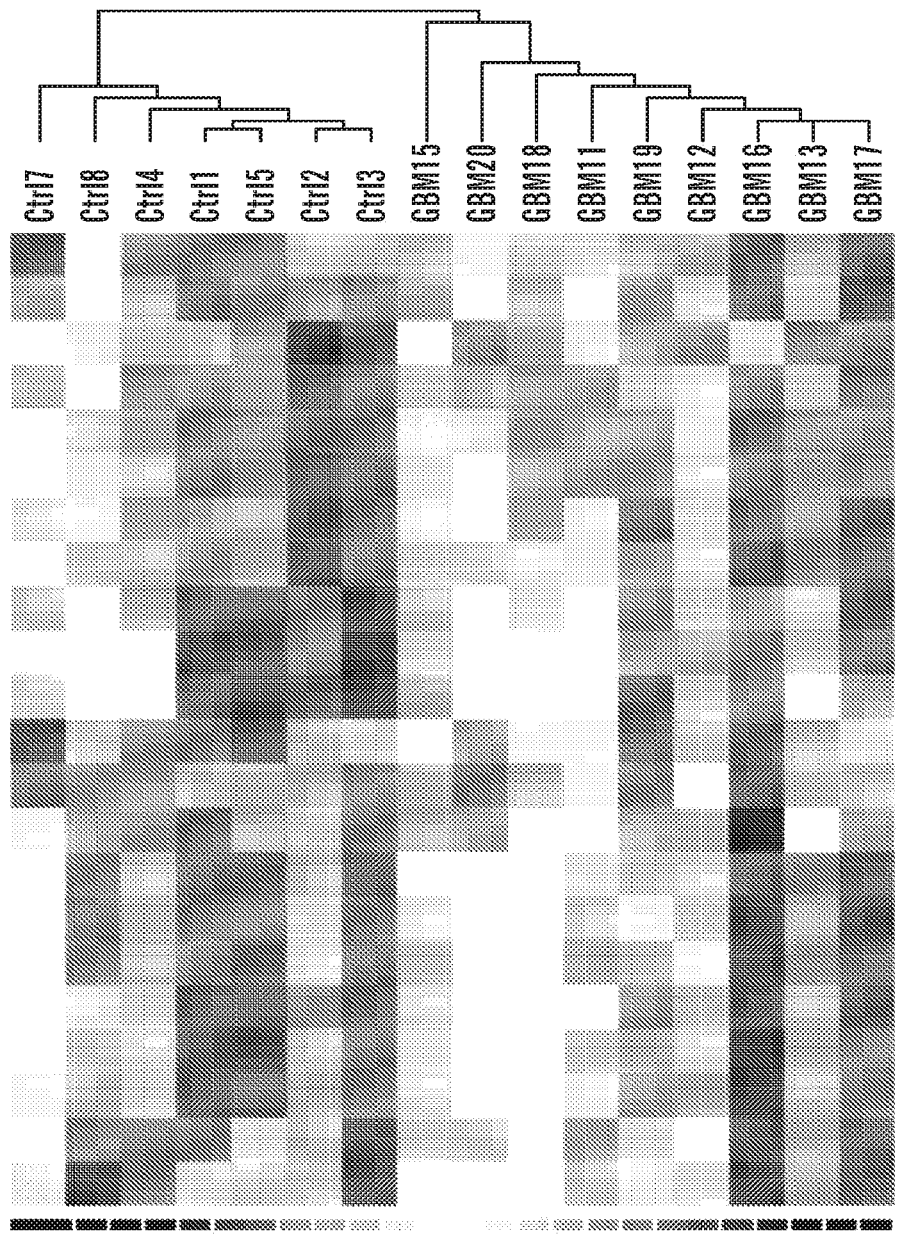
FIG. 1A. Heatmap and Clustering diagram illustrating microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $5\times10$ and with the log-median-ratio (i.e. the logarithm to the ratio between the median expression level of a given gene in GBMs and the same gene in Ctrls, log(median(GeneX(GBMs))/median(GeneX(Ctrls)))) being at least "1" or above, or with a P value less than or equal to $2\times10^{-6}$. The genes included in the data set are listed in Table 1.

Microvesicles are shed by eukaryotic cells, or budded off of the plasma membrane, to the exterior of the cell. These membrane vesicles are heterogeneous in size with diameters ranging from about 10 nm to about 5000 nm. The small microvesicles (approximately 10 to 1000 nm, and more often approximately 30 to 200 nm in diameter) that are released by exocytosis of intracellular multivesicular bodies or by double inward budding of multivesicular bodies are referred to in the art as "exosomes." The compositions, methods and uses described herein are equally applicable to microvesicles of all sizes; preferably 30 to 800 nm; and more preferably 30 to 200 nm.

In some of the literature, the term "exosome" also refers to protein complexes containing exoribonucleases which are involved in mRNA degradation and the processing of small nucleolar RNAs (snoRNAs), small nuclear RNAs (snRNAs) and ribosomal RNAs (rRNA) (Liu et al., 2006; van Dijk et al., 2007). Such protein complexes do not have membranes and are not "microvesicles" or "exosomes" as those terms are used here in.

Certain aspects of the present invention are based on the surprising finding that glioblastoma derived microvesicles can be isolated from the serum of glioblastoma patients (Skog et al., 2008). This is the first discovery of microvesicles derived from cells in the brain, present in a bodily fluid of a subject. Prior to this discovery it was not known whether glioblastoma cells produced microvesicles or whether such microvesicles could cross the blood brain bather into the rest of the body. These microvesicles were found to contain mutant mRNA associated with tumor cells (Skog et al., 2008). The microvesicles also contained microRNAs (miRNAs) which were found to be abundant in glioblastomas (Skog et al., 2008). Glioblastoma-derived microvesicles were also found to potently promote angiogenic features in primary human brain microvascular endothelial cells (HBMVEC) in culture. This angiogenic effect was mediated at least in part through angiogenic proteins present in the microvesicles (Skog et al., 2008). The nucleic acids found within these microvesicles, as well as other contents of the microvesicles such as angiogenic proteins, can be used as valuable biomarkers for tumor diagnosis, characterization and prognosis by providing a genetic profile. Contents within these microvesicles can also be used to monitor tumor progression over time by analyzing if other mutations are acquired during tumor progression as well as if the levels of certain mutations or gene expression increase or decrease over time or over a course of treatment.

Certain aspects of the present invention are based on another finding that most of the extracellular RNA in bodily fluid from a subject is contained within microvesicles and thus protected from degradation by ribonucleases (Skog et al., 2008). More than 90% of extracellular RNA in total serum can be recovered in microvesicles (Skog et al., 2008).

One aspect of the present invention relates to methods for detecting, diagnosing, monitoring, treating or evaluating a disease or other medical condition in a subject comprising the steps of, isolating exosomes from a bodily fluid of a subject, and analyzing one or more nucleic acids contained within the exosomes. The nucleic acids are analyzed qualitatively and/or quantitatively, and the results are compared to results expected or obtained for one or more other subjects who have or do not have the disease or other medical condition. The presence of a difference in microvesicular nucleic acid content of the subject, as compared to that of one or more other individuals, can indicate the presence or absence of, the progression of (e.g., changes of tumor size and tumor malignancy), or the susceptibility to a disease or other medical condition in the subject.

The isolation methods and techniques described herein provide the following heretofore unrealized advantages: 1) the opportunity to selectively analyze disease- or tumor-specific nucleic acids, which may be realized by isolating disease- or tumor-specific microvesicles apart from other microvesicles within the fluid sample; 2) significantly higher yield of nucleic acid species with higher sequence integrity as compared to the yield/integrity obtained by extracting nucleic acids directly from the fluid sample; 3) scalability, e.g. to detect nucleic acids expressed at low levels, the sensitivity can be increased by isolating more microvesicles from a larger volume of serum; 4) purer nucleic acids in that protein and lipids, debris from dead cells, and other potential contaminants and PCR inhibitors are excluded from the microvesicle preparation before the nucleic acid extraction step; and 5) more choices in nucleic acid extraction methods as microvesicle preparations are of much smaller volume than that of the starting serum, making it possible to extract nucleic acids from the microvesicle preparations using small volume column filters.

The microvesicles are preferably isolated from a bodily fluid from a subject. As used herein, a "bodily fluid" refers to a sample of fluid isolated from anywhere in the body of the subject, preferably a peripheral location, including but not limited to, for example, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof.

The term "subject" is intended to include all animals shown to or expected to have microvesicles. In particular embodiments, the subject is a mammal, a human or nonhuman primate, a dog, a cat, a horse, a cow, other farm animals, or a rodent (e.g. mice, rats, guinea pig etc.). The term "subject" and "individual" are used interchangeably herein.

Methods of isolating microvesicles from a biological sample are known in the art. For example, a method of differential centrifugation is described in a paper by Raposo et al. (Raposo et al., 1996) and a paper by Skog et. al.(Skog et al., 2008). Methods of anion exchange and/or gel permeation chromatography are described in U.S. Pat. Nos. 6,899, 863 and 6,812,023. Methods of sucrose density gradients or organelle electrophoresis are described in U.S. Pat. No. 7,198,923. A method of magnetic activated cell sorting (MACS) is described in (Taylor and Gercel-Taylor, 2008). A method of nanomembrane ultrafiltration is described in (Cheruvanky et al., 2007). Additionally, microvesicles can be identified and isolated from bodily fluid of a subject by a recently developed microchip technology that uses a microfluidic platform to separate tumor-derived microvesicles. This technology, as described in a paper by Nagrath et al. (Nagrath et al., 2007), can be adapted to identify and separate microvesicles using similar principles of capture and separation as taught in the paper. Further, a method of isolating microvesicles from urine samples is described in a paper by Miranda et. al.(Miranda et al., 2010) and in PCT/US2010/042365 by Russo et. al., filed Jul. 16, 2010 (expected to publish in 2011). Each of the foregoing references is incorporated by reference herein for its teaching of these methods.

In one embodiment, the microvesicles isolated from a bodily fluid are enriched for those originating from a specific cell type, for example, lung, pancreas, stomach, intestine, bladder, kidney, ovary, testis, skin, colorectal, breast, prostate, brain, esophagus, liver, placenta, fetus cells. Because the microvesicles often carry surface molecules such as antigens from their donor cells, surface molecules may be used to identify, isolate and/or enrich for microvesicles from a specific donor cell type (Al-Nedawi et al., 2008; Taylor and Gercel-Taylor, 2008). In this way, microvesicles originating from distinct cell populations can be analyzed for their nucleic acid content. For example, tumor (malignant and non-malignant) microvesicles carry tumor-associated surface antigens and may be detected, isolated and/or enriched via these specific tumor-associated surface antigens. In one example, the surface antigen is epithelial-cell-adhesion-molecule (EpCAM), which is specific to microvesicles from carcinomas of lung, colorectal, breast, prostate, head and neck, and hepatic origin, but not of hematological cell origin (Balzar et al., 1999; Went et al., 2004). In another example, the surface antigen is CD24, which is a glycoprotein specific to urine microvesicles (Keller et al., 2007). In yet another example, the surface antigen is selected from a group of molecules including CD70, carcinoembryonic antigen (CEA), EGFR, EGFRvIII and other variants, Fas ligand, TRAIL, tranferrin receptor, p38.5, p97 and HSP72. Additionally, tumor-specific microvesicles may be characterized by the lack of surface markers, such as CD80 and CD86.

The isolation of microvesicles from specific cell types can be accomplished, for example, by using antibodies, aptamers, aptamer analogs or molecularly imprinted polymers specific for a desired surface antigen. In one embodiment, the surface antigen is specific for a cancer type. In another embodiment, the surface antigen is specific for a cell type which is not necessarily cancerous. One example of a method of microvesicle separation based on cell surface antigen is provided in U.S. Pat. No. 7,198,923. As described in, e.g., U.S. Pat. Nos. 5,840,867 and 5,582,981, WO/2003/050290 and a publication by Johnson et al. (Johnson et al., 2008), aptamers and their analogs specifically bind surface molecules and can be used as a separation tool for retrieving cell type-specific microvesicles. Molecularly imprinted polymers also specifically recognize surface molecules as described in, e.g., U.S. Pat. Nos. 6,525,154, 7,332,553 and 7,384,589 and a publication by Bossi et al. (Bossi et al., 2007) and are a tool for retrieving and isolating cell type-specific microvesicles. Each of the foregoing reference is incorporated herein for its teaching of these methods.

It may be beneficial or otherwise desirable to extract the nucleic acid from the exosomes prior to the analysis. Nucleic acid molecules can be extracted from a microvesicle using any number of procedures, which are well-known in the art, the particular extraction procedure chosen being appropriate for the particular biological sample. In some instances, with some techniques, it may also be possible to analyze the nucleic acid without extraction from the microvesicle.

In one embodiment, the extracted nucleic acids, including DNA and/or RNA, are analyzed directly without an amplification step. Direct analysis may be performed with different methods including, but not limited to, nanostring technology. NanoString technology enables identification and quantification of individual target molecules in a biological sample by attaching a color-coded fluorescent reporter to each target molecule. This approach is similar to the concept of measuring inventory by scanning barcodes. Reporters can be made with hundreds or even thousands of different codes allowing for highly multiplexed analysis. The technology is described in a publication by Geiss et al. (Geiss et al., 2008) and is incorporated herein by reference for this teaching.

In another embodiment, it may be beneficial or otherwise desirable to amplify the nucleic acid of the microvesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a profile as described below.

In one embodiment, the extracted nucleic acid is RNA. Preferably, the RNA is reverse-transcribed into complementary DNA before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008) or any other known nucleic acid amplification methods, followed by the detection of the amplified molecules using techniques known to those of skill in the art. Especially useful are those detection schemes designed for the detection of nucleic acid molecules if such molecules are present in very low numbers. The foregoing references are incorporated herein for their teachings of these methods.

The analysis of nucleic acids present in the microvesicles is quantitative and/or qualitative. For quantitative analysis, the amounts (e.g., expression levels), either relative or absolute, of all or specific nucleic acids of interest within the microvesicles are measured with methods known in the art (described below). For qualitative analysis, all or specific species of nucleic acids of interest within the microvesicles, whether wild-type or variants, are identified with methods known in the art (described below).

A "profile" is used herein to refer to the result of a quantitative analysis, a qualitative analysis, or a combination of both. The analysis may be an analysis of the nucleic acids as well as other contents extracted from a biological sample, e.g., a microvesicle. In one embodiment, a profile of genes refers to one or more genetic aberrations of the genes. Similarly, a profile of genes also refers to a signature of genes herein.

A "genetic aberration" is used herein to refer to a nucleic acid amount as well as a nucleic acid variant within a biological sample, e.g., a microvesicle. Specifically, genetic aberrations include, without limitation, over-expression of a gene (e.g., oncogenes) or a panel of genes, under-expression of a gene (e.g., tumor suppressor genes such as p53 or RB) or a panel of genes, alternative production of splice variants of a gene or a panel of genes, gene copy number variants (CNV) (e.g. DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splicing variants and/or changes of gene expression level.

The determination of such genetic aberrations can be performed by a variety of techniques known to the skilled practitioner. For example, expression levels of nucleic acids, alternative splicing variants, chromosome rearrangement and gene copy numbers can be determined by microarray analysis (U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO 2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE)(Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590) and combinations or modifications of any of the foregoing. Notably, gene expression levels may be determined by the serial analysis of gene expression (SAGE) technique (Velculescu et al., 1995). In general, the methods for analyzing genetic aberrations are reported in numerous publications, not limited to those cited herein, and are available to skilled practitioners. The appropriate method of analysis will depend upon the specific goals of the analysis, the condition and/or history of the patient, and the specific cancer(s), diseases or other medical conditions to be detected, monitored or treated. The forgoing references are incorporated herein for their teachings of these methods.

In one embodiment, the analysis is of a profile of the amounts (levels) of all or specific nucleic acids present in the microvesicle, herein referred to as a "quantitative nucleic acid profile" of the microvesicles. In another embodiment, the analysis is of a profile of the species of all or specific nucleic acids present in the microvesicles (both wild type as well as variants), herein referred to as a "nucleic acid species profile." A term used herein to refer to a combination of these types of profiles is "genetic profile" which refers to the determination of the presence or absence of nucleotide species, variants and also increases or decreases in nucleic acid levels.

Once generated, these genetic profiles of the microvesicles are compared to those expected in, or otherwise derived from a healthy normal individual. A profile can be a genome-wide profile (representing all possible expressed genes or DNA sequences). It can be narrower as well, such as a cancer-wide profile (representing all possible genes or nucleic acids derived from or associated with cancer). Where a specific cancer is suspected or known to exist, the profile can be specific to that cancer (e.g., representing all possible genes or nucleic acids derived from or associated with the cancer or various clinically distinct subtypes of that cancer or known drug-resistant or sensitive forms of the cancer).

The methods of nucleic acid isolation, amplification and analysis are routine for one skilled in the art and examples of protocols can be found, for example, in *Molecular Cloning: A Laboratory Manual* (3-Volume Set) Ed. Joseph Sambrook, David W. Russel, and Joe Sambrook, Cold Spring Harbor Laboratory, 3rd edition (Jan. 15, 2001), ISBN: 0879695773. A particular useful protocol source for methods used in PCR amplification is *PCR Basics: From Background to Bench* by Springer Verlag; 1st edition (Oct. 15, 2000), ISBN: 0387916008.

Many methods of diagnosis performed on a tumor biopsy sample can be performed with microvesicles since tumor cells are known to shed microvesicles into bodily fluid and the genetic aberrations within these microvesicles are reflective of those within the tumor cells themselves (Skog et al., 2008). Furthermore, methods of diagnosis using microvesicles have characteristics that are absent in methods of diagnosis performed directly on a tumor biopsy sample. For example, one particular advantage of the analysis of microvesicular nucleic acids, as opposed to other forms of sampling of tumor/cancer nucleic acid, is the availability for analysis of tumor/cancer nucleic acids derived from all foci of a tumor or genetically heterogeneous tumors present in an individual. Biopsy samples are limited in that they provide information only about the specific focus of the tumor from which the biopsy is obtained. Different tumorous/cancerous foci found within the body, or even within a single tumor often have different genetic profiles, all of which are not analyzed in a standard biopsy. However, analysis of the microvesicular nucleic acids from an individual has the potential to provide a sampling of all foci within an individual. This provides valuable information with respect to recommended treatments, treatment effectiveness, disease prognosis, and analysis of disease recurrence, which cannot be provided by a simple biopsy.

Aspects of the present invention relate to a method for monitoring disease (e.g. cancer) progression in a subject, and also to a method for monitoring disease recurrence in an individual. These methods comprise the steps of isolating microvesicles from a bodily fluid of an individual, as discussed herein, and analyzing nucleic acid within the microvesicles as discussed herein (e.g. to create a genetic profile of the microvesicles). The presence or absence of a certain genetic aberration or profile is used to indicate the presence or absence of the disease (e.g., cancer) in the subject as discussed herein. The process is performed periodically over time, and the results reviewed, to monitor the progression or regression of the disease, or to determine recurrence of the disease. Put another way, a change in the microvesicular genetic profile indicates a change in the disease state in the subject. The period of time to elapse between sampling of microvesicles from the subject, for performance of the isolation and analysis of the microvesicles, will depend upon the circumstances of the subject, and is to be determined by the skilled practitioner. Such a method would be extremely beneficial when analyzing nucleic acid from a gene that is associated with the therapy undergone by the subject. For example, a gene which is targeted by the therapy can be monitored for the development of mutations which make it resistant to the therapy, upon which time the therapy can be modified accordingly. The monitored gene may also be one which indicates specific responsiveness to a specific therapy.

Aspects of the present invention also relate to the fact that a variety of non-cancer diseases and/or medical conditions also have genetic links and/or causes, and such diseases and/or medical conditions can likewise be diagnosed and/or monitored by the methods described herein. Many such diseases are metabolic, infectious or degenerative in nature. One such disease is diabetes (e.g. diabetes insipidus) in which the vasopressin type 2 receptor (V2R) is modified. Another such disease is kidney fibrosis in which genetic profiles for the genes of collagens, fibronectin and TGF-β are changed. Changes in genetic profiles due to substance abuse, viral and/or bacterial infection, and hereditary disease states can likewise be detected by the methods described herein.

Diseases or other medical conditions for which the inventions described herein are applicable include, but are not limited to, nephropathy, diabetes insipidus, diabetes mellitus, diabetes type I, diabetes II, renal disease glomerulonephritis, bacterial or viral glomerulonephritides, IgA nephropathy, Henoch-Schonlein Purpura, membranoproliferative glomerulonephritis, membranous nephropathy, Sjogren's syndrome, nephrotic syndrome minimal change disease, focal glomerulosclerosis and related disorders, acute renal failure, acute tubulointerstitial nephritis, pyelonephritis, GU tract inflammatory disease, Pre-clampsia, renal graft rejection, leprosy, reflux nephropathy, nephrolithiasis, genetic renal disease, medullary cystic, medullar sponge, polycystic kidney disease, autosomal dominant polycystic kidney disease, autosomal recessive polycystic kidney disease, tuberous sclerosis, von Hippel-Lindau disease, familial thinglomerular basement membrane disease, collagen III glomerulopathy, fibronectin glomerulopathy, Alport's syndrome, Fabry's disease, Nail-Patella Syndrome, congenital urologic anomalies, monoclonal gammopathies, multiple myeloma, amyloidosis and related disorders, febrile illness, familial Mediterranean fever, HIV infection-AIDS, inflammatory disease, systemic vasculitides, polyarteritis nodosa, Wegener's granulomatosis, polyarteritis, necrotizing and crecentic glomerulonephritis, polymyositis-dermatomyositis, pancreatitis, rheumatoid arthritis, systemic lupus erythematosus, gout, blood disorders, sickle cell disease, thrombotic thrombocytopenia purpura, Fanconi's syndrome, transplantation, acute kidney injury, irritable bowel syndrome, hemolytic-uremic syndrome, acute corticol necrosis, renal thromboembolism, trauma and surgery, extensive injury, burns, abdominal and vascular surgery, induction of anesthesia, side effect of use of drugs or drug abuse, circulatory disease myocardial infarction, cardiac failure, peripheral vascular disease, hypertension, coronary heart disease, non-atherosclerotic cardiovascular disease, atherosclerotic cardiovascular disease, skin disease, psoriasis, systemic sclerosis, respiratory disease, COPD, obstructive sleep apnoea, hypoia at high altitude or endocrine disease, or acromegaly.

Selection of an individual from whom the microvesicles are isolated is performed by the skilled practitioner based upon analysis of one or more of a variety of factors. Such factors for consideration are whether the subject has a family history of a specific disease (e.g., a cancer), has a genetic predisposition for such a disease, has an increased risk for such a disease, or has physical symptoms which indicate a predisposition, or environmental reasons. Environmental reasons include lifestyle, exposure to agents which cause or contribute to the disease such as in the air, land, water or diet. In addition, having previously had the disease, being currently diagnosed with the disease prior to therapy or after therapy, being currently treated for the disease (undergoing therapy), being in remission or recovery from the disease, are other reasons to select an individual for performing the methods.

The cancer diagnosed, monitored or otherwise profiled, can be any kind of cancer. This includes, without limitation, epithelial cell cancers such as lung, ovarian, cervical, endometrial, breast, brain, colon and prostate cancers. Also included are gastrointestinal cancer, head and neck cancer, non-small cell lung cancer, cancer of the nervous system, kidney cancer, retina cancer, skin cancer, liver cancer, pancreatic cancer, genital-urinary cancer and bladder cancer, melanoma, and leukemia. In addition, the methods and compositions of the present invention are equally applicable to detection, diagnosis and prognosis of non-malignant tumors in an individual (e.g., neurofibromas, meningiomas and schwannomas).

In one embodiment, the cancer is brain cancer. Types of brain tumors and cancer are well known in the art. Glioma is a general name for tumors that arise from the glial (supportive) tissue of the brain. Gliomas are the most common primary brain tumors. Astrocytomas, ependymomas, oligodendrogliomas, and tumors with mixtures of two or more cell types, called mixed gliomas, are the most common gliomas. The following are other common types of brain tumors: Acoustic Neuroma (Neurilemmoma, Schwannoma. Neurinoma), Adenoma, Astracytoma, Low-Grade Astrocytoma, giant cell astrocytomas, Mid- and High-Grade Astrocytoma, Recurrent tumors, Brain Stem Glioma, Chordoma, Choroid Plexus Papilloma, CNS Lymphoma (Primary Malignant Lymphoma), Cysts, Dermoid cysts, Epidermoid cysts, Craniopharyngioma, Ependymoma Anaplastic ependymoma, Gangliocytoma (Ganglioneuroma), Ganglioglioma, Glioblastoma Multiforme (GBM), Malignant Astracytoma, Glioma, Hemangioblastoma, Inoperable Brain Tumors, Lymphoma, Medulloblastoma (MDL), Meningioma, Metastatic Brain Tumors, Mixed Glioma, Neurofibromatosis, Oligodendroglioma. Optic Nerve Glioma, Pineal Region Tumors, Pituitary Adenoma, PNET (Primitive Neuroectodermal Tumor), Spinal Tumors, Subependymoma, and Tuberous Sclerosis (Bourneville's Disease).

As an exemplary embodiment of the present invention, one aspect of the present invention is a method of analyzing RNA profiles using microvesicles isolated from brain cancer serum samples. The method comprises the steps of isolating microvesicles from brain cancer serum samples and analyzing nucleic acids extracted from the isolated microvesicles.

As an exemplary embodiment of the present invention, another aspect of the present intention is the discovery of a series of brain cancer gene expression profiles or signatures. The signatures were discovered by analyzing nucleic acids extracted from brain cancer serum samples. The signatures can be used for the diagnosis and/or prognosis of brain caner, as well as treatment plan evaluation, selection and monitoring of brain cancer.

The exemplary embodiment of the present invention is illustrated in the following example for both method and signature aspects. In this example, gene signatures for glioblastoma cancer were obtained using methods and materials detailed below.

Blood samples from patients diagnosed with de-novo primary GBM were collected immediately prior to surgery, before opening of the dura mater, into a BD Vacutainer SST (#367985) at Massachusetts General Hospital (MGH). Blood from normal healthy controls was collected from volunteers recruited at the MGH blood bank. All samples were collected with informed consent according to the appropriate protocols approved by the Institutional Review Board at MGH. The blood was left to clot for 30 min and serum was isolated according to manufacturer's recommendations within two hours of collection. Serum was filtered by slowly passing it through a 0.8 μm syringe filter, aliquoted into 1.8 milliliter (ml) cryotubes and kept at −80° C. until used. Altogether, 9 serum samples from glioblastoma patients and 7 serum samples from non-glioblastoma human subjects were obtained for the following analysis.

Isolation of microvesicles from serum samples was performed as previously described (Skog et al., 2008). Briefly, 1 ml serum was centrifuged for 10 min at 300×g to eliminate any cell contamination. Supernatants were further centrifuged for 20 min at 16,500×g and filtered through a 0.22 μm filter. Microvesicles were then pelleted by ultracentrifugation at 110,000×g for 70 min. The microvesicle pellets were washed in 13 ml PBS, pelleted again and resuspended in cold PBS. Isolated microvesicles were measured for their total protein content using DC Protein Assay (Bio-Rad, Hercules, Calif., USA).

For the extraction of RNA from microvesicles, the pelleted microvesicles were incubated in an RNAse inhibitor solution for 5-10 minutes at room temperature. The RNase inhibitor can be from various known vendors, e.g., one inhibitor is "SUPERase" from Ambion Inc. Total RNA was extracted from the RNAse-treated microvesicles using various commercial RNA extraction kits such as the QIAamp RNA Blood Mini Kit or the miRNeasy mini kit from Qiagen, or the MirVana RNA isolation kit from Ambion Inc., according to the manufacturer's protocols. After treatment with DNAse according to the manufacturers' protocol, total RNA was eluted in 30 ul nuclease-free water. RNA quality and concentration was assessed with the Agilent Bioanalyzer RNA Pico Chip yielding typical concentrations of 0.4-0.8ng/μL for normal controls and 0.8-2.0ng/μL for GBM patients.

The extracted RNA was then analyzed using the Agilent 44K Whole Human Genome Oligo Microarrays (one-color), a standard gene expression analysis tool, according to standard protocols. Briefly, for the linear T7-based amplification step, from 0.07 μg up to 0.46 μg of total RNA was used, depending on the available amount of total RNA. To produce Cy3-labeled cRNA, the RNA samples were amplified and labeled using the Agilent Low RNA Input Linear Amp Kit (Agilent Technologies) following the manufacturer's protocol. Yields of cRNA and the dye incorporation rate were measured with the ND-1000 Spectrophotometer (NanoDrop Technologies). The hybridization procedure was performed according to the Agilent 60-mer oligo microarray processing protocol using the Agilent Gene Expression Hybridization Kit (Agilent Technologies). Briefly, 1.5-1.65 μg of Cy3-labeled fragmented cRNA in hybridization buffer was hybridized overnight (17 hours, 65° C.) to Agilent Whole Human Genome Oligo Microarrays 4×44K using Agilent's recommended hybridization chamber and oven. Finally, the microarrays were washed once with the Agilent Gene Expression Wash Buffer 1 for 1 min at room temperature followed by a second wash with preheated Agilent Gene Expression Wash Buffer 2 (37° C.) for 1 min. The last washing step was performed with acetonitrile. Fluorescence signals of the hybridized Agilent Microarrays were detected using Agilent's Microarray Scanner System (Agilent Technologies).

The Agilent Feature Extraction Software (FES) was used to read out and process the microarray image files. The software determines feature intensities (including background subtraction), rejects outliers and calculates statistical confidences. For the determination of differential gene expression, FES-derived output data files were further analyzed using the Rosetta Resolver gene expression data analysis system (Rosetta Biosoftware). This software offers—among other features—the ability to compare two single intensity profiles in a ratio experiment. All samples were labeled with Cy3. Here, the ratio experiments are designated as control versus (vs.) sample experiments (automated data output of the Resolver system).

The raw data from Feature Extraction was pre-processed and normalized in several different ways using R/Bioconductor and the packages limma, Agi4x44PreProcess and vsn. To ensure that the normalization procedure did not introduce unintended biases or artifacts, the data was normalized in three different ways using Quartile normalization with and without background subtraction and variance stabilized normalization (VSN), and the normalized data was compared to the raw values. Normalized data was transferred to Excel and filtered with different criteria as described below. Gene lists of interest were uploaded and analyzed with the online Gene Ontology Tool DAVID 6.7 (http://david.abcc.ncifcrf.gov/).

As a result, microvesicles (less than 0.8 μm in diameter) were isolated from serum samples from 9 GBM patients (prior to surgery) and 7 normal healthy controls. RNA from this exosomal fraction (exoRNA) was extracted, labeled and amplified by linear amplification and hybridized to Agilent 4×44K arrays. The raw data was corrected for background, normalized and submitted for deposit in the Gene Expression Omnibus database by user name/ID Mikkell Noerholm on Sep. 4, 2010 in the format of GEOarchive. The deposited file name is AgilentQuartileNorm_MeanSignal_GSMvsCTRL_GEO.zip. The deposited data are here incorporated by reference in its entirety including the array oligo sequences.

Clustering analysis, heat maps, and Principle Component Analysis of the normalized data was performed by using various softwares, e.g. GeneSifter, provided various sources, e.g., dChip (http://biosun1.harvard.edu/complab/dchip). A clustering analysis for genome-wide expression data from DNA microarray hybridization uses standard statistical algorithms to cluster genes according to similarity in pattern of gene expression (Eisen et al., 1998). A type of Principle Component Analysis is described previously (Alter et al., 2000).

Other data analysis tools, known in the art, may be substituted for the tools described and exemplified herein. In addition to Clustering Analysis, Principle Component Analysis, other analytic tools such as Linear Discriminant Analysis, Receiver Operating Characteristic Curve Analysis (Zweig and Campbell, 1993), Binary Analysis (U.S. Pat. No. 7,081,340), Cox Proportional Hazards Analysis (U.S. Pat. No. 7,081,340), Support Vector Machines and Recursive Feature Elimination (SVM-RFE) (U.S. Pat. No. 7,117,188), Classification to Nearest Centroid (Dabney, 2005) or combinations thereof may be used to analyze the expression data including microarray data.

Figure 17:
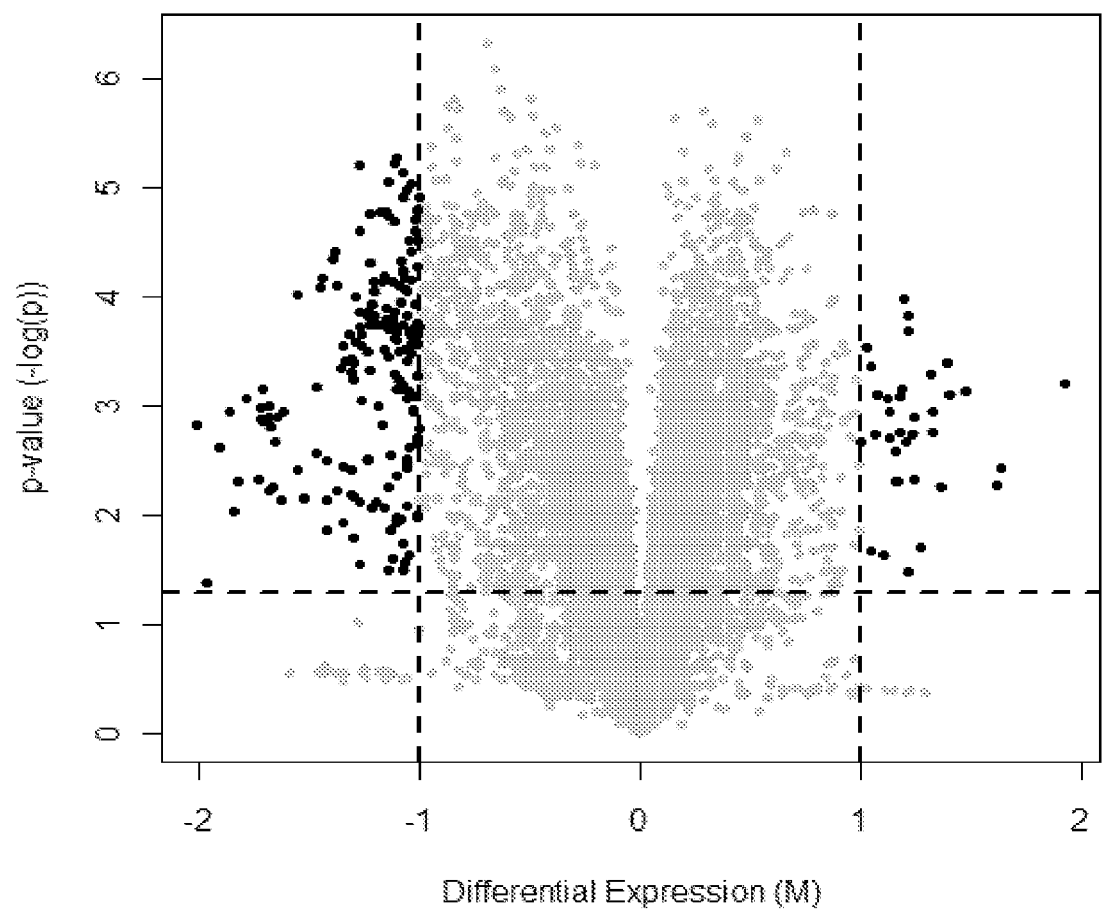
FIG. 17. Volcano plot of −log(p-value) of the t-test between the two groups (GBM vs. Non-GBM) plotted against the differential expression of each gene between groups(M=log(GBM)−log(Ctrl), i.e. M=1 means 2-fold up-regulation).
Figure 18A:
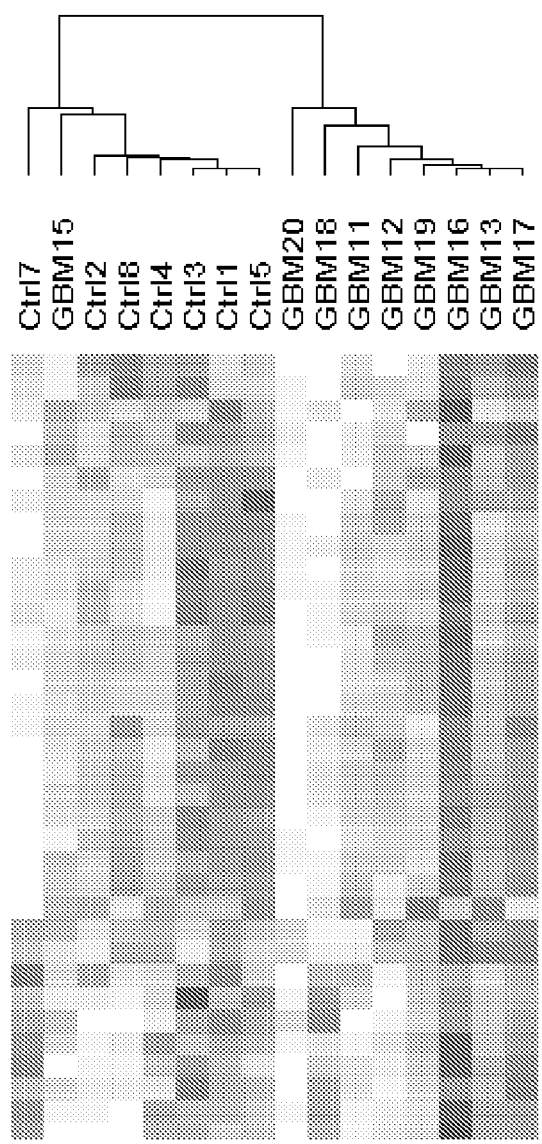
FIG. 18A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. The heatmap shown is a part of the heatmap showing the expression of the genes listed in Table 17. For each of the genes included in the data set, the expression levels in the GBM samples and in the control samples are significantly different with a $p \leq 5 \times 10^{-2}$ and the log-median-ratio being at least "1" or above or being at least "−1" or below. The p-values were corrected using Benjamin and Hochberg method.
Figure 18B:
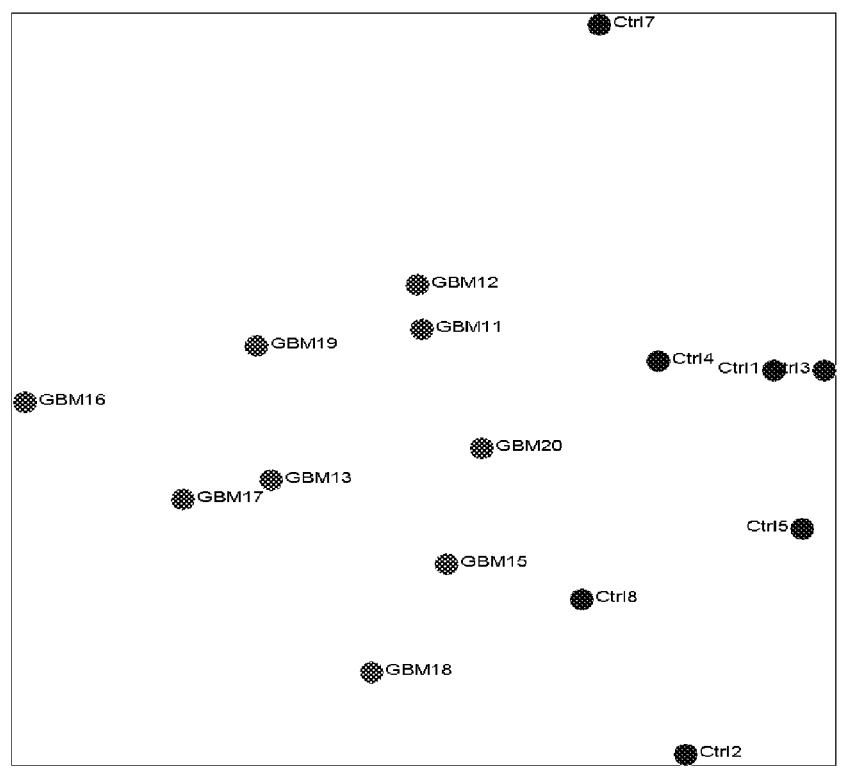
FIG. 18B. A plot showing the result of a Principle Component Analysis (PCA) performed on the data set of FIG. 18A with the same samples, the same genes and the same inclusion criteria.

We conducted a t-test between the two groups of samples on each gene in the full data set to identify the genes that best separate, distinguish, or discriminate between the two groups. As shown in FIG. 17, a volcano plot of the p-values against the level of differential expression, it is evident that substantially more genes are significantly down-regulated than up-regulated in the GBM samples. The level of differential expression is the difference of the median expression levels in the GBM and Control groups (i.e., median level in GBM—median level in Control). The typical degree of disregulation and the significance (p-value) is also higher for the down-regulated genes than for the up-regulated genes.

Based on the p values and the level of differential expression, we derived 16 different groups of genes from the above microarray data. The 16 groups of genes are listed in Tables 1-16, respectively. The criteria for inclusion of the each gene in the groups in Tables 1-16 are as follows:

Table 1: $p \leq 5 \times 10^{-4}$ and with the log-median-ratio being at least "1" or above, or $p \leq 0.000002$;
Table 2: $p \leq 5 \times 10^{-4}$ and the log-median-ratio being at least "1" or above;
Table 3: $p \leq 2 \times 10^{-3}$ and the log-median-ratio being at least "1" or above;
Table 4: $p \leq 2 \times 10^{-6}$;
Table 5: $p \leq 1 \times 10^{-5}$;
Table 6: $p \leq 5 \times 10^{-4}$ and the log-median-ratio being at least "0.8" or above, or being at least "−0.8" or below;
Table 7: $p \leq 1 \times 10^{-5}$ and the log-median-ratio being at least "0.585" or above, or being at least "−0.585" or below;
Table 8: $p \leq 1 \times 10^{-4}$ and the log-median-ratio being at least "1" or above, or being at least "−1" or below;
Table 9: $p \leq 1 \times 10^{-5}$ and the log-median-ratio being below "0";
Table 10: $p \leq 1 \times 10^{-5}$ and log-median-ratio being above "0";
Table 11: $p \leq 1 \times 10^{-4}$;
Table 12: $p \leq 1 \times 10^{-3}$ and the log-median-ratio being at least "1" or above, or being "−1" or below;
Table 13: $p \leq 0.05$ and the log-median-ratio being at least "1" or above, or being "−1" or below;
Table 14: $p \leq 0.05$ and the log-median-ratio being at least "0.585" or above;
Table 15: $p \leq 0.05$ and the log-median-ratio being at least "1" or above; and
Table 16: $p \leq 0.001$.

Each of the 16 groups can be a gene signature for glioblastoma. We tested each group for its capability as a glioblastoma signature. For each group, two independent tests were performed. One test used Clustering Analysis. The other test used Principle Component Analysis. For each group, the results (as illustrated in FIGS. 1-16, As and Bs, respectively) showed that at least one of the two tests separated the cancer group and the control group.

Accordingly, one embodiment of the present invention is a profile of one or more of genes selected from the genes in Tables 1-16. In another embodiment, the profiles are of one or more genes selected from a single Table, e.g., from Table 1. In a further embodiment, the profiles are of a group of genes comprising each of the genes in a single Table, e.g., Table1. One or more members in each group constitute a glioblastoma gene signature because either Clustering Analysis or Principle Component Analysis of the expression profiles of such one or more members in each group can separate the disease and control samples.

Another embodiment of the present invention is a method of applying the signatures for aiding the diagnosis, prognosis or therapy treatment for a subject. The method comprises first isolating microvesicles from the subject, measuring the expression levels of one or more RNA transcripts extracted from isolated microvesicles, determining a test profile of one or more RNA transcripts based on the measured expression level(s), and comparing the test profile to a reference profile to determine the characteristics of the test profile.

Figure 1B:
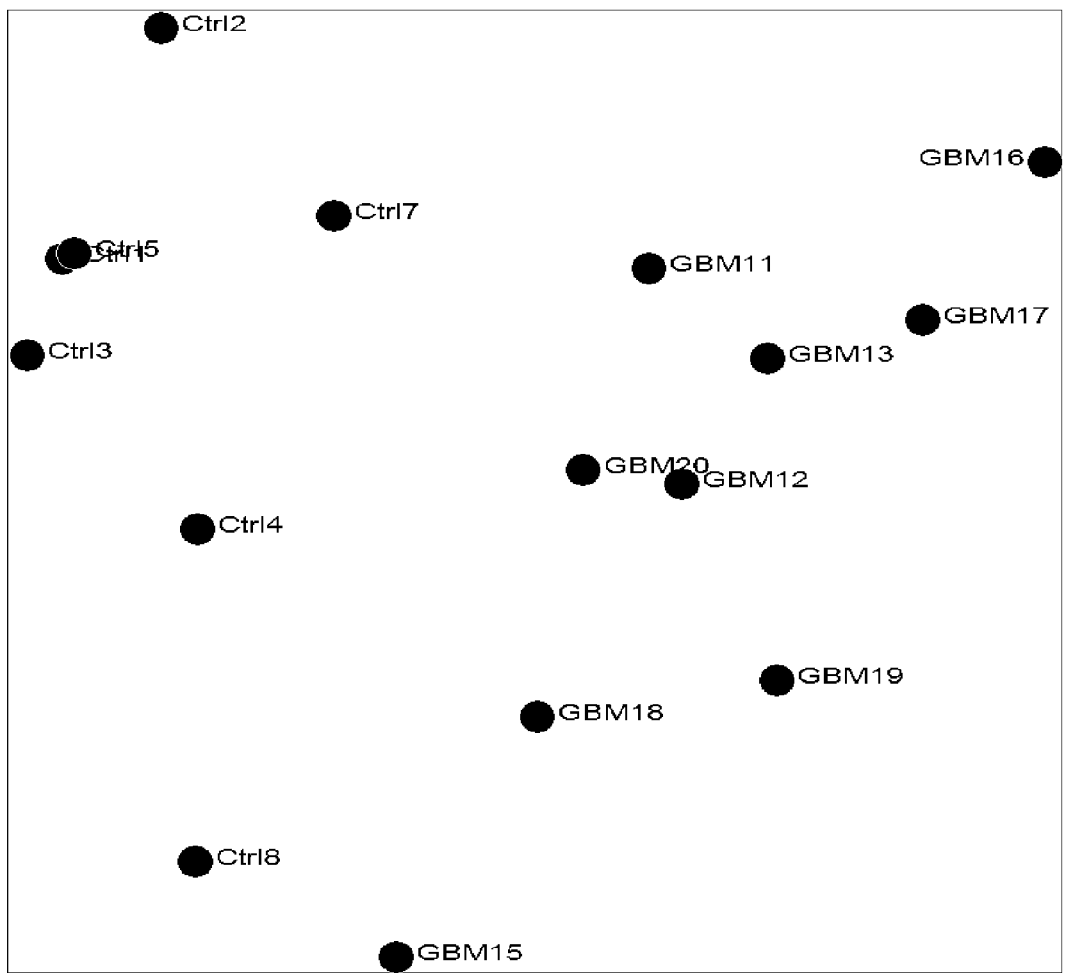
FIG. 1B. A plot showing the result of a Principle Component Analysis (PCA) performed on the data set of FIG. 1A with the same samples, the same genes and the same inclusion criteria.
Figure 2A:
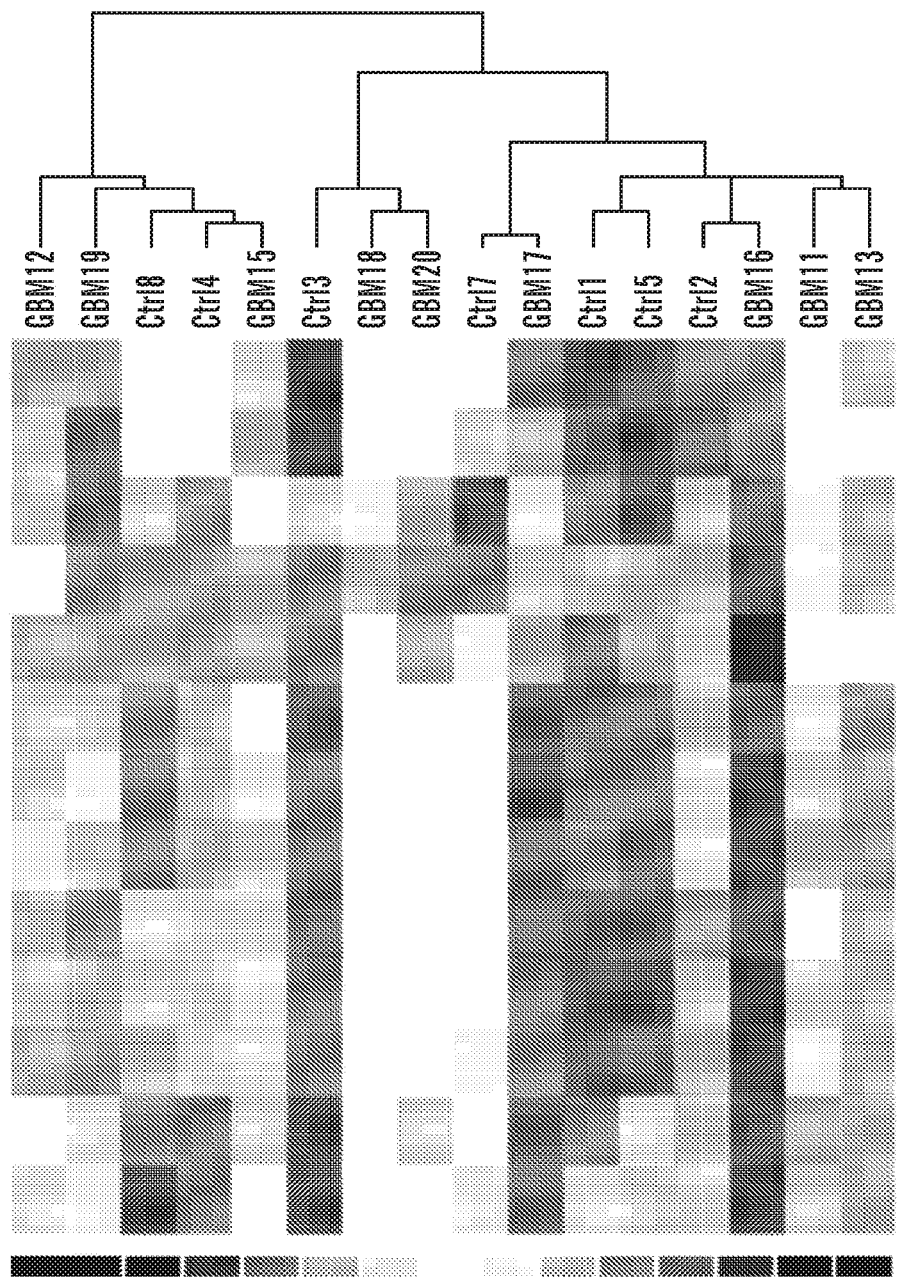
FIG. 2A. Heatmap and Clustering diagram illustrating microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $5\times10^4$ and with the log-median-ratio being at least "1" or above. The genes included in the data set are listed in Table 2.
Figure 2B:
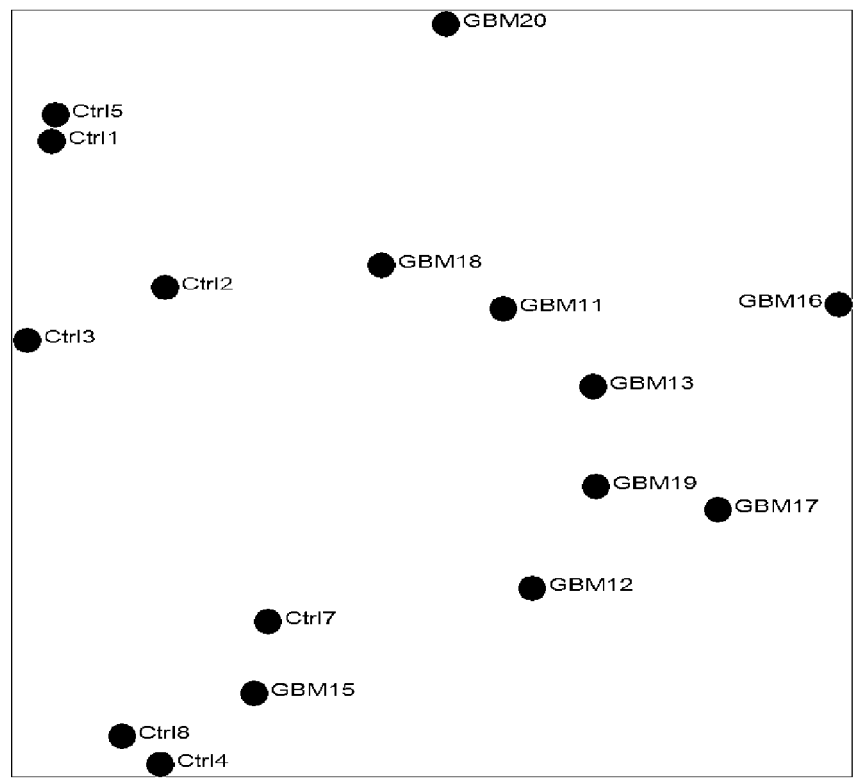
FIG. 2B. A plot showing the result of a Principle Component Analysis (PCA) performed on the data set of FIG. 2A with the same samples, the same genes and the same inclusion criteria.
Figure 3A:
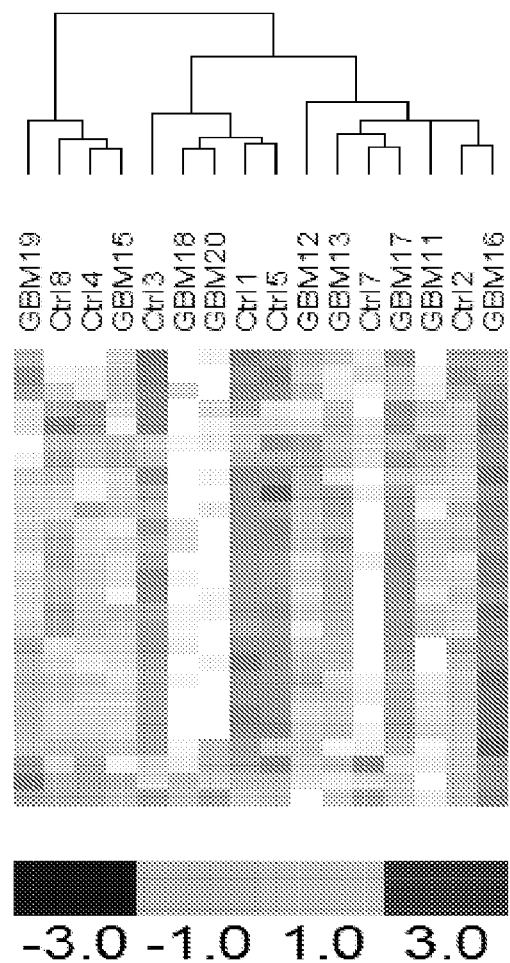
FIG. 3A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10^{-3}$ and with the log-median-ratio being at least "1" or above. The genes included in the data set are listed in Table 3.
Figure 3B:
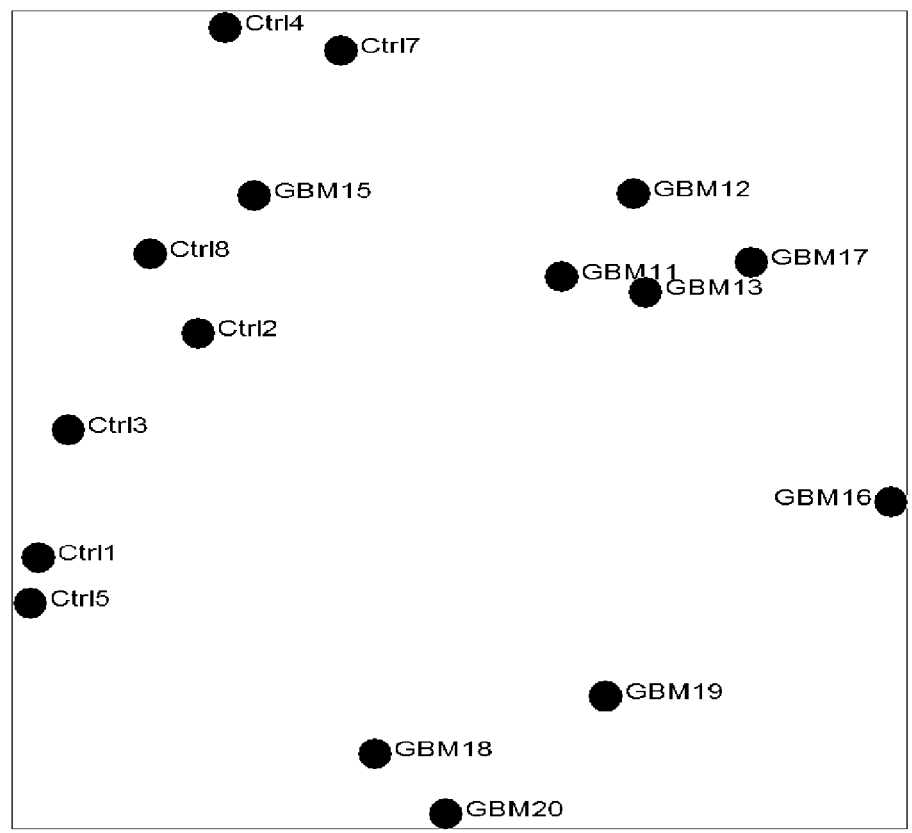
FIG. 3B. A plot showing the result of a Principle Component Analysis (PCA) performed on the data set of FIG. 3A with the same samples, the same genes and the same inclusion criteria.
Figure 4A:
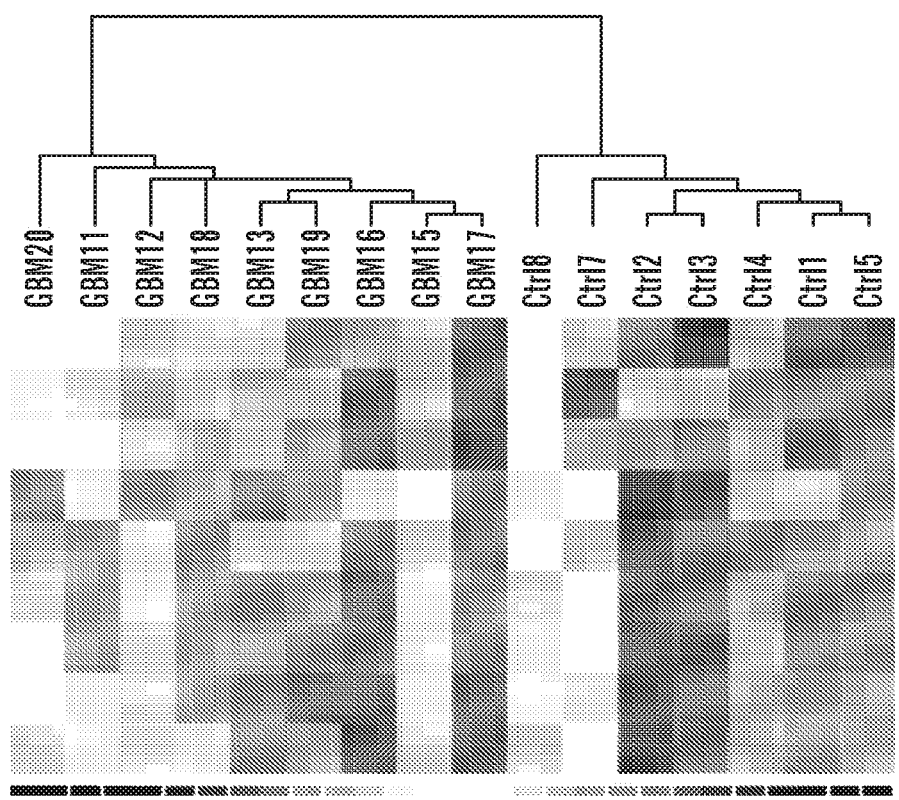
FIG. 4A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $2\times10^{-6}$. The genes included in the data set are listed in Table 4.
Figure 4B:
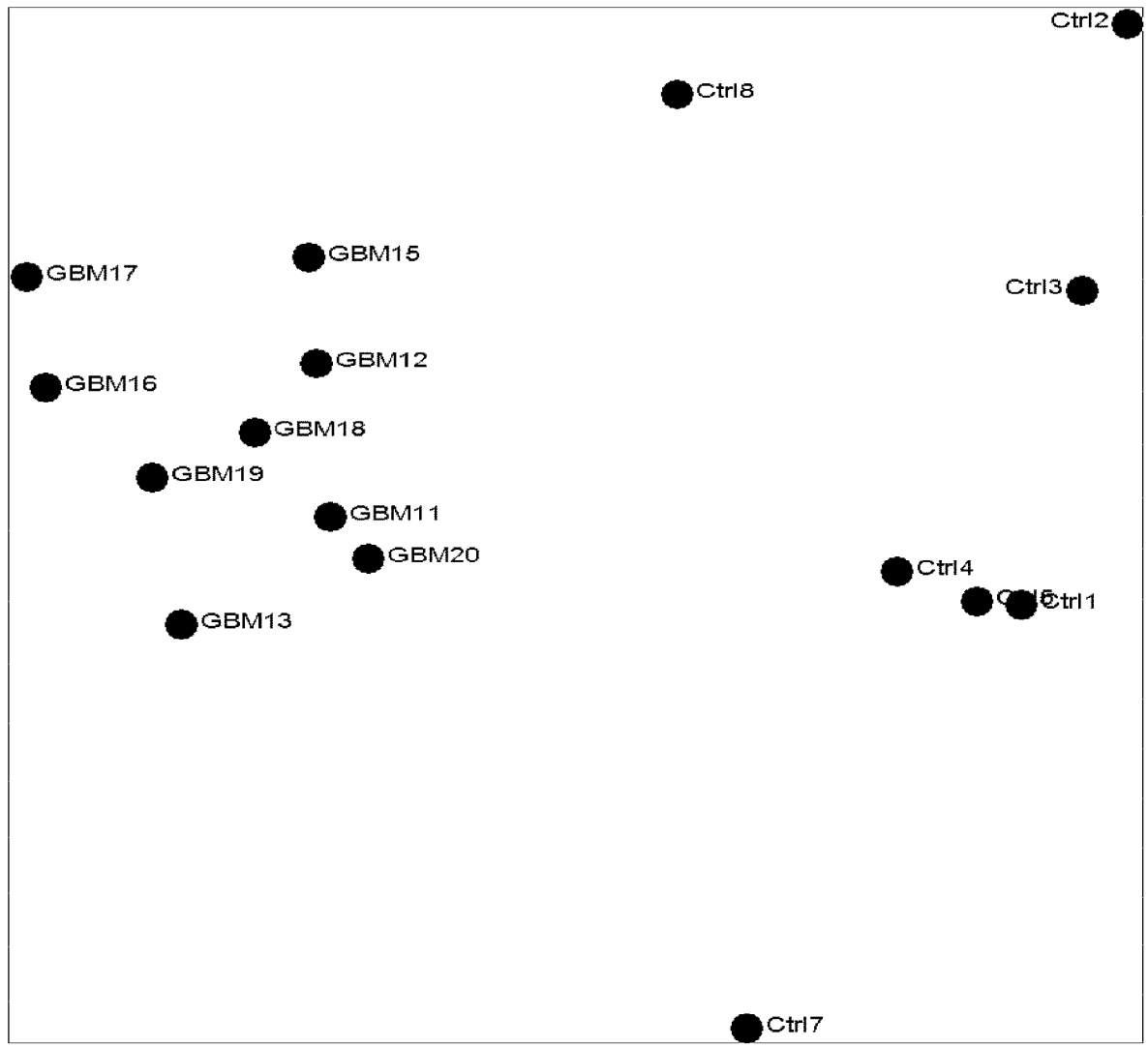
FIG. 4B. A plot showing the result of a Principle Component Analysis (PCA) performed on the data set of FIG. 4A with the same samples, the same genes and the same inclusion criteria.
Figure 5A:
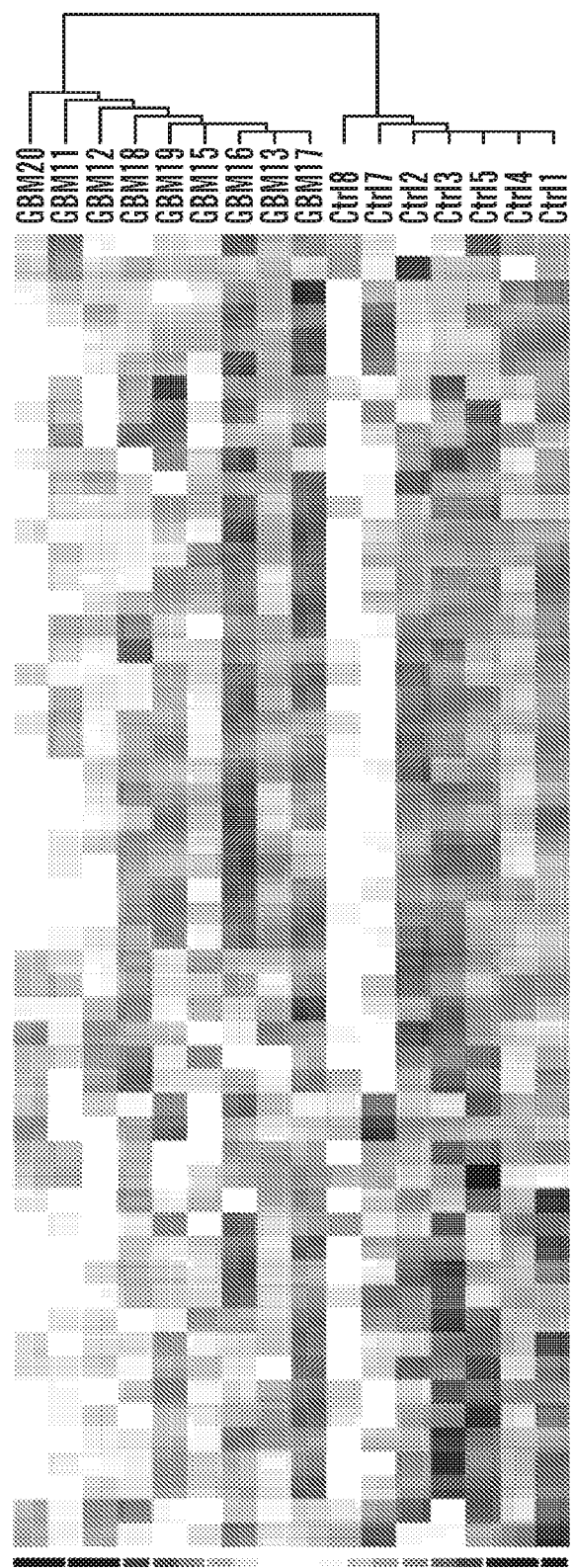
FIG. 5A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10^{-5}$. The genes included in the data set are listed in Table 5.
Figure 5B:
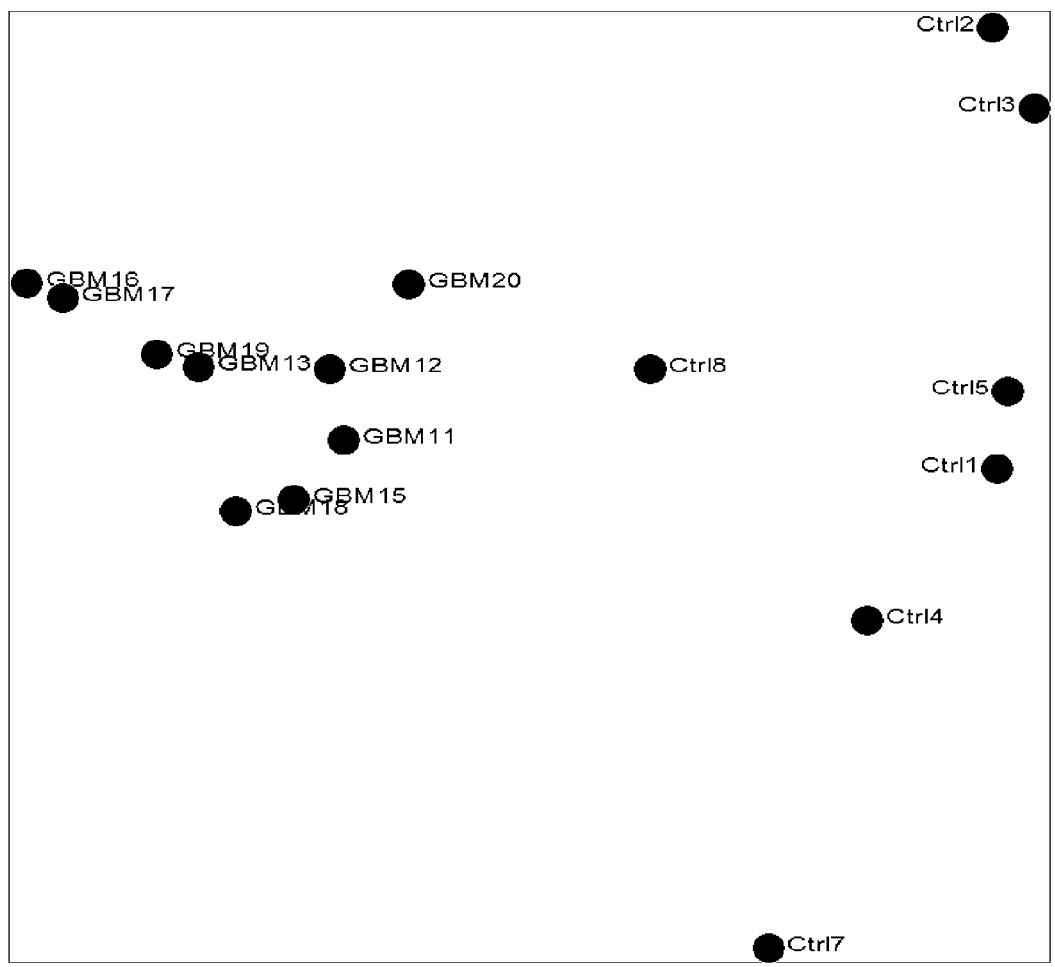
FIG. 5B. A plot showing the result of a Principle Component Analysis (PCA) performed on the data set of FIG. 5A with the same samples, the same genes and the same inclusion criteria.
Figure 6A:
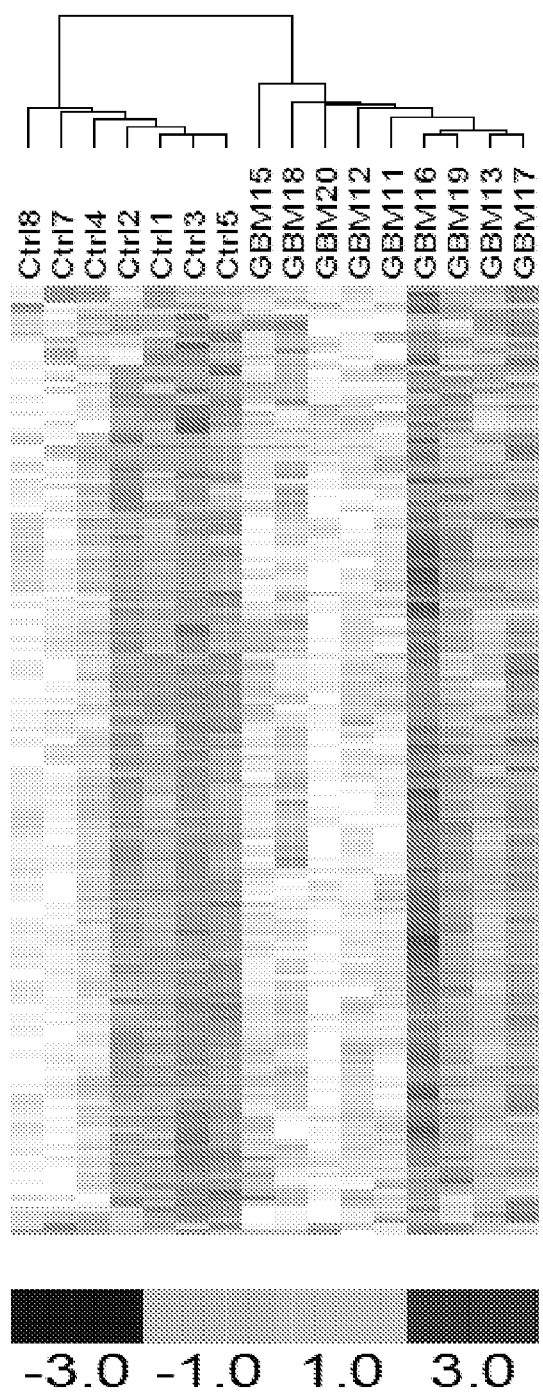
FIG. 6A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10$ and with the log-median-ratio being at least "0.8" or above, or being at least "−0.8" or below. The genes included in the data set are listed in Table 6.
Figure 6B:
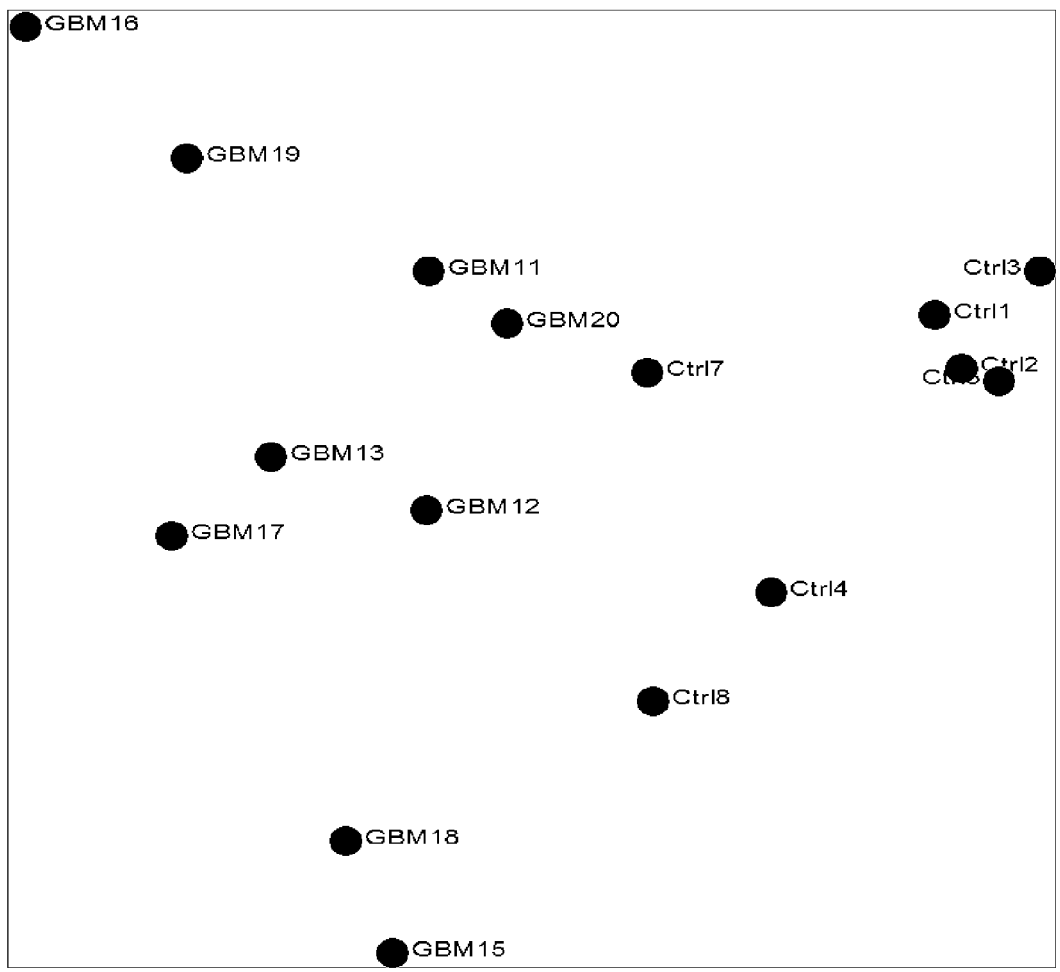
FIG. 6B. A plot showing the result of a Principle Component Analysis (PCA) performed on the data set of FIG. 6A with the same samples, the same genes and the same inclusion criteria.
Figure 7A:
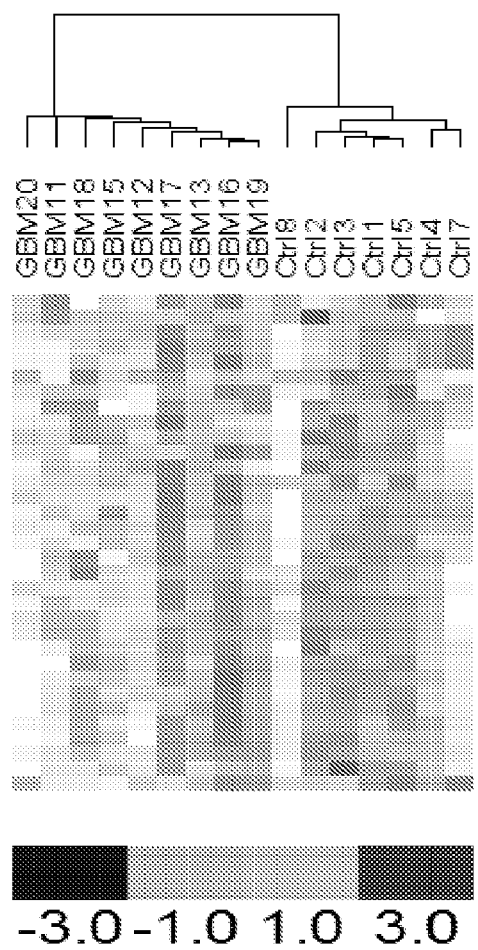
FIG. 7A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10^{-5}$ and with the log-median-ratio being at least "0.585" or above, the log-median-ratio being at least "0.8" or above, or being at least "−0.585" or below. The genes included in the data set are listed in Table 7.
Figure 7B:
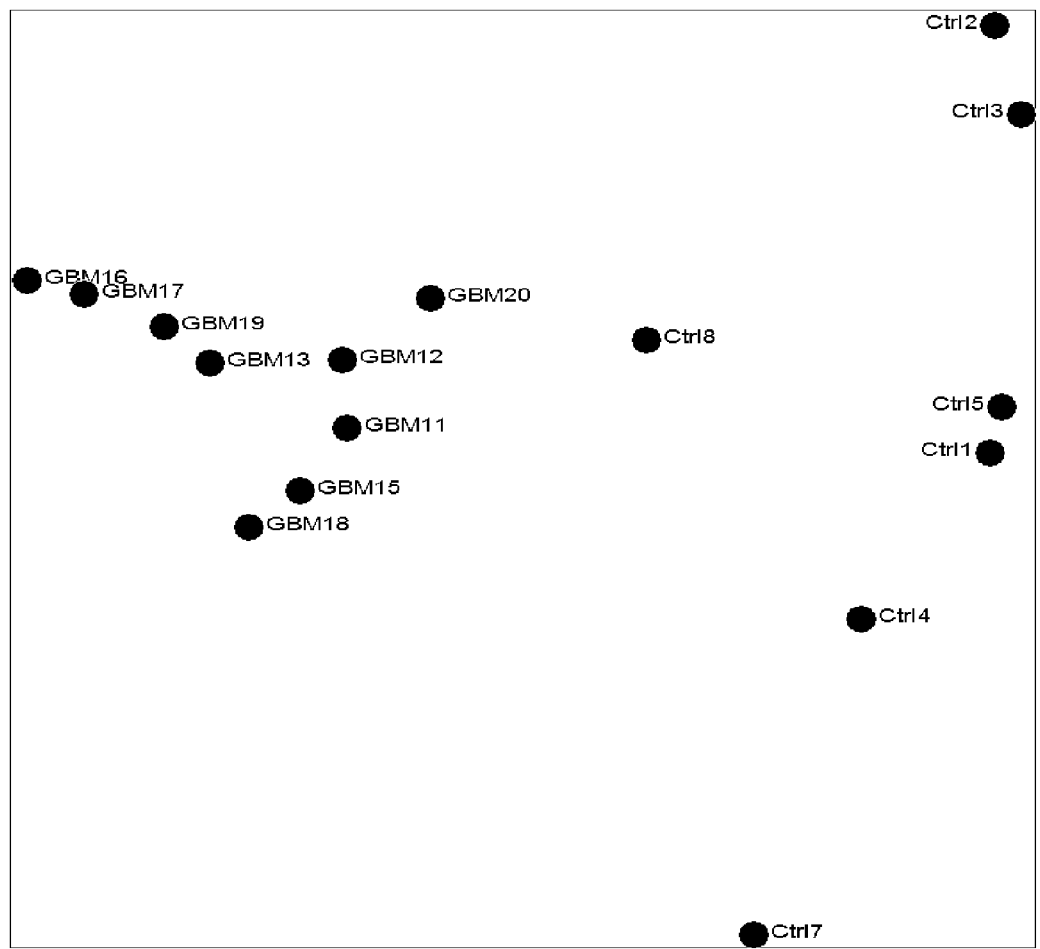
FIG. 7B. A plot showing the result of a Principle Component Analysis (PCA) performed on the data set of FIG. 7A with the same samples, the same genes and the same inclusion criteria.
Figure 8A:
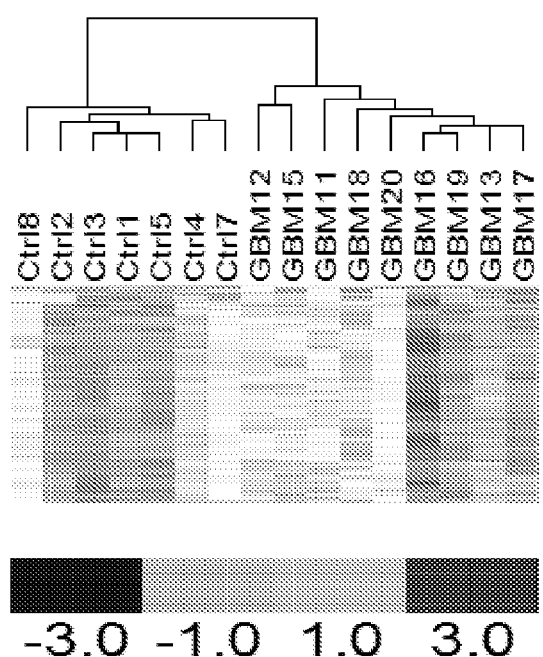
FIG. 8A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10$ and with the log-median-ratio being at least "1" or above, or being at least "−1" or below. The genes included in the data set are listed in Table 8.
Figure 8B:
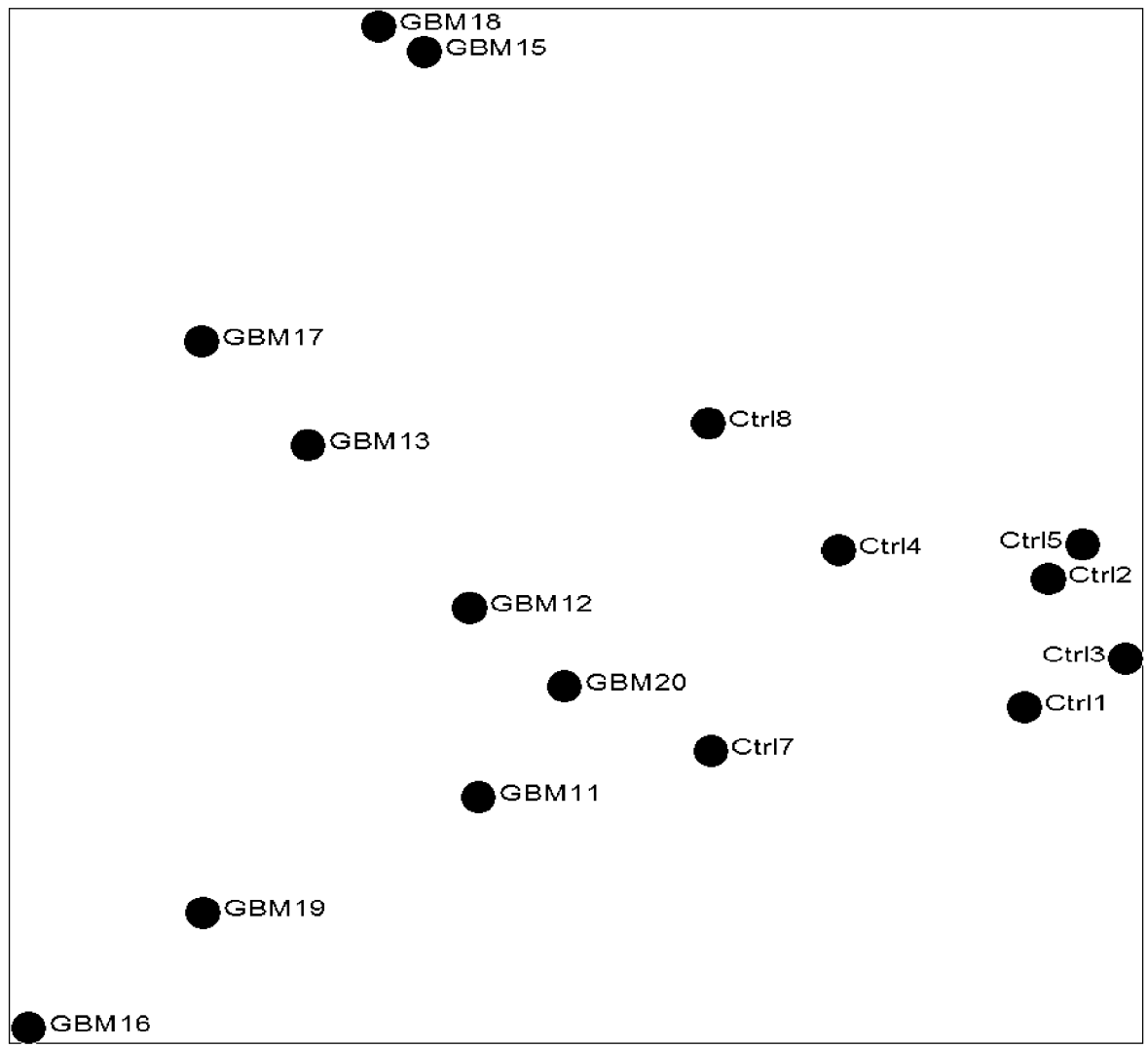
FIG. 8B. A plot showing the result of a Principle Component Analysis (PCA) performed on the data set of FIG. 8A with the same samples, the same genes and the same inclusion criteria.
Figure 9A:
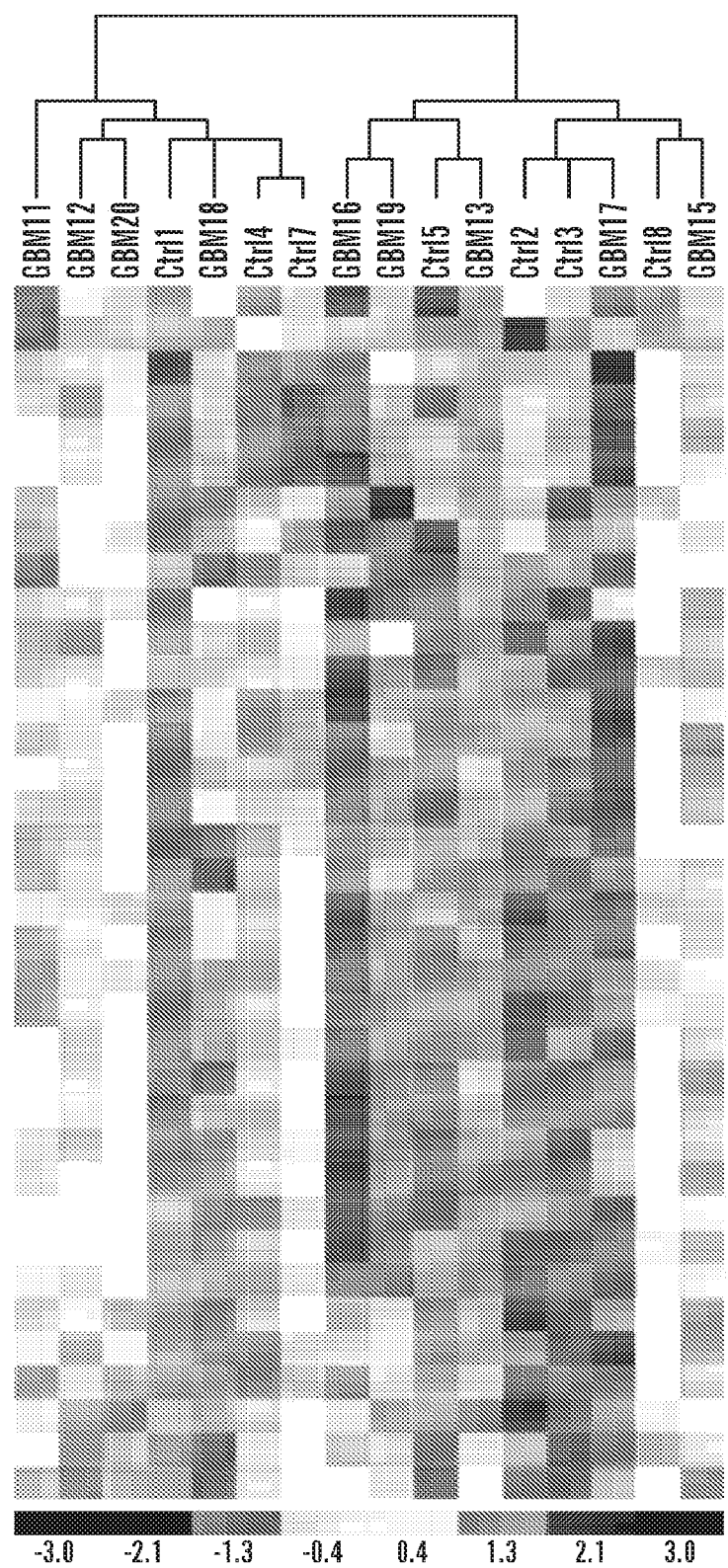
FIG. 9A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM1 8, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10^{-5}$ and with the log-median-ratio being below "0". The genes included in the data set are listed in Table 9.
Figure 9B:
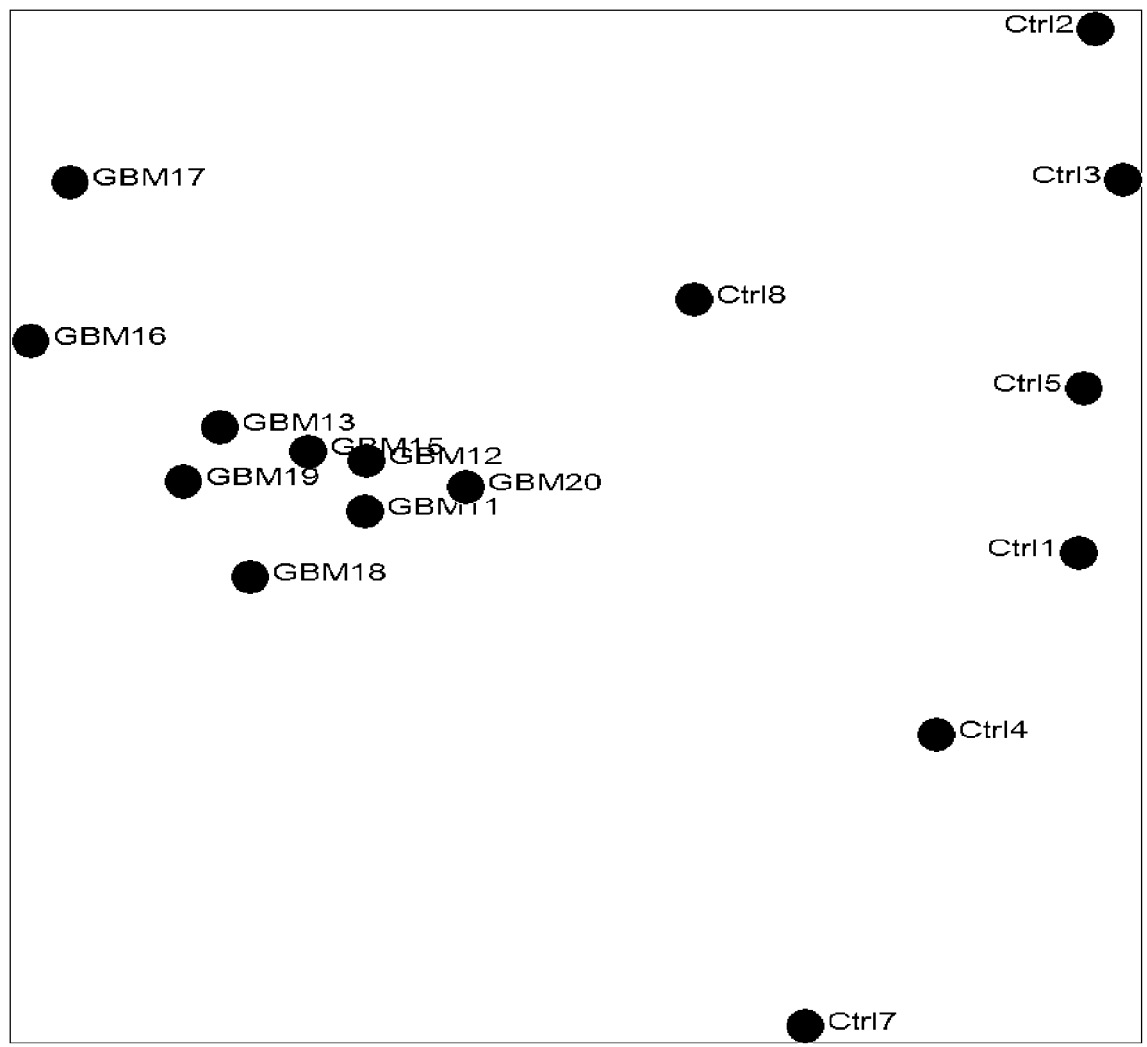
FIG. 9B. A plot showing the result of a Principle Component Analysis (PCA) performed on the data set of FIG. 9A with the same samples, the same genes and the same inclusion criteria.
Figure 10A:
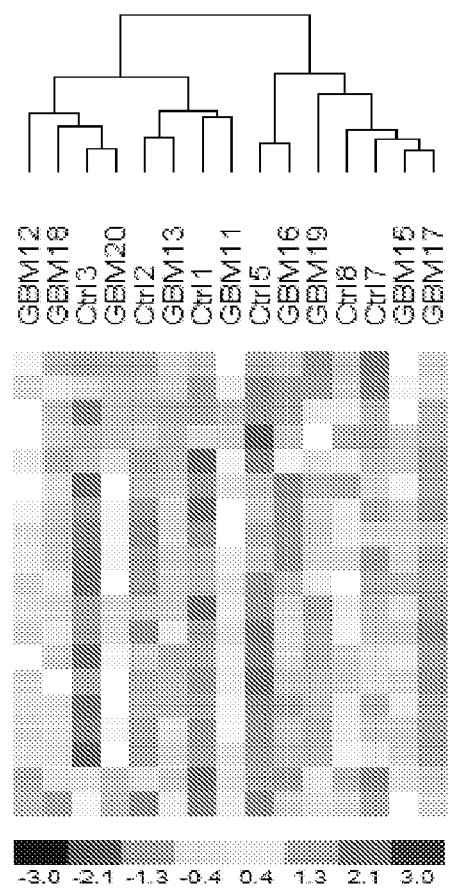
FIG. 10A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10^{-5}$ and with the log-median-ratio being above "0". The genes included in the data set are listed in Table 10.
Figure 10B:
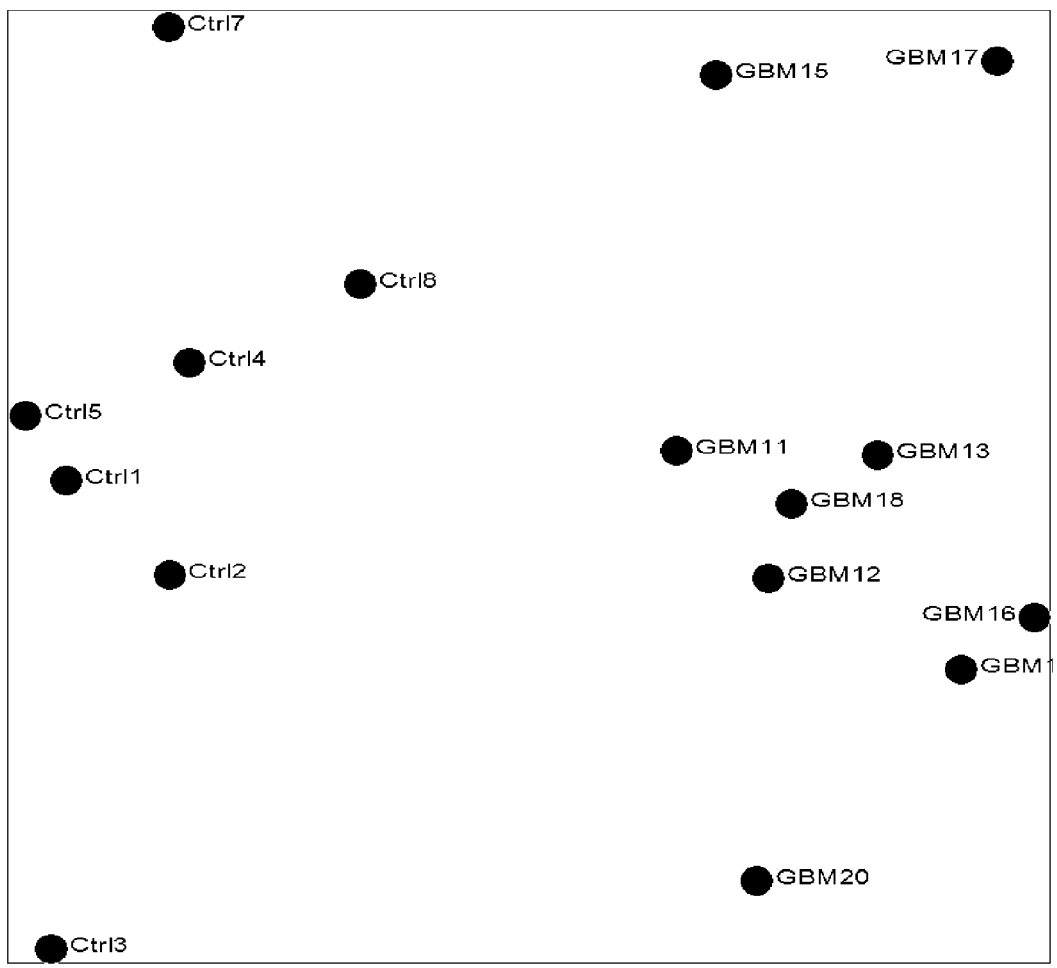
FIG. 10B. A plot showing the result of a Principle Component Analysis (PCA) performed on the data set of FIG. 10A with the same samples, the same genes and the same inclusion criteria.
Figure 11A:
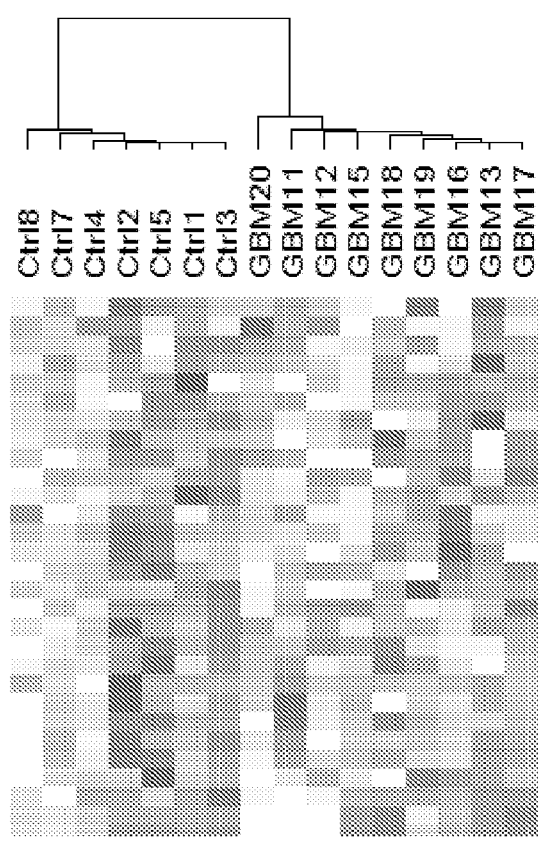
FIG. 11A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. The heatmap shown is a part of the heatmap showing the expression of the genes listed in Table 11. For each of the genes included in the data set, the expression levels in the GBM samples and in the control samples are significantly different with a P value less than or equal to $1\times10^{-4}$.
Figure 11B:
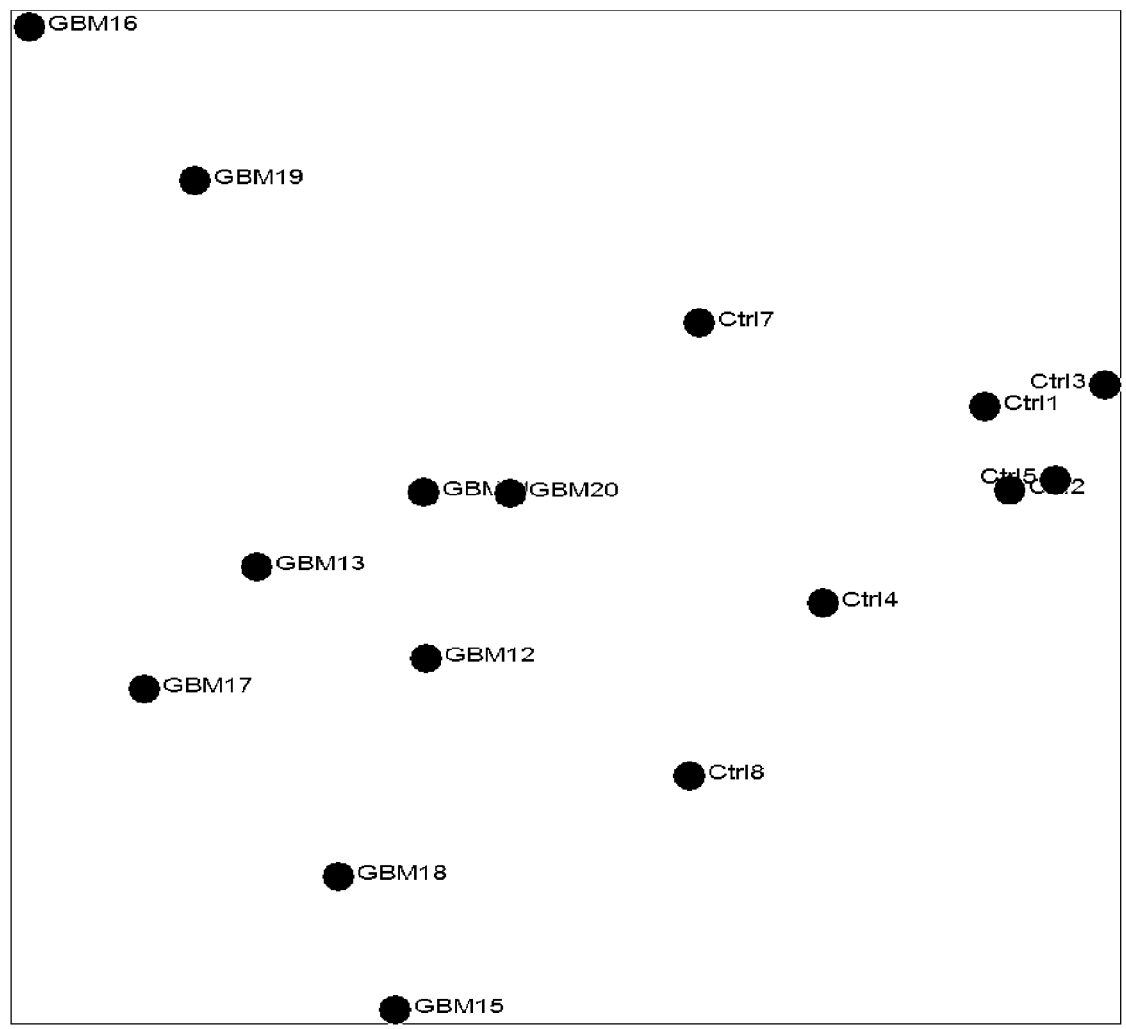
FIG. 11B. A plot showing the result of a Principle Component Analysis (PCA) performed on the data set of FIG. 11A with the same samples, the same genes and the same inclusion criteria.
Figure 12A:
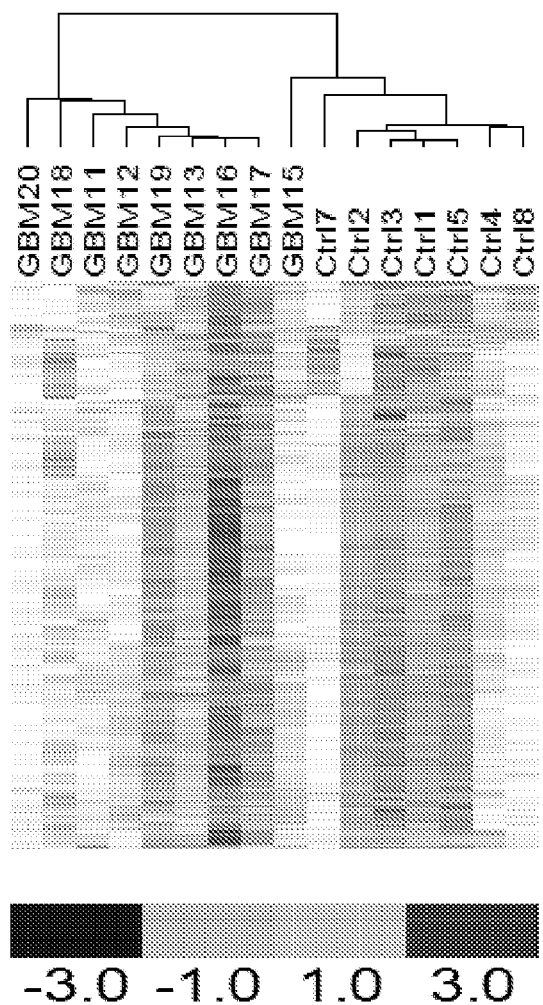
FIG. 12A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to $1\times10^{-3}$ and with the log-median-ratio being at least "1" or above, or being "−1" or below. The genes included in the data set are listed in Table 12.
Figure 12B:
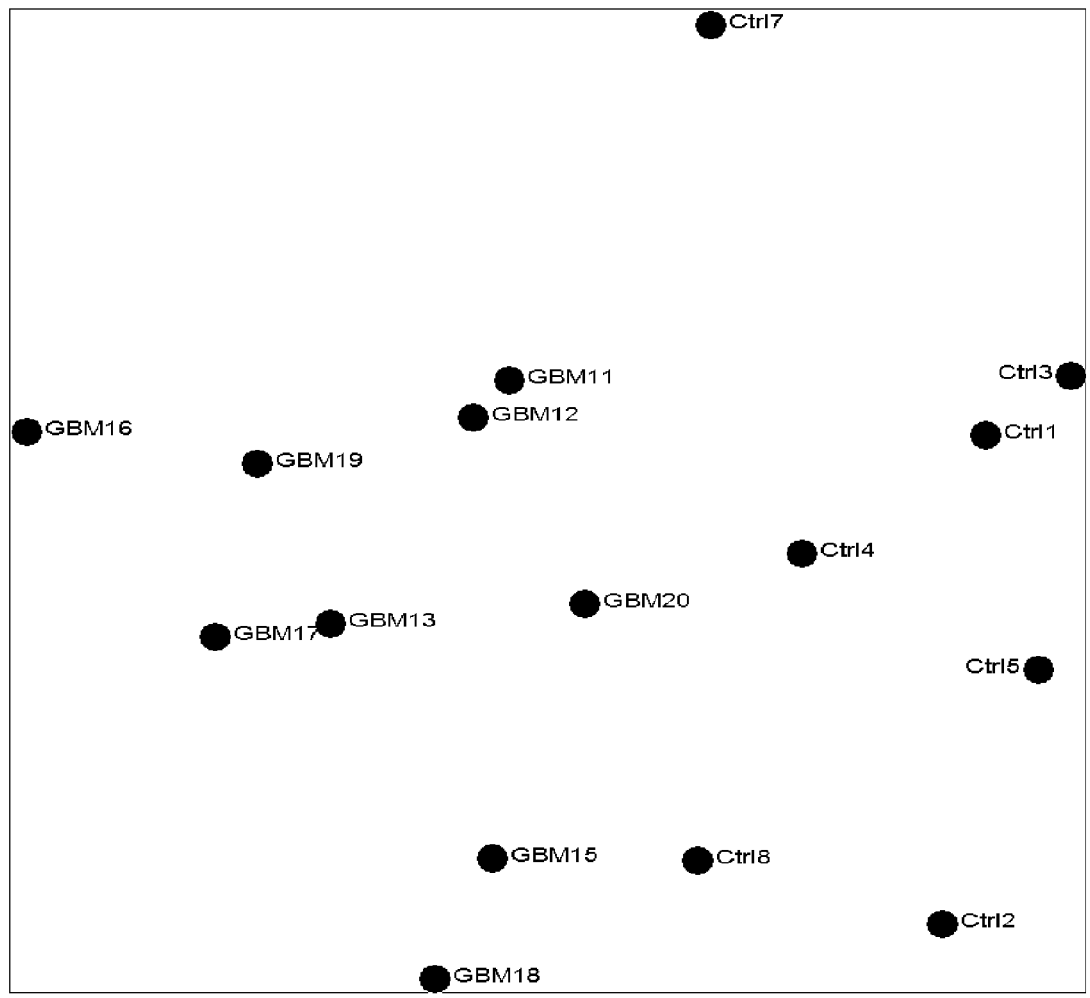
FIG. 12B. A plot showing the result of a Principle Component Analysis (PCA) performed on the data set of FIG. 12A with the same samples, the same genes and the same inclusion criteria.
Figure 13A:
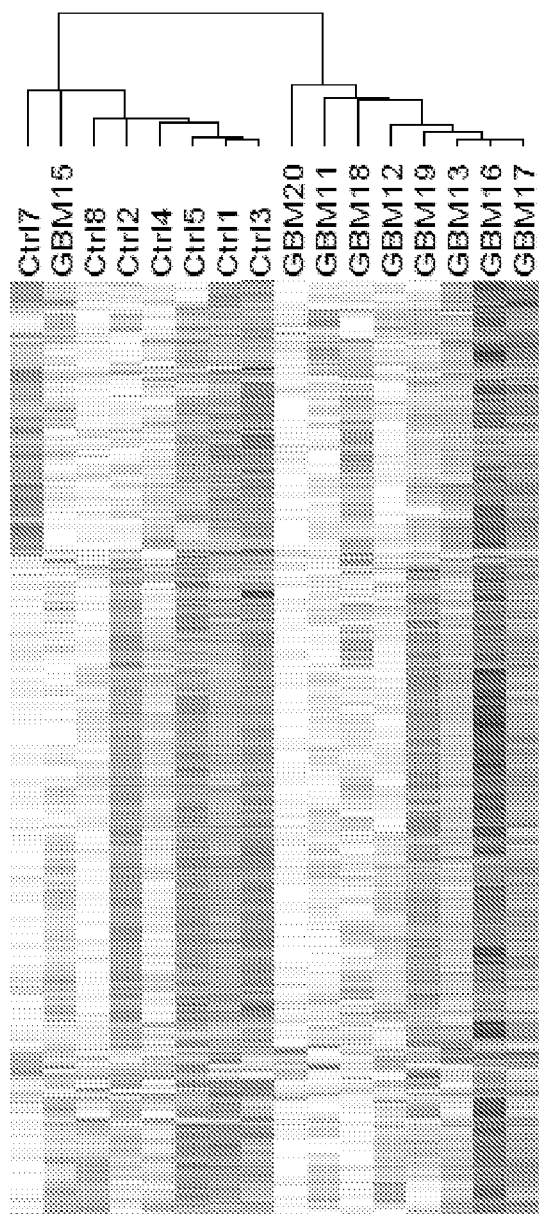
FIG. 13A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to 0.05 and with the log-median-ratio being at least "1" or above, or being "−1" or below. The genes included in the data set are listed in Table 13.
Figure 13B:
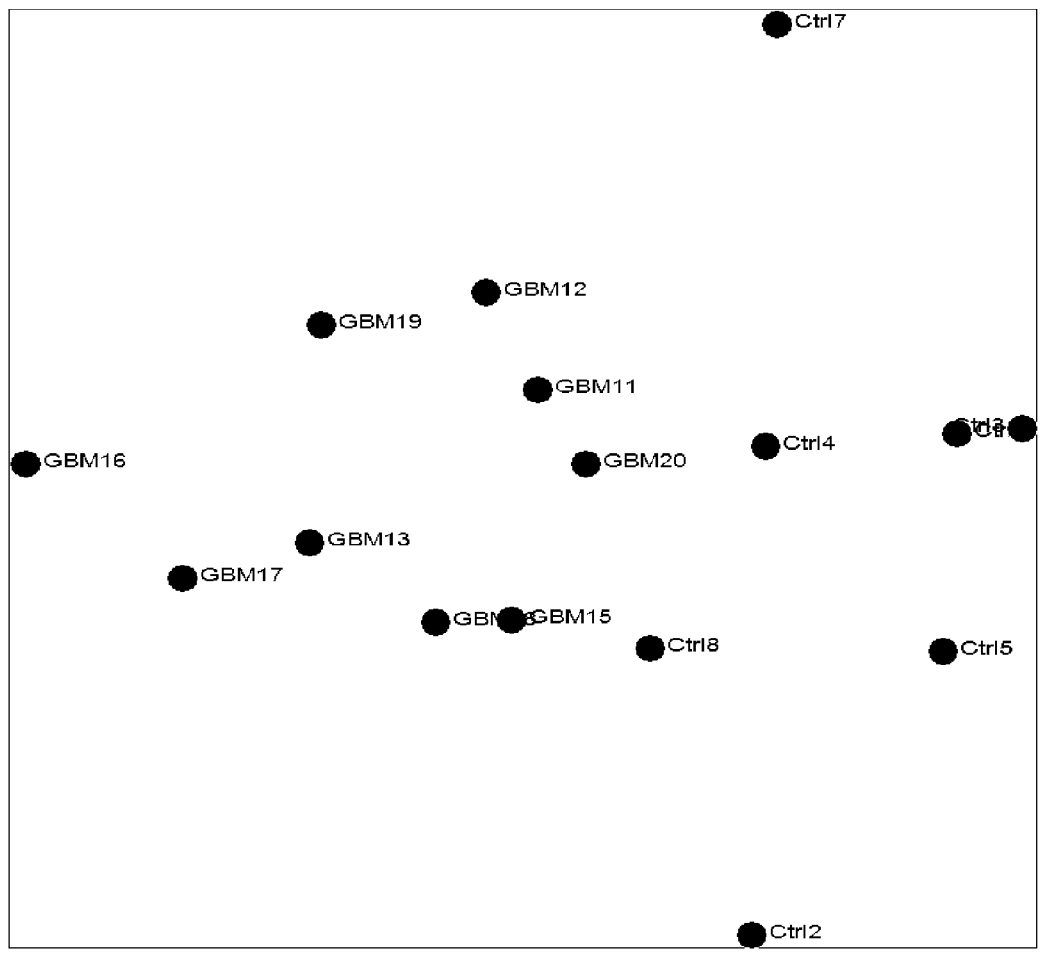
FIG. 13B. A plot showing the result of a Principle Component Analysis (PCA) performed on the data set of FIG. 13A with the same samples, the same genes and the same inclusion criteria.
Figure 14A:
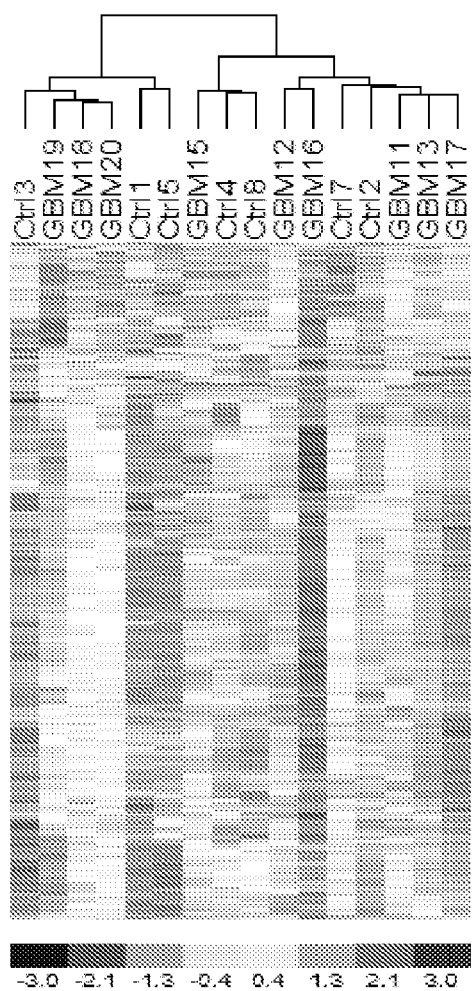
FIG. 14A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to 0.05 and with the log-median-ratio being at least "0.585" or above. The genes included in the data set are listed in Table 14.
Figure 14B:
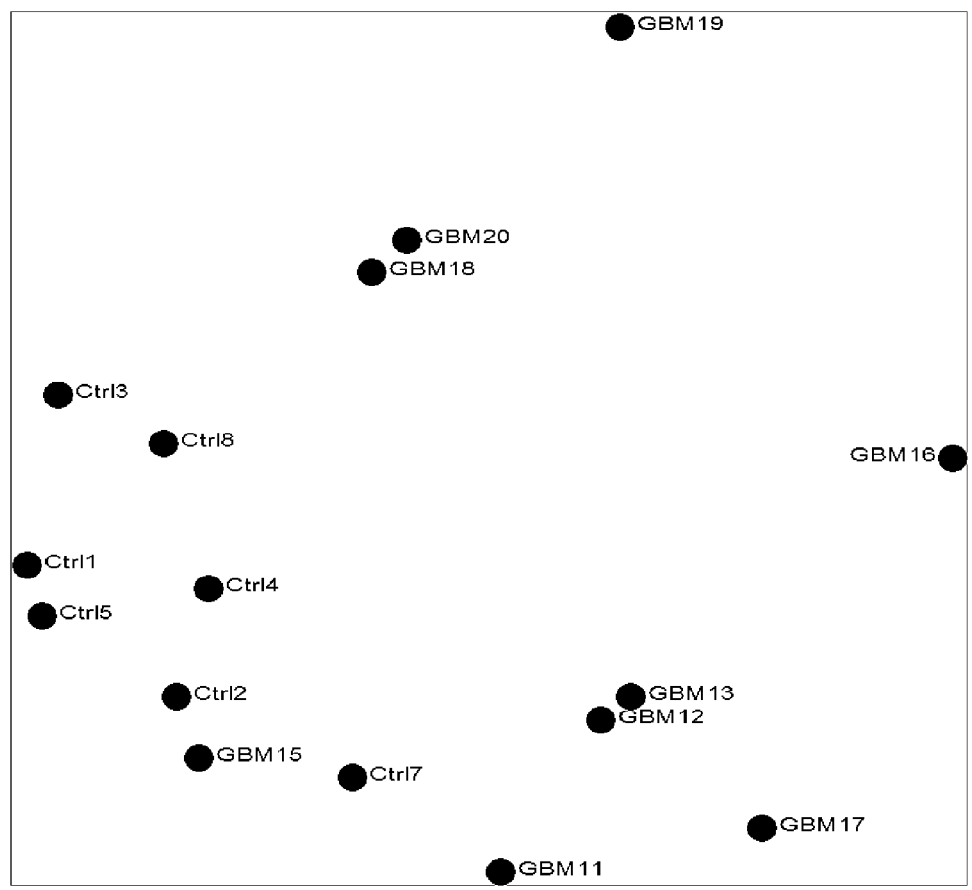
FIG. 14B. A plot showing the result of a Principle Component Analysis (PCA) performed on the data set of FIG. 14A with the same samples, the same genes and the same inclusion criteria.
Figure 15A:
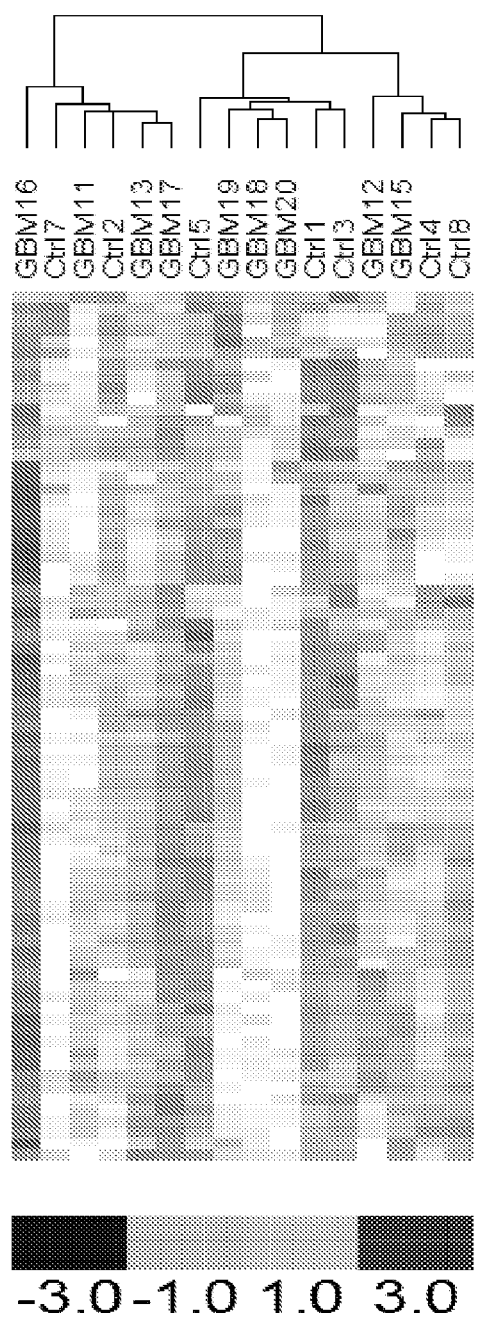
FIG. 15A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. For each of the genes included in the data set, the expression levels in the GBM samples and in the control samples are significantly different with a P value less than or equal to 0.05 and with the log-median-ratio being at least "1" or above. The genes included in the data set are listed in Table 15.
Figure 15B:
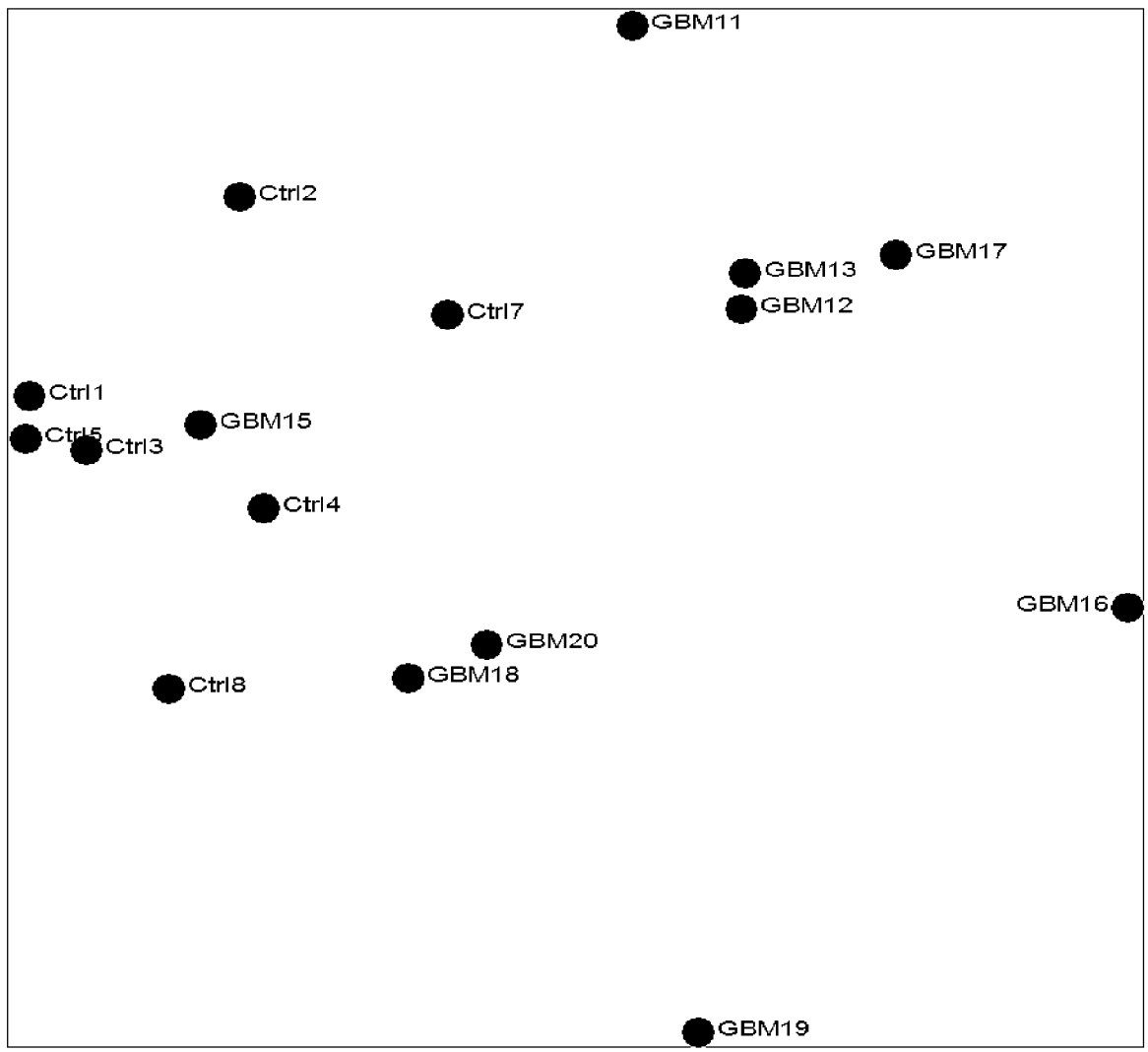
FIG. 15B. A plot showing the result of a Principle Component Analysis (PCA) performed on the data set of FIG. 15A with the same samples, the same genes and the same inclusion criteria.
Figure 16A:
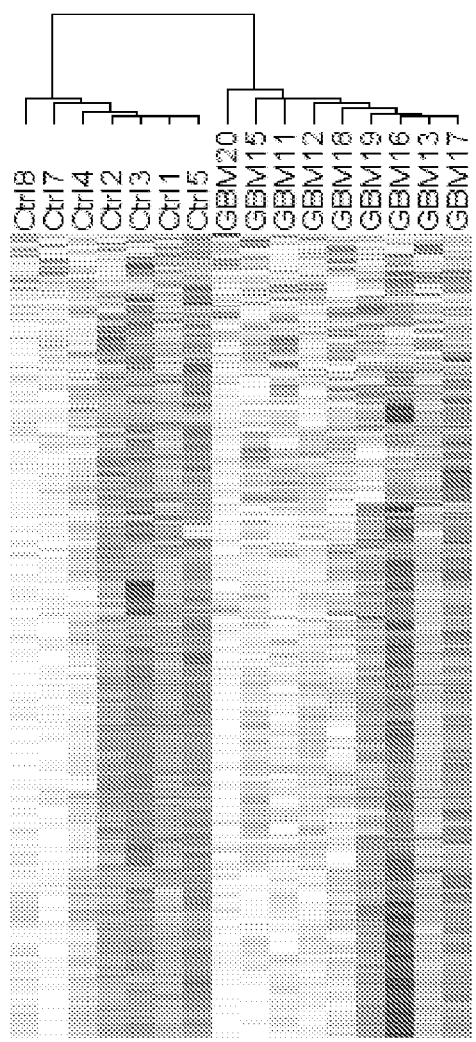
FIG. 16A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. The heatmap shown is a part of the heatmap showing the expression of the genes listed in Table 16. For each of the genes included in the data set, the expression levels in the GBM samples and in the control samples are significantly different with a P value less than or equal to 0.001.
Figure 16B:
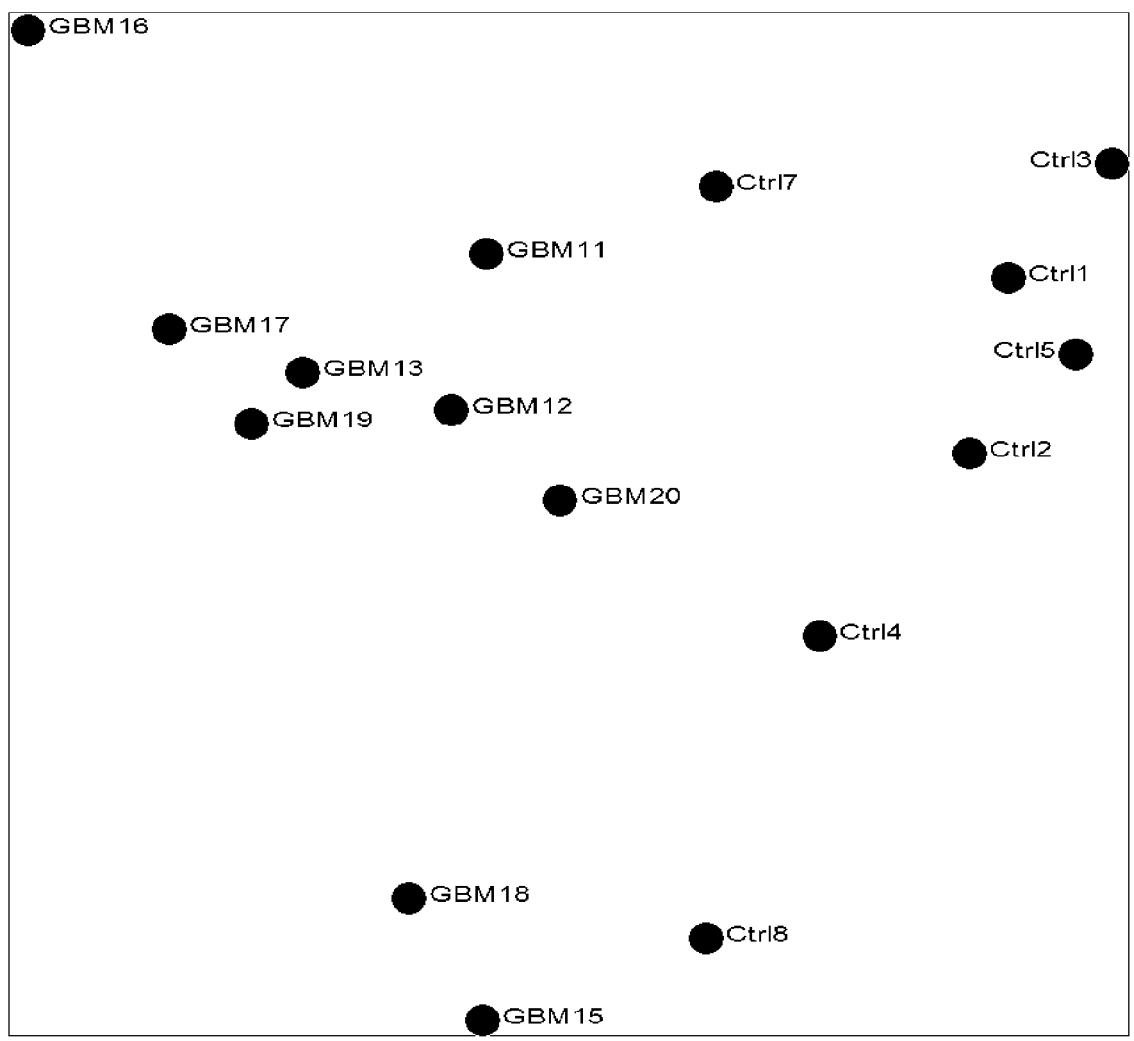
FIG. 16B. A plot showing the result of a Principle Component Analysis (PCA) performed on the data set of FIG. 16A with the same samples, the same genes and the same inclusion criteria.

For example, as shown in Table 1, the group included 22 genes based on the inclusion criteria of $p \leq 5 \times 10^{-4}$ and a log-median-ratio being at least "1" or above, or $p \leq 0.000002$. The 22 genes have functionalities including as receptors, transcription factors, and enzymes. As shown in FIG. 1A, the 22-gene signature clusters control samples together in one subgroup and disease samples together in another subgroup when subjected to a Clustering Analysis. The disease samples GBM11, GBM12, GBM13, GBM15, GBM16, GBM17, GBM18, GBM19, and GBM20 cluster together in one subgroup. The control samples from non-Glioblastoma human subjects, Ctrl1, Ctrl2, Ctrl3, Ctrl4, Ctrl5, Ctrl7 and Ctrl8, clustered in another subgroup. The separation of GBM and Control samples can be achieved by Clustering Analysis. As shown in FIG. 1B, the same 22-gene signature is validated using Principle Component Analysis. The Control group dots appear on the upper left side of the plot while the GBM group dots appear on the middle-right side of the plot.

Furthermore, an evidence-based analysis tool, optionally together with one or more of the Heuristic methods described above, may also be used for analyzing expression data. For example, a gene ontology analysis may be carried out and genes in the same biological signaling pathway group together. A signature or profile comprised of a group of genes in a relevant signaling pathway may be derived and used for the purpose of diagnosing a corresponding biological condition.

As a further analytical step, we performed a multiple testing correction analysis in which a normalized data set was subjected to an unpaired t-test. The p-values were corrected using the Benjamin and Hochberg Method (Benjamini and Hochberg, 1995) with a cut-off of corrected p<0.05 and fold change of ≥2.5. As a result of the application of this method, 275 genes were found to be down-regulated. Using the above-mentioned criteria, a Gene Ontology (GO) analysis with an enrichment score of 64.26 showed that 210 recognized genes had GO terms related to Translation elongation, Ribosome, or ribonucleoprotein. Furthermore, 24 genes were found to be upregulated. Using the above-mentioned criteria, a GO analysis with an enrichment score of 1.27 showed that 23 recognized genes had GO terms related to transcription (i.e. transcription factor activity, transcription, DNA binding, homeobox).

Based on the p values that have been corrected using the Benjamin and Hochberg Method and the level of differential expression, we derived 4 additional groups of genes from the above microarray data. The 4 groups of genes are listed in Tables 17-20, respectively. The criteria to obtain the groups in Tables 17-20 are as follows:

Table 17: $p \leq 5 \times 10^{-2}$ and with the log-median-ratio being at least "1" or above, or being at least "−1" or below;

Table 18: $p \leq 5 \times 10^{-2}$ and the log-median-ratio being at least "1" or above, or being at least "−1.5" or below;

Table 19: $p \leq 5 \times 10^{-2}$ and the log-median-ratio being at least "1" or above;

Table 20: $p \leq 5 \times 10^{-2}$ and the log-median-ratio being at least "−1.5" or below, respectively.

Each of the 4 groups can be a gene signature for glioblastoma. We tested each group for its capability as a glioblastoma signature. For each group, two independent tests were performed. One test used Clustering Analysis. The other test used Principle Component Analysis. For each group, the results (as illustrated in FIGS. 18-21 As and Bs, respectively) showed that at least one of the two tests can separate the cancer group and the control group.

Figure 19A:
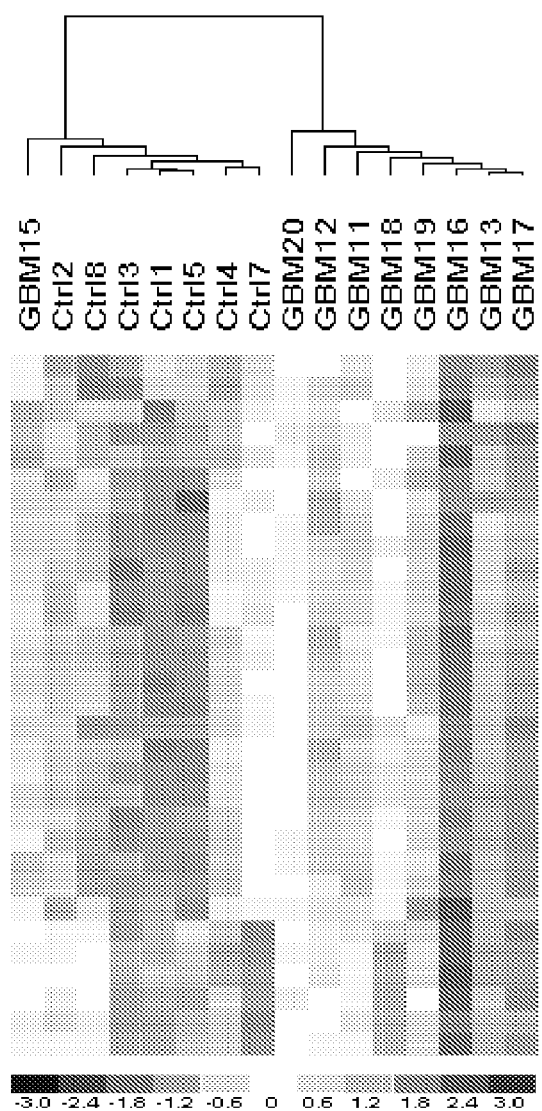
FIG. 19A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. The heatmap shows the expression of the genes listed in Table 18. For each of the genes included in the data set, the expression levels in the GBM samples and in the control samples are significantly different with a $p \leq 5 \times 10^{-2}$ and the log-median-ratio being at least "1" or above or being at least "−1.5" or below. The p-values were corrected using Benjamin and Hochberg method.
Figure 19B:
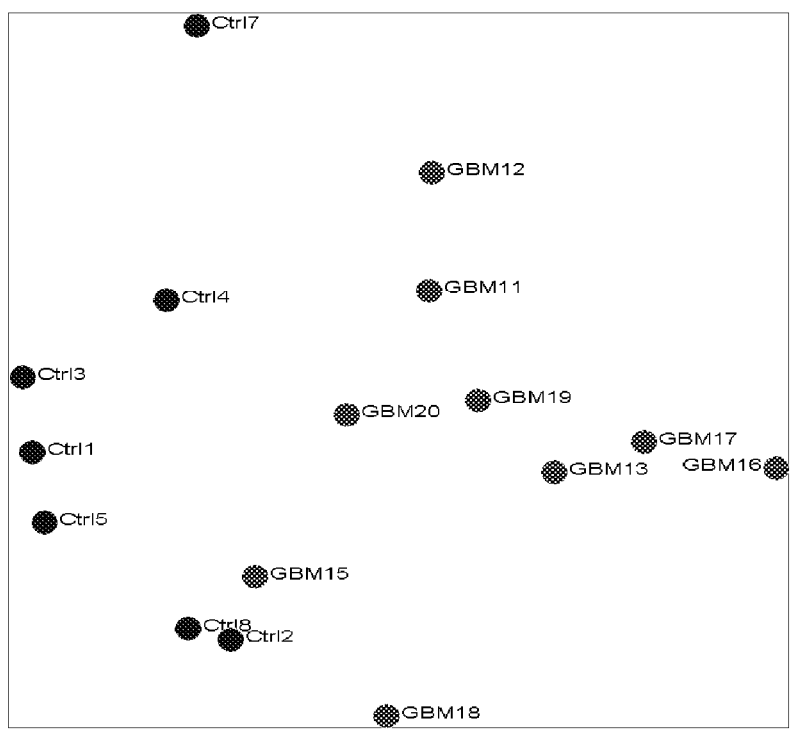
FIG. 19B. A plot showing the result of a Principle Component Analysis (PCA) performed on the data set of FIG. 19A with the same samples, the same genes and the same inclusion criteria.
Figure 20A:
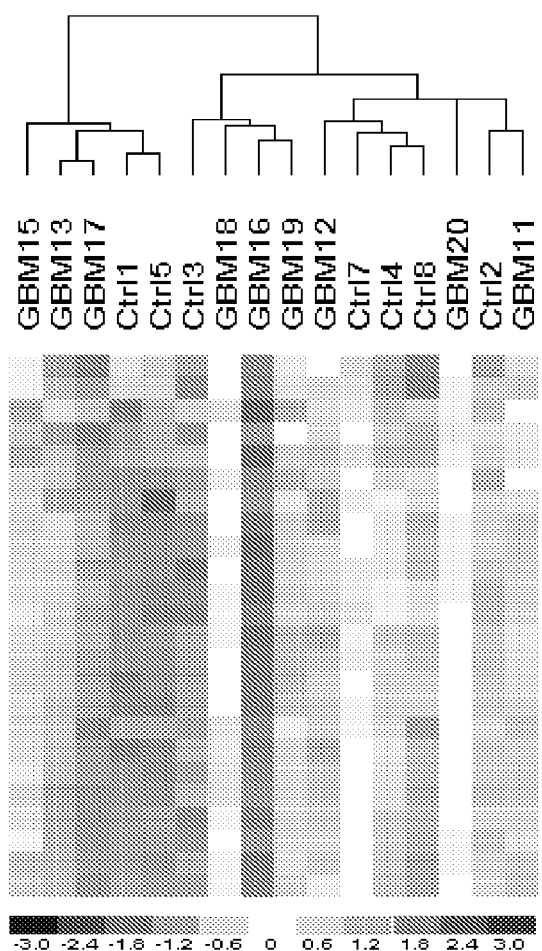
FIG. 20A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. The heatmap shows the expression of the genes listed in Table 19. For each of the genes included in the data set, the expression levels in the GBM samples and in the control samples are significantly different with a $p \leq 5 \times 10^{-2}$ and the log-median-ratio being at least "1" or above. The p-values were corrected using Benjamin and Hochberg method.
Figure 20B:
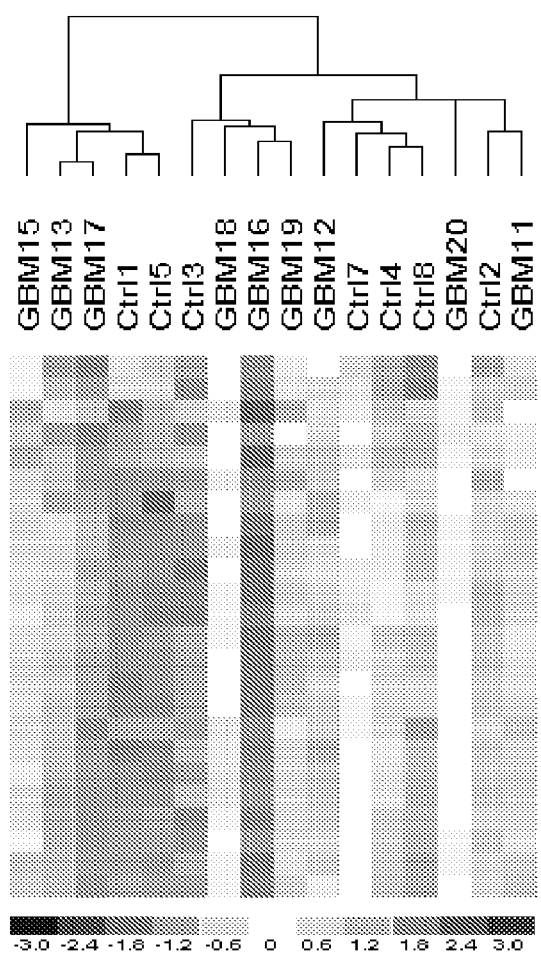
FIG. 20B. A plot showing the result of a Principle Component Analysis (PCA) performed on the data set of FIG. 20A with the same samples, the same genes and the same inclusion criteria.
Figure 21A:
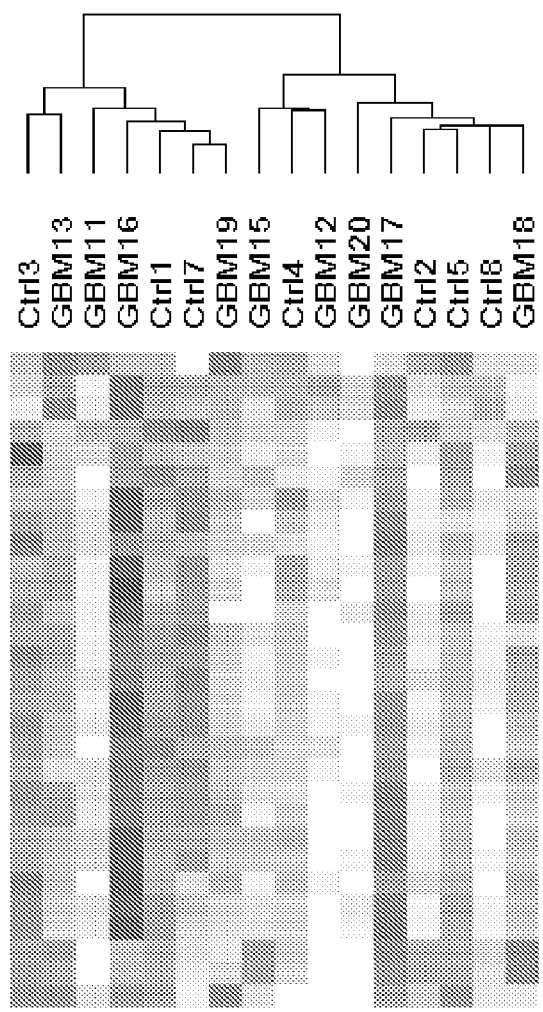
FIG. 21A. Heatmap and Clustering diagram illustrating the microarray data showing gene expression profiles from exosomes isolated from serum samples from Glioblastoma (GBM) and non-Glioblastoma human subjects (Ctrl). The GBM RNA samples from glioblastoma patients are named GBM11, GBM12, GBM13, GBM15, GBM16, GBM17, GBM18, GBM19, and GBM20. The control RNA samples from non-Glioblastoma human subjects are named Ctrl1, Ctrl2, Ctrl3, Ctrl4, Ctrl5, Ctrl7 and Ctrl8. The heatmap shown is a part of the heatmap showing the expression of the genes listed in Table 20. For each of the genes included in the data set, the expression levels in the GBM samples and in the control samples are significantly different with a $p \leq 5 \times 10^{-2}$ and the log-median-ratio being at least "−1.5" or below. The p-values were corrected using Benjamin and Hochberg method.
Figure 21B:
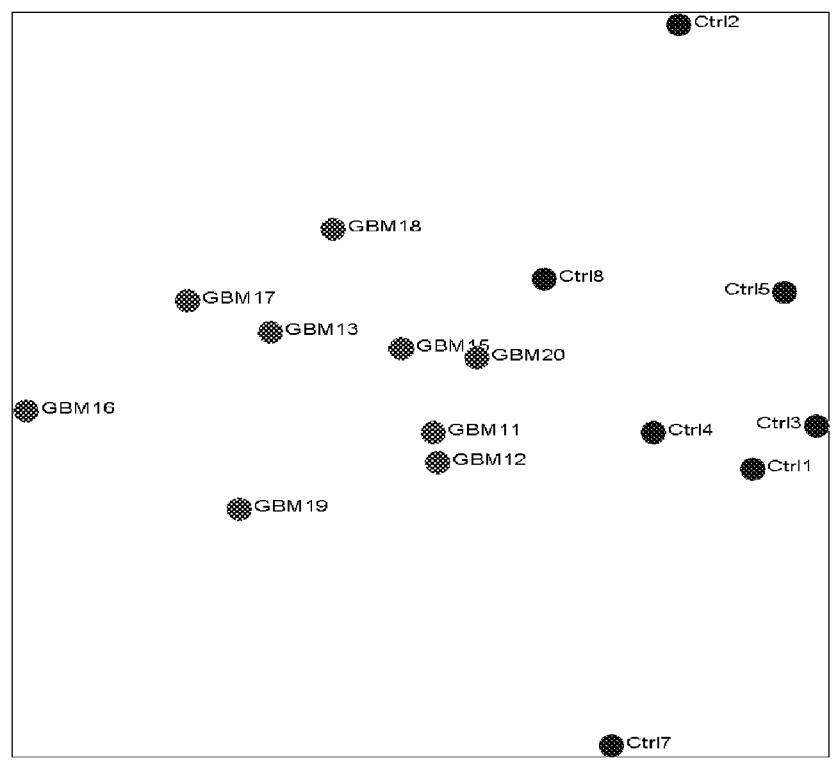
FIG. 21B. A plot showing the result of a Principle Component Analysis (PCA) performed on the data set of FIG. 21A with the same samples, the same genes and the same inclusion criteria.

For example, as shown in Table 18, the group includes 31 genes based in the inclusion criteria of $p \leq 5 \times 10^{-2}$ and the log-median-ratio being at least "1" or above, or being at least "−1.5" or below. The 31 genes have various functionalities including as receptors, transcription factors, and enzymes. As shown in FIG. 19A, the 31-gene signature clusters control samples together in one subgroup and disease samples together in another subgroup when subjected to Clustering Analysis. The 9 tumor samples are easily distinguishable from and clearly form a cluster different from the 7 Normal Controls. The disease samples GBM11, GBM12, GBM13, GBM15, GBM16, GBM17, GBM18, GBM19, and GBM20 cluster together in one subgroup. The control samples from non-Glioblastoma human subjects, Ctrl1, Ctrl2, Ctrl3, Ctrl4, Ctrl5, Ctrl7 and Ctrl8, clustered in another subgroup. The separation of GBM and Control samples can be achieved by Clustering Analysis. As shown in FIG. 19B, the same 31-genes signature was validated using Principle Component Analysis. The Control group dots appear on the upper left side of the plot. The GBM group dots appear on the middle-right side of the plot.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES

1. Abravaya, K., J. J. Canino, S. Muldoon, and H. H. Lee. 1995. Detection of point mutations with a modified ligase chain reaction (Gap-LCR). *Nucleic Acids Res.* 23:675-82.
2. Al-Nedawi, K., B. Meehan, J. Micallef, V. Lhotak, L. May, A. Guha, and J. Rak. 2008. Intercellular transfer of the oncogenic receptor EGFRvIII by microvesicles derived from tumour cells. *Nat Cell Biol.* 10:619-24.
3. Alter, O., P. O. Brown, and D. Botstein. 2000. Singular value decomposition for genome-wide expression data processing and modeling. *Proc Nail Acad Sci USA.* 97:10101-6.
4. Balzar, M., M. J. Winter, C. J. de Boer, and S. V. Litvinov. 1999. The biology of the 17-1A antigen (Ep-CAM). *J Mol Med.* 77:699-712.
5. Benjamini, J., and Y. Hochberg. 1995. Controlling the false discovery rate: a practical and powerful approach to multiple testing. *J Roy Statist Soc Ser B (Methodological).* 57:289-300.
6. Bossi, A., F. Bonini, A. P. Turner, and S. A. Piletsky. 2007. Molecularly imprinted polymers for the recognition of proteins: the state of the art. *Biosens Bioelectron.* 22:1131-7.
7. Cheruvanky, A., H. Zhou, T. Pisitkun, J. B. Kopp, M. A. Knepper, P. S. Yuen, and R. A. Star. 2007. Rapid isolation of urinary exosomal biomarkers using a nanomembrane ultrafiltration concentrator. *Am J Physiol Renal Physiol.* 292:F1 657-61.
8. Cotton, R. G., N. R. Rodrigues, and R. D. Campbell. 1988. Reactivity of cytosine and thymine in single-base-pair mismatches with hydroxylamine and osmium tetroxide and its application to the study of mutations. *Proc Natl Acad Sci USA.* 85:4397-401.
9. Cristofanilli, M., and J. Mendelsohn. 2006. Circulating tumor cells in breast cancer: Advanced tools for "tailored" therapy? *Proc Natl Acad Sci USA.* 103:17073-4.
10. Dabney, A. R. 2005. Classification of microarrays to nearest centroids. *Bioinformatics.* 21:4148-54.
11. Eisen, M. B., P. T. Spellman, P. O. Brown, and D. Botstein. 1998. Cluster analysis and display of genome-wide expression patterns. *Proc Natl Acad Sci USA.* 95:14863-8.
12. Fischer, S. G., and L. S. Lerman. 1979a. Length-independent separation of DNA restriction fragments in two-dimensional gel electrophoresis. *Cell.* 16:191-200.
13. Fischer, S. G., and L. S. Lerman. 1979b. Two-dimensional electrophoretic separation of restriction enzyme fragments of DNA. *Methods Enzymol.* 68:183-91.
14. Geiss, G. K., R. E. Bumgarner, B. Birditt, T. Dahl, N. Dowidar, D. L. Dunaway, H. P. Fell, S. Ferree, R. D. George, T. Grogan, J. J. James, M. Maysuria, J. D. Mitton, P. Oliveri, J. L. Osborn, T. Peng, A. L. Ratcliffe, P. J. Webster, E. H. Davidson, and L. Hood. 2008. Direct multiplexed measurement of gene expression with color-coded probe pairs. *Nat Biotechnol.* 26:317-25.
15. Guatelli, J. C., K. M. Whitfield, D. Y. Kwoh, K. J. Barringer, D. D. Richman, and T. R. Gingeras. 1990. Isothermal, in vitro amplification of nucleic acids by a multienzyme reaction modeled after retroviral replication. *Proc Natl Acad Sci USA.* 87:1874-8.
16. Hahn, P. J. 1993. Molecular biology of double-minute chromosomes. *Bioessays.* 15:477-84.
17. Hakonarson, H., U. S. Bjornsdottir, E. Halapi, J. Bradfield, F. Zink, M. Mouy, H. Helgadottir, A. S. Gudmundsdottir, H. Andrason, A. E. Adalsteinsdottir, K. Kristjansson, I. Birkisson, T. Amason, M. Andresdottir, D. Gislason, T. Gislason, J. R. Gulcher, and K. Stefansson. 2005. Profiling of genes expressed in peripheral blood mononuclear cells predicts glucocorticoid sensitivity in asthma patients. *Proc Natl Acad Sci USA.*102:14789-94.
18. Johnson, S., D. Evans, S. Laurenson, D. Paul, A. G. Davies, P. K. Ferrigno, and C. Walti. 2008. Surface-immobilized peptide aptamers as probe molecules for protein detection. *Anal Chem.* 80:978-83.

19. Kan, Y. W., and A. M. Dozy. 1978a. Antenatal diagnosis of sickle-cell anaemia by D.N.A. analysis of amniotic-fluid cells. *Lancet.* 2:910-2.
20. Kan, Y. W., and A. M. Dozy. 1978b. Polymorphism of DNA sequence adjacent to human beta-globin structural gene: relationship to sickle mutation. *Proc Natl Acad Sci USA.* 75:5631-5.
21. Keller, S., C. Rupp, A. Stoeck, S. Runz, M. Fogel, S. Lugert, H. D. Hager, M. S. Abdel-Bakky, P. Gutwein, and P. Altevogt. 2007. CD24 is a marker of exosomes secreted into urine and amniotic fluid. *Kidney Int.* 72:1095-102.
22. Kwoh, D. Y., G. R. Davis, K. M. Whitfield, H. L. Chappelle, L. J. DiMichele, and T. R. Gingeras. 1989. Transcription-based amplification system and detection of amplified human immunodeficiency virus type 1 with a bead-based sandwich hybridization format. *Proc Natl Acad Sci USA.* 86:1173-7.
23. Landegren, U., R. Kaiser, J. Sanders, and L. Hood. 1988. A ligase-mediated gene detection technique. *Science.* 241:1077-80.
24. Li, J., L. Wang, H. Mamon, M. H. Kulke, R. Berbeco, and G. M. Makrigiorgos. 2008. Replacing PCR with COLD-PCR enriches variant DNA sequences and redefines the sensitivity of genetic testing. *Nat Med.* 14:579-84.
25. Liu, Q., J. C. Greimann, and C. D. Lima. 2006. Reconstitution, activities, and structure of the eukaryotic RNA exosome. *Cell.* 127:1223-37.
26. Miele, E. A., D. R. Mills, and F. R. Kramer. 1983. Autocatalytic replication of a recombinant RNA. *J Mol Biol.* 171:281-95.
27. Miranda, K. C., D. T. Bond, M. McKee, J. Skog, T. G. Paunescu, N. Da Silva, D. Brown, and L. M. Russo. 2010. Nucleic acids within urinary exosomes/microvesicles are potential biomarkers for renal disease. *Kidney Int.* 78:191-9.
28. Myers, R. M., Z. Larin, and T. Maniatis. 1985. Detection of single base substitutions by ribonuclease cleavage at mismatches in RNA:DNA duplexes. *Science.* 230:1242-6.
29. Nagrath, S., L. V. Sequist, S. Maheswaran, D. W. Bell, D. Irimia, L. Ulkus, M. R. Smith, E. L. Kwak, S. Digumarthy, A. Muzikansky, P. Ryan, U. J. Balis, R. G. Tompkins, D. A. Haber, and M. Toner. 2007. Isolation of rare circulating tumour cells in cancer patients by microchip technology. *Nature.* 450:1235-9.
30. Nakazawa, H., D. English, P. L. Randell, K. Nakazawa, N. Martel, B. K. Armstrong, and H. Yamasaki. 1994. UV and skin cancer: specific p53 gene mutation in normal skin as a biologically relevant exposure measurement. *Proc Natl Acad Sci USA.* 91:360-4.
31. Orita, M., H. Iwahana, H. Kanazawa, K. Hayashi, and T. Sekiya. 1989. Detection of polymorphisms of human DNA by gel electrophoresis as single-strand conformation polymorphisms. *Proc Natl Acad Sci USA.* 86:2766-70.
32. Raposo, G., H. W. Nijman, W. Stoorvogel, R. Liejendekker, C. V. Harding, C. J. Melief, and H. J. Geuze. 1996. B lymphocytes secrete antigen-presenting vesicles. *J Exp Med.* 183:1161-72.
33. Skog, J., T. Wurdinger, S. van Rijn, D. H. Meijer, L. Gainche, M. Sena-Esteves, W. T. Curry, Jr., B. S. Carter, A. M. Krichevsky, and X. O. Breakefield. 2008. Glioblastoma microvesicles transport RNA and proteins that promote tumour growth and provide diagnostic biomarkers. *Nat Cell Biol.* 10:1470-6.
34. Steemers, F. J., W. Chang, G. Lee, D. L. Barker, R. Shen, and K. L. Gunderson. 2006. Whole-genome genotyping with the single-base extension assay. *Nat Methods.* 3:31-3.
35. Taylor, D. D., and C. Gercel-Taylor. 2008. MicroRNA signatures of tumor-derived exosomes as diagnostic biomarkers of ovarian cancer. *Gynecol Oncol.* 110:13-21.
36. van Dijk, E. L., G. Schilders, and G. J. Pruijn. 2007. Human cell growth requires a functional cytoplasmic exosome, which is involved in various mRNA decay pathways. *RNA.* 13:1027-35.
37. Velculescu, V. E., L. Zhang, B. Vogel stein, and K. W. Kinzler. 1995. Serial analysis of gene expression. *Science.* 270:484-7.
38. Went, P. T., A. Lugli, S. Meier, M. Bundi, M. Mirlacher, G. Sauter, and S. Dirnhofer. 2004. Frequent EpCam protein expression in human carcinomas. *Hum Pathol.* 35:122-8.
39. Zweig, M. H., and G. Campbell. 1993. Receiver-operating characteristic (ROC) plots: a fundamental evaluation tool in clinical medicine. *Clin Chem.* 39:561-77.

While the present invention has been disclosed with reference to certain embodiments, numerous modifications, alterations, and changes to the described embodiments are possible without departing from the scope of the present invention, as defined in the appended claims. Accordingly, it is intended that the present invention not be limited to the particular described embodiments, but that it enjoy the full scope defined by the language of the following claims, and equivalents thereof.

TABLE 1

Gene list generated at the inclusion criteria of $p \leq 5 \times 10^{-4}$ and the log-median-ratio being at least "1" or above, or $p \leq 0.000002$.

| GenBank Accession | Gene Name | Description |
| --- | --- | --- |
| NM_173833 | SCARA5 | *Homo sapiens* scavenger receptor class A, member 5 (putative) (SCARA5), mRNA [NM_173833] |
| NM_182688 | UBE2G2 | *Homo sapiens* ubiquitin-conjugating enzyme E2G 2 (UBC7 homolog, yeast) (UBE2G2), transcript variant 2, mRNA [NM_182688] |
| NM_024812 | BAALC | *Homo sapiens* brain and acute leukemia, cytoplasmic (BAALC), transcript variant 1, mRNA [NM_024812] |
| XM_372498 | LOC390427 | PREDICTED: *Homo sapiens* similar to TBP-associated factor 15 isoform 1 (LOC390427), mRNA [XM_372498] |
| THC2718728 | THC2718728 | Unknown |
| ENST00000248668 | LRFN1 | Leucine-rich repeat and fibronectin type III domain-containing protein 1 (Fragment). [Source: Uniprot/SPTREMBL; Acc: Q9P244] [ENST00000248668] |

TABLE 1-continued

Gene list generated at the inclusion criteria of $p \leq 5 \times 10^{-4}$
and the log-median-ratio being at least "1" or above, or $p \leq 0.000002$.

| GenBank Accession | Gene Name | Description |
| --- | --- | --- |
| NM_175734 | C17orf74 | *Homo sapiens* chromosome 17 open reading frame 74 (C17orf74), mRNA [NM_175734] |
| NM_004750 | CRLF1 | *Homo sapiens* cytokine receptor-like factor 1 (CRLF1), mRNA [NM_004750] |
| AA418814 | AA418814 | AA418814 zw01a02.s1 Soares_NhHMPu_S1 *Homo sapiens* cDNA clone IMAGE: 767978 3', mRNA sequence [AA418814] |
| NM_203374 | ZNF784 | *Homo sapiens* zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | *Homo sapiens* forkhead box D3 (FOXD3), mRNA [NM_012183] |
| NM_138763 | BAX | *Homo sapiens* BCL2-associated X protein (BAX), transcript variant delta, mRNA [NM_138763] |
| NM_001404 | EEF1G | *Homo sapiens* eukaryotic translation elongation factor 1 gamma (EEF1G), mRNA [NM_001404] |
| BC107865 | LOC204010 | *Homo sapiens* similar to 40S ribosomal protein SA (P40) (34/67 kDa laminin receptor) (Colon carcinoma laminin-binding protein) (NEM/1CHD4) (Multidrug resistance-associated protein MGr1-Ag), mRNA (cDNA clone MGC: 104447 IMAGE: 4095371), complete cds . . . |
| NM_203477 | MGC70863 | *Homo sapiens* similar to RPL23AP7 protein (MGC70863), transcript variant 1, mRNA [NM_203477] |
| NM_003202 | TCF7 | *Homo sapiens* transcription factor 7 (T-cell specific, HMG-box) (TCF7), transcript variant 1, mRNA [NM_003202] |
| NM_019059 | TOMM7 | *Homo sapiens* translocase of outer mitochondrial membrane 7 homolog (yeast) (TOMM7), mRNA [NM_019059] |
| NM_000661 | RPL9 | *Homo sapiens* ribosomal protein L9 (RPL9), transcript variant 1, mRNA [NM_000661] |
| NM_033060 | KRTAP4-10 | *Homo sapiens* keratin associated protein 4-10 (KRTAP4-10), mRNA [NM_033060] |
| XR_018133 | LOC389404 | PREDICTED: *Homo sapiens* similar to 60S ribosomal protein L9 (LOC389404), mRNA [XR_018133] |
| ENST00000333351 | ENST00000333351 | PREDICTED: *Homo sapiens* hypothetical LOC391504 (LOC391504), mRNA [XR_018627] |

TABLE 2

Gene list generated at the inclusion criteria of $p \leq 5 \times 10^{-4}$
and the log-median-ratio being at least "1" or above.

| GenBank Accession | Gene Name | Description |
| --- | --- | --- |
| NM_173833 | SCARA5 | *Homo sapiens* scavenger receptor class A, member 5 (putative) (SCARA5), mRNA [NM_173833] |
| NM_182688 | UBE2G2 | *Homo sapiens* ubiquitin-conjugating enzyme E2G 2 (UBC7 homolog, yeast) (UBE2G2), transcript variant 2, mRNA [NM_182688] |
| NM_024812 | BAALC | *Homo sapiens* brain and acute leukemia, cytoplasmic (BAALC), transcript variant 1, mRNA [NM_024812] |
| XM_372498 | LOC390427 | PREDICTED: *Homo sapiens* similar to TBP-associated factor 15 isoform 1 (LOC390427), mRNA [XM_372498] |
| THC2718728 | THC2718728 | Unknown |
| ENST00000248668 | LRFN1 | Leucine-rich repeat and fibronectin type III domain-containing protein 1 (Fragment). [Source: Uniprot/SPTREMBL; Acc: Q9P244] [ENST00000248668] |
| NM_175734 | C17orf74 | *Homo sapiens* chromosome 17 open reading frame 74 (C17orf74), mRNA [NM_175734] |
| NM_004750 | CRLF1 | *Homo sapiens* cytokine receptor-like factor 1 (CRLF1), mRNA [NM_004750] |
| AA418814 | AA418814 | AA418814 zw01a02.s1 Soares_NhHMPu_S1 *Homo sapiens* cDNA clone IMAGE: 767978 3', mRNA sequence [AA418814] |
| NM_203374 | ZNF784 | *Homo sapiens* zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | *Homo sapiens* forkhead box D3 (FOXD3), mRNA [NM_012183] |
| NM_138763 | BAX | *Homo sapiens* BCL2-associated X protein (BAX), transcript variant delta, mRNA [NM_138763] |

TABLE 3

Gene list generated at the inclusion criteria of $p \leq 2 \times 10^{-3}$ and the log-median-ratio being at least "1" or above.

| GenBank Accession | Gene Name | Description |
|---|---|---|
| NM_173833 | SCARA5 | Homo sapiens scavenger receptor class A, member 5 (putative) (SCARA5), mRNA [NM_173833] |
| NM_182688 | UBE2G2 | Homo sapiens ubiquitin-conjugating enzyme E2G 2 (UBC7 homolog, yeast) (UBE2G2), transcript variant 2, mRNA [NM_182688] |
| AK000420 | AK000420 | Homo sapiens cDNA FLJ20413 fis, clone KAT02170. [AK000420] |
| NM_024812 | BAALC | Homo sapiens brain and acute leukemia, cytoplasmic (BAALC), transcript variant 1, mRNA [NM_024812] |
| XM_372498 | LOC390427 | PREDICTED: Homo sapiens similar to TBP-associated factor 15 isoform 1 (LOC390427), mRNA [XM_372498] |
| THC2718728 | THC2718728 | Unknown |
| NM_198253 | TERT | Homo sapiens telomerase reverse transcriptase (TERT), transcript variant 1, mRNA [NM_198253] |
| NM_002307 | LGALS7 | Homo sapiens lectin, galactoside-binding, soluble, 7 (galectin 7) (LGALS7), mRNA [NM_002307] |
| ENST00000248668 | LRFN1 | Leucine-rich repeat and fibronectin type III domain-containing protein 1 (Fragment). [Source: Uniprot/SPTREMBL; Acc: Q9P244] [ENST00000248668] |
| ENST00000325151 | ENST00000325151 | Small inducible cytokine A27 precursor (CCL27) (CC chemokine ILC) (IL-11 R-alpha-locus chemokine) (Skinkine) (ESkine) (Cutaneous T-cell-attracting chemokine) (CTACK). [Source: Uniprot/SWISSPROT; Acc: Q9Y4X3] [ENST00000325151] |
| NM_006266 | RALGDS | Homo sapiens ral guanine nucleotide dissociation stimulator (RALGDS), transcript variant 1, mRNA [NM_006266] |
| NM_001138 | AGRP | Homo sapiens agouti related protein homolog (mouse) (AGRP), transcript variant 1, mRNA [NM_001138] |
| NM_207377 | UNQ9438 | Homo sapiens TIMM9 (UNQ9438), mRNA [NM_207377] |
| NM_015088 | TNRC6B | Homo sapiens trinucleotide repeat containing 6B (TNRC6B), transcript variant 1, mRNA [NM_015088] |
| NM_175734 | C17orf74 | Homo sapiens chromosome 17 open reading frame 74 (C17orf74), mRNA [NM_175734] |
| NM_004750 | CRLF1 | Homo sapiens cytokine receptor-like factor 1 (CRLF1), mRNA [NM_004750] |
| NM_003508 | FZD9 | Homo sapiens frizzled homolog 9 (Drosophila) (FZD9), mRNA [NM_003508] |
| AA418814 | AA418814 | AA418814 zw01a02.s1 Soares_NhHMPu_S1 Homo sapiens cDNA clone IMAGE: 767978 3', mRNA sequence [AA418814] |
| NM_203374 | ZNF784 | Homo sapiens zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | Homo sapiens forkhead box D3 (FOXD3), mRNA [NM_012183] |
| NM_019105 | TNXB | Homo sapiens tenascin XB (TNXB), transcript variant XB, mRNA [NM_019105] |
| ENST00000360514 | ENST00000360514 | Homo sapiens hypothetical LOC339483, mRNA (cDNA clone MGC: 52427 IMAGE: 4872239), complete cds. [BC041632] |
| NM_138763 | BAX | Homo sapiens BCL2-associated X protein (BAX), transcript variant delta, mRNA [NM_138763] |
| NM_203304 | RKHD1 | Homo sapiens ring finger and KH domain containing 1 (RKHD1), mRNA [NM_203304] |
| NM_018490 | LGR4 | Homo sapiens leucine-rich repeat-containing G protein-coupled receptor 4 (LGR4), mRNA [NM_018490] |
| CV575560 | CV575560 | oe37f10.y1 Human keratoconus cornea, unamplified, (od [CV575560] |

TABLE 4

Gene list generated at the inclusion criteria of $p \leq 2 \times 10^{-6}$.

| GenBank Accession | Gene Name | Description |
|---|---|---|
| NM_001404 | EEF1G | Homo sapiens eukaryotic translation elongation factor 1 gamma (EEF1G), mRNA [NM_001404] |
| BC107865 | LOC204010 | Homo sapiens similar to 40S ribosomal protein SA (P40) (34/67 kDa laminin receptor) (Colon carcinoma laminin-binding protein) (NEM/1CHD4) (Multidrug resistance-associated protein MGr1-Ag), mRNA (cDNA clone MGC: 104447 IMAGE: 4095371), complete cds . . . |

TABLE 4-continued

Gene list generated at the inclusion criteria of $p \leq 2 \times 10^{-6}$.

| GenBank Accession | Gene Name | Description |
| --- | --- | --- |
| NM_203477 | MGC70863 | *Homo sapiens* similar to RPL23AP7 protein (MGC70863), transcript variant 1, mRNA [NM_203477] |
| NM_003202 | TCF7 | *Homo sapiens* transcription factor 7 (T-cell specific, HMG-box) (TCF7), transcript variant 1, mRNA [NM_003202] |
| NM_019059 | TOMM7 | *Homo sapiens* translocase of outer mitochondrial membrane 7 homolog (yeast) (TOMM7), mRNA [NM_019059] |
| NM_000661 | RPL9 | *Homo sapiens* ribosomal protein L9 (RPL9), transcript variant 1, mRNA [NM_000661] |
| NM_033060 | KRTAP4-10 | *Homo sapiens* keratin associated protein 4-10 (KRTAP4-10), mRNA [NM_033060] |
| XR_018133 | LOC389404 | PREDICTED: *Homo sapiens* similar to 60S ribosomal protein L9 (LOC389404), mRNA [XR_018133] |
| ENST00000333351 | ENST00000333351 | PREDICTED: *Homo sapiens* hypothetical LOC391504 (LOC391504), mRNA [XR_018627] |

TABLE 5

Gene list generated at the inclusion criteria of $p \leq 1 \times 10^{-5}$.

| GenBank Accession | GeneName | Description |
| --- | --- | --- |
| THC2718728 | THC2718728 | Unknown |
| NM_203477 | MGC70863 | *Homo sapiens* similar to RPL23AP7 protein (MGC70863), transcript variant 1, mRNA [NM_203477] |
| NR_000029 | RPL23AP7 | *Homo sapiens* ribosomal protein L23a pseudogene 7 (RPL23AP7) on chromosome 2 [NR_000029] |
| BC030568 | LOC376693 | *Homo sapiens* hypothetical LOC376693, mRNA (cDNA clone MGC: 45392 IMAGE: 5526694), complete cds. [BC030568] |
| BC006438 | BC006438 | *Homo sapiens* cDNA clone MGC: 13162 IMAGE: 3010103, complete cds. [BC006438] |
| ENST00000303979 | ENST00000303979 | Unknown |
| XR_016879 | LOC388401 | PREDICTED: *Homo sapiens* similar to 60S ribosomal protein L7 (LOC388401), mRNA [XR_016879] |
| NM_001404 | EEF1G | *Homo sapiens* eukaryotic translation elongation factor 1 gamma (EEF1G), mRNA [NM_001404] |
| NM_203477 | MGC70863 | *Homo sapiens* similar to RPL23AP7 protein (MGC70863), transcript variant 1, mRNA [NM_203477] |
| NM_001040437 | C6orf48 | *Homo sapiens* chromosome 6 open reading frame 48 (C6orf48), transcript variant 1, mRNA [NM_001040437] |
| XM_001128309 | LOC730663 | PREDICTED: *Homo sapiens* similar to 60S ribosomal protein L23a (LOC730663), mRNA [XM_001128309] |
| NM_001214 | C16orf3 | *Homo sapiens* chromosome 16 open reading frame 3 (C16orf3), mRNA [NM_001214] |
| NM_001082575 | HRNBP3 | *Homo sapiens* hypothetical protein LOC146713 (HRNBP3), mRNA [NM_001082575] |
| BC107865 | LOC204010 | *Homo sapiens* similar to 40S ribosomal protein SA (P40) (34/67 kDa laminin receptor) (Colon carcinoma laminin-binding protein) (NEM/1CHD4) (Multidrug resistance-associated protein MGr1-Ag), mRNA (cDNA clone MGC: 104447 IMAGE: 4095371), complete cds . . . |
| NM_203477 | MGC70863 | *Homo sapiens* similar to RPL23AP7 protein (MGC70863), transcript variant 1, mRNA [NM_203477] |
| NM_003202 | TCF7 | *Homo sapiens* transcription factor 7 (T-cell specific, HMG-box) (TCF7), transcript variant 1, mRNA [NM_003202] |
| A_24_P93052 | A_24_P93052 | Unknown |
| NM_019059 | TOMM7 | *Homo sapiens* translocase of outer mitochondrial membrane 7 homolog (yeast) (TOMM7), mRNA [NM_019059] |
| NM_001907 | CTRL | *Homo sapiens* chymotrypsin-like (CTRL), mRNA [NM_001907] |
| XM_372331 | NKX1-2 | PREDICTED: *Homo sapiens* NK1 transcription factor related, locus 2 (*Drosophila*) (NKX1-2), mRNA [XM_372331] |
| ENST00000237840 | hCG_1642354 | PREDICTED: *Homo sapiens* similar to 60S ribosomal protein L23a (LOC341511), mRNA [XM_292109] |
| XR_015402 | LOC731170 | PREDICTED: *Homo sapiens* similar to eukaryotic translation elongation factor 1 alpha 2 (LOC731170), mRNA [XR_015402] |
| NM_138693 | KLF14 | *Homo sapiens* Kruppel-like factor 14 (KLF14), mRNA [NM_138693] |
| NM_033260 | FOXQ1 | *Homo sapiens* forkhead box Q1 (FOXQ1), mRNA [NM_033260] |
| XM_926013 | LOC642398 | PREDICTED: *Homo sapiens* hypothetical LOC642398, transcript variant 1 (LOC642398), mRNA [XM_926013] |
| NM_015417 | C20orf28 | *Homo sapiens* chromosome 20 open reading frame 28 (C20orf28), mRNA [NM_015417] |

TABLE 5-continued

Gene list generated at the inclusion criteria of $p \leq 1 \times 10^{-5}$.

| GenBank Accession | GeneName | Description |
|---|---|---|
| XR_018155 | LOC643013 | PREDICTED: *Homo sapiens* similar to laminin receptor 1 (ribosomal protein SA) (LOC643013), mRNA [XR_018155] |
| NM_004137 | KCNMB1 | *Homo sapiens* potassium large conductance calcium-activated channel, subfamily M, beta member 1 (KCNMB1), mRNA [NM_004137] |
| NM_198904 | GABRG2 | *Homo sapiens* gamma-aminobutyric acid (GABA) A receptor, gamma 2 (GABRG2), transcript variant 1, mRNA [NM_198904] |
| NM_013373 | ZDHHC8 | *Homo sapiens* zinc finger, DHHC-type containing 8 (ZDHHC8), mRNA [NM_013373] |
| AA627135 | AA627135 | nq71a04.s1 NCI_CGAP_Pr22 *Homo sapiens* cDNA clone IMAGE: 1157742 3' similar to SW: R13A_HUMAN P40429 60S RIBOSOMAL PROTEIN L13A;, mRNA sequence [AA627135] |
| NM_000661 | RPL9 | *Homo sapiens* ribosomal protein L9 (RPL9), transcript variant 1, mRNA [NM_000661] |
| XR_018553 | LOC648294 | PREDICTED: *Homo sapiens* hypothetical LOC648294 (LOC648294), mRNA [XR_018553] |
| NM_033060 | KRTAP4-10 | *Homo sapiens* keratin associated protein 4-10 (KRTAP4-10), mRNA [NM_033060] |
| NM_000984 | RPL23A | *Homo sapiens* ribosomal protein L23a (RPL23A), mRNA [NM_000984] |
| BC002431 | B4GALT2 | *Homo sapiens* cDNA clone IMAGE: 3347310, containing frame-shift errors. [BC002431] |
| NM_000983 | RPL22 | *Homo sapiens* ribosomal protein L22 (RPL22), mRNA [NM_000983] |
| XM_927514 | LOC644357 | PREDICTED: *Homo sapiens* similar to Elongation factor 1-delta (EF-1-delta) (Antigen NY-CO-4) (LOC644357), mRNA [XM_927514] |
| NM_001014373 | C19orf31 | *Homo sapiens* chromosome 19 open reading frame 31 (C19orf31), mRNA [NM_001014373] |
| XR_018133 | LOC389404 | PREDICTED: *Homo sapiens* similar to 60S ribosomal protein L9 (LOC389404), mRNA [XR_018133] |
| NM_003202 | TCF7 | *Homo sapiens* transcription factor 7 (T-cell specific, HMG-box) (TCF7), transcript variant 1, mRNA [NM_003202] |
| A_24_P213073 | A_24_P213073 | Unknown |
| THC2615996 | THC2615996 | Unknown |
| NM_016337 | EVL | *Homo sapiens* Enah/Vasp-like (EVL), mRNA [NM_016337] |
| NM_001402 | EEF1A1 | *Homo sapiens* eukaryotic translation elongation factor 1 alpha 1 (EEF1A1), mRNA [NM_001402] |
| NM_015355 | SUZ12 | *Homo sapiens* suppressor of zeste 12 homolog (*Drosophila*) (SUZ12), mRNA [NM_015355] |
| ENST00000332289 | ENST00000332289 | PREDICTED: *Homo sapiens* similar to 40S ribosomal protein SA (p40) (34 [XR_019580] |
| CR627135 | CR627135 | *Homo sapiens* mRNA; cDNA DKFZp779J0122 (from clone DKFZp779J0122). [CR627135] |
| THC2533996 | THC2533996 | HSU09954 ribosomal protein L9 {*Homo sapiens*} (exp = −1; wgp = 0; cg = 0), partial (42%) [THC2533996] |
| A_24_P714750 | A_24_P714750 | Unknown |
| ENST00000333351 | ENST00000333351 | PREDICTED: *Homo sapiens* hypothetical LOC391504 (LOC391504), mRNA [XR_018627] |
| NM_178230 | PPIAL4 | *Homo sapiens* peptidylprolyl isomerase A (cyclophilin A)-like 4 (PPIAL4), mRNA [NM_178230] |
| NM_003754 | EIF3S5 | *Homo sapiens* eukaryotic translation initiation factor 3, subunit 5 epsilon, 47 kDa (EIF3S5), mRNA [NM_003754] |
| NM_001212 | C1QBP | *Homo sapiens* complement component 1, q subcomponent binding protein (C1QBP), nuclear gene encoding mitochondrial protein, mRNA [NM_001212] |
| NM_006597 | HSPA8 | *Homo sapiens* heat shock 70 kDa protein 8 (HSPA8), transcript variant 1, mRNA [NM_006597] |

TABLE 6

Gene list generated at the inclusion criteria of $p \leq 5 \times 10^{-4}$ and the log-median-ratio being at least "0.8" or above, or being at least "−0.8" or below.

| GenBank Accession | GeneName | Description |
|---|---|---|
| NM_001039567 | RPS4Y2 | *Homo sapiens* ribosomal protein S4, Y-linked 2 (RPS4Y2), mRNA [NM_001039567] |
| NM_001008 | RPS4Y1 | *Homo sapiens* ribosomal protein S4, Y-linked 1 (RPS4Y1), mRNA [NM_001008] |

TABLE 6-continued

Gene list generated at the inclusion criteria of $p \leq 5 \times 10^{-4}$
and the log-median-ratio being at least "0.8" or above, or being at least "−0.8" or below.

| GenBank Accession | GeneName | Description |
| --- | --- | --- |
| NM_015646 | RAP1B | *Homo sapiens* RAP1B, member of RAS oncogene family (RAP1B), transcript variant 1, mRNA [NM_015646] |
| NM_033251 | RPL13 | *Homo sapiens* ribosomal protein L13 (RPL13), transcript variant 2, mRNA [NM_033251] |
| NM_001803 | CD52 | *Homo sapiens* CD52 molecule (CD52), mRNA [NM_001803] |
| NM_006597 | HSPA8 | *Homo sapiens* heat shock 70 kDa protein 8 (HSPA8), transcript variant 1, mRNA [NM_006597] |
| NM_001402 | EEF1A1 | *Homo sapiens* eukaryotic translation elongation factor 1 alpha 1 (EEF1A1), mRNA [NM_001402] |
| NM_001030 | RPS27 | *Homo sapiens* ribosomal protein S27 (metallopanstimulin 1) (RPS27), mRNA [NM_001030] |
| XR_017498 | LOC645693 | PREDICTED: *Homo sapiens* similar to eukaryotic translation elongation factor 1 alpha 2 (LOC645693), mRNA [XR_017498] |
| NM_006597 | HSPA8 | *Homo sapiens* heat shock 70 kDa protein 8 (HSPA8), transcript variant 1, mRNA [NM_006597] |
| NM_001778 | CD48 | *Homo sapiens* CD48 molecule (CD48), mRNA [NM_001778] |
| NM_001017 | RPS13 | *Homo sapiens* ribosomal protein S13 (RPS13), mRNA [NM_001017] |
| THC2544911 | THC2544911 | MUSEFTU elongation factor Tu {*Mus musculus*} (exp = −1; wgp = 0; cg = 0), partial (37%) [THC2544911] |
| NM_021104 | RPL41 | *Homo sapiens* ribosomal protein L41 (RPL41), transcript variant 1, mRNA [NM_021104] |
| NM_000981 | RPL19 | *Homo sapiens* ribosomal protein L19 (RPL19), mRNA [NM_000981] |
| NM_002300 | LDHB | *Homo sapiens* lactate dehydrogenase B (LDHB), mRNA [NM_002300] |
| NM_033251 | RPL13 | *Homo sapiens* ribosomal protein L13 (RPL13), transcript variant 2, mRNA [NM_033251] |
| NM_003973 | RPL14 | *Homo sapiens* ribosomal protein L14 (RPL14), transcript variant 2, mRNA [NM_003973] |
| NM_000978 | RPL23 | *Homo sapiens* ribosomal protein L23 (RPL23), mRNA [Nfvf_000978] |
| A_24_P392195 | A_24_P392195 | Unknown |
| NM_001028 | RPS25 | *Homo sapiens* ribosomal protein S25 (RPS25), mRNA [NM_001028] |
| NM_001032 | RPS29 | *Homo sapiens* ribosomal protein S29 (RPS29), transcript variant 1, mRNA [NM_001032] |
| XR_017260 | LOC646710 | PREDICTED: *Homo sapiens* hypothetical LOC646710 (LOC646710), mRNA [XR_017260] |
| A_24_P333112 | A_24_P333112 | Unknown |
| XR_017294 | LOC646949 | PREDICTED: *Homo sapiens* similar to ribosomal protein L23 (LOC646949), mRNA [XR_017294] |
| NM_002085 | GPX4 | *Homo sapiens* glutathione peroxidase 4 (phospholipid hydroperoxidase) (GPX4), transcript variant 1, mRNA [NM_002085] |
| XR_015548 | LOC729449 | PREDICTED: *Homo sapiens* similar to 60S ribosomal protein L7 (LOC729449), mRNA [XR_015548] |
| NM_006597 | HSPA8 | *Homo sapiens* heat shock 70 kDa protein 8 (HSPA8), transcript variant 1, mRNA [NM_006597] |
| NM_001402 | EEF1A1 | *Homo sapiens* eukaryotic translation elongation factor 1 alpha 1 (EEF1A1), mRNA [NM_001402] |
| NM_001568 | EIF3S6 | *Homo sapiens* eukaryotic translation initiation factor 3, subunit 6 48 kDa (EIF3S6), mRNA [NM_001568] |
| A_32_P128781 | A_32_P128781 | Unknown |
| ENST00000312528 | ENST00000312528 | Unknown |
| NM_001402 | EEF1A1 | *Homo sapiens* eukaryotic translation elongation factor 1 alpha 1 (EEF1A1), mRNA [NM_001402] |
| NM_025228 | TRAF3IP3 | *Homo sapiens* TRAF3 interacting protein 3 (TRAF3IP3), mRNA [NM_025228] |
| A_24_P332292 | A_24_P332292 | Unknown |
| NM_198969 | AES | *Homo sapiens* amino-terminal enhancer of split (AES), transcript variant 1, mRNA [NM_198969] |
| NM_000989 | RPL30 | *Homo sapiens* ribosomal protein L30 (RPL30), mRNA [NM_000989] |
| A_24_P878388 | A_24_P878388 | Unknown |
| XR_016879 | LOC388401 | PREDICTED: *Homo sapiens* similar to 60S ribosomal protein L7 (LOC388401), mRNA [XR_016879] |
| NM_000967 | RPL3 | *Homo sapiens* ribosomal protein L3 (RPL3), transcript variant 1, mRNA [NM_000967] |
| NM_000967 | RPL3 | *Homo sapiens* ribosomal protein L3 (RPL3), transcript variant 1, mRNA [NM_000967] |
| A_24_P84408 | A_24_P84408 | Unknown |
| NM_000661 | RPL9 | *Homo sapiens* ribosomal protein L9 (RPL9), transcript variant 1, mRNA [NM_000661] |

TABLE 6-continued

Gene list generated at the inclusion criteria of $p \leq 5 \times 10^{-4}$
and the log-median-ratio being at least "0.8" or above, or being at least "−0.8" or below.

| GenBank Accession | GeneName | Description |
| --- | --- | --- |
| NM_000661 | RPL9 | *Homo sapiens* ribosomal protein L9 (RPL9), transcript variant 1, mRNA [NM_000661] |
| A_24_P650893 | A_24_P650893 | Unknown |
| A_24_P298238 | A_24_P298238 | Unknown |
| THC2541331 | THC2541331 | HSU02032 ribosomal protein L23a {*Homo sapiens*} (exp = −1; wgp = 0; cg = 0), partial (71%) [THC2541331] |
| XR_018025 | LOC641790 | PREDICTED: *Homo sapiens* similar to ribosomal protein L31 (LOC641790), mRNA [XR_018025] |
| BC018140 | RPS21 | *Homo sapiens* ribosomal protein S21, mRNA (cDNA clone MGC: 9438 IMAGE: 3903320), complete cds. [BC018140] |
| ENST00000308989 | ENST00000308989 | PREDICTED: *Homo sapiens* similar to ribosomal protein L31 (LOC729005), mRNA [XM_001133428] |
| A_24_P212726 | A_24_P212726 | Unknown |
| NM_001028 | RPS25 | *Homo sapiens* ribosomal protein S25 (RPS25), mRNA [NM_001028] |
| XR_015402 | LOC731170 | PREDICTED: *Homo sapiens* similar to eukaryotic translation elongation factor 1 alpha 2 (LOC731170), mRNA [XR_015402] |
| A_24_P340886 | A_24_P340886 | Unknown |
| XR_019376 | LOC285260 | PREDICTED: *Homo sapiens* similar to ribosomal protein L31 (LOC285260), mRNA [XR_019376] |
| ENST00000359449 | ENST00000359449 | Sequence 237 from Patent WO0220754. [AX721277] |
| XR_018975 | LOC389644 | PREDICTED: *Homo sapiens* similar to ribosomal protein L5 (LOC389644), mRNA [XR_018975] |
| A_24_P505981 | A_24_P505981 | Unknown |
| ENST00000240349 | NACA3P | PREDICTED: *Homo sapiens* similar to nascent polypeptide-associated complex alpha polypeptide (LOC389240), mRNA [XM_371715] |
| A_24_P221375 | A_24_P221375 | Unknown |
| NM_000984 | RPL23A | *Homo sapiens* ribosomal protein L23a (RPL23A), mRNA [NM_000984] |
| XR_018231 | LOC648027 | PREDICTED: *Homo sapiens* similar to Elongation factor 1-gamma (EF-1-gamma) (eEF-1B gamma) (LOC648027), mRNA [XR_018231] |
| NM_013234 | EIF3S12 | *Homo sapiens* eukaryotic translation initiation factor 3, subunit 12 (EIF3S12), mRNA [NM_013234] |
| NM_001861 | COX4I1 | *Homo sapiens* cytochrome c oxidase subunit IV isoform 1 (COX4I1), mRNA [NM_001861] |
| XR_019544 | LOC652890 | PREDICTED: *Homo sapiens* similar to 60S ribosomal protein L7 (LOC652890), mRNA [XR_019544] |
| NM_000982 | RPL21 | *Homo sapiens* ribosomal protein L21 (RPL21), mRNA [NM_000982] |
| A_23_P210285 | A_23_P210285 | Unknown |
| XR_019361 | LOC442260 | PREDICTED: *Homo sapiens* similar to 60S ribosomal protein L23a (LOC442260), mRNA [XR_019361] |
| A_24_P289884 | A_24_P289884 | Unknown |
| A_24_P135242 | A_24_P135242 | Unknown |
| NM_003973 | RPL14 | *Homo sapiens* ribosomal protein L14 (RPL14), transcript variant 2, mRNA [NM_003973] |
| XR_019386 | LOC652558 | PREDICTED: *Homo sapiens* similar to 60S ribosomal protein L7 (LOC652558), mRNA [XR_019386] |
| THC2533996 | THC2533996 | HSU09954 ribosomal protein L9 {*Homo sapiens*} (exp = −1; wgp = 0; cg = 0), partial (42%) [THC2533996] |
| NM_000984 | RPL23A | *Homo sapiens* ribosomal protein L23a (RPL23A), mRNA [NM_000984] |
| NM_020240 | CDC42SE2 | *Homo sapiens* CDC42 small effector 2 (CDC42SE2), transcript variant 1, mRNA [NM_020240] |
| NM_007104 | RPL10A | *Homo sapiens* ribosomal protein L10a (RPL10A), mRNA [NM_007104] |
| XR_015944 | LOC731681 | PREDICTED: *Homo sapiens* similar to 60S ribosomal protein L9 (LOC731681), mRNA [XR_015944] |
| NM_001404 | EEF1G | *Homo sapiens* eukaryotic translation elongation factor 1 gamma (EEF1G), mRNA [NM_001404] |
| NM_021103 | TMSB10 | *Homo sapiens* thymosin, beta 10 (TMSB10), mRNA [NM_021103] |
| NM_001011 | RPS7 | *Homo sapiens* ribosomal protein S7 (RPS7), mRNA [NM_001011] |
| NM_016270 | KLF2 | *Homo sapiens* Kruppel-like factor 2 (lung) (KLF2), mRNA [NM_016270] |
| NM_015414 | RPL36 | *Homo sapiens* ribosomal protein L36 (RPL36), transcript variant 2, mRNA [NM_015414] |
| XR_018222 | RPL31P4 | PREDICTED: *Homo sapiens* ribosomal protein L31 pseudogene 4 (RPL31P4), mRNA [XR_018222] |
| BC028083 | TRBV5-4 | *Homo sapiens* T cell receptor beta variable 5-4, mRNA (cDNA clone MGC: 40031 IMAGE: 5217067), complete cds. [BC028083] |
| NM_033625 | RPL34 | *Homo sapiens* ribosomal protein L34 (RPL34), transcript variant 2, mRNA [NM_033625] |

TABLE 6-continued

Gene list generated at the inclusion criteria of $p \leq 5 \times 10^{-4}$
and the log-median-ratio being at least "0.8" or above, or being at least "−0.8" or below.

| GenBank Accession | GeneName | Description |
|---|---|---|
| NM_000996 | RPL35A | *Homo sapiens* ribosomal protein L35a (RPL35A), mRNA [NM_000996] |
| A_24_P144163 | A_24_P144163 | Unknown |
| A_24_P238427 | A_24_P238427 | Unknown |
| AK092748 | RP3-377H14.5 | *Homo sapiens* cDNA FLJ35429 fis, clone SMINT2002126. [AK092748] |
| THC2560098 | THC2560098 | S35960 C-terminal {*Homo sapiens*} (exp = −1; wgp = 0; cg = 0), partial (64%) [THC2560098] |
| A_24_P324224 | A_24_P324224 | Unknown |
| NM_203477 | MGC70863 | *Homo sapiens* similar to RPL23AP7 protein (MGC70863), transcript variant 1, mRNA [NM_203477] |
| XR_019277 | LOC391719 | PREDICTED: *Homo sapiens* similar to ribosomal protein L19 (LOC391719), mRNA [XR_019277] |
| AK098605 | AK098605 | *Homo sapiens* cDNA FLJ25739 fis, clone TST05834. [AK098605] |
| A_24_P127442 | A_24_P127442 | Unknown |
| NM_153236 | GIMAP7 | *Homo sapiens* GTPase, IMAP family member 7 (GIMAP7), mRNA [NM_153236] |
| NR_001577 | NME2P1 | *Homo sapiens* non-metastatic cells 2, protein (NM23B) expressed in, pseudogene 1 (NME2P1) on chromosome 12 [NR_001577] |
| XR_015767 | LOC731224 | PREDICTED: *Homo sapiens* similar to 60S ribosomal protein L9 (LOC731224), mRNA [XR_015767] |
| AK124741 | AK124741 | *Homo sapiens* cDNA FLJ42751 fis, clone BRAWH3000491, moderately similar to 40S ribosomal protein S12. [AK124741] |
| NM_000984 | RPL23A | *Homo sapiens* ribosomal protein L23a (RPL23A), mRNA [NM_000984] |
| XM_001125895 | LOC730452 | PREDICTED: *Homo sapiens* similar to 60S ribosomal protein L7 (LOC730452), mRNA [XM_001125895] |
| NM_000967 | RPL3 | *Homo sapiens* ribosomal protein L3 (RPL3), transcript variant 1, mRNA [NM_000967] |
| XR_018341 | LOC390413 | PREDICTED: *Homo sapiens* similar to 60S ribosomal protein L7 (LOC390413), mRNA [XR_018341] |
| XR_018054 | LOC392878 | PREDICTED: *Homo sapiens* hypothetical LOC392878 (LOC392878), mRNA [XR_018054] |
| NM_006013 | RPL10 | *Homo sapiens* ribosomal protein L10 (RPL10), mRNA [NM_006013] |
| ENST00000332696 | ENST00000332696 | similar to 60S ribosomal protein L23a (LOC644384), mRNA [Source: RefSeq_dna; Acc: XR_017413] [ENST00000332696] |
| A_24_P204474 | A_24_P204474 | Unknown |
| A_32_P208856 | A_32_P208856 | Unknown |
| NM_001404 | EEF1G | *Homo sapiens* eukaryotic translation elongation factor 1 gamma (EEF1G), mRNA [NM_001404] |
| THC2506377 | THC2506377 | HSU02032 ribosomal protein L23a {*Homo sapiens*}(exp = −1; wgp = 0; cg = 0), partial (92%) [THC2506377] |
| NM_080746 | RPL10L | *Homo sapiens* ribosomal protein L10-like (RPL10L), mRNA [NM_080746] |
| NM_000986 | RPL24 | *Homo sapiens* ribosomal protein L24 (RPL24), mRNA [NM_000986] |
| XM_928025 | LOC644937 | PREDICTED: *Homo sapiens* similar to 60S ribosomal protein L10 (QM protein) (Tumor suppressor QM) (Laminin receptor homolog) (LOC644937), mRNA [XM_928025] |
| XM_930195 | hCG_18290 | PREDICTED: *Homo sapiens* similar to 60S ribosomal protein L32 (LOC644907), mRNA [XM_930195] |
| NM_001080544 | LOC653314 | *Homo sapiens* similar to ribosomal protein L19 (LOC653314), mRNA [NM_001080544] |
| ENST00000333351 | ENST00000333351 | PREDICTED: *Homo sapiens* hypothetical LOC391504 (LOC391504), mRNA [XR_018627] |
| A_24_P212654 | A_24_P212654 | Unknown |
| XR_018509 | LOC391701 | PREDICTED: *Homo sapiens* similar to ribosomal protein S23 (LOC391701), mRNA [XR_018509] |
| NM_000979 | RPL18 | *Homo sapiens* ribosomal protein L18 (RPL18), mRNA [NM_000979] |
| NM_019059 | TOMM7 | *Homo sapiens* translocase of outer mitochondrial membrane 7 homolog (yeast) (TOMM7), mRNA [NM_019059] |
| A_24_P392436 | A_24_P392436 | Unknown |
| ENST00000361800 | ENST00000361800 | Unknown |
| A_24_P32207 | A_24_P32207 | Unknown |
| NM_000979 | RPL18 | *Homo sapiens* ribosomal protein L18 (RPL18), mRNA [NM_000979] |
| A_24_P384411 | A_24_P384411 | Unknown |
| NM_002258 | KLRB1 | *Homo sapiens* killer cell lectin-like receptor subfamily B, member 1 (KLRB1), mRNA [NM_002258] |
| NM_001023 | RPS20 | *Homo sapiens* ribosomal protein S20 (RPS20), mRNA [NM_001023] |
| A_24_P32836 | A_24_P32836 | Unknown |

TABLE 6-continued

Gene list generated at the inclusion criteria of $p \leq 5 \times 10^{-4}$
and the log-median-ratio being at least "0.8" or above, or being at least "−0.8" or below.

| GenBank Accession | GeneName | Description |
| --- | --- | --- |
| NM_019059 | TOMM7 | *Homo sapiens* translocase of outer mitochondrial membrane 7 homolog (yeast) (TOMM7), mRNA [NM_019059] |
| A_24_P350008 | A_24_P350008 | Unknown |
| XR_018553 | LOC648294 | PREDICTED: *Homo sapiens* hypothetical LOC648294 (LOC648294), mRNA [XR_018553] |
| XR_018303 | LOC648378 | PREDICTED: *Homo sapiens* similar to ribosomal protein S14 (LOC648378), mRNA [XR_018303] |
| NM_032378 | EEF1D | *Homo sapiens* eukaryotic translation elongation factor 1 delta (guanine nucleotide exchange protein) (EEF1D), transcript variant 1, mRNA [NM_032378] |
| A_24_P118874 | A_24_P118874 | Unknown |
| NM_001014 | RPS10 | *Homo sapiens* ribosomal protein S10 (RPS10), mRNA [NM_001014] |
| NR_000029 | RPL23AP7 | *Homo sapiens* ribosomal protein L23a pseudogene 7 (RPL23AP7) on chromosome 2 [NR_000029] |
| NM_002818 | PSME2 | *Homo sapiens* proteasome (prosome, macropain) activator subunit 2 (PA28 beta) (PSME2), mRNA [NM_002818] |
| NM_016337 | EVL | *Homo sapiens* Enah/Vasp-like (EVL), mRNA [NM_016337] |
| ENST00000237840 | hCG_1642354 | PREDICTED: *Homo sapiens* similar to 60S ribosomal protein L23a (LOC341511), mRNA [XM_292109] |
| NM_001404 | EEF1G | *Homo sapiens* eukaryotic translation elongation factor 1 gamma (EEF1G), mRNA [NM_001404] |
| XR_018970 | LOC391140 | PREDICTED: *Homo sapiens* similar to ribosomal protein L13 (LOC391140), mRNA [XR_018970] |
| NM_000969 | RPL5 | *Homo sapiens* ribosomal protein L5 (RPL5), mRNA [NM_000969] |
| THC2494410 | THC2494410 | 2113200F ribosomal protein S9. {*Homo sapiens*} (exp = −1; wgp = −1; cg = −1), complete [THC2494410] |
| A_24_P93452 | A_24_P93452 | Unknown |
| A_24_P366457 | A_24_P366457 | Unknown |
| NM_000661 | RPL9 | *Homo sapiens* ribosomal protein L9 (RPL9), transcript variant 1, mRNA [NM_000661] |
| XR_016930 | LOC645412 | PREDICTED: *Homo sapiens* similar to 40S ribosomal protein S16 (LOC645412), mRNA [XR_016930] |
| NM_001018 | RPS15 | *Homo sapiens* ribosomal protein S15 (RPS15), mRNA [NM_001018] |
| ENST00000359659 | ENST00000359659 | Q8BT90_MOUSE (Q8BT90) 10, 11 days embryo whole body cDNA, RIKEN full-length enriched library, clone: 2810021H19 product: ribosomal protein S17, full insert sequence. (Fragment), partial (98%) [THC2555910] |
| A_24_P93052 | A_24_P93052 | Unknown |
| NM_015853 | LOC51035 | *Homo sapiens* SAPK substrate protein 1 (LOC51035), mRNA [NM_015853] |
| A_24_P410070 | A_24_P410070 | Unknown |
| A_24_P170103 | A_24_P170103 | Unknown |
| AX721252 | AX721252 | Sequence 212 from Patent WO0220754. [AX721252] |
| A_24_P33213 | A_24_P33213 | Unknown |
| XR_018720 | LOC392206 | PREDICTED: *Homo sapiens* similar to ribosomal protein L10a (LOC392206), mRNA [XR_018720] |
| A_24_P341176 | A_24_P341176 | Unknown |
| NM_000971 | RPL7 | *Homo sapiens* ribosomal protein L7 (RPL7), mRNA [NM_000971] |
| XR_018133 | LOC389404 | PREDICTED: *Homo sapiens* similar to 60S ribosomal protein L9 (LOC389404), mRNA [XR_018133] |
| NM_005594 | NACA | *Homo sapiens* nascent-polypeptide-associated complex alpha polypeptide (NACA), mRNA [NM_005594] |
| NM_006013 | RPL10 | *Homo sapiens* ribosomal protein L10 (RPL10), mRNA [NM_006013] |
| A_24_P101271 | A_24_P101271 | Unknown |
| A_24_P264549 | A_24_P264549 | Unknown |
| THC2782843 | THC2782843 | RL18A_HUMAN (Q02543) 60S ribosomal protein L18a, partial (89%) [THC2782843] |
| XM_379885 | hCG_2023776 | PREDICTED: *Homo sapiens* similar to Heterogeneous nuclear ribonucleoprotein A1 (Helix-destabilizing protein) (Single-strand binding protein) (hnRNP core protein A1) (HDP-1) (Topoisomerase-inhibitor suppressed) (LOC402562), mRNA [XM_379885] |
| NM_152219 | GJC1 | *Homo sapiens* gap junction protein, chi 1, 31.9 kDa (GJC1), mRNA [NM_152219] |
| ENST00000323800 | ENST00000323800 | CDNA FLJ25155 fis, clone CBR07976. [Source: Uniprot/SPTREMBL; Acc: Q96LR6] [ENST00000323800] |
| THC2737361 | THC2737361 | Q2IMJ3_ANADE (Q2IMJ3) LigA, partial (5%) [THC2737361] |
| THC2718728 | THC2718728 | Unknown |
| AA418814 | AA418814 | AA418814 zw01a02.s1 Soares_NhHMPu_S1 *Homo sapiens* cDNA clone IMAGE: 767978 3', mRNA sequence [AA418814] |

TABLE 7

Gene list generated at the inclusion criteria of $p \leq 1 \times 10^{-5}$
and the log-median-ratio being at least "0.585" or above, or being at least "−0.585" or below.

| GenBank Accession | GeneName | Description |
|---|---|---|
| NM_006597 | HSPA8 | *Homo sapiens* heat shock 70 kDa protein 8 (HSPA8), transcript variant 1, mRNA [NM_006597] |
| NM_001402 | EEF1A1 | *Homo sapiens* eukaryotic translation elongation factor 1 alpha 1 (EEF1A1), mRNA [NM_001402] |
| XR_016879 | LOC388401 | PREDICTED: *Homo sapiens* similar to 60S ribosomal protein L7 (LOC388401), mRNA [XR_016879] |
| XR_015402 | LOC731170 | PREDICTED: *Homo sapiens* similar to eukaryotic translation elongation factor 1 alpha 2 (LOC731170), mRNA [XR_015402] |
| NM_000984 | RPL23A | *Homo sapiens* ribosomal protein L23a (RPL23A), mRNA [NM_000984] |
| THC2533996 | THC2533996 | HSU09954 ribosomal protein L9 {*Homo sapiens*} (exp = −1; wgp = 0; cg = 0), partial (42%) [THC2533996] |
| NM_203477 | MGC70863 | *Homo sapiens* similar to RPL23AP7 protein (MGC70863), transcript variant 1, mRNA [NM_203477] |
| NM_001404 | EEF1G | *Homo sapiens* eukaryotic translation elongation factor 1 gamma (EEF1G), mRNA [NM_001404] |
| ENST00000333351 | ENST00000333351 | PREDICTED: *Homo sapiens* hypothetical LOC391504 (LOC391504), mRNA [XR_018627] |
| NM_019059 | TOMM7 | *Homo sapiens* translocase of outer mitochondrial membrane 7 homolog (yeast) (TOMM7), mRNA [NM_019059] |
| XR_018553 | LOC648294 | PREDICTED: *Homo sapiens* hypothetical LOC648294 (LOC648294), mRNA [XR_018553] |
| NR_000029 | RPL23AP7 | *Homo sapiens* ribosomal protein L23a pseudogene 7 (RPL23AP7) on chromosome 2 [NR_000029] |
| NM_016337 | EVL | *Homo sapiens* Enah/Vasp-like (EVL), mRNA [NM_016337] |
| ENST00000237840 | hCG_1642354 | PREDICTED: *Homo sapiens* similar to 60S ribosomal protein L23a (LOC341511), mRNA [XM_292109] |
| NM_000661 | RPL9 | *Homo sapiens* ribosomal protein L9 (RPL9), transcript variant 1, mRNA [NM_000661] |
| A_24_P93052 | A_24_P93052 | Unknown |
| XR_018133 | LOC389404 | PREDICTED: *Homo sapiens* similar to 60S ribosomal protein L9 (LOC389404), mRNA [XR_018133] |
| BC030568 | LOC376693 | *Homo sapiens* hypothetical LOC376693, mRNA (cDNA clone MGC: 45392 IMAGE: 5526694), complete cds. [BC030568] |
| XR_018155 | LOC643013 | PREDICTED: *Homo sapiens* similar to laminin receptor 1 (ribosomal protein SA) (LOC643013), mRNA [XR_018155] |
| A_24_P213073 | A_24_P213073 | Unknown |
| NM_000983 | RPL22 | *Homo sapiens* ribosomal protein L22 (RPL22), mRNA [NM_000983] |
| NM_003202 | TCF7 | *Homo sapiens* transcription factor 7 (T-cell specific, HMG-box) (TCF7), transcript variant 1, mRNA [NM_003202] |
| NM_203477 | MGC70863 | *Homo sapiens* similar to RPL23AP7 protein (MGC70863), transcript variant 1, mRNA [NM_203477] |
| AA627135 | AA627135 | nq71a04.s1 NCI_CGAP_Pr22 *Homo sapiens* cDNA clone IMAGE: 1157742 3' similar to SW: R13A_HUMAN P40429 60S RIBOSOMAL PROTEIN L13A;, mRNA sequence [AA627135] |
| ENST00000303979 | ENST00000303979 | Unknown |
| NM_003754 | EIF3S5 | *Homo sapiens* eukaryotic translation initiation factor 3, subunit 5 epsilon, 47 kDa (EIF3S5), mRNA [NM_003754] |
| NM_001212 | C1QBP | *Homo sapiens* complement component 1, q subcomponent binding protein (C1QBP), nuclear gene encoding mitochondrial protein, mRNA [NM_001212] |
| XM_927514 | LOC644357 | PREDICTED: *Homo sapiens* similar to Elongation factor 1-delta (EF-1-delta) (Antigen NY-CO-4) (LOC644357), mRNA [XM_927514] |
| NM_178230 | PPIAL4 | *Homo sapiens* peptidylprolyl isomerase A (cyclophilin A)-like 4 (PPIAL4), mRNA [NM_178230] |
| ENST00000332289 | ENST00000332289 | PREDICTED: *Homo sapiens* similar to 40S ribosomal protein SA (p40) (34 [XR_019580] |
| XM_001128309 | LOC730663 | PREDICTED: *Homo sapiens* similar to 60S ribosomal protein L23a (LOC730663), mRNA [XM_001128309] |
| XM_372331 | NKX1-2 | PREDICTED: *Homo sapiens* NK1 transcription factor related, locus 2 (*Drosophila*) (NKX1-2), mRNA [XM_372331] |
| THC2718728 | THC2718728 | Unknown |

TABLE 8

Gene list generated at the inclusion criteria of $p \leq 1 \times 10^{-4}$ and the log-median-ratio being at least "1" or above, or being at least "−1" or below.

| GenBank Accession | GeneName | Description |
|---|---|---|
| NM_001039567 | RPS4Y2 | *Homo sapiens* ribosomal protein S4, Y-linked 2 (RPS4Y2), mRNA [NM_001039567] |
| NM_001008 | RPS4Y1 | *Homo sapiens* ribosomal protein S4, Y-linked 1 (RPS4Y1), mRNA [NM_001008] |
| NM_015646 | RAP1B | *Homo sapiens* RAP1B, member of RAS oncogene family (RAP1B), transcript variant 1, mRNA [NM_015646] |
| NM_033251 | RPL13 | *Homo sapiens* ribosomal protein L13 (RPL13), transcript variant 2, mRNA [NM_033251] |
| NM_001803 | CD52 | *Homo sapiens* CD52 molecule (CD52), mRNA [NM_001803] |
| NM_006597 | HSPA8 | *Homo sapiens* heat shock 70 kDa protein 8 (HSPA8), transcript variant 1, mRNA [NM_006597] |
| NM_001402 | EEF1A1 | *Homo sapiens* eukaryotic translation elongation factor 1 alpha 1 (EEF1A1), mRNA [NM_001402] |
| NM_001030 | RPS27 | *Homo sapiens* ribosomal protein S27 (metallopanstimulin 1) (RPS27), mRNA [NM_001030] |
| XR_017498 | LOC645693 | PREDICTED: *Homo sapiens* similar to eukaryotic translation elongation factor 1 alpha 2 (LOC645693), mRNA [XR_017498] |
| NM_006597 | HSPA8 | *Homo sapiens* heat shock 70 kDa protein 8 (HSPA8), transcript variant 1, mRNA [NM_006597] |
| NM_001778 | CD48 | *Homo sapiens* CD48 molecule (CD48), mRNA [NM_001778] |
| NM_001017 | RPS13 | *Homo sapiens* ribosomal protein S13 (RPS13), mRNA [NM_001017] |
| THC2544911 | THC2544911 | MUSEFTU elongation factor Tu {*Mus musculus*} (exp = −1; wgp = 0; cg = 0), partial (37%) [THC2544911] |
| NM_021104 | RPL41 | *Homo sapiens* ribosomal protein L41 (RPL41), transcript variant 1, mRNA [NM_021104] |
| NM_000981 | RPL19 | *Homo sapiens* ribosomal protein L19 (RPL19), mRNA [NM_000981] |
| NM_002300 | LDHB | *Homo sapiens* lactate dehydrogenase B (LDHB), mRNA [NM_002300] |
| NM_033251 | RPL13 | *Homo sapiens* ribosomal protein L13 (RPL13), transcript variant 2, mRNA [NM_033251] |
| NM_003973 | RPL14 | *Homo sapiens* ribosomal protein L14 (RPL14), transcript variant 2, mRNA [NM_003973] |
| NM_000978 | RPL23 | *Homo sapiens* ribosomal protein L23 (RPL23), mRNA [NM_000978] |
| A_24_P392195 | A_24_P392195 | Unknown |
| NM_001028 | RPS25 | *Homo sapiens* ribosomal protein S25 (RPS25), mRNA [NM_001028] |
| NM_001032 | RPS29 | *Homo sapiens* ribosomal protein S29 (RPS29), transcript variant 1, mRNA [NM_001032] |
| XR_017260 | LOC646710 | PREDICTED: *Homo sapiens* hypothetical LOC646710 (LOC646710), mRNA [XR_017260] |
| A_24_P333112 | A_24_P333112 | Unknown |
| XR_017294 | LOC646949 | PREDICTED: *Homo sapiens* similar to ribosomal protein L23 (LOC646949), mRNA [XR_017294] |
| NM_002085 | GPX4 | *Homo sapiens* glutathione peroxidase 4 (phospholipid hydroperoxidase) (GPX4), transcript variant 1, mRNA [NM_002085] |
| XR_015548 | LOC729449 | PREDICTED: *Homo sapiens* similar to 60S ribosomal protein L7 (LOC729449), mRNA [XR_015548] |
| NM_006597 | HSPA8 | *Homo sapiens* heat shock 70 kDa protein 8 (HSPA8), transcript variant 1, mRNA [NM_006597] |
| NM_001402 | EEF1A1 | *Homo sapiens* eukaryotic translation elongation factor 1 alpha 1 (EEF1A1), mRNA [NM_001402] |
| NM_001568 | EIF3S6 | *Homo sapiens* eukaryotic translation initiation factor 3, subunit 6 48 kDa (EIF3S6), mRNA [NM_001568] |
| A_32_P128781 | A_32_P128781 | Unknown |
| ENST00000312528 | ENST00000312528 | Unknown |
| NM_001402 | EEF1A1 | *Homo sapiens* eukaryotic translation elongation factor 1 alpha 1 (EEF1A1), mRNA [NM_001402] |
| NM_025228 | TRAF3IP3 | *Homo sapiens* TRAF3 interacting protein 3 (TRAF3IP3), mRNA [NM_025228] |
| A_24_P332292 | A_24_P332292 | Unknown |
| NM_198969 | AES | *Homo sapiens* amino-terminal enhancer of split (AES), transcript variant 1, mRNA [NM_198969] |
| NM_000989 | RPL30 | *Homo sapiens* ribosomal protein L30 (RPL30), mRNA [NM_000989] |
| A_24_P878388 | A_24_P878388 | Unknown |
| XR_016879 | LOC388401 | PREDICTED: *Homo sapiens* similar to 60S ribosomal protein L7 (LOC388401), mRNA [XR_016879] |
| NM_000967 | RPL3 | *Homo sapiens* ribosomal protein L3 (RPL3), transcript variant 1, mRNA [NM_000967] |

TABLE 8-continued

Gene list generated at the inclusion criteria of $p \leq 1 \times 10^{-4}$ and the log-median-ratio being at least "1" or above, or being at least "−1" or below.

| GenBank Accession | GeneName | Description |
|---|---|---|
| NM_000967 | RPL3 | *Homo sapiens* ribosomal protein L3 (RPL3), transcript variant 1, mRNA [NM_000967] |
| A_24_P84408 | A_24_P84408 | Unknown |
| NM_000661 | RPL9 | *Homo sapiens* ribosomal protein L9 (RPL9), transcript variant 1, mRNA [NM_000661] |
| NM_000661 | RPL9 | *Homo sapiens* ribosomal protein L9 (RPL9), transcript variant 1, mRNA [NM_000661] |
| A_24_P650893 | A_24_P650893 | Unknown |
| A_24_P298238 | A_24_P298238 | Unknown |
| THC2541331 | THC2541331 | HSU02032 ribosomal protein L23a {*Homo sapiens*} (exp = −1; wgp = 0; cg = 0), partial (71%) [THC2541331] |
| XR_018025 | LOC641790 | PREDICTED: *Homo sapiens* similar to ribosomal protein L31 (LOC641790), mRNA [XR_018025] |
| BC018140 | RPS21 | *Homo sapiens* ribosomal protein S21, mRNA (cDNA clone MGC: 9438 IMAGE: 3903320), complete cds. [BC018140] |
| ENST00000308989 | ENST00000308989 | PREDICTED: *Homo sapiens* similar to ribosomal protein L31 (LOC729005), mRNA [XM_001133428] |
| A_24_P212726 | A_24_P212726 | Unknown |
| NM_001028 | RPS25 | *Homo sapiens* ribosomal protein S25 (RPS25), mRNA [NM_001028] |
| XR_015402 | LOC731170 | PREDICTED: *Homo sapiens* similar to eukaryotic translation elongation factor 1 alpha 2 (LOC731170), mRNA [XR_015402] |
| A_24_P340886 | A_24_P340886 | Unknown |
| XR_019376 | LOC285260 | PREDICTED: *Homo sapiens* similar to ribosomal protein L31 (LOC285260), mRNA [XR_019376] |
| ENST00000359449 | ENST00000359449 | Sequence 237 from Patent WO0220754. [AX721277] |
| XR_018975 | LOC389644 | PREDICTED: *Homo sapiens* similar to ribosomal protein L5 (LOC389644), mRNA [XR_018975] |
| A_24_P505981 | A_24_P505981 | Unknown |
| ENST00000240349 | NACA3P | PREDICTED: *Homo sapiens* similar to nascent polypeptide-associated complex alpha polypeptide (LOC389240), mRNA [XM_371715] |
| A_24_P221375 | A_24_P221375 | Unknown |
| NM_000984 | RPL23A | *Homo sapiens* ribosomal protein L23a (RPL23A), mRNA [NM_000984] |
| XR_018231 | LOC648027 | PREDICTED: *Homo sapiens* similar to Elongation factor 1-gamma (EF-1-gamma) (eEF-1B gamma) (LOC648027), mRNA [XR_018231] |
| NM_013234 | EIF3S12 | *Homo sapiens* eukaryotic translation initiation factor 3, subunit 12 (EIF3S12), mRNA [NM_013234] |
| NM_001861 | COX4I1 | *Homo sapiens* cytochrome c oxidase subunit IV isoform 1 (COX4I1), mRNA [NM_001861] |
| XR_019544 | LOC652890 | PREDICTED: *Homo sapiens* similar to 60S ribosomal protein L7 (LOC652890), mRNA [XR_019544] |
| NM_000982 | RPL21 | *Homo sapiens* ribosomal protein L21 (RPL21), mRNA [NM_000982] |
| A_23_P210285 | A_23_P210285 | Unknown |
| XR_019361 | LOC442260 | PREDICTED: *Homo sapiens* similar to 60S ribosomal protein L23a (LOC442260), mRNA [XR_019361] |
| A_24_P289884 | A_24_P289884 | Unknown |
| A_24_P135242 | A_24_P135242 | Unknown |
| NM_003973 | RPL14 | *Homo sapiens* ribosomal protein L14 (RPL14), transcript variant 2, mRNA [NM_003973] |
| XR_019386 | LOC652558 | PREDICTED: *Homo sapiens* similar to 60S ribosomal protein L7 (LOC652558), mRNA [XR_019386] |
| THC2533996 | THC2533996 | HSU09954 ribosomal protein L9 {*Homo sapiens*} (exp = −1; wgp = 0; cg = 0), partial (42%) [THC2533996] |
| NM_000984 | RPL23A | *Homo sapiens* ribosomal protein L23a (RPL23A), mRNA [NM_000984] |
| NM_020240 | CDC42SE2 | *Homo sapiens* CDC42 small effector 2 (CDC42SE2), transcript variant 1, mRNA [NM_020240] |
| NM_007104 | RPL10A | *Homo sapiens* ribosomal protein L10a (RPL10A), mRNA [NM_007104] |
| XR_015944 | LOC731681 | PREDICTED: *Homo sapiens* similar to 60S ribosomal protein L9 (LOC731681), mRNA [XR_015944] |
| NM_001404 | EEF1G | *Homo sapiens* eukaryotic translation elongation factor 1 gamma (EEF1G), mRNA [NM_001404] |
| NM_021103 | TMSB10 | *Homo sapiens* thymosin, beta 10 (TMSB10), mRNA [NM_021103] |
| NM_001011 | RPS7 | *Homo sapiens* ribosomal protein S7 (RPS7), mRNA [NM_001011] |
| NM_016270 | KLF2 | *Homo sapiens* Kruppel-like factor 2 (lung) (KLF2), mRNA [NM_016270] |
| NM_015414 | RPL36 | *Homo sapiens* ribosomal protein L36 (RPL36), transcript variant 2, mRNA [NM_015414] |

TABLE 8-continued

Gene list generated at the inclusion criteria of $p \leq 1 \times 10^{-4}$ and the log-median-ratio being at least "1" or above, or being at least "−1" or below.

| GenBank Accession | GeneName | Description |
|---|---|---|
| XR_018222 | RPL31P4 | PREDICTED: *Homo sapiens* ribosomal protein L31 pseudogene 4 (RPL31P4), mRNA [XR_018222] |
| BC028083 | TRBV5-4 | *Homo sapiens* T cell receptor beta variable 5-4, mRNA (cDNA clone MGC: 40031 IMAGE: 5217067), complete cds. [BC028083] |
| NM_033625 | RPL34 | *Homo sapiens* ribosomal protein L34 (RPL34), transcript variant 2, mRNA [NM_033625] |
| NM_000996 | RPL35A | *Homo sapiens* ribosomal protein L35a (RPL35A), mRNA [NM_000996] |
| A_24_P144163 | A_24_P144163 | Unknown |
| A_24_P238427 | A_24_P238427 | Unknown |
| AK092748 | RP3-377H14.5 | *Homo sapiens* cDNA FLJ35429 fis, clone SMINT2002126. [AK092748] |
| THC2560098 | THC2560098 | S35960 C-terminal {*Homo sapiens*} (exp = −1; wgp = 0; cg = 0), partial (64%) [THC2560098] |
| A_24_P324224 | A_24_P324224 | Unknown |
| NM_203477 | MGC70863 | *Homo sapiens* similar to RPL23AP7 protein (MGC70863), transcript variant 1, mRNA [NM_203477] |
| XR_019277 | LOC391719 | PREDICTED: *Homo sapiens* similar to ribosomal protein L19 (LOC391719), mRNA [XR_019277] |
| AK098605 | AK098605 | *Homo sapiens* cDNA FLJ25739 fis, clone TST05834. [AK098605] |
| A_24_P127442 | A_24_P127442 | Unknown |
| NM_153236 | GIMAP7 | *Homo sapiens* GTPase, IMAP family member 7 (GIMAP7), mRNA [NM_153236] |
| NR_001577 | NME2P1 | *Homo sapiens* non-metastatic cells 2, protein (NM23B) expressed in, pseudogene 1 (NME2P1) on chromosome 12 [NR_001577] |
| XR_015767 | LOC731224 | PREDICTED: *Homo sapiens* similar to 60S ribosomal protein L9 (LOC731224), mRNA [XR_015767] |
| AK124741 | AK124741 | *Homo sapiens* cDNA FLJ42751 fis, clone BRAWH3000491, moderately similar to 40S ribosomal protein S12. [AK124741] |
| NM_000984 | RPL23A | *Homo sapiens* ribosomal protein L23a (RPL23A), mRNA [NM_000984] |
| XM_001125895 | LOC730452 | PREDICTED: *Homo sapiens* similar to 60S ribosomal protein L7 (LOC730452), mRNA [XM_001125895] |
| NM_000967 | RPL3 | *Homo sapiens* ribosomal protein L3 (RPL3), transcript variant 1, mRNA [NM_000967] |
| XR_018341 | LOC390413 | PREDICTED: *Homo sapiens* similar to 60S ribosomal protein L7 (LOC390413), mRNA [XR_018341] |
| XR_018054 | LOC392878 | PREDICTED: *Homo sapiens* hypothetical LOC392878 (LOC392878), mRNA [XR_018054] |
| NM_006013 | RPL10 | *Homo sapiens* ribosomal protein L10 (RPL10), mRNA [NM_006013] |
| ENST00000332696 | ENST00000332696 | similar to 60S ribosomal protein L23a (LOC644384), mRNA [Source: RefSeq_dna; Acc: XR_017413] [ENST00000332696] |
| A_24_P204474 | A_24_P204474 | Unknown |
| A_32_P208856 | A_32_P208856 | Unknown |
| NM_001404 | EEF1G | *Homo sapiens* eukaryotic translation elongation factor 1 gamma (EEF1G), mRNA [NM_001404] |
| THC2506377 | THC2506377 | HSU02032 ribosomal protein L23a {*Homo sapiens*} (exp = −1; wgp = 0; cg = 0), partial (92%) [THC2506377] |
| NM_080746 | RPL10L | *Homo sapiens* ribosomal protein L10-like (RPL10L), mRNA [NM_080746] |
| NM_000986 | RPL24 | *Homo sapiens* ribosomal protein L24 (RPL24), mRNA [NM_000986] |
| XM_928025 | LOC644937 | PREDICTED: *Homo sapiens* similar to 60S ribosomal protein L10 (QM protein) (Tumor suppressor QM) (Laminin receptor homolog) (LOC644937), mRNA [XM_928025] |
| XM_930195 | hCG_18290 | PREDICTED: *Homo sapiens* similar to 60S ribosomal protein L32 (LOC644907), mRNA [XM_930195] |
| NM_001080544 | LOC653314 | *Homo sapiens* similar to ribosomal protein L19 (LOC653314), mRNA [NM_001080544] |
| ENST00000333351 | ENST00000333351 | PREDICTED: *Homo sapiens* hypothetical LOC391504 (LOC391504), mRNA [XR_018627] |
| THC2718728 | THC2718728 | Unknown |
| AA418814 | AA418814 | AA418814 zw01a02.s1 Soares_NhHMPu_S1 *Homo sapiens* cDNA clone IMAGE: 767978 3', mRNA sequence [AA418814] |

TABLE 9

Gene list generated at the inclusion criteria of $p \leq 1 \times 10^{-5}$
and the log-median-ratio being below "0".

| GenBank Accession | GeneName | Description |
|---|---|---|
| NM_006597 | HSPA8 | *Homo sapiens* heat shock 70 kDa protein 8 (HSPA8), transcript variant 1, mRNA [NM_006597] |
| NM_019059 | TOMM7 | *Homo sapiens* translocase of outer mitochondrial membrane 7 homolog (yeast) (TOMM7), mRNA [NM_019059] |
| NM_001402 | EEF1A1 | *Homo sapiens* eukaryotic translation elongation factor 1 alpha 1 (EEF1A1), mRNA [NM_001402] |
| NM_203477 | MGC70863 | *Homo sapiens* similar to RPL23AP7 protein (MGC70863), transcript variant 1, mRNA [NM_203477] |
| XR_016879 | LOC388401 | PREDICTED: *Homo sapiens* similar to 60S ribosomal protein L7 (LOC388401), mRNA [XR_016879] |
| XR_015402 | LOC731170 | PREDICTED: *Homo sapiens* similar to eukaryotic translation elongation factor 1 alpha 2 (LOC731170), mRNA[XR_015402] |
| THC2533996 | THC2533996 | HSU09954 ribosomal protein L9 {*Homo sapiens*} (exp = −1; wgp = 0; cg = 0), partial (42%) [THC2533996] |
| NR_000029 | RPL23AP7 | *Homo sapiens* ribosomal protein L23a pseudogene 7 (RPL23AP7) on chromosome 2 [NR_000029] |
| NM_001404 | EEF1G | *Homo sapiens* eukaryotic translation elongation factor 1 gamma (EEF1G), mRNA [NM_001404] |
| NM_000984 | RPL23A | *Homo sapiens* ribosomal protein L23a (RPL23A), mRNA [NM_000984] |
| ENST00000333351 | ENST00000333351 | PREDICTED: *Homo sapiens* hypothetical LOC391504 (LOC391504), mRNA [XR_018627] |
| XR_018553 | LOC648294 | PREDICTED: *Homo sapiens* hypothetical LOC648294 (LOC648294), mRNA [XR_018553] |
| BC030568 | LOC376693 | *Homo sapiens* hypothetical LOC376693, mRNA (cDNA clone MGC: 45392 IMAGE: 5526694), complete cds. [BC030568] |
| ENST00000237840 | hCG_1642354 | PREDICTED: *Homo sapiens* similar to 60S ribosomal protein L23a (LOC341511), mRNA [XM_292109] |
| A_24_P93052 | A_24_P93052 | Unknown |
| NM_016337 | EVL | *Homo sapiens* Enah/Vasp-like (EVL), mRNA [NM_016337] |
| NM_000661 | RPL9 | *Homo sapiens* ribosomal protein L9 (RPL9), transcript variant 1, mRNA [NM_000661] |
| ENST00000303979 | ENST00000303979 | Unknown |
| NM_003202 | TCF7 | *Homo sapiens* transcription factor 7 (T-cell specific, HMG-box) (TCF7), transcript variant 1, mRNA [NM_003202] |
| XR_018133 | LOC389404 | PREDICTED: *Homo sapiens* similar to 60S ribosomal protein L9 (LOC389404), mRNA [XR_018133] |
| A_24_P213073 | A_24_P213073 | Unknown |
| NM_000983 | RPL22 | *Homo sapiens* ribosomal protein L22 (RPL22), mRNA [NM_000983] |
| XR_018155 | LOC643013 | PREDICTED: *Homo sapiens* similar to laminin receptor 1 (ribosomal protein SA) (LOC643013), mRNA [XR_018155] |
| NM_203477 | MGC70863 | *Homo sapiens* similar to RPL23AP7 protein (MGC70863), transcript variant 1, mRNA [NM_203477] |
| NM_001212 | C1QBP | *Homo sapiens* complement component 1, q subcomponent binding protein (C1QBP), nuclear gene encoding mitochondrial protein, mRNA [NM_001212] |
| XM_001128309 | LOC730663 | PREDICTED: *Homo sapiens* similar to 60S ribosomal protein L23a (LOC730663), mRNA [XM_001128309] |
| AA627135 | AA627135 | nq71a04.s1 NCI_CGAP_Pr22 *Homo sapiens* cDNA clone IMAGE: 1157742 3' similar to SW: R13A_HUMAN P40429 60S RIBOSOMAL PROTEIN L13A;, mRNA sequence [AA627135] |
| NM_003754 | EIF3S5 | *Homo sapiens* eukaryotic translation initiation factor 3, subunit 5 epsilon, 47 kDa (EIF3S5), mRNA [NM_003754] |
| NM_178230 | PPIAL4 | *Homo sapiens* peptidylprolyl isomerase A (cyclophilin A)-like 4 (PPIAL4), mRNA [NM_178230] |
| XM_927514 | LOC644357 | PREDICTED: *Homo sapiens* similar to Elongation factor 1-delta (EF-1-delta) (Antigen NY-CO-4) (LOC644357), mRNA [XM_927514] |
| NM_003202 | TCF7 | *Homo sapiens* transcription factor 7 (T-cell specific, HMG-box) (TCF7), transcript variant 1, mRNA [NM_003202] |
| ENST00000332289 | ENST00000332289 | PREDICTED: *Homo sapiens* similar to 40S ribosomal protein SA (p40) (34 [XR_019580] |
| BC107865 | LOC204010 | *Homo sapiens* similar to 40S ribosomal protein SA (P40) (34/67 kDa laminin receptor) (Colon carcinoma laminin-binding protein) (NEM/1CHD4) (Multidrug resistance-associated protein MGr1-Ag), mRNA (cDNA clone MGC: 104447 IMAGE: 4095371), complete cds . . . |
| NM_203477 | MGC70863 | *Homo sapiens* similar to RPL23AP7 protein (MGC70863), transcript variant 1, mRNA [NM_203477] |

TABLE 9-continued

Gene list generated at the inclusion criteria of $p \leq 1 \times 10^{-5}$
and the log-median-ratio being below "0".

| GenBank Accession | GeneName | Description |
|---|---|---|
| NM_001040437 | C6orf48 | *Homo sapiens* chromosome 6 open reading frame 48 (C6orf48), transcript variant 1, mRNA [NM_001040437] |
| BC006438 | BC006438 | *Homo sapiens* cDNA clone MGC: 13162 IMAGE: 3010103, complete cds. [BC006438] |

TABLE 10

Gene list generated at the inclusion criteria of $p \leq 1 \times 10^{-5}$
and the log-median-ratio being above "0".

| GenBank Accession | GeneName | Description |
|---|---|---|
| NM_001082575 | HRNBP3 | *Homo sapiens* hypothetical protein LOC146713 (HRNBP3), mRNA [NM_0010825751 |
| NM_015355 | SUZ12 | *Homo sapiens* suppressor of zeste 12 homolog (*Drosophila*) (SUZ12), mRNA [NM_015355] |
| NM_001014373 | C19orf31 | *Homo sapiens* chromosome 19 open reading frame 31 (C19orf31), mRNA [NM_001014373] |
| NM_004137 | KCNMB1 | *Homo sapiens* potassium large conductance calcium-activated channel, subfamily M, beta member 1 (KCNMB1), mRNA [NM_004137] |
| CR627135 | CR627135 | *Homo sapiens* mRNA; cDNA DKFZp779J0122 (from clone DKFZp779J0122). [CR627135] |
| NM_198904 | GABRG2 | *Homo sapiens* gamma-aminobutyric acid (GABA) A receptor, gamma 2 (GABRG2), transcript variant 1, mRNA [NM_198904] |
| NM_001907 | CTRL | *Homo sapiens* chymotrypsin-like (CTRL), mRNA [NM_001907] |
| XM_926013 | LOC642398 | PREDICTED: *Homo sapiens* hypothetical LOC642398, transcript variant 1 (LOC642398), mRNA [XM_926013] |
| NM_015417 | C20orf28 | *Homo sapiens* chromosome 20 open reading frame 28 (C20orf28), mRNA [NM_015417] |
| BC002431 | B4GALT2 | *Homo sapiens* cDNA clone IMAGE: 3347310, containing frame-shift errors. [BC002431] |
| NM_013373 | ZDHHC8 | *Homo sapiens* zinc finger, DHHC-type containing 8 (ZDHHC8), mRNA [NM_013373] |
| A_242714750 | A_24_P714750 | Unknown |
| NM_138693 | KLF14 | *Homo sapiens* Kruppel-like factor 14 (KLF14), mRNA [NM_138693] |
| NM_033060 | KRTAP4-10 | *Homo sapiens* keratin associated protein 4-10 (KRTAP4-10), mRNA [NM_033060] |
| NM_033260 | FOXQ1 | *Homo sapiens* forkhead box Q1 (FOXQ1), mRNA [NM_033260] |
| THC2615996 | THC2615996 | Unknown |
| XM_372331 | NKX1-2 | PREDICTED: *Homo sapiens* NK1 transcription factor related, locus 2 (*Drosophila*) (NKX1-2), mRNA [XM_372331] |
| NM_001214 | C16orf3 | *Homo sapiens* chromosome 16 open reading frame 3 (C16orf3), mRNA [NM_001214] |
| THC2718728 | THC2718728 | Unknown |

TABLE 11

Gene list generated at the inclusion criteria of $p \leq 1 \times 10^{-4}$.

| GenBank Accession | Gene Name | Description |
|---|---|---|
| NM_000978 | RPL23 | *Homo sapiens* ribosomal protein L23 (RPL23), mRNA [NM_000978] |
| NM_000979 | RPL18 | *Homo sapiens* ribosomal protein L 18 (RPL18), mRNA [NM_000979] |
| A_32_P230059 | A_32_P230059 | Unknown |
| A_24_P144163 | A_24_P144163 | Unknown |
| NM_013328 | PYCR2 | *Homo sapiens* pyrroline-5-carboxylate reductase family, member 2 (PYCR2), mRNA [NM_013328] |
| A_32_P128781 | A_32_P128781 | Unknown |
| THC2718728 | THC2718728 | Unknown |
| NM_002085 | GPX4 | *Homo sapiens* glutathione peroxidase 4 (phospholipid hydroperoxidase) (GPX4), transcript variant 1, mRNA [NM_002085] |
| NM_000996 | RPL35A | *Homo sapiens* ribosomal protein L35a (RPL35A), mRNA [NM_000996] |

TABLE 11-continued

Gene list generated at the inclusion criteria of $p \leq 1 \times 10^{-4}$.

| GenBank Accession | Gene Name | Description |
| --- | --- | --- |
| ENST00000333650 | ENST00000333650 | PREDICTED: *Homo sapiens* similar to 60S ribosomal protein L14 (CAG-ISL 7) (LOC730747), mRNA [XR_015398] |
| CR594528 | CR594528 | full-length cDNA clone CS0DM002YC17 of Fetal liver of *Homo sapiens* (human) [CR594528] |
| A_32_P11425 | A_32_P11425 | Unknown |
| NM_001028 | RPS25 | *Homo sapiens* ribosomal protein S25 (RPS25), mRNA [NM_001028] |
| NM_025004 | CCDC15 | *Homo sapiens* coiled-coil domain containing 15 (CCDC15), mRNA [NM_025004] |
| A_24_P333112 | A_24_P333112 | Unknown |
| NM_001803 | CD52 | *Homo sapiens* CD52 molecule (CD52), mRNA [NM_001803] |
| NM_000984 | RPL23A | *Homo sapiens* ribosomal protein L23a (RPL23A), mRNA [NM_000984] |
| NM_001568 | EIF3S6 | *Homo sapiens* eukaryotic translation initiation factor 3, subunit 6 48 kDa (EIF3S6), mRNA [NM_001568] |
| NM_001032 | RPS29 | *Homo sapiens* ribosomal protein S29 (RPS29), transcript variant 1, mRNA [NM_001032] |
| NM_175863 | ARID1B | *Homo sapiens* AT rich interactive domain 1B (SWI1-like) (ARID1B), transcript variant 3, mRNA [NM_175863] |
| NM_030915 | LBH | *Homo sapiens* limb bud and heart development homolog (mouse) (LBH), mRNA [NM_030915] |
| NM_001014 | RPS10 | *Homo sapiens* ribosomal protein S 10 (RPS10), mRNA [NM_001014] |
| ENST00000312528 | ENST00000312528 | Unknown |
| NM_015414 | RPL36 | *Homo sapiens* ribosomal protein L36 (RPL36), transcript variant 2, mRNA [NM_015414] |
| CR933606 | C20orf80 | *Homo sapiens* mRNA; cDNA DKFZp686M08106 (from clone DKFZp686M08106). [CR933606] |
| NM_003973 | RPL14 | *Homo sapiens* ribosomal protein L14 (RPL14), transcript variant 2, mRNA [NM_003973] |
| NM_032378 | EEF1D | *Homo sapiens* eukaryotic translation elongation factor 1 delta (guanine nucleotide exchange protein) (EEF1D), transcript variant 1, mRNA [NM_032378] |
| XM_379885 | hCG_2023776 | PREDICTED: *Homo sapiens* similar to Heterogeneous nuclear ribonucleoprotein A1 (Helix-destabilizing protein) (Single-strand binding protein) (hnRNP core protein A1) (HDP-1) (Topoisomerase-inhibitor suppressed) (LOC402562), mRNA [XM_379885] |
| NM_203477 | MGC70863 | *Homo sapiens* similar to RPL23AP7 protein (MGC70863), transcript variant 1, mRNA [NM_203477] |
| XR_018975 | LOC389644 | PREDICTED: *Homo sapiens* similar to ribosomal protein L5 (LOC389644), mRNA [XR_018975] |
| NM_194302 | CCDC108 | *Homo sapiens* coiled-coil domain containing 108 (CCDC108), transcript variant 1, mRNA [NM_194302] |
| NM_173680 | ZNF775 | *Homo sapiens* zinc finger protein 775 (ZNF775), mRNA [NM_173680] |
| NM_016085 | C2orf28 | *Homo sapiens* chromosome 2 open reading frame 28 (C2orf28), transcript variant 1, mRNA [NM_016085] |
| NR_000029 | RPL23AP7 | *Homo sapiens* ribosomal protein L23a pseudogene 7 (RPL23AP7) on chromosome 2 [NR_000029] |
| NM_007104 | RPL10A | *Homo sapiens* ribosomal protein L10a (RPL10A), mRNA [NM_007104] |
| NM_003752 | EIF3S8 | *Homo sapiens* eukaryotic translation initiation factor 3, subunit 8, 110 kDa (EIF3S8), transcript variant 1, mRNA [NM_003752] |
| A_24_P358578 | A_24_P358578 | Unknown |
| NM_000989 | RPL30 | *Homo sapiens* ribosomal protein L30 (RPL30), mRNA [NM_000989] |
| NM_024600 | C16orf30 | *Homo sapiens* chromosome 16 open reading frame 30 (C16orf30), mRNA [NM_024600] |
| BC030568 | LOC376693 | *Homo sapiens* hypothetical LOC376693, mRNA (cDNA clone MGC: 45392 IMAGE: 5526694), complete cds. [BC030568] |
| XM_087499 | LOC152663 | PREDICTED: *Homo sapiens* similar to 60S ribosomal protein L7a (LOC152663), mRNA [XM_087499] |
| A_24_P650893 | A_24_P650893 | Unknown |
| XR_019277 | LOC391719 | PREDICTED: *Homo sapiens* similar to ribosomal protein L19 (LOC391719), mRNA [XR_019277] |
| NM_001005472 | LOC388524 | *Homo sapiens* similar to Laminin receptor 1 (LOC388524), mRNA [NM_001005472] |
| BC006438 | BC006438 | *Homo sapiens* cDNA clone MGC: 13162 IMAGE: 3010103, complete cds. [BC006438] |
| NM_001030 | RPS27 | *Homo sapiens* ribosomal protein S27 (metallopanstimulin 1) (RPS27), mRNA [NM_001030] |
| NM_015444 | TMEM158 | *Homo sapiens* transmembrane protein 158 (TMEM158), mRNA [NM_015444] |

TABLE 11-continued

Gene list generated at the inclusion criteria of $p \leq 1 \times 10^{-4}$.

| GenBank Accession | Gene Name | Description |
|---|---|---|
| NM_021103 | TMSB10 | *Homo sapiens* thymosin, beta 10 (TMSB10), mRNA [NM_021103] |
| XR_018222 | RPL31P4 | PREDICTED: *Homo sapiens* ribosomal protein L31 pseudogene 4 (RPL31P4), mRNA [XR_018222] |
| NM_006098 | GNB2L1 | *Homo sapiens* guanine nucleotide binding protein (G protein), beta polypeptide 2-like 1 (GNB2L1), mRNA [NM_006098] |
| A_32_P167577 | A_32_P167577 | Unknown |
| NM_003973 | RPL14 | *Homo sapiens* ribosomal protein L14 (RPL14), transcript variant 2, mRNA [NEM_003973] |
| NM_000967 | RPL3 | *Homo sapiens* ribosomal protein L3 (RPL3), transcript variant 1, mRNA [NM_000967] |
| NM_033251 | RPL13 | *Homo sapiens* ribosomal protein L13 (RPL13), transcript variant 2, mRNA [NM_033251] |
| XM_001131279 | LOC343851 | PREDICTED: *Homo sapiens* similar to 40S ribosomal protein S10 (LOC343851), mRNA [XM_001131279] |
| A_32_P233211 | A_32_P233211 | Unknown |
| NM_001018 | RPS15 | *Homo sapiens* ribosomal protein S15 (RPS15), mRNA [NM_001018] |
| A_24_P307255 | A_24_P307255 | Unknown |
| NM_000661 | RPL9 | *Homo sapiens* ribosomal protein L9 (RPL9), transcript variant 1, mRNA [NM_000661] |
| NM_206833 | CTXN1 | *Homo sapiens* cortexin 1 (CTXN1), mRNA [NM_206833] |
| A_24_P84408 | A_24_P84408 | Unknown |
| ENST00000303979 | ENST00000303979 | Unknown |
| NM_014765 | TOMM20 | *Homo sapiens* translocase of outer mitochondrial membrane 20 homolog (yeast) (TOMM20), mRNA [NM_014765] |
| A_24_P93452 | A_24_P93452 | Unknown |
| NM_005594 | NACA | *Homo sapiens* nascent-polypeptide-associated complex alpha polypeptide (NACA), mRNA [NM_005594] |
| XR_016879 | LOC388401 | PREDICTED: *Homo sapiens* similar to 60S ribosomal protein L7 (LOC388401), mRNA [XR_016879] |
| NM_001404 | EEF1G | *Homo sapiens* eukaryotic translation elongation factor 1 gamma (EEF1G), mRNA [NM_001404] |
| NM_001028 | RPS25 | *Homo sapiens* ribosomal protein S25 (RPS25), mRNA [NM_001028] |
| NM_021631 | FKSG2 | *Homo sapiens* apoptosis inhibitor (FKSG2), mRNA [NM_021631] |
| NM_203477 | MGC70863 | *Homo sapiens* similar to RPL23AP7 protein (MGC70863), transcript variant 1, mRNA [NM_203477] |
| A_24_P881608 | A_24_P881608 | Unknown |
| XR_018970 | LOC391140 | PREDICTED: *Homo sapiens* similar to ribosomal protein L13 (LOC391140), mRNA [XR_018970] |
| A_32_P95502 | A_32_P95502 | Unknown |
| NM_001040437 | C6orf48 | *Homo sapiens* chromosome 6 open reading frame 48 (C6orf48), transcript variant 1, mRNA [NM_001040437] |
| XM_001128309 | LOC730663 | PREDICTED: *Homo sapiens* similar to 60S ribosomal protein L23a (LOC730663), mRNA [XM_001128309] |
| NM_000986 | RPL24 | *Homo sapiens* ribosomal protein L24 (RPL24), mRNA [NM_000986] |
| NM_001214 | C16orf3 | *Homo sapiens* chromosome 16 open reading frame 3 (C16orf3), mRNA [NM_001214] |
| A_24_P366457 | A_24_P366457 | Unknown |
| AK092748 | RP3-377H14.5 | *Homo sapiens* cDNA FLJ35429 fis, clone SMINT2002126. [AK092748] |
| AK090412 | LOC375010 | *Homo sapiens* mRNA for FLJ00310 protein. [AK090412] |
| A_24_P118874 | A_24_P118874 | Unknown |
| NM_001778 | CD48 | *Homo sapiens* CD48 molecule (CD48), triRNA [NM_001778] |
| NM_000967 | RPL3 | *Homo sapiens* ribosomal protein L3 (RPL3), transcript variant 1, mRNA [NM_000967] |
| NM_000610 | CD44 | *Homo sapiens* CD44 molecule (Indian blood group) (CD44), transcript variant 1, mRNA [NM_000610] |
| NM_144601 | CMTM3 | *Homo sapiens* CKLF-like MARVEL transmembrane domain containing 3 (CMTM3), transcript variant 1, mRNA [NM_144601] |
| NM_198969 | AES | *Homo sapiens* amino-terminal enhancer of split (AES), transcript variant 1, mRNA [NM_198969] |
| NM_021978 | ST14 | *Homo sapiens* suppression of tumorigenicity 14 (colon carcinoma) (ST14), mRNA [NM_021978] |
| NM_001082575 | HRNBP3 | *Homo sapiens* hypothetical protein LOC146713 (HRNBP3), mRNA [NM_001082575] |
| NM_032378 | EEF1D | *Homo sapiens* eukaryotic translation elongation factor 1 delta (guanine nucleotide exchange protein) (EEF1D), transcript variant 1, mRNA [NM_032378] |
| XR_016930 | LOC645412 | PREDICTED: *Homo sapiens* similar to 40S ribosomal protein S16 (LOC645412), mRNA [XR_016930] |

TABLE 11-continued

Gene list generated at the inclusion criteria of $p \leq 1 \times 10^{-4}$.

| GenBank Accession | Gene Name | Description |
|---|---|---|
| BC107865 | LOC204010 | *Homo sapiens* similar to 40S ribosomal protein SA (P40) (34/67 kDa laminin receptor) (Colon carcinoma laminin-binding protein) (NEM/1CHD4) (Multidrug resistance-associated protein MGr1-Ag), mRNA (cDNA clone MGC: 104447 IMAGE: 4095371), complete cds . . . |
| BC040156 | LOC284570 | *Homo sapiens*, clone IMAGE: 4941949, mRNA. [BC040156] |
| XR_015767 | LOC731224 | PREDICTED: *Homo sapiens* similar to 60S ribosomal protein L9 (LOC731224), mRNA [XR_015767] |
| ENST00000240349 | NACA3P | PREDICTED: *Homo sapiens* similar to nascent polypeptide-associated complex alpha polypeptide (LOC389240), mRNA [XM_371715] |
| NM_007286 | SYNPO | *Homo sapiens* synaptopodin (SYNPO), mRNA [NM_007286] |
| NM_203477 | MGC70863 | *Homo sapiens* similar to RPL23AP7 protein (MGC70863), transcript variant 1, mRNA [NM_203477] |
| BC047708 | BC047708 | *Homo sapiens*, clone IMAGE: 5750141, mRNA. [BC047708] |
| NM_003202 | TCF7 | *Homo sapiens* transcription factor 7 (T-cell specific, HMG-box) (TCF7), transcript variant 1, mRNA [NM_003202] |
| A_23_P210285 | A_23_P210285 | Unknown |
| BC028232 | BC028232 | *Homo sapiens*, clone IMAGE: 5221276, mRNA, partial cds. [BC028232] |
| A_24_P93052 | A_24_P93052 | Unknown |
| XR_018303 | LOC648378 | PREDICTED: *Homo sapiens* similar to ribosomal protein S14 (LOC648378), mRNA [XR_018303] |
| NM_001005472 | LOC388524 | *Homo sapiens* similar to Laminin receptor 1 (LOC388524), mRNA [NM_001005472] |
| NM_001023 | RPS20 | *Homo sapiens* ribosomal protein S20 (RPS20), mRNA [NM_001023] |
| NM_012320 | LYPLA3 | *Homo sapiens* lysophospholipase 3 (lysosomal phospholipase A2) (LYPLA3), mRNA [NM_012320] |
| NM_001039567 | RPS4Y2 | *Homo sapiens* ribosomal protein S4, Y-linked 2 (RPS4Y2), mRNA [NM_001039567] |
| AK124741 | AK124741 | *Homo sapiens* cDNA FLJ42751 fis, clone BRAWH3000491, moderately similar to 40S ribosomal protein S12. [AK124741] |
| NM_020212 | LOC56964 | *Homo sapiens* hypothetical protein from EUROIMAGE 384293 (LOC56964), mRNA [NM_020212] |
| AK095213 | AK095213 | *Homo sapiens* cDNA FLJ37894 fis, clone BRTHA2004639. [AK095213] |
| THC2679528 | THC2679528 | Unknown |
| ENST00000335083 | LOC728449 | annexin A8 [Source: RefSeq_peptide; Acc: NP_001621] [ENST00000335083] |
| NM_019059 | TOMM7 | *Homo sapiens* translocase of outer mitochondrial membrane 7 hotnolog (yeast) (TOMM7), mRNA [NM_019059] |
| NM_025228 | TRAF3IP3 | *Homo sapiens* TRAF3 interacting protein 3 (TRAF3IP3), mRNA [NM_025228] |
| XR_018231 | LOC648027 | PREDICTED: *Homo sapiens* similar to Elongation factor 1-gamma (EF-1-gamma) (eEF-1B gamma) (LOC648027), mRNA [XR_018231] |
| AK096498 | AK096498 | *Homo sapiens* cDNA FLJ39179 fis, clone OCBBF2004147. [AK096498] |
| NM_001907 | CTRL | *Homo sapiens* chymotrypsin-like (CTRL), mRNA [NM_001907] |
| ENST00000321214 | C16orf81 | Uncharacterized protein C16orf81. [Source: Uniprot/SPTREMBL; Acc: Q8N9R0] [ENST00000321214] |
| NM_174918 | C19orf59 | *Homo sapiens* chromosome 19 open reading frame 59 (C19orf59), mRNA [NM_174918] |
| XR_016196 | LOC642652 | PREDICTED: *Homo sapiens* hypothetical LOC642652 (LOC642652), mRNA [XR_016196] |
| XM_372331 | NKX1-2 | PREDICTED: *Homo sapiens* NK1 transcription factor related, locus 2 (*Drosophila*) (NKX1-2), mRNA [XM_372331] |
| A_24_P135242 | A_24_P135242 | Unknown |
| NM_033625 | RPL34 | *Homo sapiens* ribosomal protein L34 (RPL34), transcript variant 2, mRNA [NM_033625] |
| ENST00000321566 | ENST00000321566 | PREDICTED: *Homo sapiens* similar to 60S ribosomal protein L7a, transcript variant 3 (LOC388474), mRNA [XM_938181] |
| XM_060535 | hCG_1641703 | PREDICTED: *Homo sapiens* similar to ribosomal protein L18a (LOC127545), mRNA [XM_060535] |
| XR_019248 | LOC130728 | PREDICTED: *Homo sapiens* similar to 60S ribosomal protein L7 (LOC130728), mRNA [XR_019248] |
| NM_032087 | PCDHGA7 | *Homo sapiens* protocadherin gamma subfamily A, 7 (PCDHGA7), transcript variant 2, mRNA [NM_032087] |
| NM_004420 | DUSP8 | *Homo sapiens* dual specificity phosphatase 8 (DUSP8), mRNA [NM_004420] |
| ENST00000237840 | hCG_1642354 | PREDICTED: *Homo sapiens* similar to 60S ribosomal protein L23a (LOC341511), mRNA [XM_292109] |
| A_24_P340886 | A_24_P340886 | Unknown |
| A_24_P464798 | A_24_P464798 | Unknown |

TABLE 11-continued

Gene list generated at the inclusion criteria of $p \leq 1 \times 10^{-4}$.

| GenBank Accession | Gene Name | Description |
|---|---|---|
| AA418814 | AA418814 | AA418814 zw01a02.s1 Soares_NhHMPu_S1 *Homo sapiens* cDNA clone IMAGE: 767978 3', mRNA sequence [AA418814] |
| XM_928025 | LOC644937 | PREDICTED: *Homo sapiens* similar to 60S ribosomal protein L10 (QM protein) (Tumor suppressor QM) (Laminin receptor homolog) (LOC644937), mRNA [XM_928025] |
| NM_006032 | CPNE6 | *Homo sapiens* copine VI (neuronal) (CPNE6), mRNA [NM_006032] |
| XR_015402 | LOC731170 | PREDICTED: *Homo sapiens* similar to eukaryotic translation elongation factor 1 alpha 2 (LOC731170), mRNA [XR_015402] |
| NM_002512 | NME2 | *Homo sapiens* non-metastatic cells 2, protein (NM23B) expressed in (NME2), transcript variant 1, mRNA [NM_002512] |
| AK074447 | FIJ23867 | *Homo sapiens* cDNA FLJ23867 fis, clone LNG09729. [AK074447] |
| NM_138693 | KLF14 | *Homo sapiens* Kruppel-like factor 14 (KLF14), mRNA [NM_138693] |
| BG209258 | LOC728315 | RST28773 Athersys RAGE Library *Homo sapiens* cDNA, mRNA sequence [BG209258] |
| AK025430 | AK025430 | *Homo sapiens* cDNA: FLJ21777 fis, clone HEP00173. [AK025430] |
| ENST00000273794 | LOC90113 | *Homo sapiens* mRNA; cDNA DKFZp761K032 (from clone DKFZp761K032). [AL834499] |
| THC2541331 | THC2541331 | HSU02032 ribosomal protein L23a {*Homo sapiens*} (exp = −1; wgp = 0; cg = 0), partial (71%) [THC2541331] |
| A_24_P32207 | A_24_P32207 | Unknown |
| BX115782 | BX115782 | BX115782 Soares_testis_NHT *Homo sapiens* cDNA clone IMAGp998E224413, mRNA sequence [BX115782] |
| NM_001014 | RPS10 | *Homo sapiens* ribosomal protein S10 (RPS10), mRNA [NM_001014] |
| THC2704973 | THC2704973 | Unknown |
| NM_000984 | RPL23A | *Homo sapiens* ribosomal protein L23a (RPL23A), mRNA [NM_000984] |
| NM_006302 | GCS1 | *Homo sapiens* glucosidase I (GCS1), mRNA [NM_006302] |
| NM_006597 | HSPA8 | *Homo sapiens* heat shock 70 kDa protein 8 (HSPA8), transcript variant 1, mRNA [NM_006597] |
| XR_019376 | LOC285260 | PREDICTED: *Homo sapiens* similar to ribosomal protein L31 (LOC285260), mRNA [XR_019376] |
| NM_006235 | POU2AF1 | *Homo sapiens* POU domain, class 2, associating factor 1 (POU2AF1), mRNA [NM_006235] |
| AK095945 | AK095945 | *Homo sapiens* cDNA FLJ38626 fis, clone HEART2009599. [AK095945] |
| A_24_P221375 | A_24_P221375 | Unknown |
| A_24_P341386 | A_24_P341386 | Unknown |
| NM_194278 | C14orf43 | *Homo sapiens* chromosome 14 open reading frame 43 (C14orf43), transcript variant 1, mRNA [NM_194278] |
| NM_033625 | RPL34 | *Homo sapiens* ribosomal protein L34 (RPL34), transcript variant 2, mRNA [NM_033625] |
| NM_003202 | TCF7 | *Homo sapiens* transcription factor 7 (T-cell specific, HMG-box) (TCF7), transcript variant 1, mRNA [NM_003202] |
| A_24_P878388 | A_24_P878388 | Unknown |
| NM_033260 | FOXQ1 | *Homo sapiens* forkhead box Q1 (FOXQ1), mRNA [NM_033260] |
| XR_018786 | LOC649303 | PREDICTED: *Homo sapiens* similar to ribosomal protein S10 (LOC649303), mRNA [XR_018786] |
| NM_005356 | LCK | *Homo sapiens* lymphocyte-specific protein tyrosine kinase (LCK), transcript variant 2, mRNA [NM_005356] |
| NM_024099 | C11orf48 | *Homo sapiens* chromosome 11 open reading frame 48 (C11orf48), mRNA [NM_024099] |
| THC2540532 | THC2540532 | Unknown |
| ENST00000372073 | TMEM164 | Transmembrane protein 164. [Source: Uniprot/SWISSPROT; Acc: Q5U3C3] [ENST00000372073] |
| BC006438 | BC006438 | *Homo sapiens* cDNA clone MGC: 13162 IMAGE: 3010103, complete cds. [BC006438] |
| A_24_P32836 | A_24_P32836 | Unknown |
| ENST00000359659 | ENST00000359659 | Q8BT90_MOUSE (Q8BT90) 10, 11 days embryo whole body cDNA, RIKEN full-length enriched library, clone: 2810021H19 product: ribosomal protein S17, full insert sequence. (Fragment), partial (98%) [THC2555910] |
| AK057177 | L3MBTL2 | *Homo sapiens* cDNA FLJ32615 fis, clone STOMA2000148. [AK057177] |
| AK025353 | AK025353 | *Homo sapiens* cDNA: FLJ21700 fis, clone COL09849, highly similar to HSU14972 Human ribosomal protein S10 mRNA. [AK025353] |
| ENST00000359449 | ENST00000359449 | Sequence 237 from Patent WO0220754. [AX721277] |
| XM_926013 | LOC642398 | PREDICTED: *Homo sapiens* hypothetical LOC642398, transcript variant 1 (LOC642398), mRNA [XM_926013] |
| NM_052952 | DIRC1 | *Homo sapiens* disrupted in renal carcinoma 1 (DIRC1), mRNA [NM_052952] |
| NM_003202 | TCF7 | *Homo sapiens* transcription factor 7 (T-cell specific, HMG-box) (TCF7), transcript variant 1, mRNA [NM_003202] |

TABLE 11-continued

Gene list generated at the inclusion criteria of $p \leq 1 \times 10^{-4}$.

| GenBank Accession | Gene Name | Description |
|---|---|---|
| NM_052940 | LRRC42 | *Homo sapiens* leucine rich repeat containing 42 (LRRC42), mRNA [NM_052940] |
| NM_015417 | C20orf28 | *Homo sapiens* chromosome 20 open reading frame 28 (C20orf28), mRNA [NM_015417] |
| A_24_P341176 | A_24_P341176 | Unknown |
| XR_019059 | LOC654170 | PREDICTED: *Homo sapiens* similar to 40S ribosomal protein S16 (LOC654170), mRNA [XR_019059] |
| NM_014343 | CLDN15 | *Homo sapiens* claudin 15 (CLDN15), transcript variant 1, mRNA [NM_014343] |
| A_23_P58072 | A_23_P58072 | Unknown |
| THC2611974 | THC2611974 | AY250221 nogo receptor-like 3 {*Homo sapiens*} (exp = −1; wgp = 0; cg = 0), partial (12%) [THC2611974] |
| NM_153236 | GIMAP7 | *Homo sapiens* GTPase, IMAP family member 7 (GIMAP7), mRNA [NM_153236] |
| NM_032810 | ATAD1 | *Homo sapiens* ATPase family, AAA domain containing 1 (ATAD1), mRNA [NM_0328101 |
| NM_000164 | GIPR | *Homo sapiens* gastric inhibitory polypeptide receptor (GIPR), mRNA [NM_000164] |
| BC011940 | BC011940 | *Homo sapiens* cDNA clone IMAGE: 4329532, partial cds. [BC011940] |
| NM_001798 | CDK2 | *Homo sapiens* cyclin-dependent kinase 2 (CDK2), transcript variant 1, mRNA [NM_001798] |
| A_24_P551530 | A_24_P551530 | Unknown |
| NM_021130 | PPIA | *Homo sapiens* peptidylprolyl isomerase A (cyclophilin A) (PPIA), mRNA [NM_021130] |
| XR_018155 | LOC643013 | PREDICTED: *Homo sapiens* similar to laminin receptor 1 (ribosomal protein SA) (LOC643013), mRNA [XR_018155] |
| NM_020240 | CDC42SE2 | *Homo sapiens* CDC42 small effector 2 (CDC42SE2), transcript variant 1, mRNA [NM_020240] |
| NM_005828 | WDR68 | *Homo sapiens* WD repeat domain 68 (WDR68), mRNA [NM_005828] |
| NM_004137 | KCNMB1 | *Homo sapiens* potassium large conductance calcium-activated channel, subfamily M, beta member 1 (KCNMB1), mRNA [NM_004137] |
| NM_005309 | GPT | *Homo sapiens* glutamic-pyruvate transaminase (alanine aminotransferase) (GPT), mRNA [NM_005309] |
| NM_198904 | GABRG2 | *Homo sapiens* gamma-aminobutyric acid (GABA) A receptor, gamma 2 (GABRG2), transcript variant 1, mRNA [NM_198904] |
| NM_013373 | ZDHHC8 | *Homo sapiens* zinc finger, DHHC-type containing 8 (ZDHHC8), mRNA [NM_013373] |
| NM_001077710 | FAM110C | *Homo sapiens* family with sequence similarity 110, member C (FAM110C), mRNA [NM_001077710] |
| BC018140 | RPS21 | *Homo sapiens* ribosomal protein S21, mRNA (cDNA clone MGC: 9438 IMAGE: 3903320), complete cds. [BC018140] |
| AA627135 | AA627135 | nq71a04.s1 NCI_CGAP_Pr22 *Homo sapiens* cDNA clone IMAGE: 1157742 3' similar to SW: R13A_HUMAN P40429 60S RIBOSOMAL PROTEIN L13A;, mRNA sequence [AA627135] |
| NM_000661 | RPL9 | *Homo sapiens* ribosomal protein L9 (RPL9), transcript variant 1, mRNA [NM_000661] |
| XR_018720 | LOC392206 | PREDICTED: *Homo sapiens* similar to ribosomal protein L10a (LOC392206), mRNA [XR_018720] |
| A_24_P127442 | A_24_P127442 | Unknown |
| NM_016155 | MMP17 | *Homo sapiens* matrix metallopeptidase 17 (membrane-inserted) (MMP17), mRNA [NM_016155] |
| A_24_P384411 | A_24_P384411 | Unknown |
| THC2506377 | THC2506377 | HSU02032 ribosomal protein L23a {*Homo sapiens*} (exp = −1; wgp = 0; cg = 0), partial (92%) [THC2506377] |
| NM_001080544 | LOC653314 | *Homo sapiens* similar to ribosomal protein L19 (LOC653314), mRNA [NM_001080544] |
| NM_024324 | CRELD2 | *Homo sapiens* cysteine-rich with EGF-like domains 2 (CRELD2), mRNA [NM_024324] |
| BC067080 | FCRLB | *Homo sapiens* Fc receptor-like B, mRNA (cDNA clone MGC: 71141 IMAGE: 3529386), complete cds. [BC067080] |
| NM_004689 | MTA1 | *Homo sapiens* metastasis associated 1 (MTA1), mRNA [NM_004689] |
| NM_002333 | LRP3 | *Homo sapiens* low density lipoprotein receptor-related protein 3 (LRP3), mRNA [NM_002333] |
| THC2618720 | THC2618720 | Unknown |
| NM_021104 | RPL41 | *Homo sapiens* ribosomal protein L41 (RPL41), transcript variant 1, mRNA [NM_021104] |
| AL834350 | PPP2R5C | *Homo sapiens* mRNA; cDNA DKFZp761H0317 (from clone DKFZp761H0317). [AL834350] |
| BC028083 | TRBV5-4 | *Homo sapiens* T cell receptor beta variable 5-4, mRNA (cDNA clone MGC: 40031 IMAGE: 5217067), complete cds. [BC028083] |

TABLE 11-continued

Gene list generated at the inclusion criteria of $p \leq 1 \times 10^{-4}$.

| GenBank Accession | Gene Name | Description |
|---|---|---|
| ENST00000332696 | ENST00000332696 | similar to 60S ribosomal protein L23a (LOC644384), mRNA [Source: RefSeq dna; Acc: XR_017413] [ENST00000332696] |
| XR_015944 | LOC731681 | PREDICTED: *Homo sapiens* similar to 60S ribosomal protein L9 (LOC731681), mRNA [XR_015944] |
| XR_019544 | LOC652890 | PREDICTED: *Homo sapiens* similar to 60S ribosomal protein L7 (LOC652890), mRNA [XR_019544] |
| ENST00000361800 | ENST00000361800 | Unknown |
| N47494 | N47494 | N47494 yy90a12.s1 Soares_multiple_sclerosis_2NbHMSP *Homo sapiens* cDNA clone IMAGE: 280798 3' similar to gb: M23115 CALCIUM-TRANSPORTING ATPASE SARCOPLASMIC RETICULUM TYPE, SLOW (HUMAN);, mRNA sequence [N47494] |
| XR_018553 | LOC648294 | PREDICTED: *Homo sapiens* hypothetical LOC648294 (LOC648294), mRNA [XR_018553] |
| AK096778 | AK096778 | *Homo sapiens* cDNA FLJ39459 fis, clone PROST2011439. [AK096778] |
| CN304251 | CN304251 | 17000532640995 GRN_ES *Homo sapiens* cDNA 5', mRNA sequence [CN304251] |
| NM_000545 | TCF1 | *Homo sapiens* transcription factor 1, hepatic; LF-B1, hepatic nuclear factor (HNF1), albumin proximal factor (TCF1), mRNA [NM_000545] |
| XM_929928 | LOC646960 | PREDICTED: *Homo sapiens* similar to transmembrane protease, serine 9 (LOC646960), mRNA [XM_929928] |
| NM_002258 | KLRB1 | *Homo sapiens* killer cell lectin-like receptor subfamily B, member 1 (KLRB1), mRNA [NM_002258] |
| NM_031478 | FAM57B | *Homo sapiens* family with sequence similarity 57, member B (FAM57B), mRNA [NM_031478] |
| A_24_P238427 | A_24_P238427 | Unknown |
| NM_000971 | RPL7 | *Homo sapiens* ribosomal protein L7 (RPL7), mRNA [NM_000971] |
| NR_002797 | LOC255783 | *Homo sapiens* hypothetical protein LOC255783 (LOC255783) on chromosome 19 [NR_002797] |
| NM_015284 | KIAA0467 | *Homo sapiens* KIAA0467 (KIAA0467), mRNA [NM_015284] |
| NM_033060 | KRTAP4-10 | *Homo sapiens* keratin associated protein 4-10 (KRTAP4-10), mRNA [NM_033060] |
| AA451906 | AA451906 | AA451906 zx16h04.s1 Soares_total_fetus_Nb2HF8_9w *Homo sapiens* cDNA clone IMAGE: 786679 3', mRNA sequence [AA451906] |
| AK093171 | AK093171 | *Homo sapiens* cDNA FLJ35852 fis, clone TEST12007074. [AK093171] |
| THC2658813 | THC2658813 | Unknown |
| BF822111 | BF822111 | BF822111 CM3-RT0011-051200-531-f10 RT0011 *Homo sapiens* cDNA, mRNA sequence [BF822111] |
| NM_022139 | GFRA4 | *Homo sapiens* GDNF family receptor alpha 4 (GFRA4), transcript variant 1, mRNA [NM_022139] |
| AL133632 | AL133632 | PREDICTED: *Homo sapiens* hypothetical LOC648245 (LOC648245), mRNA [XM_001127731] |
| NM_152219 | GJC1 | *Homo sapiens* gap junction protein, chi 1, 31.9 kDa (GJC1), mRNA [NM_152219] |
| A_24_P264549 | A_24_P264549 | Unknown |
| NM_006013 | RPL10 | *Homo sapiens* ribosomal protein L10 (RPL10), mRNA [NM_006013] |
| A_24_P789842 | A_24_P789842 | Unknown |
| NM_005356 | LCK | *Homo sapiens* lymphocyte-specific protein tyrosine kinase (LCK), transcript variant 2, mRNA [NM_005356] |
| XR_019361 | LOC442260 | PREDICTED: *Homo sapiens* similar to 60S ribosomal protein L23a (LOC442260), mRNA [XR_019361] |
| NM_000972 | RPL7A | *Homo sapiens* ribosomal protein L7a (RPL7A), mRNA [NM_000972] |
| ENST00000308989 | ENST00000308989 | PREDICTED: *Homo sapiens* similar to ribosomal protein L31 (LOC729005), mRNA [XM_001133428] |
| NM_003202 | TCF7 | *Homo sapiens* transcription factor 7 (T-cell specific, HMG-box) (TCF7), transcript variant 1, mRNA [NM_003202] |
| NM_003775 | EDG6 | *Homo sapiens* endothelial differentiation, lysophosphatidic acid G-protein-coupled receptor, 6 (EDG6), mRNA [NM_003775] |
| ENST00000323800 | ENST00000323800 | CDNA FLJ25155 fis, clone CBR07976. [Source: Uniprot/SPTREMBL; Acc: Q96LR6] [ENST00000323800] |
| NM_002300 | LDHB | *Homo sapiens* lactate dehydrogenase B (LDHB), mRNA [NM_002300] |
| NM_000984 | RPL23A | *Homo sapiens* ribosomal protein L23a (RPL23A), mRNA [NM_000984] |
| NM_130759 | GIMAP1 | *Homo sapiens* GTPase, IMAP family member 1 (GIMAP1), mRNA [NM_130759] |
| ENST00000307437 | ENST00000307437 | PREDICTED: *Homo sapiens* similar to ribosomal protein S12 (LOC727997), mRNA [XM_001127053] |

TABLE 11-continued

Gene list generated at the inclusion criteria of $p \leq 1 \times 10^{-4}$.

| GenBank Accession | Gene Name | Description |
| --- | --- | --- |
| BC002431 | B4GALT2 | *Homo sapiens* cDNA clone IMAGE: 3347310, containing frame-shift errors. [BC002431] |
| NM_033405 | PRIC285 | *Homo sapiens* peroxisomal proliferator-activated receptor A interacting complex 285 (PRIC285), transcript variant 2, mRNA [NM_033405] |
| NM_000983 | RPL22 | *Homo sapiens* ribosomal protein L22 (RPL22), mRNA [NM_000983] |
| NM_152636 | METT5D1 | *Homo sapiens* methyltransferase 5 domain containing 1 (METT5D1), mRNA [NM_152636] |
| NM_015481 | ZNF385 | *Homo sapiens* zinc finger protein 385 (ZNF385), mRNA [NM_015481] |
| AY090769 | AY090769 | *Homo sapiens* ribosomal protein S18/S6-like mRNA, complete sequence. [AY090769] |
| NM_001402 | EEF1A1 | *Homo sapiens* eukaryotic translation elongation factor 1 alpha 1 (EEF1A1), mRNA [NM_001402] |
| NM_182796 | MAT2B | *Homo sapiens* methionine adenosyltransferase II, beta (MAT2B), transcript variant 2, mRNA [NM_182796] |
| XM_927514 | LOC644357 | PREDICTED: *Homo sapiens* similar to Elongation factor 1-delta (EF-1-delta) (Antigen NY-CO-4) (LOC644357), mRNA [XM_927514] |
| NM_002818 | PSME2 | *Homo sapiens* proteasome (prosome, macropain) activator subunit 2 (PA28 beta) (PSME2), mRNA [NM_002818] |
| NM_176812 | CHMP4B | *Homo sapiens* chromatin modifying protein 4B (CHMP4B), mRNA [NM_176812] |
| A_24_P298238 | A_24_P298238 | Unknown |
| NM_003202 | TCF7 | *Homo sapiens* transcription factor 7 (T-cell specific, HMG-box) (TCF7), transcript variant 1, mRNA [NM_003202] |
| A_24_P212654 | A_24_P212654 | Unknown |
| A_24_P392436 | A_24_P392436 | Unknown |
| A_24_P350008 | A_24_P350008 | Unknown |
| ENST00000367058 | CR2 | Complement receptor type 2 precursor (Cr2) (Complement C3d receptor) (Epstein-Barr virus receptor) (EBV receptor) (CD21 antigen). [Source: Uniprot/SWISSPROT; Acc: P20023] [ENST00000367058] |
| A_24_P33213 | A_24_P33213 | Unknown |
| NM_001014373 | C19orf31 | *Homo sapiens* chromosome 19 open reading frame 31 (C19orf31), mRNA [NM_001014373] |
| NM_001039842 | LOC339229 | *Homo sapiens* hypothetical protein LOC339229 (LOC339229), mRNA [NM_001039842] |
| NM_012423 | RPL13A | *Homo sapiens* ribosomal protein L13a (RPL13A), mRNA [NM_012423] |
| NM_025247 | ACAD10 | *Homo sapiens* acyl-Coenzyme A dehydrogenase family, member 10 (ACAD10), mRNA [NM_025247] |
| THC2494410 | THC2494410 | 2113200F ribosomal protein S9. {*Homo sapiens*} (exp = −1; wgp = −1; cg = −1), complete [THC2494410] |
| NM_005581 | BCAM | *Homo sapiens* basal cell adhesion molecule (Lutheran blood group) (BCAM), transcript variant 1, mRNA [NM_005581] |
| XR_018133 | LOC389404 | PREDICTED: *Homo sapiens* similar to 60S ribosomal protein L9 (LOC389404), mRNA [XR_018133] |
| AK025669 | AK025669 | *Homo sapiens* cDNA: FLJ22016 fis, clone HEP07422. [AK025669] |
| NM_201286 | USP51 | *Homo sapiens* ubiquitin specific peptidase 51 (USP51), mRNA [NM_201286] |
| NM_003202 | TCF7 | *Homo sapiens* transcription factor 7 (T-cell specific, HMG-box) (TCF7), transcript variant 1, mRNA [NM_003202] |
| XR_019386 | LOC652558 | PREDICTED: *Homo sapiens* similar to 60S ribosomal protein L7 (LOC652558), mRNA [XR_0193861 |
| A_24_P213073 | A_24_P213073 | Unknown |
| NM_021173 | POLD4 | *Homo sapiens* polymerase (DNA-directed), delta 4 (POLD4), mRNA [NM_021173] |
| A_24_P392195 | A_24_P392195 | Unknown |
| THC2782843 | THC2782843 | RL18A_HUMAN (Q02543) 60S ribosomal protein L18a, partial (89%) [THC2782843] |
| NM_152889 | CHST13 | *Homo sapiens* carbohydrate (chondroitin 4) sulfotransferase 13 (CHST13), mRNA [NM_152889] |
| NM_001017 | RPS13 | *Homo sapiens* ribosomal protein S13 (RPS13), mRNA [NM_001017] |
| THC2737361 | THC2737361 | Q2IMJ3_ANADE (Q2IMJ3) LigA, partial (5%) [THC2737361] |
| XR_018509 | LOC391701 | PREDICTED: *Homo sapiens* similar to ribosomal protein S23 (LOC391701), mRNA [XR_018509] |
| THC2615996 | THC2615996 | Unknown |
| NM_080660 | ZC3HAV1L | *Homo sapiens* zinc finger CCCH-type, antiviral 1-like (ZC3HAV1L), mRNA [NM_080660] |
| NM_203305 | FAM102A | *Homo sapiens* family with sequence similarity 102, member A (FAM102A), transcript variant 2, mRNA [NM_203305] |

TABLE 11-continued

Gene list generated at the inclusion criteria of $p \leq 1 \times 10^{-4}$.

| GenBank Accession | Gene Name | Description |
|---|---|---|
| XM_930195 | hCG_18290 | PREDICTED: *Homo sapiens* similar to 60S ribosomal protein L32 (LOC644907), mRNA [XM_930195] |
| NM_013284 | POLM | *Homo sapiens* polymerase (DNA directed), mu (POLM), mRNA [NM_013284] |
| NM_138425 | C12orf57 | *Homo sapiens* chromosome 12 open reading frame 57 (C12orf37), mRNA [NM_138425] |
| AK098605 | AK098605 | *Homo sapiens* cDNA FLJ25739 fis, clone TST05834. [AK098605] |
| THC2544911 | THC2544911 | MUSEFTU elongation factor Tu {*Mus musculus*} (exp = −1; wgp = 0; cg = 0), partial (37%) [THC2544911] |
| BC063671 | LOC92659 | *Homo sapiens* hypothetical protein BC009233, mRNA (cDNA clone IMAGE: 3924188), partial cds. [BC063671] |
| NM_001404 | EEF1G | *Homo sapiens* eukaryotic translation elongation factor 1 gamma (EEF1G), mRNA [NM_001404] |
| NM_014931 | SAPS1 | *Homo sapiens* SAPS domain family, member 1 (SAPS1), mRNA [NM_014931] |
| XM_001125895 | LOC730452 | PREDICTED: *Homo sapiens* similar to 60S ribosomal protein L7 (LOC730452), mRNA [XM_001125895] |
| AK021957 | COL27A1 | *Homo sapiens* cDNA FLJ11895 fis, clone HEMBA1007301, weakly similar to COLLAGEN ALPHA 1(III) CHAIN. [AK021957] |
| NM_006291 | TNFAIP2 | *Homo sapiens* tumor necrosis factor, alpha-induced protein 2 (TNFAIP2), mRNA [NM_006291] |
| NM_006597 | HSPA8 | *Homo sapiens* heat shock 70 kDa protein 8 (HSPA8), transcript variant 1, mRNA [NM_006597] |
| THC2694215 | THC2694215 | Q3W9Q7_9ACTO (Q3W9Q7) Pyridoxamine 5'-phosphate oxidase, partial (3%) [THC2694215] |
| NM_021959 | PPP1R11 | *Homo sapiens* protein phosphatase 1, regulatory (inhibitor) subunit 11 (PPP1R11), mRNA [NM_021959] |
| A_32_P208856 | A_32_P208856 | Unknown |
| NM_177458 | LYNX1 | *Homo sapiens* Ly6/neurotoxin 1 (LYNX1), transcript variant SLURP2, mRNA [NM_177458] |
| THC2650296 | THC2650296 | RL18A_MOUSE (P62717) 60S ribosomal protein L18a, complete [THC2650296] |
| NM_138732 | NRXN2 | *Homo sapiens* neurexin 2 (NRXN2), transcript variant alpha-2, mRNA [NM_138732] |
| NM_080746 | RPL10L | *Homo sapiens* ribosomal protein L10-like (RPL10L), mRNA [NM_080746] |
| NM_001005291 | SREBF1 | *Homo sapiens* sterol regulatory element binding transcription factor 1 (SREBF1), transcript variant 1, mRNA [NM_001005291] |
| A_24_P194954 | A_24_P194954 | Unknown |
| NM_145245 | EVI5L | *Homo sapiens* ecotropic viral integration site 5-like (EVI5L), mRNA [NM_145245] |
| NM_016337 | EVL | *Homo sapiens* Enah/Vasp-like (EVL), mRNA [NM_016337] |
| NM_032152 | PRAM1 | *Homo sapiens* PML-RARA regulated adaptor molecule 1 (PRAM1), mRNA [NM_032152] |
| NM_003202 | TCF7 | *Homo sapiens* transcription factor 7 (T-cell specific, HMG-box) (TCF7), transcript variant 1, mRNA [NM_003202] |
| THC2560098 | THC2560098 | S35960 C-terminal {*Homo sapiens*} (exp = −1; wgp = 0; cg = 0), partial (64%) [THC2560098] |
| A_24_P273074 | A_24_P273074 | Unknown |
| AX721252 | AX721252 | Sequence 212 from Patent WO0220754. [AX721252] |
| NM_000972 | RPL7A | *Homo sapiens* ribosomal protein L7a (RPL7A), mRNA [NM_000972] |
| NM_006013 | RPL10 | *Homo sapiens* ribosomal protein L10 (RPL10), mRNA [NM_006013] |
| NM_003202 | TCF7 | *Homo sapiens* transcription factor 7 (T-cell specific, HMG-box) (TCF7), transcript variant 1, mRNA [NM_003202] |
| A_24_P101271 | A_24_P101271 | Unknown |
| XR_019375 | LOC645326 | PREDICTED; *Homo sapiens* similar to laminin receptor 1 (ribosomal protein SA) (LOC645326), mRNA [XR_019375] |
| A_24_P332292 | A_24_P332292 | Unknown |
| NM_001402 | EEF1A1 | *Homo sapiens* eukaryotic translation elongation factor 1 alpha 1 (EEF1A1), mRNA [NM_001402] |
| NM_000981 | RPL19 | *Homo sapiens* ribosomal protein L19 (RPL19), mRNA [NM_000981] |
| NM_152525 | ALS2CR11 | *Homo sapiens* amyotrophic lateral sclerosis 2 (juvenile) chromosome region, candidate 11 (ALS2CR11), mRNA [NM_152525] |
| NM_000661 | RPL9 | *Homo sapiens* ribosomal protein L9 (RPL9), transcript variant 1, mRNA [NM_000661] |
| NM_033625 | RPL34 | *Homo sapiens* ribosomal protein L34 (RPL34), transcript variant 2, mRNA [NM_033625] |
| NM_175065 | HIST2H2AB | *Homo sapiens* histone cluster 2, H2ab (HIST2H2AB), mRNA [NM_175065] |
| NM_015355 | SUZ12 | *Homo sapiens* suppressor of zeste 12 homolog (*Drosophila*) (SUZ12), mRNA [NM_015355] |

TABLE 11-continued

Gene list generated at the inclusion criteria of $p \leq 1 \times 10^{-4}$.

| GenBank Accession | Gene Name | Description |
|---|---|---|
| A_24_P170103 | A_24_P170103 | Unknown |
| A_32_P25838 | A_32_P25838 | Unknown |
| ENST00000332289 | ENST00000332289 | PREDICTED: *Homo sapiens* similar to 40S ribosomal protein SA (p40) (34 [XR_019580] |
| CR627135 | CR627135 | *Homo sapiens* mRNA; cDNA DKEZp779J0122 (from clone DKFZp77910122). [CR627135] |
| A_32_P101195 | A_32_P101195 | Unknown |
| NM_000969 | RPL5 | *Homo sapiens* ribosomal protein L5 (RPL5), mRNA [NM_000969] |
| NM_033184 | KRTAP2-4 | *Homo sapiens* keratin associated protein 2-4 (KRTAP2-4), mRNA [NM_033184] |
| NM_024012 | HTR5A | *Homo sapiens* 5-hydroxytryptamine (serotonin) receptor 5A (HTR5A), mRNA [NM_024012] |
| A_24_P410070 | A_24_P410070 | Unknown |
| XM_374010 | LOC389033 | PREDICTED: *Homo sapiens* hypothetical LOC389033 (LOC389033), mRNA [XM_374010] |
| NM_033251 | RPL13 | *Homo sapiens* ribosomal protein L13 (RPL13), transcript variant 2, mRNA [NM_033251] |
| XR_015548 | LOC729449 | PREDICTED: *Homo sapiens* similar to 60S ribosomal protein L7 (LOC729449), mRNA [XR_015548] |
| THC2533996 | THC2533996 | HSU09954 ribosomal protein L9 {*Homo sapiens*} (exp = -1; wgp = 0; cg = 0), partial (42%) [THC2533996] |
| NM_015937 | PIGT | *Homo sapiens* phosphatidylinositol glycan anchor biosynthesis, class T (PIGT), mRNA [NM_015937] |
| NM_019059 | TOMM7 | *Homo sapiens* translocase of outer mitochondrial membrane 7 homolog (yeast) (TOMM7), mRNA [NM_019059] |
| NM_001778 | CD48 | *Homo sapiens* CD48 molecule (CD48), mRNA [NM_001778] |
| NR_002778 | RPL29P2 | *Homo sapiens* ribosomal protein L29 pseudogene 2 (RPL29P2) on chromosome 17 [NR_002778] |
| THC2689192 | THC2689192 | Q7XC69_ORYSA (Q7XC69) Expressed protein, partial (6%) [THC2689192] |
| BE843546 | BE843546 | BE843546 CM3-TN0066-080800-269-g03 TN0066 *Homo sapiens* cDNA, mRNA sequence [BE843546] |
| A_24_P714750 | A_24_P714750 | Unknown |
| NM_017801 | CMTM6 | *Homo sapiens* CKLF-like MARVEL transmembrane domain containing 6 (CMTM6), mRNA [NM_017801] |
| NM_016270 | KLF2 | *Homo sapiens* Kruppel-like factor 2 (lung) (KLF2), mRNA [NM_016270] |
| XR_017260 | LOC646710 | PREDICTED: *Homo sapiens* hypothetical LOC646710 (LOC646710), mRNA [XR_017260] |
| XR_018341 | LOC390413 | PREDICTED: *Homo sapiens* similar to 60S ribosomal protein L7 (LOC390413), mRNA [XR_018341] |
| NM_023078 | PYCRL | *Homo sapiens* pyrroline-5-carboxylate reductase-like (PYCRL), mRNA [NM_023078] |
| NM_000979 | RPL18 | *Homo sapiens* ribosomal protein L18 (RPL18), mRNA [NM_000979] |
| XR_018054 | LOC392878 | PREDICTED: *Homo sapiens* hypothetical LOC392878 (LOC392878), mRNA [XR_018054] |
| NM_001005472 | LOC388524 | *Homo sapiens* similar to Laminin receptor 1 (LOC388524), mRNA [NM_001005472] |
| NM_018326 | GIMAP4 | *Homo sapiens* GTPase, IMAP family member 4 (GIMAP4), mRNA [NM_018326] |
| NM_013234 | EIF3S12 | *Homo sapiens* eukaryotic translation initiation factor 3, subunit 12 (EIF3S12), mRNA [NM_013234] |
| BC024303 | FLJ35390 | *Homo sapiens* hypothetical protein FLJ35390, mRNA (cDNA clone IMAGE: 4328569), with apparent retained intron. [BC024303] |
| NM_000982 | RPL21 | *Homo sapiens* ribosomal protein L21 (RPL21), mRNA [NM_000982] |
| NM_032611 | PTP4A3 | *Homo sapiens* protein tyrosine phosphatase type IVA, member 3 (PTP4A3), transcript variant 1, mRNA [NM_0326111 |
| A_24_P67308 | A_24_P67308 | Unknown |
| NM_001404 | EEF1G | *Homo sapiens* eukaryotic translation elongation factor 1 gamma (EEF1G), mRNA [NM_001404] |
| NM_001039211 | ATAD3C | *Homo sapiens* ATPase family, AAA domain containing 3C (ATAD3C), mRNA [NM_001039211] |
| NM_001967 | EIF4A2 | *Homo sapiens* eukaryotic translation initiation factor 4A, isoform 2 (EIF4A2), mRNA [NM_001967] |
| NM_001011 | RPS7 | *Homo sapiens* ribosomal protein S7 (RPS7), mRNA [NM_001011] |
| ENST00000333351 | ENST00000333351 | PREDICTED: *Homo sapiens* hypothetical LOC391504 (LOC391504), mRNA [XR_018627] |
| A_24_P204474 | A_24_P204474 | Unknown |
| NM_001861 | COX4I1 | *Homo sapiens* cytochrome c oxidase subunit IV isoform 1 (COX4I1), mRNA [NM_001861] |
| NM_178230 | PPIAL4 | *Homo sapiens* peptidylprolyl isomerase A (cyclophilin A)-like 4 (PPIAL4), mRNA [NM_178230] |

TABLE 11-continued

Gene list generated at the inclusion criteria of $p \leq 1 \times 10^{-4}$.

| GenBank Accession | Gene Name | Description |
|---|---|---|
| NM_017549 | EPDR1 | Homo sapiens ependymin related protein 1 (zebrafish) (EPDR1), mRNA [NM_017549] |
| AL547890 | AL547890 | AL547890 AL547890 Homo sapiens PLACENTA COT 25-NORMALIZED Homo sapiens cDNA clone CS0D1033YB095-PRIME, mRNA sequence [AL547890] |
| A_24_P392790 | A_24_P392790 | Unknown |
| XR_017498 | LOC645693 | PREDICTED: Homo sapiens similar to eukaryotic translation elongation factor 1 alpha 2 (LOC645693), mRNA [XR_017498] |
| NM_003754 | EIF3S5 | Homo sapiens eukaryotic translation initiation factor 3, subunit 5 epsilon, 47 kDa (EIF3S5), mRNA [NM_003754] |
| NM_001008 | RPS4Y1 | Homo sapiens ribosomal protein S4, Y-linked 1 (RPS4Y1), mRNA [NM_001008] |
| NM_002405 | MFNG | Homo sapiens MFNG O-fucosylpeptide 3-beta-N-acetylglucosaminyltransferase (MFNG), mRNA [NM_002405] |
| A_24_P324224 | A_24_P324224 | Unknown |
| A_24_P714620 | A_24_P714620 | Unknown |
| NM_001017418 | SPRR2B | Homo sapiens small proline-rich protein 2B (SPRR2B), mRNA [NM_001017418] |
| NM_015853 | LOC51035 | Homo sapiens SAPK substrate protein 1 (LOC51035), mRNA [NM_015853] |
| NM_018949 | UTS2R | Homo sapiens urotensin 2 receptor (UTS2R), mRNA [NM_018949] |
| NM_001005472 | LOC388524 | Homo sapiens similar to Laminin receptor 1 (LOC388524), mRNA [NM_001005472] |
| A_24_P375435 | A_24_P375435 | Unknown |
| NM_000967 | RPL3 | Homo sapiens ribosomal protein L3 (RPL3), transcript variant 1, mRNA [NM_000967] |
| NM_015646 | RAP1B | Homo sapiens RAP1B, member of RAS oncogene family (RAP1B), transcript variant 1, mRNA [NM_015646] |
| A_24_P212726 | A_24_P212726 | Unknown |
| NM_006682 | FGL2 | Homo sapiens fibrinogen-like 2 (FGL2), mRNA [NM_006682] |
| NM_001014 | RPS10 | Homo sapiens ribosomal protein S10 (RPS10), mRNA [NM_001014] |
| XR_017294 | LOC646949 | PREDICTED: Homo sapiens similar to ribosomal protein L23 (LOC646949), mRNA [XR_017294] |
| NM_001212 | C1QBP | Homo sapiens complement component 1, q subcomponent binding protein (C1QBP), nuclear gene encoding mitochondrial protein, mRNA [NM_001212] |
| XR_018025 | LOC641790 | PREDICTED: Homo sapiens similar to ribosomal protein L31 (LOC641790), mRNA [XR_018025] |
| A_24_P289884 | A_24_P289884 | Unknown |
| NR_001577 | NME2P1 | Homo sapiens non-metastatic cells 2, protein (NM23B) expressed in, pseudogene 1 (NME2P1) on chromosome 12 [NR_001577] |
| NM_006597 | HSPA8 | Homo sapiens heat shock 70 kDa protein 8 (HSPA8), transcript variant 1, mRNA [NM_006597] |
| BC005008 | CEACAM6 | Homo sapiens carcinoembryonic antigen-related cell adhesion molecule 6 (non-specific cross reacting antigen), mRNA (cDNA clone MGC: 10467 IMAGE: 3640231), complete cds. [BC005008] |
| NM_003757 | EIF3S2 | Homo sapiens eukaryotic translation initiation factor 3, subunit 2 beta, 36 kDa (EIF3S2), mRNA [NM_003757] |
| NM_001402 | EEF1A1 | Homo sapiens eukaryotic translation elongation factor 1 alpha 1 (EEF1A1), mRNA [NM_001402] |
| NM_001005472 | LOC388524 | Homo sapiens similar to Laminin receptor 1 (LOC388524), mRNA [NM_001005472] |
| NM_021130 | PP1A | Homo sapiens peptidylprolyl isomerase A (cyclophilin A) (PPIA), mRNA [NM_021130] |
| A_24_P505981 | A_24_P505981 | Unknown |
| NM_005401 | PTPN14 | Homo sapiens protein tyrosine phosphatase, non-receptor type 14 (PTPN14), mRNA [NM_005401] |
| NM_031918 | KLF16 | Homo sapiens Kruppel-like factor 16 (KLF16), mRNA [NM_031918] |

TABLE 12

Gene list generated at the inclusion criteria of $p \leq 1 \times 10^{-3}$ and the log-median-ratio being below being at least "1" or above, or being "−1" or below.

| GenBank Accession | GeneName | Description |
|---|---|---|
| NM_001039567 | RPS4Y2 | Homo sapiens ribosomal protein S4, Y-linked 2 (RPS4Y2), mRNA [NM_001039567] |
| NM_001008 | RPS4Y1 | Homo sapiens ribosomal protein S4, Y-linked 1 (RPS4Y1), mRNA [NM_001008] |
| NM_002985 | CCL5 | Homo sapiens chemokine (C—C motif) ligand 5 (CCL5), mRNA [NM_002985] |
| NM_004907 | IER2 | Homo sapiens immediate early response 2 (IER2), mRNA [NM_004907] |
| NM_015646 | RAP1B | Homo sapiens RAP1B, member of RAS oncogene family (RAP1B), transcript variant 1, mRNA [NM_015646] |
| NM_002490 | NDUFA6 | Homo sapiens NADH dehydrogenase (ubiquinone) 1 alpha subcomplex, 6, 14 kDa (NDUFA6), nuclear gene encoding mitochondrial protein, mRNA [NM_002490] |
| AL049447 | AL049447 | Homo sapiens mRNA; cDNA DKFZp586A0722 (from clone DKFZp586A0722). [AL049447] |
| NM_012329 | MMD | Homo sapiens monocyte to macrophage differentiation-associated (MMD), mRNA [NM_012329] |
| NM_004048 | B2M | Homo sapiens beta-2-microglobulin (B2M), mRNA [NM_004048] |
| NM_001004 | RPLP2 | Homo sapiens ribosomal protein, large, P2 (RPLP2), mRNA [NM_001004] |
| NM_033251 | RPL13 | Homo sapiens ribosomal protein L13 (RPL13), transcript variant 2, mRNA [NM_033251] |
| ENST00000383061 | ENST00000383061 | PREDICTED: Homo sapiens similar to myosin regulatory light chain-like (LOC442204), mRNA [XM_498088] |
| NM_004907 | IER2 | Homo sapiens immediate early response 2 (IER2), mRNA [NM_004907] |
| NM_001803 | CD52 | Homo sapiens CD52 molecule (CD52), mRNA [NM_001803] |
| NM_145113 | MAX | Homo sapiens MYC associated factor X (MAX), transcript variant 3, mRNA [NM_145113] |
| NM_002954 | RPS27A | Homo sapiens ribosomal protein S27a (RPS27A), mRNA [NM_002954] |
| A_24_P144383 | A_24_P144383 | Unknown |
| NM_006471 | MRCL3 | Homo sapiens myosin regulatory light chain MRCL3 (MRCL3), mRNA [NM_006471] |
| NM_006597 | HSPA8 | Homo sapiens heat shock 70 kDa protein 8 (HSPA8), transcript variant 1, mRNA [NM_006597] |
| NM_001402 | EEF1A1 | Homo sapiens eukaryotic translation elongation factor 1 alpha 1 (EEF1A1), mRNA [NM_001402] |
| NM_001030 | RPS27 | Homo sapiens ribosomal protein S27 (metallopanstimulin 1) (RPS27), mRNA [NM_001030] |
| NM_080425 | GNAS | Homo sapiens GNAS complex locus (GNAS), transcript variant 2, mRNA [NM_080425] |
| NM_001032 | RPS29 | Homo sapiens ribosomal protein S29 (RPS29), transcript variant 1, mRNA [NM_001032] |
| NM_004048 | B2M | Homo sapiens beta-2-microglobulin (B2M), mRNA [NM_004048] |
| NM_007262 | PARK7 | Homo sapiens Parkinson disease (autosomal recessive, early onset) 7 (PARK7), mRNA [NM_007262] |
| NM_001012 | RPS8 | Homo sapiens ribosomal protein S8 (RPS8), mRNA [NM_001012] |
| NM_005594 | NACA | Homo sapiens nascent-polypeptide-associated complex alpha polypeptide (NACA), mRNA [NM_005594] |
| XR_017498 | LOC645693 | PREDICTED: Homo sapiens similar to eukaryotic translation elongation factor 1 alpha 2 (LOC645693), mRNA [XR_017498] |
| NM_006597 | HSPA8 | Homo sapiens heat shock 70 kDa protein 8 (HSPA8), transcript variant 1, mRNA [NM_006597] |
| NM_001778 | CD48 | Homo sapiens CD48 molecule (CD48), mRNA [NM_001778] |
| NM_001017 | RPS13 | Homo sapiens ribosomal protein S13 (RPS13), mRNA [NM_001017] |
| NM_001030 | RPS27 | Homo sapiens ribosomal protein S27 (metallopanstimulin 1) (RPS27), mRNA [NM_001030] |
| NM_000968 | RPL4 | Homo sapiens ribosomal protein L4 (RPL4), mRNA [NM_000968] |
| NM_004657 | SDPR | Homo sapiens serum deprivation response (phosphatidylserine binding protein) (SDPR), mRNA [NM_004657] |
| XR_018386 | LOC392358 | PREDICTED: Homo sapiens similar to 40S ribosomal protein S6 (LOC392358), mRNA [XR_018386] |
| NM_002945 | RPA1 | Homo sapiens replication protein A1, 70 kDa (RPA1), mRNA [NM_002945] |
| THC2544911 | THC2544911 | MUSEFTU elongation factor Tu {Mus musculus} (exp = −1; wgp = 0; cgo), partial (37%) [THC2544911] |
| NM_001017 | RPS13 | Homo sapiens ribosomal protein S13 (RPS13), mRNA [NM_001017] |
| NM_021104 | RPL41 | Homo sapiens ribosomal protein L41 (RPL41), transcript variant 1, mRNA [NM_021104] |
| NM_000981 | RPL19 | Homo sapiens ribosomal protein L19 (RPL19), mRNA [NM_000981] |

TABLE 12-continued

Gene list generated at the inclusion criteria of $p \leq 1 \times 10^{-3}$ and the log-median-ratio being below being at least "1" or above, or being "−1" or below.

| GenBank Accession | GeneName | Description |
| --- | --- | --- |
| THC2527647 | THC2527647 | Q59GY2_HUMAN (Q59GY2) Ribosomal protein L4 variant (Fragment), partial (51%) [THC2527647] |
| A_24_P929974 | A_24_P929974 | Unknown |
| NM_002300 | LDHB | Homo sapiens lactate dehydrogenase B (LDHB), mRNA [NM_002300] |
| NM_033251 | RPL13 | Homo sapiens ribosomal protein L13 (RPL13), transcript variant 2, mRNA [NM_033251] |
| NM_001031 | RPS28 | Homo sapiens ribosomal protein S28 (RPS28), mRNA [NM_001031] |
| M36647 | UQCRH | Homo sapiens mitochondrial hinge protein precursor, mRNA, complete cds. [M36647] |
| NM_003973 | RPL14 | Homo sapiens ribosomal protein L14 (RPL14), transcript variant 2, mRNA [NM_003973] |
| NM_000978 | RPL23 | Homo sapiens ribosomal protein L23 (RPL23), mRNA [NM_000978] |
| NM_033251 | RPL13 | Homo sapiens ribosomal protein LI3 (RPL13), transcript variant 2, mRNA [NM_033251] |
| NM_001003 | RPLP1 | Homo sapiens ribosomal protein, large, P1 (RPLP1), transcript variant 1, mRNA [NM_001003] |
| NM_001568 | EIF3S6 | Homo sapiens eukaryotic translation initiation factor 3, subunit 6 48 kDa (EIF3S6), mRNA [NM_001568] |
| A_24_P392195 | A_24_P392195 | Unknown |
| NM_001028 | RPS25 | Homo sapiens ribosomal protein S25 (RPS25), mRNA [NM_001028] |
| NM_003756 | EIF3S3 | Homo sapiens eukaryotic translation initiation factor 3, subunit 3 gamma, 40 kDa (EIF3S3), mRNA [NM_003756] |
| NM_001032 | RPS29 | Homo sapiens ribosomal protein S29 (RPS29), transcript variant 1, mRNA [NM_001032] |
| A_24_P238426 | A_24_P238426 | Unknown |
| BX096698 | BX096698 | BX096698 Soares breast 2NbHBst Homo sapiens cDNA clone IMAGp998E11242, mRNA sequence [BX096698] |
| XR_017260 | LOC646710 | PREDICTED: Homo sapiens hypothetical LOC646710 (LOC646710), mRNA [XR_017260] |
| A_24_P333112 | A_24_P333112 | Unknown |
| NM_001003 | RPLP1 | Homo sapiens ribosomal protein, large, P1 (RPLP1), transcript variant 1, mRNA [NM_001003] |
| NM_002823 | PTMA | Homo sapiens prothymosin, alpha (gene sequence 28) (PTMA), mRNA [NM_002823] |
| NM_033251 | RPL13 | Homo sapiens ribosomal protein L13 (RPL13), transcript variant 2, mRNA [NM_033251] |
| XR_017294 | LOC646949 | PREDICTED: Homo sapiens similar to ribosomal protein L23 (LOC646949), mRNA [XR_017294] |
| XR_016779 | LOC440311 | PREDICTED: Homo sapiens similar to Glioma tumor suppressor candidate region gene 2 protein (p60) (LOC440311), mRNA [XR_016779] |
| NM_002085 | GPX4 | Homo sapiens glutathione peroxidase 4 (phospholipid hydroperoxidase) (GPX4), transcript variant 1, mRNA [NM_002085] |
| NM_000993 | RPL31 | Homo sapiens ribosomal protein L31 (RPL31), mRNA [NM_000993] |
| XR_015548 | LOC729449 | PREDICTED: Homo sapiens similar to 60S ribosomal protein L7 (LOC729449), mRNA KR_015548] |
| NM_199290 | NACA2 | Homo sapiens nascent-polypeptide-associated complex alpha polypeptide-like (NACAL), mRNA [NM_1992901 |
| BC052613 | LOC728131 | Homo sapiens cDNA clone MGC: 59872 YMAGE: 6301163, complete cds. [BC052613] |
| A_24_P306968 | A_24_P306968 | Unknown |
| A_32_P49392 | A_32_P49392 | Unknown |
| XM_497657 | LOC441876 | PREDICTED: Homo sapiens similar to 40S ribosomal protein S16, transcript variant 1 (LOC441876), mRNA [XM_497657] |
| NM_001025 | RPS23 | Homo sapiens ribosomal protein S23 (RPS23), mRNA [NM_001025] |
| BU956542 | BU956542 | BU956542 AGENCOURT_10615527 NIH_MGC_107 Homo sapiens cDNA clone IMAGE: 6730153 5', mRNA sequence [BU956542] |
| AK027315 | AK027315 | Homo sapiens cDNA FLJ14409 fis, clone HEMBA1004408, moderately similar to PEPTIDYL-PROLYL CIS-TRANS ISOMERASE 10 (EC 5.2.1.8). [AK027315] |
| NM_006597 | HSPA8 | Homo sapiens heat shock 70 kDa protein 8 (HSPA8), transcript variant 1, mRNA [NM_006597] |
| NM_001006 | RPS3A | Homo sapiens ribosomal protein S3A (RPS3A), mRNA [NM_001006] |
| NM_001402 | EEF1A1 | Homo sapiens eukaryotic translation elongation factor 1 alpha 1 (EEF1A1), mRNA [NM_001402] |

TABLE 12-continued

Gene list generated at the inclusion criteria of $p \leq 1 \times 10^{-3}$ and the log-median-ratio being below being at least "1" or above, or being "−1" or below.

| GenBank Accession | GeneName | Description |
| --- | --- | --- |
| NM_001568 | EIF3S6 | *Homo sapiens* eukaryotic translation initiation factor 3, subunit 6 48 kDa (EIF3S6), mRNA [NM_001568] |
| NM_001436 | FBL | *Homo sapiens* fibrillarin (FBL), mRNA [NM_001436] |
| NM_000975 | RPL11 | *Homo sapiens* ribosomal protein L11 (RPL11), mRNA [NM_000975] |
| NM_033546 | MRLC2 | *Homo sapiens* myosin regulatory light chain MRLC2 (MRLC2), mRNA [NM_033546] |
| A_32_P128781 | A_32_P128781 | Unknown |
| XR_018063 | LOC392030 | PREDICTED: *Homo sapiens* hypothetical LOC392030 (LOC392030), mRNA [XR_018063] |
| A_24_P298835 | A_24_P298835 | Unknown |
| A_23_P200955 | A_23_P200955 | Unknown |
| A_24_P341376 | A_24_P341376 | Unknown |
| NM_080392 | PTP4A2 | *Homo sapiens* protein tyrosine phosphatase type IVA, member 2 (PTP4A2), transcript variant 2, mRNA [NM_080392] |
| ENST00000312528 | ENST00000312528 | Unknown |
| NM_015710 | GLTSCR2 | *Homo sapiens* glioma tumor suppressor candidate region gene 2 (GLTSCR2), mRNA [NM_015710] |
| NM_001402 | EEF1A1 | *Homo sapiens* eukaryotic translation elongation factor 1 alpha 1 (EEF1A1), mRNA [NM_001402] |
| NM_025228 | TRAF3IP3 | *Homo sapiens* TRAF3 interacting protein 3 (TRAF3IP3), mRNA [NM_025228] |
| NM_002624 | PFDN5 | *Homo sapiens* prefoldin subunit 5 (PFDN5), transcript variant 1, mRNA [NM_002624] |
| A_24_P160920 | A_24_P160920 | Unknown |
| A_24_P332292 | A_24_P332292 | Unknown |
| NM_198969 | AES | *Homo sapiens* amino-terminal enhancer of split (AES), transcript variant 1, mRNA [NM_198969] |
| NM_000989 | RPL30 | *Homo sapiens* ribosomal protein L30 (RPL30), mRNA [NM_000989] |
| A_24_P878388 | A_24_P878388 | Unknown |
| NM_001402 | EEF1A1 | *Homo sapiens* eukaryotic translation elongation factor 1 alpha 1 (EEF1A1), mRNA [NM_001402] |
| NM_000989 | RPL30 | *Homo sapiens* ribosomal protein L30 (RPL30), mRNA [NM_000989] |
| XR_016879 | LOC388401 | PREDICTED: *Homo sapiens* similar to 60S ribosomal protein L7 (LOC388401), mRNA [XR_016879] |
| NM_000967 | RPL3 | *Homo sapiens* ribosomal protein L3 (RPL3), transcript variant 1, mRNA [NM_0009671 |
| ENST00000337102 | ENST00000337102 | 40S ribosomal protein S21. [Source: Uniprot/SWISSPROT;Acc: P63220] [ENST00000337102] |
| NM_006263 | PSME1 | *Homo sapiens* proteasome (prosome, macropain) activator subunit 1 (PA28 alpha) (PSME1), transcript variant 1, mRNA [NM_006263] |
| XR_018138 | LOC392497 | PREDICTED: *Homo sapiens* similar to 40S ribosomal protein S6 (LOC392497), mRNA [XR_018138] |
| NM_002341 | LTB | *Homo sapiens* lymphotoxin beta (TNF superfamily, member 3) (LTB), transcript variant 1, mRNA [NM_002341] |
| NM_000967 | RPL3 | *Homo sapiens* ribosomal protein L3 (RPL3), transcript variant 1, mRNA [NM_000967] |
| A_24_P84408 | A_24_P84408 | Unknown |
| NM_002121 | HLA-DPB1 | *Homo sapiens* major histocompatibility complex, class II, DP beta 1 (HLA-DPB1), mRNA [NM_002121] |
| NM_000661 | RPL9 | *Homo sapiens* ribosomal protein L9 (RPL9), transcript variant 1, mRNA [NM_000661] |
| NM_000991 | RPL28 | *Homo sapiens* ribosomal protein L28 (RPL28), mRNA [NM_000991] |
| NM_001006 | RPS3A | *Homo sapiens* ribosomal protein S3A (RPS3A), mRNA [NM_001006] |
| NM_001006 | RPS3A | *Homo sapiens* ribosomal protein S3A (RPS3A), mRNA [NM_001006] |
| NM_000661 | RPL9 | *Homo sapiens* ribosomal protein L9 (RPL9), transcript variant 1, mRNA [NM_000661] |
| A_24_P650893 | A_24_P650893 | Unknown |
| A_24_P50567 | A_24_P50567 | Unknown |
| A_24_P136011 | A_24_P136011 | Unknown |
| A_24_P298238 | A_24_P298238 | Unknown |
| THC2541331 | THC2541331 | HSU02032 ribosomal protein L23a {*Homo sapiens*} (exp = −1; wgp = 0; cg = 0), partial (71%) [THC2541331] |
| XR_018025 | LOC641790 | PREDICTED: *Homo sapiens* similar to ribosomal protein L31 (LOC641790), mRNA [XR_0180251 |
| NM_003295 | TPT1 | *Homo sapiens* tumor protein, translationally-controlled 1 (TPT I), mRNA [NM_003295] |
| NM_001867 | COX7C | *Homo sapiens* cytochrome c oxidase subunit VIIc (COX7C), nuclear gene encoding mitochondrial protein, mRNA [NM_001867] |

TABLE 12-continued

Gene list generated at the inclusion criteria of $p \leq 1 \times 10^{-3}$ and the log-median-ratio being below being at least "1" or above, or being "−1" or below.

| GenBank Accession | GeneName | Description |
|---|---|---|
| BC018140 | RPS21 | *Homo sapiens* ribosomal protein S21, mRNA (cDNA clone MGC: 9438 IMAGE: 3903320), complete cds. [BC018140] |
| NM_005340 | HINT1 | *Homo sapiens* histidine triad nucleotide binding protein 1 (HINT1), mRNA [NM_005340] |
| BC067891 | LOC645683 | *Homo sapiens* cDNA clone MGC: 87657 IMAGE: 5271409, complete cds. [BC067891] |
| ENST00000308989 | ENST00000308989 | PREDICTED: *Homo sapiens* similar to ribosomal protein L31 (LOC729005), mRNA [XM_001133428] |
| A_24_P212726 | A_24_P212726 | Unknown |
| NM_001028 | RPS25 | *Homo sapiens* ribosomal protein S25 (RPS25), mRNA [NM_001028] |
| NM_000998 | RPL37A | *Homo sapiens* ribosomal protein L37a (RPL37A), mRNA [NM_000998] |
| XR_015402 | LOC731170 | PREDICTED: *Homo sapiens* similar to eukaryotic translation elongation factor 1 alpha 2 (LOC731170), mRNA [XR_015402] |
| A_24_P340886 | A_24_P340886 | Unknown |
| NM_016480 | PAIP2 | *Homo sapiens* poly(A) binding protein interacting protein 2 (PAIP2), transcript variant 2, mRNA [NM_016480] |
| THC2567891 | THC2567891 | Q6NXR8_HUMAN (Q6NXR8) Ribosomal protein S3a, partial (91%) [THC2567891] |
| XR_019376 | LOC285260 | PREDICTED: *Homo sapiens* similar to ribosomal protein L31 (LOC285260), mRNA [XR_019376] |
| ENST00000359449 | ENST00000359449 | Sequence 237 from Patent WO0220754. [AX721277] |
| NM_000988 | RPL27 | *Homo sapiens* ribosomal protein L27 (RPL27), mRNA [NM_000988] |
| XR_018975 | LOC389644 | PREDICTED: *Homo sapiens* similar to ribosomal protein L5 (LOC389644), mRNA [XR_018975] |
| XR_019168 | LOC391847 | PREDICTED: *Homo sapiens* similar to ribosomal protein L19 (LOC391847), mRNA [XR_019168] |
| A_24_P505981 | A_24_P505981 | Unknown |
| CD174733 | CD174733 | CD174733 AGENCOURT_13961604 NIH_MGC_172 *Homo sapiens* cDNA 5', mRNA sequence [CD174733] |
| ENST00000240349 | NACA3P | PREDICTED: *Homo sapiens* similar to nascent polypeptide-associated complex alpha polypeptide (LOC389240), mRNA [XM_371715] |
| A_24_P221375 | A_24_P221375 | Unknown |
| NM_000984 | RPL23A | *Homo sapiens* ribosomal protein L23a (RPL23A), mRNA [NM_000984] |
| XR_018231 | LOC648027 | PREDICTED: *Homo sapiens* similar to Elongation factor 1-gamma (EF-1-gamma) (eEF-1B gamma) (LOC648027), mRNA [XR_018231] |
| NM_003753 | EIF3S7 | *Homo sapiens* eukaryotic translation initiation factor 3, subunit 7 zeta, 66/67 kDa (EIF3S7), mRNA [NM_003753] |
| NM_000978 | RPL23 | *Homo sapiens* ribosomal protein L23 (RPL23), mRNA [NM_000978] |
| BC001697 | RPS15A | *Homo sapiens* ribosomal protein S15a, mRNA (cDNA clone MGC: 2466 IMAGE: 2967511), complete cds. [BC001697] |
| NM_013234 | EIF3S12 | *Homo sapiens* eukaryotic translation initiation factor 3, subunit 12 (EIF3S12), mRNA [NM_0132341] |
| NM_001022 | RPS19 | *Homo sapiens* ribosomal protein S19 (RPS19), mRNA [NM_001022] |
| NM_001007074 | RPL32 | *Homo sapiens* ribosomal protein L32 (RPL32), transcript variant 3, mRNA [NM_001007074] |
| NM_001861 | COX4I1 | *Homo sapiens* cytochrome c oxidase subunit IV isoform 1 (COX4I1), mRNA [NM_001861] |
| XR_019544 | LOC652890 | PREDICTED: *Homo sapiens* similar to 60S ribosomal protein L7 (LOC652890), mRNA [XR_019544] |
| A_24_P41979 | A_24_P41979 | Unknown |
| NM_003746 | DYNLL1 | *Homo sapiens* dynein, light chain, LC8-type 1 (DYNLL1), transcript variant 3, mRNA [NM_003746] |
| NM_000982 | RPL21 | *Homo sapiens* ribosomal protein L21 (RPL21), mRNA [NM_000982] |
| A_23_P210285 | A_23_P210285 | Unknown |
| NM_002539 | ODC1 | *Homo sapiens* ornithine decarboxylase 1 (ODC1), mRNA [NM_002539] |
| XR_019361 | LOC442260 | PREDICTED: *Homo sapiens* similar to 60S ribosomal protein L23a (LOC442260), mRNA [XR_019361] |
| A_24_P289884 | A_24_P289884 | Unknown |
| A_24_P135242 | A_24_P135242 | Unknown |
| NM_003973 | RPL14 | *Homo sapiens* ribosomal protein L14 (RPL14), transcript variant 2, mRNA [NM_003973] |
| XR_019386 | LOC652558 | PREDICTED: *Homo sapiens* similar to 60S ribosomal protein L7 (LOC652558), mRNA [XR_019386] |

TABLE 12-continued

Gene list generated at the inclusion criteria of $p \leq 1 \times 10^{-3}$ and the log-median-ratio being below being at least "1" or above, or being "−1" or below.

| GenBank Accession | GeneName | Description |
| --- | --- | --- |
| ENST00000381140 | ENST00000381140 | Transcription factor IIIA (Factor A) (TFIIIA). [Source: Uniprot/SWISSPROT; Acc: Q92664] [ENST00000381140] |
| NM_003145 | SSR2 | *Homo sapiens* signal sequence receptor, beta (translocon-associated protein beta) (SSR2), mRNA [NM_003145] |
| THC2533996 | THC2533996 | HSU09954 ribosomal protein L9 {*Homo sapiens*} (exp = −1; wgp = 0; cg = 0), partial (42%) [THC2533996] |
| NM_001344 | DAD1 | *Homo sapiens* defender against cell death 1 (DAD1), mRNA [NM_001344] |
| A_24_P255252 | A_24_P255252 | Unknown |
| NM_002954 | RPS27A | *Homo sapiens* ribosomal protein S27a (RPS27A), mRNA [NM_002954] |
| NM_145808 | MTPN | *Homo sapiens* myotrophin (MTPN), mRNA [NM_145808] |
| NM_000984 | RPL23A | *Homo sapiens* ribosomal protein L23a (RPL23A), mRNA [NM_000984] |
| NM_020240 | CDC42SE2 | *Homo sapiens* CDC42 small effector 2 (CDC42SE2), transcript variant 1, mRNA [NM_020240] |
| NM_001016 | RPS12 | *Homo sapiens* ribosomal protein S12 (RPS12), mRNA [NM_001016] |
| NM_175738 | RAB37 | *Homo sapiens* RAB37, member RAS oncogene family (RAB37), transcript variant 3, mRNA [NM_175738] |
| A_24_P170147 | A_24_P170147 | Unknown |
| NM_007104 | RPL10A | *Homo sapiens* ribosomal protein L10a (RPL10A), mRNA [NM_007104] |
| XR_015944 | LOC731681 | PREDICTED: *Homo sapiens* similar to 60S ribosomal protein L9 (LOC731681), mRNA [XR_015944] |
| XR_018963 | LOC442237 | PREDICTED: *Homo sapiens* similar to 40S ribosomal protein S7 (S8) (LOC442237), mRNA [XR_018963] |
| NM_021149 | COTL1 | *Homo sapiens* coactosin-like 1 (*Dictyostelium*) (COTL1), mRNA [NM_021149] |
| NM_003295 | TPT1 | *Homo sapiens* tumor protein, translationally-controlled 1 (TPT1), mRNA [NM_003295] |
| NM_016269 | LEF1 | *Homo sapiens* lymphoid enhancer-binding factor 1 (LEF1), mRNA [NM_016269] |
| NM_016274 | PLEKHO1 | *Homo sapiens* pleckstrin homology domain containing, family O member 1 (PLEKHO1), mRNA [NM_016274] |
| NM_006830 | UQCR | *Homo sapiens* ubiquinol-cytochrome c reductase, 6.4 kDa subunit (UQCR), mRNA [NM_006830] |
| NM_001404 | EEF1G | *Homo sapiens* eukaryotic translation elongation factor 1 gamma (EEF1G), mRNA [NM_001404] |
| A_24_P755505 | A_24_P755505 | Unknown |
| ENST00000078131 | ENST00000078131 | OTTHUMP00000016594. [Source: Uniprot/SPTREMBL;Acc: Q9NU98] [ENST00000078131] |
| NM_021103 | TMSB10 | *Homo sapiens* thymosin, beta 10 (TMSB10), mRNA [NM_021103] |
| XR_018554 | LOC402219 | PREDICTED: *Homo sapiens* similar to ribosomal protein L5 (LOC402219), mRNA [XR_018554] |
| NM_033625 | RPL34 | *Homo sapiens* ribosomal protein L34 (RPL34), transcript variant 2, mRNA [NM_033625] |
| XR_015936 | LOC731457 | PREDICTED: *Homo sapiens* similar to ribosomal protein S27a (LOC731457), mRNA [XR_015936] |
| AF147412 | AF147412 | *Homo sapiens* full length insert cDNA clone YP59C02. [AF147412] |
| NM_001011 | RPS7 | *Homo sapiens* ribosomal protein S7 (RPS7), mRNA [NM_001011] |
| A_24_P730256 | A_24_P730256 | Unknown |
| A_24_P587803 | A_24_P587803 | Unknown |
| NM_016270 | KLF2 | *Homo sapiens* Kruppel-like factor 2 (lung) (KLF2), mRNA [NM_016270] |
| NM_015414 | RPL36 | *Homo sapiens* ribosomal protein L36 (RPL36), transcript variant 2, mRNA [NM_015414] |
| XR_017130 | LOC158345 | PREDICTED: *Homo sapiens* similar to ribosomal protein L4 (LOC158345), mRNA [XR_017130] |
| XR_018222 | RPL31P4 | PREDICTED: *Homo sapiens* ribosomal protein L31 pseudogene 4 (RPL31P4), mRNA [XR_018222] |
| BC028083 | TRBV5-4 | *Homo sapiens* T cell receptor beta variable 5-4, mRNA (cDNA clone MGC: 40031 IMAGE: 5217067), complete cds. [BC028083] |
| NM_000997 | RPL37 | *Homo sapiens* ribosomal protein L37 (RPL37), mRNA [NM_000997] |
| A_24_P367063 | A_24_P367063 | Unknown |
| NM_001010 | RPS6 | *Homo sapiens* ribosomal protein S6 (RPS6), mRNA [NM_001010] |
| THC2553216 | THC2553216 | HUMRRL3A ribosomal protein L3 {*Homo sapiens*} (exp = −1; wgp = 0; cg = 0), partial (24%) [THC2553216] |
| NM_033625 | RPL34 | *Homo sapiens* ribosomal protein L34 (RPL34), transcript variant 2, mRNA [NM_033625] |
| A_24_P685729 | A_24_P685729 | Unknown |
| NM_022551 | RPS18 | *Homo sapiens* ribosomal protein S18 (RPS18), mRNA [NM_022551] |

TABLE 12-continued

Gene list generated at the inclusion criteria of $p \leq 1 \times 10^{-3}$ and the log-median-ratio being below being at least "1" or above, or being "−1" or below.

| GenBank Accession | GeneName | Description |
|---|---|---|
| NM_001028 | RPS25 | *Homo sapiens* ribosomal protein S25 (RPS25), mRNA [NM_001028] |
| NM_000996 | RPL35A | *Homo sapiens* ribosomal protein L35a (RPL35A), mRNA [NM_000996] |
| XR_018695 | RPL31P10 | PREDICTED: *Homo sapiens* similar to ribosomal protein L31 (LOC390283), mRNA [XR_018695] |
| A_24_P144163 | A_24_P144163 | Unknown |
| A_24_P238427 | A_24_P238427 | Unknown |
| AK092748 | RP3-377H14.5 | *Homo sapiens* cDNA FLJ35429 fis, clone SMINT2002126. [AK092748] |
| THC2560098 | THC2560098 | S35960 C-terminal {*Homo sapiens*} (exp = −1; wgp = 0; cg = 0), partial (64%) [THC2560098] |
| DW451363 | DW451363 | HHAGE004093 Human liver regeneration after partial hepatectomy *Homo sapiens* cDNA, mRNA sequence [DW451363] |
| A_24_P324224 | A_24_P324224 | Unknown |
| NM_000970 | RPL6 | *Homo sapiens* ribosomal protein L6 (RPL6), transcript variant 2, mRNA [NM_000970] |
| ENST00000356196 | hCG_26523 | PREDICTED: *Homo sapiens* similar to 60S ribosomal protein L26 (LOC646161), mRNA [XR_018048] |
| NM_203477 | MGC70863 | *Homo sapiens* similar to RPL23AP7 protein (MGC70863), transcript variant 1, mRNA [NM_203477] |
| ENST00000356196 | hCG_26523 | PREDICTED: *Homo sapiens* similar to 60S ribosomal protein L26 (Silica-induced gene 20 protein) (SIG-20) (LOC400055), mRNA [XM_374987] |
| NM_005617 | RPS14 | *Homo sapiens* ribosomal protein S14 (RPS14), transcript variant 3, mRNA [NM_005617] |
| NM_000454 | SOD1 | *Homo sapiens* superoxide dismutase 1, soluble (amyotrophic lateral sclerosis 1 (adult)) (SOD1), mRNA [NM_000454] |
| NM_001013 | RPS9 | *Homo sapiens* ribosomal protein S9 (RPS9), mRNA [NM_001013] |
| XR_018048 | LOC646161 | PREDICTED: *Homo sapiens* similar to 60S ribosomal protein L26 (LOC646161), mRNA [XR_018048] |
| THC2584902 | THC2584902 | Q5M9L9_MOUSE (Q5M9L9) Ribosomal protein S8, partial (73%) [THC2584902] |
| XR_015398 | LOC730747 | PREDICTED: *Homo sapiens* similar to 60S ribosomal protein L14 (CAG-ISL 7) (LOC730747), mRNA [XR_015398] |
| XR_019277 | LOC391719 | PREDICTED: *Homo sapiens* similar to ribosomal protein L19 (LOC391719), mRNA [XR_019277] |
| XR_019597 | LOC401863 | PREDICIED: *Homo sapiens* similar to ribosomal protein L10a (LOC401863), mRNA [XR_019597] |
| AK098605 | AK098605 | *Homo sapiens* cDNA FLJ25739 fis, clone TST05834. [AK098605] |
| A_24_P127442 | A_24_P127442 | Unknown |
| NM_203495 | COMMD6 | *Homo sapiens* COMM domain containing 6 (COMMD6), transcript variant 2, mRNA [NM_203495] |
| NM_153236 | GIMAP7 | *Homo sapiens* GTPase, IMAP family member 7 (GIMAP7), mRNA [NM_153236] |
| XM_935576 | LOC641827 | PREDICTED: *Homo sapiens* similar to eukaryotic translation elongation factor 1 beta 2 (LOC641827), mRNA [XM_935576] |
| NR_001577 | NME2P1 | *Homo sapiens* non-metastatic cells 2, protein (NM23B) expressed in, pseudogene 1 (NME2P1) on chromosome 12 [NR_001577] |
| XR_015767 | LOC731224 | PREDICTED: *Homo sapiens* similar to 60S ribosomal protein L9 (LOC731224), mRNA [XR_015767] |
| NM_007104 | RPL10A | *Homo sapiens* ribosomal protein L10a (RPL10A), mRNA [NM_007104] |
| NM_003295 | TPT1 | *Homo sapiens* tumor protein, translationally-controlled 2 (TPT1), mRNA [NM_003295] |
| AK124741 | AK124741 | *Homo sapiens* cDNA FLJ42751 fis, clone BRAWH3000491, moderately similar to 40S ribosomal protein S12. [AK124741] |
| NM_005617 | RPS14 | *Homo sapiens* ribosomal protein S14 (RPS14), transcript variant 3, mRNA [NM_005617] |
| NM_000986 | RPL24 | *Homo sapiens* ribosomal protein L24 (RPL24), mRNA [NM_000986] |
| NM_000984 | RPL23A | *Homo sapiens* ribosomal protein L23a (RPL23A), mRNA [NM_000984] |
| XM_001125895 | LOC730452 | PREDICTED: *Homo sapiens* similar to 60S ribosomal protein L7 (LOC730452), mRNA [XM_001125895] |
| NM_001011 | RPS7 | *Homo sapiens* ribosomal protein S7 (RPS7), mRNA [NM_001011] |
| XR_018994 | LOC391181 | PREDICTED: *Homo sapiens* similar to 60S ribosomal protein L6 (TAX-responsive enhancer element-binding protein 107) (TAXREB107) (Neoplasm-related protein C140) (LOC391181), mRNA [XR_018994] |
| A_24_P332441 | A_24_P332441 | Unknown |
| NM_000967 | RPL3 | *Homo sapiens* ribosomal protein L3 (RPL3), transcript variant 1, mRNA [NM_000967] |

TABLE 12-continued

Gene list generated at the inclusion criteria of $p \leq 1 \times 10^{-3}$ and the log-median-ratio being below being at least "1" or above, or being "−1" or below.

| GenBank Accession | GeneName | Description |
|---|---|---|
| NM_006013 | RPL10 | Homo sapiens ribosomal protein L10 (RPL10), mRNA [NM_006013] |
| NM_000982 | RPL21 | Homo sapiens ribosomal protein L21 (RPL21), mRNA [NM_000982] |
| XR_018341 | LOC390413 | PREDICTED: Homo sapiens similar to 60S ribosomal protein L7 (LOC390413), mRNA [XR_018341] |
| XR_018054 | LOC392878 | PREDICTED: Homo sapiens hypothetical LOC392878 (LOC392878), mRNA [XR_018054] |
| NM_006013 | RPL10 | Homo sapiens ribosomal protein L10 (RPL10), mRNA [NM_006013] |
| NM_001011 | RPS7 | Homo sapiens ribosomal protein S7 (RPS7), mRNA [NM_001011] |
| ENST00000332696 | ENST00000332696 | similar to 60S ribosomal protein L23a (LOC644384), mRNA [Source: RefSeq_dna;Acc: XR_017413] [ENST00000332696] |
| NM_006360 | PCID1 | Homo sapiens PCI domain containing 1 (herpesvirus entry mediator) (PCID1), mRNA [NM_006360] |
| A_24_P204474 | A_24_P204474 | Unknown |
| A_32_P208856 | A_32_P208856 | Unknown |
| NM_001404 | EEF1G | Homo sapiens eukaryotic translation elongation factor 1 gamma (EEF1G), mRNA [NM_001404] |
| ENST00000313620 | LOC342994 | PREDICTED: Homo sapiens similar to ribosomal protein L34 (LOC342994), mRNA [XM_938484] |
| A_24_P126902 | A_24_P126902 | Unknown |
| THC2506377 | THC2506377 | HSU02032 ribosomal protein L23a {Homo sapiens} (exp = −1; wgp = 0; cg = 0), partial (92%) [THC2506377] |
| NM_000998 | RPL37A | Homo sapiens ribosomal protein L37a (RPL37A), mRNA [NM_000998] |
| NM_000454 | SOD1 | Homo sapiens superoxide dismutase 1, soluble (amyotrophic lateral sclerosis 1 (adult)) (SOD1), mRNA [NM_000454] |
| NM_005340 | HINT1 | Homo sapiens histidine triad nucleotide binding protein 1 (HINT1), mRNA [NM_005340] |
| NM_006013 | RPL10 | Homo sapiens ribosomal protein L10 (RPL10), mRNA [NM_006013] |
| NM_080746 | RPL10L | Homo sapiens ribosomal protein L10-like (RPL10L), mRNA [NM_080746] |
| A_24_P50489 | A_24_P50489 | Unknown |
| XR_019242 | LOC402149 | PREDICTED: Homo sapiens similar to ribosomal protein L28 (LOC402149), mRNA [XR_019242] |
| NM_002568 | PABPC1 | Homo sapiens poly(A) binding protein, cytoplasmic 1 (PABPC1), mRNA [NM_002568] |
| NP1252191 | NP1252191 | GB|AACC02000041.1|EAL24419.1 similar to 60S ribosomal protein L32 [Homo sapiens] [NP1252191] |
| NM_000997 | RPL37 | Homo sapiens ribosomal protein L37 (RPL37), mRNA [NM_000997] |
| NM_000986 | RPL24 | Homo sapiens ribosomal protein L24 (RPL24), mRNA [NM_000986] |
| XR_019052 | LOC391738 | PREDICTED: Homo sapiens similar to 60S ribosomal protein L29 (Cell surface heparin-binding protein HIP) (LOC391738), mRNA [XR_019052] |
| XR_018303 | LOC648378 | PREDICTED: Homo sapiens similar to ribosomal protein S14 (LOC648378), mRNA [XR_018303] |
| XM_928025 | LOC644937 | PREDICTED: Homo sapiens similar to 60S ribosomal protein L10 (QM protein) (Tumor suppressor QM) (Laminin receptor homolog) (LOC644937), mRNA [XM_928025] |
| AL137354 | AL137354 | Homo sapiens mRNA; cDNA DKFZp434A0326 (from clone DKFZp434A0326). [AL137354] |
| XM_930195 | hCG_18290 | PREDICTED: Homo sapiens similar to 60S ribosomal protein L32 (LOC644907), mRNA [XM_930195] |
| NM_001080544 | LOC653314 | Homo sapiens similar to ribosomal protein L19 (LOC653314), mRNA [NM_001080544] |
| ENST00000333351 | ENST00000333351 | PREDICTED: Homo sapiens hypothetical LOC391504 (LOC391504), mRNA [XR_018627] |
| NM_173833 | SCARA5 | Homo sapiens scavenger receptor class A, member 5 (putative) (SCARA5), mRNA [NM_173833] |
| NM_182688 | UBE2G2 | Homo sapiens ubiquitin-conjugating enzyme E2G 2 (UBC7 homolog, yeast) (UBE2G2), transcript variant 2, mRNA [NM_182688] |
| AK000420 | AK000420 | Homo sapiens cDNA FLJ20413 fis, clone KAT02170. [AK000420] |
| NM_024812 | BAALC | Homo sapiens brain and acute leukemia, cytoplasmic (BAALC), transcript variant 1, mRNA [NM_024812] |
| XM_372498 | LOC390427 | PREDICTED: Homo sapiens similar to TBP-associated factor 15 isoform 1 (LOC390427), mRNA [XM_372498] |
| THC2718728 | THC2718728 | Unknown |
| NM_198253 | TERT | Homo sapiens telomerase reverse transcriptase (TERT), transcript variant 1, mRNA [NM_198253] |

TABLE 12-continued

Gene list generated at the inclusion criteria of $p \le 1 \times 10^{-3}$ and the log-median-ratio being below being at least "1" or above, or being "−1" or below.

| GenBank Accession | GeneName | Description |
|---|---|---|
| NM_002307 | LGALS7 | *Homo sapiens* lectin, galactoside-binding, soluble, 7 (galectin 7) (LGALS7), mRNA [NM_002307] |
| ENST00000248668 | LRFN1 | Leucine-rich repeat and fibronectin type III domain-containing protein 1 (Fragment). [Source: Uniprot/SPTREMBL;Acc: Q9P244] LENST000002486681 |
| ENST00000325151 | ENST00000325151 | Small inducible cytokine A27 precursor (CCL27) (CC chemokine ILC) (IL-11 R-alpha-locus chemokine) (Skinkine) (ESkine) (Cutaneous T-cell-attracting chemokine) (CTACK). [Source: Uniprot/SWISSPROT;Acc: Q9Y4X3] [ENST00000325151] |
| NM_006266 | RALGDS | *Homo sapiens* ral guanine nucleotide dissociation stimulator (RALGDS), transcript variant 1, mRNA [NM_006266] |
| NM_001138 | AGRP | *Homo sapiens* agouti related protein homolog (mouse) (AGRP), transcript variant 1, mRNA [NM_001138] |
| NM_207377 | UNQ9438 | *Homo sapiens* TIMM9 (UNQ9438), mRNA [NM_207377] |
| NM_015088 | TNRC6B | *Homo sapiens* trinucleotide repeat containing 6B (TNRC6B), transcript variant 1, mRNA [NM_015088] |
| NM_175734 | C17orf74 | *Homo sapiens* chromosome 17 open reading frame 74 (C17orf74), mRNA [NM_175734] |
| NM_004750 | CRLF1 | *Homo sapiens* cytokine receptor-like factor 1 (CRLF1), mRNA [NM_004750] |
| NM_003508 | FZD9 | *Homo sapiens* frizzled homolog 9 (*Drosophila*) (FZD9), mRNA [NM_003508] |
| AA418814 | AA418814 | AA418814 zw01a02.s1 Soares_NhHMPu_S1 *Homo sapiens* cDNA clone IMAGE: 767978 3', mRNA sequence [AA418814] |
| NM_203374 | ZNF784 | *Homo sapiens* zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT;Acc: P30740] [ENST00000380739] |
| NM_012183 | FOXD3 | *Homo sapiens* forkhead box D3 (FOXD3), mRNA [NM_012183] |
| NM_019105 | TNXB | *Homo sapiens* tenascin XB (TNXB), transcript variant XB, mRNA [NM_019105] |
| ENST00000360514 | ENST00000360514 | *Homo sapiens* hypothetical LOC339483, mRNA (cDNA clone MGC: 52427 IMAGE: 4872239), complete cds. [BC041632] |
| NM_138763 | BAX | *Homo sapiens* BCL2-associated X protein (BAX), transcript variant delta, mRNA [NM_138763] |
| NM_203304 | RKHD1 | *Homo sapiens* ring finger and KH domain containing 1 (RKHD1), mRNA [NM_203304] |
| NM_018490 | LGR4 | *Homo sapiens* leucine-rich repeat-containing G protein-coupled receptor 4 (LGR4), mRNA [NM_018490] |
| CV575560 | CV575560 | oe37f10.y1 Human keratoconus cornea, unamplified, (od [CV575560] |

TABLE 13

Gene list generated at the inclusion criteria of $p \le 0.05$ and the log-median-ratio being below being at least "1" or above, or being "−1" or below.

| GenBank Accession | GeneName | Description |
|---|---|---|
| NM_002619 | PF4 | *Homo sapiens* platelet factor 4 (chemokine (C-X-C motif) ligand 4) (PF4), mRNA [NM_002619] |
| NM_001039567 | RPS4Y2 | *Homo sapiens* ribosomal protein S4, Y-linked 2 (RPS4Y2), mRNA [NM_001039567] |
| NM_183049 | TMSL3 | *Homo sapiens* thymosin-like 3 (TMSL3), mRNA [NM_183049] |
| NM_001008 | RPS4Y1 | *Homo sapiens* ribosomal protein S4, Y-linked 1 (RPS4Y1), mRNA [NM_001008] |
| NM_004126 | GNG11 | *Homo sapiens* guanine nucleotide binding protein (G protein), gamma 11 (GNG11), mRNA [NM_004126] |
| NM_002985 | CCL5 | *Homo sapiens* chemokine (C—C motif) ligand 5 (CCL5), mRNA [NM_002985] |
| NM_002704 | PPBP | *Homo sapiens* pro-platelet basic protein (chemokine (C-X-C motif) ligand 7) (PPBP), mRNA [NM_002704] |
| NM_183049 | TMSL3 | *Homo sapiens* thymosin-like 3 (TMSL3), mRNA [NM_183049] |
| A_24_P530977 | A_24_P530977 | Unknown |
| NM_004048 | B2M | *Homo sapiens* beta-2-microglobulin (B2M), mRNA [NM_004048] |
| ENST00000334647 | ENST00000334647 | Thymosin-like 4. [Source: Uniprot/SPTREMBL;Acc: Q5T4B6] [ENST00000334647] |
| NM_004907 | IER2 | *Homo sapiens* immediate early response 2 (IER2), mRNA [NM_004907] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| NM_004048 | B2M | *Homo sapiens* beta-2-microglobulin (B2M), mRNA [NM_004048] |
| NM_001005339 | RGS10 | *Homo sapiens* regulator of G-protein signalling 10 (RGS10), transcript variant 1, mRNA [NM_001005339] |
| NM_201397 | GPX1 | *Homo sapiens* glutathione peroxidase 1 (GPX1), transcript variant 2, mRNA [NM_201397] |
| NM_006176 | NRGN | *Homo sapiens* neurogranin (protein kinase C substrate, RC3) (NRGN), mRNA [NM_006176] |
| NM_015646 | RAP1B | *Homo sapiens* RAP1B, member of RAS oncogene family (RAP1B), transcript variant 1, mRNA [NM_015646] |
| NM_130782 | RGS18 | *Homo sapiens* regulator of G-protein signalling 18 (RGS18), mRNA [NM_130782] |
| NM_015714 | G0S2 | *Homo sapiens* G0/G1switch 2 (G0S2), mRNA [NM_015714] |
| NM_002490 | NDUFA6 | *Homo sapiens* NADH dehydrogenase (ubiquinone) 1 alpha subcomplex, 6, 14 kDa (NDUFA6), nuclear gene encoding mitochondrial protein, mRNA [NM_002490] |
| AL049447 | AL049447 | *Homo sapiens* mRNA; cDNA DKEZp586A0722 (from clone DKFZp586A0722). [AL049447] |
| NM_031286 | SH3BGRL3 | *Homo sapiens* SH3 domain binding glutamic acid-rich protein like 3 (SH3BGRL3), mRNA [NM_031286] |
| NM_004048 | B2M | *Homo sapiens* beta-2-microglobulin (B2M), mRNA [NM_004048] |
| ENST00000375806 | C6orf25 | G6b protein precursor. [Source: Uniprot/SWISSPROT;Acc: O95866] [ENST00000375806] |
| NM_021109 | TMSB4X | *Homo sapiens* thymosin, beta 4, X-linked (TMSB4X), mRNA [NM_021109] |
| NM_000407 | GP1BB | *Homo sapiens* glycoprotein Ib (platelet), beta polypeptide (GP1BB), mRNA [NM_000407] |
| BC000845 | BC000845 | *Homo sapiens* cDNA done IMAGE: 3457769, partial cds. [BC000845] |
| NM_012329 | MMD | *Homo sapiens* monocyte to macrophage differentiation-associated (MMD), mRNA [NM_012329] |
| AK025280 | THRAP2 | *Homo sapiens* cDNA: FLJ21627 fis, clone COL08058. [AK025280] |
| NM_004048 | B2M | *Homo sapiens* beta-2-microglobulin (B2M), mRNA [NM_004048] |
| NM_002620 | PF4V1 | *Homo sapiens* platelet factor 4 variant 1 (PF4V1), mRNA [NM_002620] |
| NM_032489 | ACRBP | *Homo sapiens* acrosin binding protein (ACRBP), mRNA [NM_032489] |
| NM_001004 | RPLP2 | *Homo sapiens* ribosomal protein, large, P2 (RPLP2), mRNA [NM_001004] |
| NM_033251 | RPL13 | *Homo sapiens* ribosomal protein L13 (RPL13), transcript variant 2, mRNA [NM_033251] |
| NM_002073 | GNAZ | *Homo sapiens* guanine nucleotide binding protein (G protein), alpha z polypeptide (GNAZ), mRNA [NM_002073] |
| NM_203339 | CLU | *Homo sapiens* clusterin (CLU), transcript variant 2, mRNA [NM_203339] |
| NM_014857 | RABGAP1L | *Homo sapiens* RAB GTPase activating protein 1-like (RABGAP1L), transcript variant 1, mRNA [NM_014857] |
| ENST00000383061 | ENST00000383061 | PREDICTED: *Homo sapiens* similar to myosin regulatory light chain-like (LOC442204), mRNA [XM_498088] |
| NM_004152 | OAZ1 | *Homo sapiens* ornithine decarboxylase antizyme 1 (OAZ1), mRNA [NM_004152] |
| NM_004907 | IER2 | *Homo sapiens* immediate early response 2 (IER2), mRNA [NM_004907] |
| NM_001803 | CD52 | *Homo sapiens* CD52 molecule (CD52), mRNA [NM_001803] |
| NM_004048 | B2M | *Homo sapiens* beta-2-microglobulin (B2M), mRNA [NM_004048] |
| NM_145113 | MAX | *Homo sapiens* MYC associated factor X (MAX), transcript variant 3, mRNA [NM_145113] |
| NM_002954 | RPS27A | *Homo sapiens* ribosomal protein S27a (RPS27A), mRNA [NM_002954] |
| A_24_P144383 | A_24_P144383 | Unknown |
| NM_006471 | MRCL3 | *Homo sapiens* myosin regulatory light chain MRCL3 (MRCL3), mRNA [NM_006471] |
| NM_014380 | NGFRAP1 | *Homo sapiens* nerve growth factor receptor (TNFRSF16) associated protein 1 (NGFRAP1), transcript variant 3, mRNA [NM_014380] |
| NM_006597 | HSPA8 | *Homo sapiens* heat shock 70 kDa protein 8 (HSPA8), transcript variant 1, mRNA [NM_006597] |
| NM_004048 | B2M | *Homo sapiens* beta-2-microglobulin (B2M), mRNA [NM_004048] |
| NM_001402 | EEF1A1 | *Homo sapiens* eukaryotic translation elongation factor 1 alpha I (EEF1A1), mRNA [NM_001402] |
| NM_004048 | B2M | *Homo sapiens* beta-2-microglobulin (B2M), mRNA [NM_004048] |
| NM_004048 | B2M | *Homo sapiens* beta-2-microglobulin (B2M), mRNA [NM_004048] |
| AY029066 | AY029066 | *Homo sapiens* Humanin (HN1) mRNA, complete cds. [AY029066] |
| NM_001030 | RPS27 | *Homo sapiens* ribosomal protein S27 (metallopanstimulin 1) (RPS27), mRNA [NM_001030] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| NM_080425 | GNAS | Homo sapiens GNAS complex locus (GNAS), transcript variant 2, mRNA [NM_080425] |
| NM_001032 | RPS29 | Homo sapiens ribosomal protein S29 (RPS29), transcript variant 1, mRNA [NM_001032] |
| NM_014372 | RNF11 | Homo sapiens ring finger protein 11 (RNF11), mRNA [NM_014372] |
| NM_004048 | B2M | Homo sapiens beta-2-microglobulin (B2M), mRNA [NM_004048] |
| NM_007262 | PARK7 | Homo sapiens Parkinson disease (autosomal recessive, early onset) 7 (PARK7), mRNA [NM_007262] |
| NM_001012 | RPS8 | Homo sapiens ribosomal protein S8 (RPS8), mRNA [NM_001012] |
| NM_006000 | TUBA4A | Homo sapiens tubulin, alpha 4a (TUBA4A), mRNA [NM_006000] |
| NM_005594 | NACA | Homo sapiens nascent-polypeptide-associated complex alpha polypeptide (NACA), roRNA [NM_005594] |
| XR_017498 | LOC645693 | PREDICTED: Homo sapiens similar to eukaryotic translation elongation factor 1 alpha 2 (LOC645693), mRNA [XR_017498] |
| NM_006597 | HSPA8 | Homo sapiens heat shock 70 kDa protein 8 (HSPA8), transcript variant 1, mRNA [NM_006597] |
| NM_001778 | CD48 | Homo sapiens CD48 molecule (CD48), mRNA [NM_001778] |
| NM_016489 | NT5C3 | Homo sapiens 5'-nucleotidase, cytosolic III (NT5C3), transcript variant 3, mRNA [NM_016489] |
| ENST00000361789 | CYTB | Cytochrome b. [Source: Uniprot/SWISSPROT;Acc: P00156] [ENST00000361789] |
| NM_001800 | CDKN2D | Homo sapiens cyclin-dependent kinase inhibitor 2D (p19, inhibits CDK4) (CDKN2D), transcript variant 1, mRNA [NM_001800] |
| NM_001017 | RPS13 | Homo sapiens ribosomal protein S13 (RPS13), mRNA [NM_001017] |
| NM_001030 | RPS27 | Homo sapiens ribosomal protein S27 (metallopanstimulin 1) (RPS27), mRNA [NM_001030] |
| NM_000968 | RPL4 | Homo sapiens ribosomal protein L4 (RPL4), mRNA [NM_000968] |
| NM_004657 | SDPR | Homo sapiens serum deprivation response (phosphatidylserine binding protein) (SDPR), mRNA [NM_004657] |
| NM_002032 | FTH1 | Homo sapiens ferritin, heavy polypeptide 1 (FTH1), mRNA [NM_002032] |
| NM_002032 | FTH1 | Homo sapiens ferritin, heavy polypeptide 1 (FTH1), mRNA [NM_002032] |
| XR_018386 | LOC392358 | PREDICTED: Homo sapiens similar to 40S ribosomal protein S6 (LOC392358), mRNA [XR_018386] |
| NM_002436 | MPP1 | Homo sapiens membrane protein, palmitoylated 1, 55 kDa (MPP1), mRNA [NM_002436] |
| A_24_P229756 | A_24_P229756 | Unknown |
| NM_004048 | B2M | Homo sapiens beta-2-microglobulin (B2M), mRNA [NM_004048] |
| NM_024299 | C20orf149 | Homo sapiens chromosome 20 open reading frame 149 (C20orf149), mRNA [NM_024299] |
| NM_002945 | RPA1 | Homo sapiens replication protein A1, 70 kDa (RPA1), mRNA [NM_002945] |
| NM_002032 | FTH1 | Homo sapiens ferritin, heavy polypeptide 1 (FTH1), mRNA [NM_002032] |
| THC2544911 | THC2544911 | MUSEFTU elongation factor Tu {Mus musculus} (exp = −1; wgp = 0; cg = 0), partial (37%) [THC2544911] |
| NM_001017 | RPS13 | Homo sapiens ribosomal protein S13 (RPS13), mRNA [NM_001017] |
| NM_002107 | H3F3A | Homo sapiens H3 histone, family 3A (H3F3A), mRNA [NM_002107] |
| NM_001005 | RPS3 | Homo sapiens ribosomal protein S3 (RPS3), mRNA [NM_001005] |
| NM_021104 | RPL41 | Homo sapiens ribosomal protein L41 (RPL41), transcript variant 1, mRNA [NM_021104] |
| NM_000981 | RPL19 | Homo sapiens ribosomal protein L19 (RPL19), mRNA [NM_000981] |
| THC2527647 | THC2527647 | Q59GY2_HUMAN (Q59GY2) Ribosomal protein L4 variant (Fragment), partial (51%) [THC2527647] |
| A_24_P929974 | A_24_P929974 | Unknown |
| NM_002300 | LDHB | Homo sapiens lactate dehydrogenase B (LDHB), mRNA [NM_002300] |
| NM_152793 | C7orf41 | Homo sapiens chromosome 7 open reading frame 41 (C7orf41), mRNA [NM_152793] |
| NM_033251 | RPL13 | Homo sapiens ribosomal protein L13 (RPL13), transcript variant 2, mRNA [NM_033251] |
| NM_001031 | RPS28 | Homo sapiens ribosomal protein S28 (RPS28), mRNA [NM_001031] |
| M36647 | UQCRH | Homo sapiens mitochondrial hinge protein precursor, mRNA, complete cds. [M36647] |
| NM_003973 | RPL14 | Homo sapiens ribosomal protein L14 (RPL14), transcript variant 2, mRNA [NM_003973] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| NM_000978 | RPL23 | Homo sapiens ribosomal protein L23 (RPL23), mRNA [NM_000978] |
| NM_003118 | SPARC | Homo sapiens secreted protein, acidic, cysteine-rich (osteonectin) (SPARC), mRNA [NM_003118] |
| NM_033251 | RPL13 | Homo sapiens ribosomal protein L13 (RPL13), transcript variant 2, mRNA [NM_033251] |
| NM_001003 | RPLP1 | Homo sapiens ribosomal protein, large, P1 (RPLP1), transcript variant 1, mRNA [NM_001003] |
| NM_001568 | EIF3S6 | Homo sapiens eukaryotic translation initiation factor 3, subunit 6 48 kDa (EIF3S6), mRNA [NM_001568] |
| A_24_P392195 | A_24_P392195 | Unknown |
| NM_000129 | F13A1 | Homo sapiens coagulation factor XIII, A1 polypeptide (F13A1), mRNA [NM_000129] |
| NM_001028 | RPS25 | Homo sapiens ribosomal protein S25 (RPS25), mRNA [NM_001028] |
| NM_003756 | EIF3S3 | Homo sapiens eukaryotic translation initiation factor 3, subunit 3 gamma, 40 kDa (EIF3S3), mRNA [NM_003756] |
| NM_001032 | RPS29 | Homo sapiens ribosomal protein S29 (RPS29), transcript variant 1, mRNA [NM_001032] |
| NM_002107 | H3F3A | Homo sapiens H3 histone, family 3A (H3F3A), mRNA [NM_002107] |
| A_24_P238426 | A_24_P238426 | Unknown |
| NM_018447 | TMEM111 | Homo sapiens transmembrane protein 111 (TMEM111), mRNA [NM_018447] |
| A_24_P127051 | A_24_P127051 | Unknown |
| BX096698 | BX096698 | BX096698 Soares breast 2NbHBst Homo sapiens cDNA clone IMAGp998E11242, mRNA sequence [BX096698] |
| XR_017260 | LOC646710 | PREDICTED: Homo sapiens hypothetical LOC646710 (LOC646710), mRNA [XR_017260] |
| A_24_P333112 | A_24_P333112 | Unknown |
| NM_001003 | RPLP1 | Homo sapiens ribosomal protein, large, P1 (RPLP1), transcript variant 1, mRNA [NM_001003] |
| NM_002823 | PTMA | Homo sapiens prothymosin, alpha (gene sequence 28) (PTMA), mRNA [NM_0028231 |
| NM_033251 | RPL13 | Homo sapiens ribosomal protein L13 (RPL13), transcript variant 2, mRNA [NM_033251] |
| XR_017294 | LOC646949 | PREDICTED: Homo sapiens similar to ribosomal protein L23 (LOC646949), mRNA [XR_017294] |
| XR_016779 | LOC440311 | PREDICTED: Homo sapiens similar to Glioma tumor suppressor candidate region gene 2 protein (p60) (LOC440311), mRNA [XR_016779] |
| NM_002085 | GPX4 | Homo sapiens glutathione peroxidase 4 (phospholipid hydroperoxidase) (GPX4), transcript variant 1, mRNA [NM_002085] |
| NM_000993 | RPL31 | Homo sapiens ribosomal protein L31 (RPL31), m_RNA [NM_000993] |
| XR_015548 | LOC729449 | PREDICTED: Homo sapiens similar to 60S ribosomal protein L7 (LOC729449), mRNA [XR_015548] |
| NM_001964 | EGR1 | Homo sapiens early growth response 1 (EGR1), mRNA [NM_001964] |
| NM_199290 | NACA2 | Homo sapiens nascent-polypeptide-associated complex alpha polypeptide-like (NACAL), mRNA [NM_199290] |
| BC052613 | LOC728131 | Homo sapiens cDNA clone MGC: 59872 IMAGE: 6301163, complete cds. [BC052613] |
| A_24_P306968 | A_24_P306968 | Unknown |
| A_32_P49392 | A_32_P49392 | Unknown |
| XM_497657 | LOC441876 | PREDICTED: Homo sapiens similar to 40S ribosomal protein S16, transcript variant 1 (LOC441876), mRNA [XM_497657] |
| NM_001025 | RPS23 | Homo sapiens ribosomal protein S23 (RPS23), mRNA [NM_0010251 |
| BU956542 | BU956542 | BU956542 AGENCOURT_10615527 NIH_MGC_107 Homo sapiens cDNA clone IMAGE: 6730153 5', mRNA sequence [BU956542] |
| AK027315 | AK027315 | Homo sapiens cDNA FLJ14409 fis, clone HEMBA1004408, moderately similar to PEPTIDYL-PROLYL CIS-TRANS ISOMERASE 10 (EC 5.2.1.8). [AK027315] |
| NIvI_001997 | FAU | Homo sapiens Finkel-Biskis-Reilly murine sarcoma virus (FBR-MuSV) ubiquitously expressed (fox derived); ribosomal protein S30 (FAU), mRNA [NM_001997] |
| NM_006597 | HSPA8 | Homo sapiens heat shock 70 kDa protein 8 (HSPA8), transcript variant 1, mRNA [NM_006597] |
| NM_007285 | GABARAPL2 | Homo sapiens GABA(A) receptor-associated protein-like 2 (GABARAPL2), mRNA [NM_007285] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| NM_001006 | RPS3A | Homo sapiens ribosomal protein S3A (RPS3A), mRNA [NM_001006] |
| NM_001402 | EEF1A1 | Homo sapiens eukaryotic translation elongation factor 1 alpha 1 (EEF1A1), mRNA [NM_001402] |
| NM_001568 | EIF3S6 | Homo sapiens eukaryotic translation initiation factor 3, subunit 6 48 kDa (EIF3S6), mRNA [NM_001568] |
| NM_001436 | FBL | Homo sapiens fibrillarin (FBL), mRNA [NM_001436] |
| NM_000975 | RPL11 | Homo sapiens ribosomal protein L11 (RPL11), mRNA [NM_000975] |
| NM_033546 | MRLC2 | Homo sapiens myosin regulatory light chain MRLC2 (MRLC2), mRNA [NM_033546] |
| NR_003038 | SNHG5 | Homo sapiens small nucleolar RNA host gene (non-protein coding) 5 (SNHG5) on chromosome 6 [NR_003038] |
| A_32_P128781 | A_32_P128781 | Unknown |
| XR_018063 | LOC392030 | PREDICTED: Homo sapiens hypothetical LOC392030 (LOC392030), mRNA [XR_018063] |
| NM_003407 | ZFP36 | Homo sapiens zinc finger protein 36, C3H type, homolog (mouse) (ZFP36), mRNA [NM_003407] |
| A_24_P298835 | A_24_P298835 | Unknown |
| THC2740013 | THC2740013 | Q2U8W6_ASPOR (Q2U8W6) Predicted protein, partial (14%) [THC2740013] |
| ENST00000343149 | ENST00000343149 | Unknown |
| A_32_P200955 | A_23_P200955 | Unknown |
| A_24_P341376 | A_24_P341376 | Unknown |
| NM_003498 | SNN | Homo sapiens stannin (SNN), mRNA [NM_003498] |
| NM_080392 | PTP4A2 | Homo sapiens protein tyrosine phosphatase type IVA, member 2 (PTP4A2), transcript variant 2, mRNA [NM_080392] |
| NM_020152 | C21orf7 | Homo sapiens chromosome 21 open reading frame 7 (C21orf7), mRNA [NM_020152] |
| NM_213611 | SLC25A3 | Homo sapiens solute carrier family 25 (mitochondrial carrier; phosphate carrier), member 3 (SLC25A3), nuclear gene encoding mitochondrial protein, transcript variant 3, mRNA [NM_213611] |
| NM_003279 | TNNC2 | Homo sapiens troponin C type 2 (fast) (TNNC2), mRNA [NM_003279] |
| ENST00000312528 | ENST00000312528 | Unknown |
| NM_015710 | GLTSCR2 | Homo sapiens glioma tumor suppressor candidate region gene 2 (GLTSCR2), mRNA [NM_015710] |
| NR_002205 | FTHL12 | Homo sapiens ferritin, heavy polypeptide-like 12 (FTHL12) on chromosome 9 [NR_002205] |
| NM_001402 | EEF1A1 | Homo sapiens eukaryotic translation elongation factor 1 alpha 1 (EEF1A1), mRNA [NM_001402] |
| AY029066 | AY029066 | Homo sapiens Humanin (HN1) mRNA, complete cds. [AY029066] |
| NM_025228 | TRAF3IP3 | Homo sapiens TRAF3 interacting protein 3 (TRAF3IP3), mRNA [NM_025228] |
| NM_003529 | HIST1H3A | Homo sapiens histone cluster 1, H3a (HIST1H3A), mRNA [NM_003529] |
| NM_002624 | PFDN5 | Homo sapiens prefoldin subunit 5 (PFDN5), transcript variant 1, mRNA [NM_002624] |
| NM_005801 | EIF1 | Homo sapiens eukaryotic translation initiation factor 1 (EIF1), mRNA [NM_005801] |
| THC2567111 | THC2567111 | RL37_HUMAN (P61927) 60S ribosomal protein L37 (G1.16), complete [THC2567111] |
| ENST00000361789 | CYTB | Cytochrome b. [Source: Uniprot/SWISSPROT;Acc: P00156] [ENST00000361789] |
| A_24_P160920 | A_24_P160920 | Unknown |
| A_24_P332292 | A_24_P332292 | Unknown |
| NM_198969 | AES | Homo sapiens amino-terminal enhancer of split (AES), transcript variant 1, mRNA [NM_198969] |
| NM_000989 | RPL30 | Homo sapiens ribosomal protein L30 (RPL30), mRNA [NM_000989] |
| A_24_P878388 | A_24_P878388 | Unknown |
| NM_003532 | HIST1H3E | Homo sapiens histone cluster 1, H3e (HIST1H3E), mRNA [NM_003532] |
| NM_001402 | EEF1A1 | Homo sapiens eukaryotic translation elongation factor 1 alpha 1 (EEF1A1), mRNA [NM_001402] |
| NM_000989 | RPL30 | Homo sapiens ribosomal protein L30 (RPL30), mRNA [NM_000989] |
| XR_016879 | LOC388401 | PREDICTED: Homo sapiens similar to 60S ribosomal protein L7 (LOC388401), mRNA [XR_016879] |
| CR620748 | LOC729329 | full-length cDNA clone CS0DK011YI14 of HeLa cells Cot 25-normalized of Homo sapiens (human) [CR620748] |
| NM_000967 | RPL3 | Homo sapiens ribosomal protein L3 (RPL3), transcript variant 1, mRNA [NM_000967] |

TABLE 13-continued

Gene list generated at the inclusion criteria of p ≤ 0.05 and the log-median-ratio
being below being at least "1" or above, or being "−1" or below.

| GenBank Accession | GeneName | Description |
|---|---|---|
| ENST00000337102 | ENST00000337102 | 40S ribosomal protein S21. [Source: Uniprot/SWISSPROT;Ace: P63220] [ENST00000337102] |
| A_24_P384239 | A_24_P384239 | Unknown |
| NM_006263 | PSME1 | *Homo sapiens* proteasome (prosome, macropain) activator subunit 1 (PA28 alpha) (PSME1), transcript variant 1, mRNA [NM_006263] |
| XR_018138 | LOC392497 | PREDICTED: *Homo sapiens* similar to 40S ribosomal protein S6 (LOC392497), mRNA [XR_018138] |
| NM_002341 | LTB | *Homo sapiens* lymphotoxin beta (TNF superfamily, member 3) (LTB), transcript variant 1, mRNA [NM_002341] |
| NM_000967 | RPL3 | *Homo sapiens* ribosomal protein L3 (RPL3), transcript variant 1, mRNA [NM_000967] |
| A_24_P84408 | A_24_P84408 | Unknown |
| NM_004566 | PFKFB3 | *Homo sapiens* 6-phosphofructo-2-kinase/fructose-2,6-biphosphatase 3 (PFKFB3), mRNA [NM_004566] |
| A_24_P918875 | A_24_P918875 | Unknown |
| NM_002121 | HLA-DPB1 | *Homo sapiens* major histocompatibility complex, class II, DP beta 1 (HLA-DPB1), mRNA [NM_002121] |
| NM_007161 | LST1 | *Homo sapiens* leukocyte specific transcript 1 (LST1), transcript variant 1, mRNA [NM_007161] |
| NM_000661 | RPL9 | *Homo sapiens* ribosomal protein L9 (RPL9), transcript variant 1, mRNA [NM_000661] |
| NM_002107 | H3F3A | *Homo sapiens* H3 histone, family 3A (H3F3A), mRNA [NM_002107] |
| NM_000991 | RPL28 | *Homo sapiens* ribosomal protein L28 (RPL28), mRNA [NM_000991] |
| XR_018482 | LOC120318 | PREDICTED: *Homo sapiens* similar to 40S ribosomal protein S6 (LOC120318), mRNA [XR_018482] |
| NM_003333 | LTBA52 | *Homo sapiens* ubiquitin A-52 residue ribosomal protein fusion product 1 (UBA52), transcript variant 2, mRNA [NM_003333] |
| NM_001006 | RPS3A | *Homo sapiens* ribosomal protein S3A (RPS3A), mRNA [NM_001006] |
| NM_001006 | RPS3A | *Homo sapiens* ribosomal protein S3A (RPS3A), mRNA [NM_001006] |
| NM_000661 | RPL9 | *Homo sapiens* ribosomal protein L9 (RPL9), transcript variant 1, mRNA [NM_000661] |
| NM_002952 | RPS2 | *Homo sapiens* ribosomal protein S2 (RPS2), mRNA [NM_002952] |
| A_24_P650893 | A_24_P650893 | Unknown |
| A_24_P50567 | A_24_P50567 | Unknown |
| A_24_P136011 | A_24_P136011 | Unknown |
| A_24_P298238 | A_24_P298238 | Unknown |
| THC2541331 | THC2541331 | HSU02032 ribosomal protein L23a {*Homo sapiens*} (exp = −1; wgp = 0; cg = 0), partial (71%) [THC2541331] |
| XR_018025 | LOC641790 | PREDICTED: *Homo sapiens* similar to ribosomal protein L31 (LOC641790), mRNA [XR_018025] |
| NM_014301 | ISCU | *Homo sapiens* iron-sulfur cluster scaffold homolog (*E. coli*) (ISCU), nuclear gene encoding mitochondrial protein, transcript variant 1, mRNA [NM_014301] |
| NM_003295 | TPT1 | *Homo sapiens* tumor protein, translationally-controlled 1 (TPT1), mRNA [NM_003295] |
| ENST00000332101 | ENST00000332101 | PREDICTED: *Homo sapiens* similar to HIStone family member (his-72) (LOC391769), mRNA [XM_373079] |
| NM_001867 | COX7C | *Homo sapiens* cytochrome c oxidase subunit VIIc (COX7C), nuclear gene encoding mitochondrial protein, mRNA [NM_001867] |
| BC018140 | RPS21 | *Homo sapiens* ribosomal protein S21, mRNA (cDNA clone MGC: 9438 IMAGE: 3903320), complete cds. [BC018140] |
| NM_005340 | HINT1 | *Homo sapiens* histidine triad nucleotide binding protein 1 (HINT1), mRNA [NM_005340] |
| BC067891 | LOC645683 | *Homo sapiens* cDNA clone MGC: 87657 IMAGE: 5271409, complete cds. [BC067891] |
| NM_001018108 | SERF2 | *Homo sapiens* small EDRK-rich factor 2 (SERF2), mRNA [NM_001018108] |
| ENST00000308989 | ENST00000308989 | PREDICTED: *Homo sapiens* similar to ribosomal protein L31 (LOC729005), mRNA [XM_001133428] |
| A_24_P212726 | A_24_P212726 | Unknown |
| NM_001028 | RPS25 | *Homo sapiens* ribosomal protein S25 (RPS25), mRNA [NM_001028] |
| NM_000998 | RPL37A | *Homo sapiens* ribosomal protein L37a (RPL37A), mRNA [NM_000998] |
| XR_015402 | LOC731170 | PREDICTED: *Homo sapiens* similar to eukaryotic translation elongation factor 1 alpha 2 (LOC731170), mRNA [XR_015402] |
| A_24_P340886 | A_24_P340886 | Unknown |
| NM_016480 | PAIP2 | *Homo sapiens* poly(A) binding protein interacting protein 2 (PAIP2), transcript variant 2, mRNA [NM_016480] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| THC2567891 | THC2567891 | Q6NXR8_HUMAN (Q6NXR8) Ribosomal protein S3a, partial (91%) [THC2567891] |
| ENST00000361227 | ND3 | NADH-ubiquinone oxidoreductase chain 3 (EC 1.6.5.3) (NADH dehydrogenase subunit 3). [Source: Uniprot/SWISSPROT;Acc: P03897] [ENST00000361227] |
| XR_019376 | LOC285260 | PREDICTED: *Homo sapiens* similar to ribosomal protein L31 (LOC285260), mRNA [XR_019376] |
| ENST00000359449 | ENST00000359449 | Sequence 237 from Patent WO0220754. [AX721277] |
| NM_000988 | RPL27 | *Homo sapiens* ribosomal protein L27 (RPL27), mRNA [NM_000988] |
| A_24_P410256 | A_24_P410256 | Unknown |
| NM_021009 | UBC | *Homo sapiens* ubiquitin C (UBC), mRNA [NM_021009] |
| XR_018975 | LOC389644 | PREDICTED: *Homo sapiens* similar to ribosomal protein L5 (LOC389644), mRNA [XR_018975] |
| XR_019168 | LOC391847 | PREDICTED: *Homo sapiens* similar to ribosomal protein L19 (LOC391847), mRNA [XR_019168] |
| NM_079423 | MYL6 | *Homo sapiens* myosin, light chain 6, alkali, smooth muscle and non-muscle (MYL6), transcript variant 2, mRNA [NM_079423] |
| A_24_P505981 | A_24_P505981 | Unknown |
| CD174733 | CD174733 | CD174733 AGENCOURT_13961604 NIH_MGC_172 Homo sapiens cDNA 5', mRNA sequence [CD174733] |
| ENST00000240349 | NACA3P | PREDICTED: *Homo sapiens* similar to nascent polypeptide-associated complex alpha polypeptide (LOC389240), mRNA [XM_371715] |
| A_24_P221375 | A_24_P221375 | Unknown |
| NM_001743 | CALM2 | *Homo sapiens* calmodulin 2 (phosphorylase kinase, delta) (CALM2), mRNA [NM_0017431] |
| NM_005801 | EIF1 | *Homo sapiens* eukaryotic translation initiation factor 1 (EIF1), mRNA [NM_005801] |
| NM_000984 | RPL23A | *Homo sapiens* ribosomal protein L23a (RPL23A), mRNA [NM_000984] |
| NM_003746 | DYNLL1 | *Homo sapiens* dynein, light chain, LC8-type 1 (DYNLL1), transcript variant 3, mRNA [NM_003746] |
| XR_018231 | LOC648027 | PREDICTED: *Homo sapiens* similar to Elongation factor 1-gamma (EF-1-gamma) (eEF-1B gamma) (LOC648027), mRNA [XR_018231] |
| NM_003753 | EIF3S7 | *Homo sapiens* eukaryotic translation initiation factor 3, subunit 7 zeta, 66/67 kDa (EIF357), mRNA [NM_003753] |
| NM_000978 | RPL23 | *Homo sapiens* ribosomal protein L23 (RPL23), mRNA [NM_000978] |
| BC001697 | RPS15A | *Homo sapiens* ribosomal protein S15a, mRNA (cDNA clone MGC: 2466 IMAGE: 2967511), complete cds. [BC001697] |
| NM_013234 | EIF3S12 | *Homo sapiens* eukaryotic translation initiation factor 3, subunit 12 (EIF3S12), mRNA [NM_013234] |
| NM_001022 | RPS19 | *Homo sapiens* ribosomal protein S19 (RPS19), mRNA [NM_001022] |
| A_24_P862524 | A_24_P862524 | Unknown |
| NM_001007074 | RPL32 | *Homo sapiens* ribosomal protein L32 (RPL32), transcript variant 3, mRNA [NM_001007074] |
| NM_001861 | COX4I1 | *Homo sapiens* cytochrome c oxidase subunit IV isoform 1 (COX4I1), mRNA [NM_001861] |
| NM_006004 | UQCRH | *Homo sapiens* ubiquinol-cytochrome c reductase hinge protein (UQCRH), mRNA [NM_006004] |
| NM_006930 | SKP1A | *Homo sapiens* S-phase kinase-associated protein 1A (p19A) (SKP1A), transcript variant 1, mRNA [NM_006930] |
| XR_019544 | LOC652890 | PREDICTED: *Homo sapiens* similar to 60S ribosomal protein L7 (LOC652890), mRNA [XR_019544] |
| NM_021009 | UBC | *Homo sapiens* ubiquitin C (UBC), mRNA [NM_021009] |
| A_24_P41979 | A_24_P41979 | Unknown |
| NM_003746 | DYNLL1 | *Homo sapiens* dynein, light chain, LC8-type 1 (DYNLL1), transcript variant 3, mRNA [NM_003746] |
| NM_001344 | DAD1 | *Homo sapiens* defender against cell death 1 (DAD1), mRNA [NM_001344] |
| NM_000982 | RPL21 | *Homo sapiens* ribosomal protein L21 (RPL21), mRNA [NM_000982] |
| A_32_P210285 | A_32_P210285 | Unknown |
| NM_002539 | ODC1 | *Homo sapiens* ornithine decarboxylase 1 (ODC1), mRNA [NM_002539] |
| XR_019361 | LOC442260 | PREDICTED: *Homo sapiens* similar to 60S ribosomal protein L23a (LOC442260), mRNA [XR_019361] |
| A_24_P289884 | A_24_P289884 | Unknown |
| NM_006357 | UBE2E3 | *Homo sapiens* ubiquitin-conjugating enzyme E2E 3 (UBC4/5 homolog, yeast) (UBE2E3), transcript variant 1, mRNA [NM_006357] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| NM_000990 | RPL27A | Homo sapiens ribosomal protein L27a (RPL27A), mRNA [NM_000990] |
| NM_003404 | YWHAB | Homo sapiens tyrosine 3-monooxygenase/tryptophan 5-monooxygenase activation protein, beta polypeptide (YWHAB), transcript variant 1, mRNA [NM_003404] |
| A_24_P135242 | A_24_P135242 | Unknown |
| NM_003973 | RPL14 | Homo sapiens ribosomal protein L14 (RPL14), transcript variant 2, mRNA [NM_003973] |
| XR_019386 | LOC652558 | PREDICTED: Homo sapiens similar to 60S ribosomal protein L7 (LOC652558), mRNA [XR_019386] |
| NM_021009 | UBC | Homo sapiens ubiquitin C (UBC), mRNA [NM_021009] |
| ENST00000381140 | ENST00000381140 | Transcription factor IIIA (Factor A) (TFIIIA). [Source: Uniprot/SWISSPROT;Acc: Q92664] [ENST00000381140] |
| NM_003145 | SSR2 | Homo sapiens signal sequence receptor, beta (translocon-associated protein beta) (SSR2), mRNA [NM_003145] |
| NM_004905 | PRDX6 | Homo sapiens peroxiredoxin 6 (PRDX6), mRNA [NM_004905] |
| THC2533996 | THC2533996 | HSU09954 ribosomal protein L9 {Homo sapiens} (exp = −1; wgp cg = 0), partial (42%) [THC2533996] |
| NM_002796 | PSMB4 | Homo sapiens proteasome (prosome, macropain) subunit, beta type, 4 (PSMB4), mRNA [NM_002796] |
| NM_001344 | DAD1 | Homo sapiens defender against cell death 1 (DAD1), mRNA [NM_001344] |
| A_24_P255252 | A_24_P255252 | Unknown |
| ENST00000361453 | ND2 | NADH-ubiquinone oxidoreductase chain 2 (EC 1.6.5.3) (NADH dehydrogenase subunit 2). [Source: Uniprot/SWISSPROT;Acc: P03891] [ENST00000361453] |
| NM_002954 | RPS27A | Homo sapiens ribosomal protein S27a (RPS27A), mRNA [NM_002954] |
| NM_079423 | MYL6 | Homo sapiens myosin, light chain 6, alkali, smooth muscle and non-muscle (MYL6), transcript variant 2, mRNA [NM_079423] |
| NM_145808 | MTPN | Homo sapiens myotrophin (MTPN), mRNA [NM_145808] |
| NM_003277 | CLDN5 | Homo sapiens claudin 5 (transmembrane protein deleted in velocardiofacial syndrome) (CLDN5), mRNA [NM_003277] |
| NM_000984 | RPL23A | Homo sapiens ribosomal protein L23a (RPL23A), mRNA [NM_000984] |
| NM_020240 | CDC42SE2 | Homo sapiens CDC42 small effector 2 (CDC42SE2), transcript variant 1, mRNA [NM_020240] |
| NM_001016 | RPS12 | Homo sapiens ribosomal protein S12 (RPS12), mRNA [NM_001016] |
| NM_175738 | RAB37 | Homo sapiens RAB37, member RAS oncogene family (RAB37), transcript variant 3, mRNA [NM_175738] |
| A_24_P170147 | A_24_P170147 | Unknown |
| NM_007104 | RPL10A | Homo sapiens ribosomal protein L10a (RPL 10A), mRNA [NM_007104] |
| XR_015944 | LOC731681 | PREDICTED: Homo sapiens similar to 60S ribosomal protein L9 (LOC731681), mRNA [XR_015944] |
| XR_018963 | LOC442237 | PREDICTED: Homo sapiens similar to 40S ribosomal protein S7 (S8) (LOC442237), mRNA [XR_018963] |
| NM_021149 | COTL1 | Homo sapiens coactosin-like 1 (Dictyostelium) (COTL1), mRNA [NM_021149] |
| NM_003295 | TPT1 | Homo sapiens tumor protein, translationally-controlled 1 (TPT1), mRNA [NM_003295] |
| NM_016269 | LEF1 | Homo sapiens lymphoid enhancer-binding factor 1 (LEF1), mRNA [NM_016269] |
| NM_016274 | PLEKHO1 | Homo sapiens pleckstrin homology domain containing, family O member 1 (PLEKHO1), mRNA [NM_016274] |
| NM_006830 | UQCR | Homo sapiens ubiquinol-cytochrome c reductase, 6.4 kDa subunit (UQCR), mRNA [NM_006830] |
| NM_080425 | GNAS | Homo sapiens GNAS complex locus (GNAS), transcript variant 2, mRNA [NM_080425] |
| NM_001404 | EEF1G | Homo sapiens eukaryotic translation elongation factor 1 gamma (EEF1G), mRNA [NM_001404] |
| A_24_P755505 | A_24_P755505 | Unknown |
| ENST00000078131 | ENST00000078131 | OTTHUMP00000016594. [Source: Uniprot/SPTREMBL;Acc: Q9NU98] [ENST00000078131] |
| NM_021103 | TmsB10 | Homo sapiens thymosin, beta 10 (TMSB10), mRNA [NM_021103] |
| XR_018554 | LOC402219 | PREDICTED: Homo sapiens similar to ribosomal protein L5 (LOC402219), mRNA [XR_018554] |
| NM_033625 | RPL34 | Homo sapiens ribosomal protein L34 (RPL34), transcript variant 2, mRNA [NM_033625] |
| NM_004152 | OAZ1 | Homo sapiens ornithine decarboxylase antizyme 1 (OAZ1), mRNA [NM_004152] |
| XR_015936 | LOC731457 | PREDICTED: Homo sapiens similar to ribosomal protein S27a (LOC731457), mRNA [XR_015936] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| AF147412 | AF147412 | *Homo sapiens* full length insert cDNA clone YP59C02. [AF147412] |
| NM_001011 | RPS7 | *Homo sapiens* ribosomal protein S7 (RPS7), mRNA [NM_001011] |
| A_24_P730256 | A_24_P730256 | Unknown |
| A_24_P587803 | A_24_P587803 | Unknown |
| NM_016270 | KLF2 | *Homo sapiens* Kruppel-like factor 2 (lung) (KLF2), mRNA [NM_016270] |
| NM_015414 | RPL36 | *Homo sapiens* ribosomal protein L36 (RPL36), transcript variant 2, mRNA [NM_015414] |
| NM_001658 | ARF1 | *Homo sapiens* ADP-ribosylation factor 1 (ARF1), transcript variant 4, mRNA [NM_001658] |
| XR_017130 | LOC158345 | PREDICTED: *Homo sapiens* similar to ribosomal protein L4 (LOC158345), mRNA [XR_017130] |
| A_24_P281853 | A_24_P281853 | Unknown |
| XR_018222 | RPL31P4 | PREDICTED: *Homo sapiens* ribosomal protein L31 pseudogene 4 (RPL31P4), mRNA [XR_018222] |
| XR_015278 | LOC730588 | PREDICTED: *Homo sapiens* similar to suppressor of initiator codon mutations, related sequence 1 (LOC730588), mRNA [XR_015278] |
| NM_003333 | UBA52 | *Homo sapiens* ubiquitin A-52 residue ribosomal protein fusion product 1 (UBA52), transcript variant 2, mRNA [NM_003333] |
| BC028083 | TRBV5-4 | *Homo sapiens* T cell receptor beta variable 5-4, mRNA (cDNA clone MGC: 40031 IMAGE: 5217067), complete cds. [BC028083] |
| NM_001101 | ACTB | *Homo sapiens* actin, beta (ACTB), mRNA [NM_001101] |
| NM_000997 | RPL37 | *Homo sapiens* ribosomal protein L37 (RPL37), mRNA [NM_000997] |
| A_24_P367063 | A_24_P367063 | Unknown |
| NM_001010 | RPS6 | *Homo sapiens* ribosomal protein S6 (RPS6), mRNA [NM_001010] |
| THC2553216 | THC2553216 | HUMRRL3A ribosomal protein L3 {*Homo sapiens*} (exp = −1; wgp = 0; cg = 0), partial (24%) [THC2553216] |
| NM_033625 | RPL34 | *Homo sapiens* ribosomal protein L34 (RPL34), transcript variant 2, mRNA [NM_033625] |
| A_24_P685729 | A_24_P685729 | Unknown |
| NM_022551 | RPS18 | *Homo sapiens* ribosomal protein S18 (RPS18), mRNA [NM_022551] |
| NM_001028 | RPS25 | *Homo sapiens* ribosomal protein S25 (RPS25), mRNA [NM_001028] |
| NM_000996 | RPL35A | *Homo sapiens* ribosomal protein L35a (RPL35A), mRNA [NM_000996] |
| NM_003493 | HIST3H3 | *Homo sapiens* histone cluster 3, H3 (HIST3H3), mRNA [NM_003493] |
| BC089454 | BC089454 | *Homo sapiens* cDNA clone MGC: 105145 IMAGE: 30563285, complete cds. [BC089454] |
| XR_018695 | RPL31P10 | PREDICTED: *Homo sapiens* similar to ribosomal protein L31 (LOC390283), mRNA [XR_018695] |
| NM_005184 | CALM3 | *Homo sapiens* calmodulin 3 (phosphorylase kinase, delta) (CALM3), mRNA [NM_005184] |
| A_24_P144163 | A_24_P144163 | Unknown |
| A_24_P238427 | A_24_P238427 | Unknown |
| NM_000636 | SOD2 | *Homo sapiens* superoxide dismutase 2, mitochondrial (SOD2), nuclear gene encoding mitochondrial protein, transcript variant 1, mRNA [NM_000636] |
| NM_004152 | OAZ1 | *Homo sapiens* ornithine decarboxylase antizyme 1 (OAZ1), mRNA [NM_004152] |
| AK092748 | RP3-377H14.5 | *Homo sapiens* cDNA FLJ35429 fis, clone SMINT2002126. [AK092748] |
| THC2560098 | THC2560098 | S35960 C-terminal {*Homo sapiens*} (exp = −1; wgp = 0; cg = 0), partial (64%) [THC2560098] |
| NM_002121 | HLA-DPB1 | *Homo sapiens* major histocompatibility complex, class II, DP beta 1 (HLA-DPB1), mRNA [NM_002121] |
| NM_002107 | H3F3A | *Homo sapiens* H3 histone, family 3A (H3F3A), mRNA [NM_002107] |
| DW451363 | DW451363 | HHAGE004093 Human liver regeneration after partial hepatectomy *Homo sapiens* cDNA, mRNA sequence [DW451363] |
| A_24_P324224 | A_24_P324224 | Unknown |
| NM_000970 | RPL6 | *Homo sapiens* ribosomal protein L6 (RPL6), transcript variant 2, mRNA [NM_000970] |
| ENST00000356196 | hCG_26523 | PREDICTED: *Homo sapiens* similar to 60S ribosomal protein L26 (LOC646161), mRNA [XR_018048] |
| NM_203477 | MGC70863 | *Homo sapiens* similar to RPL23AP7 protein (MGC70863), transcript variant 1, mRNA [NM_203477] |
| ENST00000356196 | hCG_26523 | PREDICTED: *Homo sapiens* similar to 60S ribosomal protein L26 (Silica-induced gene 20 protein) (SIG-20) (LOC400055), mRNA [XM_374987] |

TABLE 13-continued

Gene list generated at the inclusion criteria of p ≤ 0.05 and the log-median-ratio
being below being at least "1" or above, or being "−1" or below.

| GenBank Accession | GeneName | Description |
|---|---|---|
| NM_004832 | GSTO1 | Homo sapiens glutathione S-transferase omega 1 (GSTO1), mRNA lNM_004832] |
| NM_005617 | RPS14 | Homo sapiens ribosomal protein S14 (RPS14), transcript variant 3, mRNA [NM_005617] |
| NM_000454 | SOD1 | Homo sapiens superoxide dismutase 1, soluble (amyotrophic lateral sclerosis 1 (adult)) (SOD1), mRNA [NM_000454] |
| A_32_P165819 | A_23_P165819 | Unknown |
| NM_002298 | LCP1 | Homo sapiens lymphocyte cytosolic protein 1 (L-plastin) (LCP1), mRNA [NM_002298] |
| NM_001013 | RPS9 | Homo sapiens ribosomal protein S9 (RPS9), mRNA [NM_001013] |
| XR_018048 | LOC646161 | PREDICTED: Homo sapiens similar to 60S ribosomal protein L26 (LOC646161), mRNA [XR_018048] |
| NM_005252 | FOS | Homo sapiens v-fos FBJ murine osteosarcoma viral oncogene homolog (FOS), mRNA [NM_005252] |
| THC2584902 | THC2584902 | Q5M9L9_MOUSE (Q5M9L9) Ribosomal protein S8, partial (73%) [THC2584902] |
| XR_015398 | LOC730747 | PREDICTED: Homo sapiens similar to 60S ribosomal protein L14 (CAG-ISL 7) (LOC730747), mRNA [XR_015398] |
| XR_019277 | LOC391719 | PREDICTED: Homo sapiens similar to ribosomal protein L19 (LOC391719), mRNA [XR_019277] |
| XR_019597 | LOC401863 | PREDICTED: Homo sapiens similar to ribosomal protein L10a (LOC401863), mRNA [XR_019597] |
| AK098605 | AK098605 | Homo sapiens cDNA FLJ25739 fis, clone TST05834. [AK098605] |
| A_24_P127442 | A_24_P127442 | Unknown |
| NM_022736 | MFSD1 | Homo sapiens major facilitator superfamily domain containing 1 (MESD1), mRNA [NM_022736] |
| NM_203495 | COMMD6 | Homo sapiens COMM domain containing 6 (COMMD6), transcript variant 2, mRNA [NM_203495] |
| NM_153236 | GIMAP7 | Homo sapiens GTPase, IMAP family member 7 (GIMAP7), mRNA [NM_153236] |
| XM_935576 | LOC641827 | PREDICTED: Homo sapiens similar to eukaryotic translation elongation factor 1 beta 2 (LOC641827), mRNA [XM_935576] |
| NM_004713 | SDCCAG1 | Homo sapiens serologically defined colon cancer antigen 1 (SDCCAG1), mRNA [NM_004713] |
| NR_001577 | NME2P1 | Homo sapiens non-metastatic cells 2, protein (NM23B) expressed in, pseudogene 1 (NME2P1) on chromosome 12 [NR_001577] |
| NM_000569 | FCGR3A | Homo sapiens Fc fragment of IgG, low affinity Ma, receptor (CD16a) (FCGR3A), mRNA [NM_000569] |
| NM_007308 | SNCA | Homo sapiens synuclein, alpha (non A4 component of amyloid precursor) (SNCA), transcript variant NACP112, mRNA [NM_007308] |
| XR_015767 | LOC731224 | PREDICTED: Homo sapiens similar to 60S ribosomal protein L9 (LOC731224), mRNA [XR_015767] |
| NM_007104 | RPL10A | Homo sapiens ribosomal protein L10a (RPL10A), mRNA [NM_007104] |
| NM_016039 | C14orf166 | Homo sapiens chromosome 14 open reading frame 166 (C14orf166), mRNA [NM_016039] |
| NM_003295 | TPT1 | Homo sapiens tumor protein, translationally-controlled 1 (TPT1), mRNA [NM_003295] |
| AK124741 | AK124741 | Homo sapiens cDNA FLJ42751 fis, clone BRAWH3000491, moderately similar to 40S ribosomal protein S12. [AK124741] |
| NM_005617 | RPS14 | Homo sapiens ribosomal protein S14 (RPS14), transcript variant 3, mRNA [NM_005617] |
| NM_000986 | RPL24 | Homo sapiens ribosomal protein L24 (RPL24), mRNA [NM_000986] |
| NM_000984 | RPL23A | Homo sapiens ribosomal protein L23a (RPL23A), mRNA [NM_000984] |
| XM_001125895 | LOC730452 | PREDICTED: Homo sapiens similar to 60S ribosomal protein L7 (LOC730452), mRNA [XM_001125895] |
| NM_001011 | RPS7 | Homo sapiens ribosomal protein S7 (RPS7), mRNA [NM_001011] |
| XR_018994 | LOC391181 | PREDICTED: Homo sapiens similar to 60S ribosomal protein L6 (TAX-responsive enhancer element-binding protein 107) (TAXREB107) (Neoplasm-related protein C140) (LOC391181), mRNA [XR_018994] |
| A_24_P332441 | A_24_P332441 | Unknown |
| NM_000967 | RPL3 | Homo sapiens ribosomal protein L3 (RPL3), transcript variant 1, mRNA [NM_000967] |
| NM_002414 | CD99 | Homo sapiens CD99 molecule (CD99), mRNA [NM_002414] |
| NM_006013 | RPL10 | Homo sapiens ribosomal protein L10 (RPL10), mRNA [NM_006013] |
| NM_000982 | RPL21 | Homo sapiens ribosomal protein L21 (RPL21), mRNA [NM_000982] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| NM_000969 | RPL5 | Homo sapiens ribosomal protein L5 (RPL5), mRNA [NM_000969] |
| XR_018341 | LOC390413 | PREDICTED: Homo sapiens similar to 60S ribosomal protein L7 (LOC390413), mRNA [XR_018341] |
| NM_014369 | PTPN18 | Homo sapiens protein tyrosine phosphatase, non-receptor type 18 (brain-derived) (PTPN18), mRNA [NM_014369] |
| XR_018054 | LOC392878 | PREDICTED: Homo sapiens hypothetical LOC392878 (LOC392878), mRNA [XR_018054] |
| NM_006013 | RPL10 | Homo sapiens ribosomal protein L10 (RPL10), mRNA [NM_006013] |
| A_24_P608790 | A_24_P608790 | Unknown |
| NM_001011 | RPS7 | Homo sapiens ribosomal protein S7 (RPS7), mRNA [NM_001011] |
| ENST00000332696 | ENST00000332696 | similar to 60S ribosomal protein L23a (LOC644384), mRNA [Source: RefSeq_dna;Acc: XR_017413] [ENST00000332696] |
| NM_006360 | PCID1 | Homo sapiens PCI domain containing 1 (herpesvirus entry mediator) (PCID1), mRNA [NM_006360] |
| A_24_P204474 | A_24_P204474 | Unknown |
| NM_018943 | TUBA8 | Homo sapiens tubulin, alpha 8 (TUBA8), mRNA [NM_018943] |
| A_32_P208856 | A_32_P208856 | Unknown |
| NM_001404 | EEF1G | Homo sapiens eukaryotic translation elongation factor 1 gamma (EEF1G), mRNA [NM_001404] |
| ENST00000313620 | LOC342994 | PREDICTED: Homo sapiens similar to ribosomal protein L34 (LOC342994), mRNA [XM_938484] |
| A_24_P126902 | A_24_P126902 | Unknown |
| THC2506377 | THC2506377 | HSU02032 ribosomal protein L23a {Homo sapiens} (exp = −1; wgp = 0; cg = 0), partial (92%) [THC2506377] |
| NM_000998 | RPL37A | Homo sapiens ribosomal protein L37a (RPL37A), mRNA [NM_000998] |
| AY033611 | AY033611 | Homo sapiens placenta immunoregulatory factor PLIF mRNA, complete cds. [AY033611] |
| NM_000454 | SOD1 | Homo sapiens superoxide dismutase 1, soluble (amyotrophic lateral sclerosis 1 (adult)) (SOD1), mRNA [NM_000454] |
| NM_005340 | HINT1 | Homo sapiens histidine triad nucleotide binding protein 1 (HINT 1), mRNA [NM_005340] |
| NM_006013 | RPL10 | Homo sapiens ribosomal protein L10 (RPL10), mRNA [NM_006013] |
| NM_080746 | RPL10L | Homo sapiens ribosomal protein L10-like (RPL10L), mRNA [NM_080746] |
| ENST00000361390 | ND1 | NADH-ubiquinone oxidoreductase chain 1 (EC 1.6.5.3) (NADH dehydrogenase subunit 1). [Source: Uniprot/SWISSPROT;Acc: P03886] [ENST00000361390] |
| A_24_P50489 | A_24_P50489 | Unknown |
| NM_005437 | NCOA4 | Homo sapiens nuclear receptor coactivator 4 (NCOA4), mRNA [NM_005437] |
| NM_175839 | SMOX | Homo sapiens spertnine oxidase (SMOX), transcript variant 1, mRNA [NM_175839] |
| XR_019242 | LOC402149 | PREDICTED: Homo sapiens similar to ribosomal protein L28 (LOC402149), mRNA [XR_019242] |
| NM_002568 | PABPC1 | Homo sapiens poly(A) binding protein, cytoplasmic 1 (PABPC1), mRNA [NM_002568] |
| NP1252191 | NP1252191 | GB|AACCO2000041.1|EAL24419.1 similar to 60S ribosomal protein L32 [Homo sapiens] [NP1252191] |
| NM_000997 | RPL37 | Homo sapiens ribosomal protein L37 (RPL37), mRNA [NM_000997] |
| NM_000986 | RPL24 | Homo sapiens ribosomal protein L24 (RPL24), mRNA [NM_000986] |
| NM_003752 | EIF3S8 | Homo sapiens eukaryotic translation initiation factor 3, subunit 8, 110 kDa (EIF3S8), transcript variant 1, mRNA [NM_003752] |
| NM_015933 | CCDC72 | Homo sapiens coiled-coil domain containing 72 (CCDC72), mRNA [NM_015933] |
| XR_019052 | LOC391738 | PREDICTED: Homo sapiens similar to 60S ribosomal protein L29 (Cell surface heparin-binding protein HIP) (LOC391738), mRNA [XR_019052] |
| NM_004548 | NDUFB10 | Homo sapiens NADH dehydrogenase (ubiquinone) 1 beta subcomplex, 10, 22 kDa (NDUFB10), mRNA [NM_004548] |
| XR_018303 | LOC648378 | PREDICTED: Homo sapiens similar to ribosomal protein S14 (LOC648378), mRNA [XR_018303] |
| XM_928025 | LOC644937 | PREDICTED: Homo sapiens similar to 60S ribosomal protein L10 (QM protein) (Tumor suppressor QM) (Laminin receptor homolog) (LOC644937), mRNA [XM_928025] |
| NM_032310 | C9orf89 | Homo sapiens chromosome 9 open reading frame 89 (C9orf89), mRNA [NM_032310] |
| AL137354 | AL137354 | Homo sapiens mRNA; cDNA DKEZp434A0326 (from clone DKEZp434A0326). [AL137354] |

TABLE 13-continued

Gene list generated at the inclusion criteria of p ≤ 0.05 and the log-median-ratio
being below being at least "1" or above, or being "−1" or below.

| GenBank Accession | GeneName | Description |
| --- | --- | --- |
| NM_002032 | FTH1 | Homo sapiens ferritin, heavy polypeptide 1 (FTH1), mRNA [NM_002032] |
| NM_001101 | ACTB | Homo sapiens actin, beta (ACTB), mRNA [NM_001101] |
| XM_930195 | hCG_18290 | PREDICTED: Homo sapiens similar to 60S ribosomal protein L32 (LOC644907), mRNA [XM_930195] |
| BC089454 | BC089454 | Homo sapiens cDNA clone MGC: 105145 IMAGE: 30563285, complete cds. [BC089454] |
| NM_001865 | COX7A2 | Homo sapiens cytochrome c oxidase subunit VIIa polypeptide 2 (liver) (COX7A2), mRNA [NM_001865] |
| NM_005319 | HIST1H1C | Homo sapiens histone cluster 1, H1c (HIST1H1C), mRNA [NM_005319] |
| NM_001080544 | LOC653314 | Homo sapiens similar to ribosomal protein L19 (LOC653314), mRNA [NM_001080544] |
| NM_021009 | UBC | Homo sapiens ubiquitin C (UBC), mRNA [NM_021009] |
| ENST00000333351 | ENST00000333351 | PREDICTED: Homo sapiens hypothetical LOC391504 (LOC391504), mRNA [XR_018627] |
| A_24_P843921 | A_24_P843921 | Unknown |
| NM_198253 | TERT | Homo sapiens telomerase reverse transcriptase (TERT), transcript variant 1, mRNA [NM_198253] |
| NM_198253 | TERT | Homo sapiens telomerase reverse transcriptase (TERT), transcript variant 1, mRNA [NM_198253] |
| NM_130766 | SKIP | Homo sapiens skeletal muscle and kidney enriched inositol phosphatase (SKIP), transcript variant 2, mRNA [NM_130766] |
| NM_002617 | PEX10 | Homo sapiens peroxisome biogenesis factor 10 (PEX10), transcript variant 2, mRNA [NM_002617] |
| NM_173833 | SCARA5 | Homo sapiens scavenger receptor class A, member 5 (putative) (SCARA5), mRNA [NM_173833] |
| NM_152339 | SPATA2L | Homo sapiens spermatogenesis associated 2-like (SPATA2L), mRNA [NM_152339] |
| NM_007185 | TNRC4 | Homo sapiens trinucleotide repeat containing 4 (TNRC4), mRNA [NM_007185] |
| NM_182688 | UBE2G2 | Homo sapiens ubiquitin-conjugating enzyme E2G 2 (UBC7 homolog, yeast) (UBE2G2), transcript variant 2, mRNA [NM_182688] |
| A_24_P636974 | A_24_P636974 | Unknown |
| NM_015901 | NUDT13 | Homo sapiens nudix (nucleoside diphosphate linked moiety X)-type motif 13 (NUDT13), mRNA [NM_015901] |
| NM_002141 | HOXA4 | Homo sapiens homeobox A4 (HOXA4), mRNA [NM_002141] |
| NM_001837 | CCR3 | Homo sapiens chemokine (C—C motif) receptor 3 (CCR3), transcript variant 1, mRNA [NM_001837] |
| NM_201999 | ELF2 | Homo sapiens E74-like factor 2 (ets domain transcription factor) (ELF2), transcript variant 1, mRNA [NM_201999] |
| AK000420 | AK000420 | Homo sapiens cDNA FLJ20413 fis, clone KAT02170. [AK000420] |
| NM_024812 | BAALC | Homo sapiens brain and acute leukemia, cytoplasmic (BAALC), transcript variant 1, mRNA [NM_024812] |
| A_23_P129405 | A_23_P129405 | Unknown |
| NM_000539 | RHO | Homo sapiens rhodopsin (opsin 2, rod pigment) (retinitis pigmentosa 4, autosomal dominant) (RHO), mRNA [NM_000539] |
| NM_198253 | TERT | Homo sapiens telomerase reverse transcriptase (TERT), transcript variant 1, mRNA [NM_198253] |
| XM_372498 | LOC390427 | PREDICTED: Homo sapiens similar to TBP-associated factor 15 isoform 1 (LOC390427), mRNA [XM_372498] |
| THC2726959 | THC2726959 | Unknown |
| THC2760960 | THC2760960 | Unknown |
| THC2718728 | THC2718728 | Unknown |
| NM_173728 | ARHGEF15 | Homo sapiens Rho guanine nucleotide exchange factor (GEF) 15 (ARHGEF15), mRNA [NM_173728] |
| NM_198253 | TERT | Homo sapiens telomerase reverse transcriptase (TERT), transcript variant 1, mRNA [NM_198253] |
| THC2667666 | THC2667666 | Unknown |
| A_24_P636834 | A_24_P636834 | Unknown |
| NM_173078 | SLITRK4 | Homo sapiens SLIT and NTRK-like family, member 4 (SLITRK4), mRNA [NM_173078] |
| NM_002307 | LGALS7 | Homo sapiens lectin, galactoside-binding, soluble, 7 (galectin 7) (LGALS7), mRNA [NM_002307] |
| ENST00000248668 | LRFN1 | Leucine-rich repeat and fibronectin type III domain-containing protein 1 (Fragment). [Source: Uniprot/SPTREMBL;Acc: Q9P244] [ENST00000248668] |
| THC2532155 | THC2532155 | Q8K2W0_MOUSE (Q8K2W0) Procollagen, type IX, alpha 2, partial (3%) [THC2532155] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| ENST00000325151 | ENST00000325151 | Small inducible cytokine A27 precursor (CCL27) (CC chemokine ILC) (IL-11R-alpha-locus chemokine) (Skinkine) (ESkine) (Cutaneous T-cell-attracting chemokine) (CTACK). [Source: Uniprot/SWISSPROT;Acc: Q9Y4X3] [ENST00000325151] |
| NM_006266 | RALGDS | Homo sapiens ral guanine nucleotide dissociation stimulator (RALGDS), transcript variant 1, mRNA [NM_006266] |
| NM_198253 | TERT | Homo sapiens telomerase reverse transcriptase (TERT), transcript variant 1, mRNA [NM_198253] |
| NM_004703 | RABEP1 | Homo sapiens rabaptin, RAB GTPase binding effector protein 1 (RABEPI), transcript variant 1, mRNA [NM_004703] |
| NM_001138 | AGRP | Homo sapiens agouti related protein homolog (mouse) (AGRP), transcript variant 1, mRNA [NM_001138] |
| XM_001133403 | LOC732417 | PREDICTED: Homo sapiens hypothetical protein LOC732417 (LOC732417), mRNA [XM_001133403] |
| NM_207377 | UNQ9438 | Homo sapiens TIMM9 (UNQ9438), mRNA [NM_207377] |
| NM_002307 | LGALS7 | Homo sapiens lectin, galactoside-binding, soluble, 7 (galectin 7) (LGALS7), mRNA [NM_002307] |
| BI262095 | BI262095 | BI262095 602953519T1 NIH_MGC_99 Homo sapiens cDNA clone IMAGE: 5087621 3', mRNA sequence [BI262095] |
| NM_145234 | CHRDL1 | Homo sapiens chordin-like 1 (CHRDL1), mRNA [NM_145234] |
| NM_016219 | MAN1B1 | Homo sapiens mannosidase, alpha, class 1B, member 1 (MAN1B1), mRNA [NM_0162191 |
| NM_018670 | MESP1 | Homo sapiens mesoderm posterior 1 homolog (mouse) (MESP1), mRNA [NM_018670] |
| NM_004819 | SYMPK | Homo sapiens symplekin (SYMPK), mRNA [NM_004819] |
| BU561469 | BU561469 | AGENCOURT_10278709 NIH_MGC_82 Homo sapiens cDNA clone 1MAGE: 6592525 5', mRNA sequence [BU561469] |
| NM_015088 | TNRC6B | Homo sapiens trinucleotide repeat containing 6B (TNRC6B), transcript variant 1, mRNA [NM_015088] |
| EN5T00000299974 | ENST00000299974 | ATP/GTP binding protein-like 1 [Source: RefSeq peptide;Acc: NP 689549] [ENST00000299974] |
| NM_175734 | C17orf74 | Homo sapiens chromosome 17 open reading frame 74 (C17orf74), mRNA [NM_175734] |
| NM_152384 | BBS5 | Homo sapiens Bardet-Biedl syndrome 5 (BBS5), mRNA [NM_152384] |
| J03651 | J03651 | Human DF3 breast carcinoma-associated antigen mRNA, partial cds. [J03651] |
| A_23_P46070 | A_23_P46070 | Unknown |
| NM_004750 | CRLF1 | Homo sapiens cytokine receptor-like factor 1 (CRLF1), mRNA [NM_004750] |
| NM_003508 | FZD9 | Homo sapiens frizzled homolog 9 (Drosophila) (FZD9), mRNA [NM_003508] |
| AL566332 | AL566332 | AL566332 AL566332 Homo sapiens FETAL BRAIN Homo sapiens cDNA clone CS0DF015YB18 3-PRIME, mRNA sequence [AL566332] |
| A_24_P144625 | A_24_P144625 | Unknown |
| AA418814 | AA418814 | AA418814 zw01a02.s1 Soares_NhHMPu_S1 Homo sapiens cDNA clone IMAGE: 767978 3', mRNA sequence [AA418814] |
| A_32_P186382 | A_32_P186382 | Unknown |
| NM_203374 | ZNF784 | Homo sapiens zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT;Acc: P30740] [ENST00000380739] |
| NM_012183 | FOXD3 | Homo sapiens forkhead box D3 (FOXD3), mRNA [NM_012183] |
| ENST00000328043 | ENST00000328043 | LRP11 protein (Fragment). [Source: Uniprot/SPTREMBL;Acc: Q96AT3] [ENST00000328043] |
| NM_019105 | TNXB | Homo sapiens tenascin XB (TNXB), transcript variant XB, mRNA [NM_019105] |
| ENST00000325371 | ENST00000325371 | Homo sapiens cDNA clone IMAGE: 4819956. [BC018035] |
| THC2504037 | THC2504037 | ALU1_HUMAN (P39188) Alu subfamily J sequence contamination warning entry, partial (7%) [THC2504037] |
| NM_174903 | RNF151 | Homo sapiens ring finger protein 151 (RNF151), mRNA [NM_174903] |
| NM_022555 | HLA-DRB3 | Homo sapiens major histocompatibility complex, class II, DR beta 3 (HLA-DRB3), mRNA [NM_022555] |
| ENST00000360514 | ENST00000360514 | Homo sapiens hypothetical LOC339483, mRNA (cDNA clone MGC: 52427 IMAGE: 4872239), complete cds. [BC041632] |
| THC2694242 | THC2694242 | Unknown |
| NM_138763 | BAX | Homo sapiens BCL2-associated X protein (BAX), transcript variant delta, mRNA [NM_1387631 |
| NM_002691 | POLD1 | Homo sapiens polymerase (DNA directed), delta 1, catalytic subunit 125 kDa (POLD1), mRNA [NM_002691] |

TABLE 13-continued

Gene list generated at the inclusion criteria of p ≤ 0.05 and the log-median-ratio being below being at least "1" or above, or being "−1" or below.

| GenBank Accession | GeneName | Description |
|---|---|---|
| ENST00000331849 | FLJ20581 | CDNA FLJ20581 fis, clone REC00491. [Source: Uniprot/SPTREMBL;Acc: Q9NWV3] [ENST00000331849] |
| XR_018717 | FDPSL4 | PREDICTED: Homo sapiens similar to farnesyl diphosphate synthase (LOC390580), mRNA [XR_018717] |
| NM_152418 | WDR21C | Homo sapiens WD repeat domain 21C (WDR21C), mRNA [NM_152418] |
| NM_203304 | RKHD1 | Homo sapiens ring finger and KH domain containing 1 (RKHD1), mRNA [NM_203304] |
| NM_018490 | LGR4 | Homo sapiens leucine-rich repeat-containing G protein-coupled receptor 4 (LGR4), mRNA [NM_018490] |
| NM_001611 | ACP5 | Homo sapiens acid phosphatase 5, tartrate resistant (ACP5), mRNA [NM_001611] |
| NM_174976 | ZDHHC22 | Homo sapiens zinc finger, DHHC-type containing 22 (ZDHHC22), mRNA [NM_174976] |
| CV575560 | CV575560 | oe37f10.y1 Human keratoconus cornea, unamplified, (od [CV575560] |

TABLE 14

Gene list generated at the inclusion criteria of p ≤ 0.05 and the log-median-ratio being at least "0.585" or above.

| GenBank Accession | Gene Name | Description |
|---|---|---|
| NR_001543 | TTTY14 | Homo sapiens testis-specific transcript, Y-linked 14 (TTTY14) on chromosome Y [NR_001543] |
| NM_004864 | GDF15 | Homo sapiens growth differentiation factor 15 (GDF15), mRNA [NM_004864] |
| BF822111 | BF822111 | BF822111 CM3-RT0011-051200-531-f10 RT0011 Homo sapiens cDNA, mRNA sequence [BF822111] |
| A_23_P329062 | A_23_P329062 | Unknown |
| NM_019064 | SDK2 | Homo sapiens sidekick homolog 2 (chicken) (SDK2), mRNA [NM_019064] |
| NM_145173 | DIRAS1 | Homo sapiens DIRAS family, GTP-binding RAS-like 1 (DIRAS1), mRNA [NM_145173] |
| NM_016434 | RTEL1 | Homo sapiens regulator of telomere elongation helicase 1 (RTEL1), transcript variant 1, mRNA [NM_016434] |
| NM_013246 | CLCF1 | Homo sapiens cardiotrophin-like cytokine factor 1 (CLCF1), mRNA [NM_013246] |
| THC2726026 | THC2726026 | Q3X600_9ACTN (Q3X600) Adenine deaminase, partial (4%) [THC2726026] |
| NM_178013 | PRIMA1 | Homo sapiens proline rich membrane anchor 1 (PRIMA1), mRNA [NM_178013] |
| AK091355 | LOC284926 | Homo sapiens cDNA FLJ34036 fis, clone FCBBF2005069. [AK091355] |
| A_24_P853410 | A_24_P853410 | Unknown |
| A_24_P780709 | A_24_P780709 | Unknown |
| NM_178428 | LCE2A | Homo sapiens late cornified envelope 2A (LCE2A), mRNA [NM_178428] |
| NM_006864 | LILRB3 | Homo sapiens leukocyte immunoglobulin-like receptor, subfamily B (with TM and ITIM domains), member 3 (LILRB3), transcript variant 2, mRNA [NM_006864] |
| AK057167 | AK057167 | Homo sapiens cDNA FLJ32605 fis, clone STOMA1000175. [AK057167] |
| NM_003748 | ALDH4A1 | Homo sapiens aldehyde dehydrogenase 4 family, member A1 (ALDH4A1), nuclear gene encoding mitochondrial protein, transcript variant P5CDhL, mRNA [NM_003748] |
| THC2679528 | THC2679528 | Unknown |
| AF355801 | CYP3A5 | Homo sapiens CYP3A5 mRNA, allele CYP3A5*3, exon 4B and partial cds, alternatively spliced. [AF355801] |
| NM_001005862 | ERBB2 | Homo sapiens v-erb-b2 erythroblastic leukemia viral oncogene homolog 2, neuro/glioblastoma derived oncogene homolog (avian) (ERBB2), transcript variant 2, mRNA [NM_001005862] |
| A_24_P471099 | A_24_P471099 | Unknown |
| NM_006283 | TACC1 | Homo sapiens transforming, acidic coiled-coil containing protein 1 (TACC1), mRNA [NM_006283] |
| NM_025004 | CCDC15 | Homo sapiens coiled-coil domain containing 15 (CCDC15), mRNA [NM_025004] |

TABLE 14-continued

Gene list generated at the inclusion criteria of p ≤ 0.05 and the
log-median-ratio being at least "0.585" or above.

| GenBank Accession | Gene Name | Description |
|---|---|---|
| NM_002124 | HLA-DRB1 | *Homo sapiens* major histocompatibility complex, class II, DR beta 1 (HLA-DRB1), mRNA [NM_002124] |
| NM_012435 | SHC2 | *Homo sapiens* SHC (Src homology 2 domain containing) transforming protein 2 (SHC2), mRNA [NM_012435] |
| AF116688 | AF116688 | *Homo sapiens* PRO2133 mRNA, complete cds. [AF116688] |
| NM_021959 | PPP1R11 | *Homo sapiens* protein phosphatase 1, regulatory (inhibitor) subunit 11 (PPP1R11), mRNA [NM_021959] |
| A_24_P786912 | A_24_P786912 | Unknown |
| NM_030914 | URM1 | *Homo sapiens* ubiquitin related modifier 1 homolog (*S. cerevisiae*) (URM1), mRNA [NM_030914] |
| NM_014408 | TRAPPC3 | *Homo sapiens* trafficking protein particle complex 3 (TRAPPC3), mRNA [NM_014408] |
| NM_003142 | SSB | *Homo sapiens* Sjogren syndrome antigen B (autoantigen La) (SSB), mRNA [NM_003142] |
| NM_031918 | KLF16 | *Homo sapiens* Kruppel-like factor 16 (KLF16), mRNA [NM_031918] |
| THC2700213 | THC2700213 | Q5VZP2_HUMAN (Q5VZP2) HERV-H LTR-associating 3, partial (21%) [THC2700213] |
| THC2553131 | THC2553131 | Q59FA2_HUMAN (Q59FA2) Splicing factor, arginine/serine-rich 1 (Splicing factor 2, alternate splicing factor) variant (Fragment), partial (18%) [THC2553131] |
| THC2729352 | THC2729352 | Unknown |
| NM_001492 | GDF1 | *Homo sapiens* growth differentiation factor 1 (GDF1), mRNA [NM_001492] |
| NM_006907 | PYCR1 | *Homo sapiens* pyrroline-5-carboxylate reductase 1 (PYCR1), transcript variant 1, mRNA [NM_006907] |
| NM_006653 | FRS3 | *Homo sapiens* fibroblast growth factor receptor substrate 3 (FRS3), mRNA [NM_006653] |
| AL096727 | AL096727 | *Homo sapiens* mRNA; cDNA DKFZp434B104 (from clone DKFZp434B104). [AL096727] |
| NM_022139 | GFRA4 | *Homo sapiens* GDNF family receptor alpha 4 (GFRA4), transcript variant 1, mRNA [NM_022139] |
| A_32_P161913 | A_32_P161913 | Unknown |
| AK074447 | FLJ23867 | *Homo sapiens* cDNA FLJ23867 fis, clone LNG09729. [AK074447] |
| NM_015271 | TRIM2 | *Homo sapiens* tripartite motif-containing 2 (TRIM2), mRNA [NM_015271] |
| A_32_P101195 | A_32_P101195 | Unknown |
| U19144 | GAGE3 | Human GAGE-3 protein mRNA, complete cds. [U19144] |
| THC2503819 | THC2503819 | BC010854 amyloid beta A4 precursor protein-binding, family B, member 1, isoform delta E9 {*Homo sapiens*} (exp = −1; wgp = 0; cg = 0), partial (22%) [THC2503819] |
| THC2618720 | THC2618720 | Unknown |
| NM_194248 | OTOF | *Homo sapiens* otoferlin (OTOF), transcript variant 1, mRNA [NM_194248] |
| NM_014580 | SLC2A8 | *Homo sapiens* solute carrier family 2, (facilitated glucose transporter) member 8 (SLC2A8), mRNA [NM_014580] |
| NM_080606 | BHLHB4 | *Homo sapiens* basic helix-loop-helix domain containing, class B, 4 (BHLHB4), mRNA [NM_080606] |
| NM_032478 | MRPL38 | *Homo sapiens* mitochondrial ribosomal protein L38 (MRPL38), nuclear gene encoding mitochondrial protein, mRNA [NM_032478] |
| A_32_P90178 | A_32_P90178 | Unknown |
| N75427 | N75427 | za82f07.s1 Soares_fetal_lung_NbHL19W *Homo sapiens* cDNA clone IMAGE: 299077 3' similar to gb: X69654 40S RIBOSOMAL PROTEIN S26 (HUMAN);, mRNA sequence [N75427] |
| A_32_P144634 | A_32_P144634 | Unknown |
| NM_015481 | ZNF385 | *Homo sapiens* zinc finger protein 385 (ZNF385), mRNA [NM_015481] |
| NM_001988 | EVPL | *Homo sapiens* envoplakin (EVPL), mRNA [NM_001988] |
| AK097411 | FLJ40092 | *Homo sapiens* cDNA FLJ40092 fis, clone TESTI2003756. [AK097411] |
| AA436686 | AA436686 | AA436686 zv59a12.s1 Soares_testis_NHT *Homo sapiens* cDNA clone IMAGE: 757918 3' similar to contains Alu repetitive element;, mRNA sequence [AA436686] |
| A_32_P227496 | A_32_P227496 | Unknown |
| BC024303 | FLJ35390 | *Homo sapiens* hypothetical protein FLJ35390, mRNA (cDNA clone IMAGE: 4328569), with apparent retained intron. [BC024303] |
| NM_003833 | MATN4 | *Homo sapiens* matrilin 4 (MATN4), transcript variant 1, mRNA [NM_003833] |
| XM_926898 | LOC643594 | PREDICTED: *Homo sapiens* similar to CG13731-PA (LOC643594), mRNA [XM_926898] |
| BX111592 | BX111592 | BX111592 Soares_testis_NHT *Homo sapiens* cDNA clone IMAGp998D162621, mRNA sequence [BX111592] |

TABLE 14-continued

Gene list generated at the inclusion criteria of p ≤ 0.05 and the
log-median-ratio being at least "0.585" or above.

| GenBank Accession | Gene Name | Description |
|---|---|---|
| NM_080825 | C20orf144 | Homo sapiens chromosome 20 open reading frame 144 (C20orf144), mRNA [NM_080825] |
| AF161342 | AF161342 | Homo sapiens HSPC079 mRNA, partial cds. [AF161342] |
| NM_003614 | GALR3 | Homo sapiens galanin receptor 3 (GALR3), mRNA [NM_003614] |
| NM_001005862 | ERBB2 | Homo sapiens v-erb-b2 erythroblastic leukemia viral oncogene homolog 2, neuro/glioblastoma derived oncogene homolog (avian) (ERBB2), transcript variant 2, mRNA [NM_001005862] |
| A_24_P461664 | A_24_P461664 | Unknown |
| NM_004609 | TCF15 | Homo sapiens transcription factor 15 (basic helix-loop-helix) (TCF15), mRNA [NM_004609] |
| X56681 | JUND | Human junD mRNA. [X56681] |
| ENST00000330598 | ENST00000330598 | Homo sapiens HSPC088 mRNA, partial cds. [AF161351] |
| NM_006270 | RRAS | Homo sapiens related RAS viral (r-ras) oncogene homolog (RRAS), mRNA [NM_006270] |
| NM_030974 | SHARPIN | Homo sapiens SHANK-associated RH domain interactor (SHARPIN), mRNA [NM_030974] |
| THC2744561 | THC2744561 | Unknown |
| NM_178430 | LCE2D | Homo sapiens late cornified envelope 2D (LCE2D), mRNA [NM_178430] |
| THC2529614 | THC2529614 | Q3VHI9_9SPHN (Q3VHI9) Manganese and iron superoxide dismutase precursor, partial (8%) [THC2529614] |
| AK096674 | AK096674 | Homo sapiens cDNA FLJ39355 fis, clone PEBLM2003426. [AK096674] |
| ENST00000356572 | ENST00000356572 | FAM39B protein. [Source: Uniprot/SPTREMBL; Acc: Q6GMS0] [ENST00000356572] |
| A_23_P105732 | A_23_P105732 | Unknown |
| NM_032789 | PARP10 | Homo sapiens poly (ADP-ribose) polymerase family, member 10 (PARP10), mRNA [NM_032789] |
| NM_005634 | SOX3 | Homo sapiens SRY (sex determining region Y)-box 3 (SOX3), mRNA [NM_005634] |
| BC035978 | ATP6V1B1 | Homo sapiens ATPase, H+ transporting, lysosomal 56/58 kDa, V1 subunit B1 (Renal tubular acidosis with deafness), mRNA (cDNA clone MGC: 32642 IMAGE: 4594171), complete cds. [BC035978] |
| A_32_P11425 | A_32_P11425 | Unknown |
| BX094246 | BX094246 | BX094246 Soares_testis_NHT Homo sapiens cDNA clone IMAGp998N201862, mRNA sequence [BX094246] |
| THC2646425 | THC2646425 | Unknown |
| BC000408 | ACAT2 | Homo sapiens acetyl-Coenzyme A acetyltransferase 2 (acetoacetyl Coenzyme A thiolase), mRNA (cDNA clone MGC: 8573 IMAGE: 2823036), complete cds. [BC000408] |
| AK055960 | AK055960 | Homo sapiens cDNA FLJ31398 fis, clone NT2NE1000175. [AK055960] |
| AF116619 | AF116619 | Homo sapiens PRO1051 mRNA, complete cds. [AF116619] |
| THC2641678 | THC2641678 | Unknown |
| NM_005781 | TNK2 | Homo sapiens tyrosine kinase, non-receptor, 2 (TNK2), transcript variant 1, mRNA [NM_005781] |
| A_32_P220567 | A_32_P220567 | Unknown |
| AF095737 | SARDH | Homo sapiens SARDH mRNA, alternatively spliced, complete cds. [AF095737] |
| NM_004364 | CEBPA | Homo sapiens CCAAT/enhancer binding protein (C/EBP), alpha (CEBPA), mRNA [NM_004364] |
| A_32_P138939 | A_32_P138939 | Unknown |
| XM_209227 | LOC653464 | PREDICTED: Homo sapiens similar to SLIT-ROBO Rho GTPase-activating protein 2 (srGAP2) (Formin-binding protein 2) (LOC653464), mRNA [XM_209227] |
| NM_033506 | FBXO24 | Homo sapiens F-box protein 24 (FBXO24), transcript variant 1, mRNA [NM_033506] |
| THC2688313 | THC2688313 | Q6NUK7_HUMAN (Q6NUK7) LYN protein (Fragment), partial (9%) [THC2688313] |
| CN304251 | CN304251 | 17000532640995 GRN_ES Homo sapiens cDNA 5', mRNA sequence [CN304251] |
| A_32_P15706 | A_32_P15706 | Unknown |
| ENST00000332863 | ENST00000332863 | Q3RT01_RALME (Q3RT01) 2OG-Fe(II) oxygenase superfamily, partial (6%) [THC2740296] |
| AK027211 | AK027211 | Homo sapiens cDNA: FLJ23558 fis, clone LNG09703. [AK027211] |
| NM_001004321 | FLJ45445 | Homo sapiens FLJ45445 protein (FLJ45445), mRNA [NM_001004321] |
| A_24_P533990 | A_24_P533990 | Unknown |
| AF010315 | TP53I11 | Homo sapiens Pig11 (PIG11) mRNA, complete cds. [AF010315] |
| NM_022036 | GPRC5C | Homo sapiens G protein-coupled receptor, family C, group 5, member C (GPRC5C), transcript variant 1, mRNA [NM_022036] |

TABLE 14-continued

Gene list generated at the inclusion criteria of p ≤ 0.05 and the log-median-ratio being at least "0.585" or above.

| GenBank Accession | Gene Name | Description |
|---|---|---|
| NM_001005862 | ERBB2 | *Homo sapiens* v-erb-b2 erythroblastic leukemia viral oncogene homolog 2, neuro/glioblastoma derived oncogene homolog (avian) (ERBB2), transcript variant 2, mRNA [NM_001005862] |
| NM_019067 | GNL3L | *Homo sapiens* guanine nucleotide binding protein-like 3 (nucleolar)-like (GNL3L), mRNA [NM_019067] |
| NM_020182 | TMEPAI | *Homo sapiens* transmembrane, prostate androgen induced RNA (TMEPAI), transcript variant 1, mRNA [NM_020182] |
| THC2654007 | THC2654007 | Unknown |
| NM_006522 | WNT6 | *Homo sapiens* wingless-type MMTV integration site family, member 6 (WNT6), mRNA [NM_006522] |
| BC037255 | LOC389634 | *Homo sapiens* hypothetical LOC389634, mRNA (cDNA clone IMAGE: 4157715). [BC037255] |
| THC2693842 | THC2693842 | Unknown |
| A_32_P112100 | A_32_P112100 | Unknown |
| NM_005772 | RCL1 | *Homo sapiens* RNA terminal phosphate cyclase-like 1 (RCL1), mRNA [NM_005772] |
| THC2557053 | THC2557053 | Q95HC0_HUMAN (Q95HC0) HLA-F protein (Fragment), partial (15%) [THC2557053] |
| NM_024407 | NDUFS7 | *Homo sapiens* NADH dehydrogenase (ubiquinone) Fe—S protein 7, 20 kDa (NADH-coenzyme Q reductase) (NDUFS7), mRNA [NM_024407] |
| AI751518 | AI751518 | AI751518 cn10d09.y1 Normal Human Trabecular Bone Cells *Homo sapiens* cDNA clone NHTBC_cn10d09 random, mRNA sequence [AI751518] |
| NM_152636 | METT5D1 | *Homo sapiens* methyltransferase 5 domain containing 1 (METT5D1), mRNA [NM_152636] |
| THC2694215 | THC2694215 | Q3W9Q7_9ACTO (Q3W9Q7) Pyridoxamine 5'-phosphate oxidase, partial (3%) [THC2694215] |
| A_24_P350252 | A_24_P350252 | Unknown |
| NM_006885 | ATBF1 | *Homo sapiens* AT-binding transcription factor 1 (ATBF1), mRNA [NM_006885] |
| NM_020654 | SENP7 | *Homo sapiens* SUMO1/sentrin specific peptidase 7 (SENP7), transcript variant 1, mRNA [NM_020654] |
| NM_016148 | SHANK1 | *Homo sapiens* SH3 and multiple ankyrin repeat domains 1 (SHANK1), mRNA [NM_016148] |
| NP111770 | NP111770 | GB|M18679.1|AAA67373.1 putative [NP111770] |
| NM_018991 | DKFZP434A0131 | *Homo sapiens* DKFZp434A0131 protein (DKFZP434A0131), transcript variant 1, mRNA [NM_018991] |
| NM_000761 | CYP1A2 | *Homo sapiens* cytochrome P450, family 1, subfamily A, polypeptide 2 (CYP1A2), mRNA [NM_000761] |
| ENST00000355748 | ENST00000355748 | Endogenous retrovirus H D1 leader region/integrase-derived ORF1, ORF2, and putative envelope protein (Endogenous retrovirus H protease/integrase-derived ORF1, ORF2, and putative envelope protein). [Source: Uniprot/SPTREMBL; Acc: O00627] [ENST00000355748] |
| NM_145316 | C6orf128 | *Homo sapiens* chromosome 6 open reading frame 128 (C6orf128), mRNA [NM_145316] |
| NM_022978 | SERF1B | *Homo sapiens* small EDRK-rich factor 1B (centromeric) (SERF1B), mRNA [NM_022978] |
| NM_021637 | TMEM35 | *Homo sapiens* transmembrane protein 35 (TMEM35), mRNA [NM_021637] |
| XM_372331 | NKX1-2 | PREDICTED: *Homo sapiens* NK1 transcription factor related, locus 2 (*Drosophila*) (NKX1-2), mRNA [XM_372331] |
| NM_005581 | BCAM | *Homo sapiens* basal cell adhesion molecule (Lutheran blood group) (BCAM), transcript variant 1, mRNA [NM_005581] |
| AF119889 | AF119889 | *Homo sapiens* PRO2667 mRNA, complete cds. [AF119889] |
| NM_018231 | FLJ10815 | *Homo sapiens* amino acid transporter (FLJ10815), mRNA [NM_018231] |
| NM_032792 | ZBTB45 | *Homo sapiens* zinc finger and BTB domain containing 45 (ZBTB45), mRNA [NM_032792] |
| BC047032 | BC047032 | *Homo sapiens*, clone IMAGE: 3894105, mRNA. [BC047032] |
| ENST00000302932 | ENST00000302932 | Uncharacterized protein C20orf181 (Fragment). [Source: Uniprot/SPTREMBL; Acc: Q92884] [ENST00000302932] |
| BC040051 | BC040051 | *Homo sapiens*, clone IMAGE: 6018828, mRNA. [BC040051] |
| NM_139025 | ADAMTS13 | *Homo sapiens* ADAM metallopeptidase with thrombospondin type 1 motif, 13 (ADAMTS13), transcript variant 1, mRNA [NM_139025] |
| NM_152764 | C16orf73 | *Homo sapiens* chromosome 16 open reading frame 73 (C16orf73), mRNA [NM_152764] |
| NM_015444 | TMEM158 | *Homo sapiens* transmembrane protein 158 (TMEM158), mRNA [NM_015444] |
| NM_021170 | HES4 | *Homo sapiens* hairy and enhancer of split 4 (*Drosophila*) (HES4), mRNA [NM_021170] |

TABLE 14-continued

Gene list generated at the inclusion criteria of p ≤ 0.05 and the
log-median-ratio being at least "0.585" or above.

| GenBank Accession | Gene Name | Description |
|---|---|---|
| ENST00000380295 | ENST00000380295 | *Homo sapiens* cDNA clone IMAGE: 4794059, partial cds. [BC022562] |
| NM_184041 | ALDOA | *Homo sapiens* aldolase A, fructose-bisphosphate (ALDOA), transcript variant 2, mRNA [NM_184041] |
| NM_178354 | LCE1F | *Homo sapiens* late cornified envelope 1F (LCE1F), mRNA [NM_178354] |
| NM_020764 | CASKIN1 | *Homo sapiens* CASK interacting protein 1 (CASKIN1), mRNA [NM_020764] |
| NM_000427 | LOR | *Homo sapiens* loricrin (LOR), mRNA [NM_000427] |
| NM_031213 | FAM108A1 | *Homo sapiens* family with sequence similarity 108, member A1 (FAM108A1), mRNA [NM_031213] |
| NM_006778 | TRIM10 | *Homo sapiens* tripartite motif-containing 10 (TRIM10), transcript variant 1, mRNA [NM_006778] |
| ENST00000302932 | ENST00000302932 | Uncharacterized protein C20orf181 (Fragment). [Source: Uniprot/SPTREMBL; Acc: Q92884] [ENST00000302932] |
| THC2707284 | THC2707284 | Q214U3_RHOPA (Q214U3) Penicillin-binding protein 1C precursor, partial (3%) [THC2707284] |
| XR_015423 | LOC731262 | PREDICTED: *Homo sapiens* hypothetical protein LOC731262 (LOC731262), mRNA [XR_015423] |
| M14087 | M14087 | Human HL14 gene encoding beta-galactoside-binding lectin, 3' end, clone 2. [M14087] |
| A_32_P138933 | A_32_P138933 | Unknown |
| THC2728513 | THC2728513 | Q26195_PLAVI (Q26195) Pva1 protein, partial (20%) [THC2728513] |
| NM_001080414 | KIAA1509 | *Homo sapiens* KIAA1509 (KIAA1509), mRNA [NM_001080414] |
| X74861 | HPX-2 | *H. sapiens* HPX-2 mRNA. [X74861] |
| NM_020857 | VPS18 | *Homo sapiens* vacuolar protein sorting 18 homolog (*S. cerevisiae*) (VPS18), mRNA [NM_020857] |
| NM_001395 | DUSP9 | *Homo sapiens* dual specificity phosphatase 9 (DUSP9), mRNA [NM_001395] |
| NM_024742 | ARMC5 | *Homo sapiens* armadillo repeat containing 5 (ARMC5), mRNA [NM_024742] |
| BC063531 | SIN3B | *Homo sapiens* SIN3 homolog B, transcription regulator (yeast), mRNA (cDNA clone IMAGE: 4417458), complete cds. [BC063531] |
| NM_000501 | ELN | *Homo sapiens* elastin (supravalvular aortic stenosis, Williams-Beuren syndrome) (ELN), transcript variant 1, mRNA [NM_000501] |
| NM_020644 | TMEM9B | *Homo sapiens* TMEM9 domain family, member B (TMEM9B), mRNA [NM_020644] |
| THC2718728 | THC2718728 | Unknown |
| NM_032391 | PRAC | *Homo sapiens* small nuclear protein PRAC (PRAC), mRNA [NM_032391] |
| NM_033184 | KRTAP2-4 | *Homo sapiens* keratin associated protein 2-4 (KRTAP2-4), mRNA [NM_033184] |
| AK124097 | AK124097 | *Homo sapiens* cDNA FLJ42103 fis, clone TESOP2007041. [AK124097] |
| NM_014417 | BBC3 | *Homo sapiens* BCL2 binding component 3 (BBC3), mRNA [NM_014417] |
| AA151106 | AA151106 | zl48e07.s1 Soares_pregnant_uterus_NbHPU *Homo sapiens* cDNA clone IMAGE: 505188 3', mRNA sequence [AA151106] |
| A_24_P417922 | A_24_P417922 | Unknown |
| THC2666258 | THC2666258 | P13985_HUMAN (P13985) P25 protein, partial (97%) [THC2666258] |
| A_23_P47220 | A_23_P47220 | Unknown |
| NM_030966 | KRTAP1-3 | *Homo sapiens* keratin associated protein 1-3 (KRTAP1-3), mRNA [NM_030966] |
| BC017972 | BC017972 | *Homo sapiens*, clone IMAGE: 4693260, mRNA. [BC017972] |
| THC2610890 | THC2610890 | Q54TC3_DICDI (Q54TC3) FVYE domain-containing protein, partial (3%) [THC2610890] |
| ENST00000248606 | PMS2L3 | postmeiotic segregation increased 2-like 3 isoform 2 [Source: RefSeq_peptide; Acc: NP_001003686] [ENST00000248606] |
| M55405 | MUC3A | *Homo sapiens* mucin (MUC-3) mRNA, partial cds. [M55405] |
| NM_032560 | SMEK1 | *Homo sapiens* SMEK homolog 1, suppressor of mek1 (*Dictyostelium*) (SMEK1), mRNA [NM_032560] |
| NM_016378 | VCX2 | *Homo sapiens* variable charge, X-linked 2 (VCX2), mRNA [NM_016378] |
| NM_024029 | YIPF2 | *Homo sapiens* Yip1 domain family, member 2 (YIPF2), mRNA [NM_024029] |
| BC067830 | LOC653391 | *Homo sapiens* similar to hypothetical protein LOC153561, mRNA (cDNA clone MGC: 87375 IMAGE: 5299741), complete cds. [BC067830] |

TABLE 14-continued

Gene list generated at the inclusion criteria of p ≤ 0.05 and the
log-median-ratio being at least "0.585" or above.

| GenBank Accession | Gene Name | Description |
|---|---|---|
| CD607715 | CD607715 | CD607715 56025722H1 FLP *Homo sapiens* cDNA, mRNA sequence [CD607715] |
| BC080624 | BC080624 | *Homo sapiens* cDNA clone MGC: 99790 IMAGE: 6304510, complete cds. [BC080624] |
| NM_004386 | NCAN | *Homo sapiens* neurocan (NCAN), mRNA [NM_004386] |
| A_32_P62137 | A_32_P62137 | Unknown |
| NM_015559 | SETBP1 | *Homo sapiens* SET binding protein 1 (SETBP1), mRNA [NM_015559] |
| THC2664581 | THC2664581 | Q948Y7_VOLCA (Q948Y7) VMP3 protein, partial (3%) [THC2664581] |
| AK024440 | OXCT2 | *Homo sapiens* mRNA for FLJ00030 protein, partial cds. [AK024440] |
| NM_018645 | HES6 | *Homo sapiens* hairy and enhancer of split 6 (*Drosophila*) (HES6), mRNA [NM_018645] |
| XR_018458 | LOC440181 | PREDICTED: *Homo sapiens* hypothetical LOC440181 (LOC440181), mRNA [XR_018458] |
| NM_001037582 | SCD5 | *Homo sapiens* stearoyl-CoA desaturase 5 (SCD5), transcript variant 1, mRNA [NM_001037582] |
| ENST00000379563 | VISA | Mitochondrial antiviral-signaling protein (Interferon-beta promoter stimulator protein 1) (IPS-1) (Virus-induced-signaling adapter) (CARD adapter inducing interferon-beta) (Cardif) (Putative NF-kappa-B-activating protein 031N) . . . |
| THC2658813 | THC2658813 | Unknown |
| NM_017592 | IXL | *Homo sapiens* intersex-like (*Drosophila*) (IXL), mRNA [NM_017592] |
| THC2679528 | THC2679528 | Unknown |
| BU540282 | BU540282 | AGENCOURT_10326456 NIH_MGC_141 *Homo sapiens* cDNA clone IMAGE: 6571686 5', mRNA sequence [BU540282] |
| A_24_P392910 | A_24_P392910 | Unknown |
| NM_001080395 | AATK | *Homo sapiens* apoptosis-associated tyrosine kinase (AATK), mRNA [NM_001080395] |
| NM_032536 | NTNG2 | *Homo sapiens* netrin G2 (NTNG2), mRNA [NM_032536] |
| THC2579650 | THC2579650 | N47124 yy53b06.r1 Soares_multiple_sclerosis_2NbHMSP *Homo sapiens* cDNA clone IMAGE: 277235 5', mRNA sequence [N47124] |
| NM_147150 | PALM2-AKAP2 | *Homo sapiens* PALM2-AKAP2 protein (PALM2-AKAP2), transcript variant 2, mRNA [NM_147150] |
| A_24_P341616 | A_24_P341616 | Unknown |
| AA484677 | AA484677 | AA484677 ne64a07.s1 NCI_CGAP_Alv1 *Homo sapiens* cDNA clone IMAGE: 909012, mRNA sequence [AA484677] |
| XR_015273 | LOC728371 | PREDICTED: *Homo sapiens* similar to ankyrin repeat domain 20A (LOC728371), mRNA [XR_015273] |
| AB014602 | SLC24A1 | *Homo sapiens* mRNA for KIAA0702 protein, partial cds. [AB014602] |
| NM_024897 | PAQR6 | *Homo sapiens* progestin and adipoQ receptor family member VI (PAQR6), transcript variant 1, mRNA [NM_024897] |
| NM_181688 | KRTAP10-10 | *Homo sapiens* keratin associated protein 10-10 (KRTAP10-10), mRNA [NM_181688] |
| THC2654039 | THC2654039 | ALU2_HUMAN (P39189) Alu subfamily SB sequence contamination warning entry, partial (4%) [THC2654039] |
| NM_033377 | CGB1 | *Homo sapiens* chorionic gonadotropin, beta polypeptide 1 (CGB1), mRNA [NM_033377] |
| AW467174 | AW467174 | AW467174 ha35g06.x1 NCI_CGAP_Kid12 *Homo sapiens* cDNA clone IMAGE: 2875738 3' similar to gb: X60673_rna1 GTP: AMP PHOSPHOTRANSFERASE MITOCHONDRIAL (HUMAN);, mRNA sequence [AW467174] |
| NM_001080209 | TTMA | *Homo sapiens* two transmembrane domain family member A (TTMA), mRNA [NM_001080209] |
| A_32_P235293 | A_32_P235293 | Unknown |
| NM_004785 | SLC9A3R2 | *Homo sapiens* solute carrier family 9 (sodium/hydrogen exchanger), member 3 regulator 2 (SLC9A3R2), mRNA [NM_004785] |
| NM_007056 | SFRS16 | *Homo sapiens* splicing factor, arginine/serine-rich 16 (SFRS16), mRNA [NM_007056] |
| NM_012148 | DUX3 | *Homo sapiens* double homeobox, 3 (DUX3), mRNA [NM_012148] |
| NM_001005862 | ERBB2 | *Homo sapiens* v-erb-b2 erythroblastic leukemia viral oncogene homolog 2, neuro/glioblastoma derived oncogene homolog (avian) (ERBB2), transcript variant 2, mRNA [NM_001005862] |
| ENST00000340381 | ENST00000340381 | Novel protein. [Source: Uniprot/SPTREMBL; Acc: Q5SNT2] [ENST00000340381] |
| AK096255 | AK096255 | *Homo sapiens* cDNA FLJ38936 fis, clone NT2NE2015275. [AK096255] |

TABLE 14-continued

Gene list generated at the inclusion criteria of p ≤ 0.05 and the
log-median-ratio being at least "0.585" or above.

| GenBank Accession | Gene Name | Description |
| --- | --- | --- |
| A_23_P211603 | A_23_P211603 | Unknown |
| AK098372 | AK098372 | Homo sapiens cDNA FLJ25506 fis, clone CBR05185. [AK098372] |
| NM_000683 | ADRA2C | Homo sapiens adrenergic, alpha-2C-, receptor (ADRA2C), mRNA [NM_000683] |
| A_23_P113762 | A_23_P113762 | Unknown |
| A_23_P119407 | A_23_P119407 | Unknown |
| AK127569 | AK127569 | Homo sapiens cDNA FLJ45662 fis, clone CTONG2027150. [AK127569] |
| NM_014460 | CSDC2 | Homo sapiens cold shock domain containing C2, RNA binding (CSDC2), mRNA [NM_014460] |
| NM_033315 | RASL10B | Homo sapiens RAS-like, family 10, member B (RASL10B), mRNA [NM_033315] |
| NM_013356 | SLC16A8 | Homo sapiens solute carrier family 16, member 8 (monocarboxylic acid transporter 3) (SLC16A8), mRNA [NM_013356] |
| NM_152219 | GJC1 | Homo sapiens gap junction protein, chi 1, 31.9 kDa (GJC1), mRNA [NM_152219] |
| NM_013452 | VCX | Homo sapiens variable charge, X-linked (VCX), mRNA [NM_013452] |
| NM_015654 | NAT9 | Homo sapiens N-acetyltransferase 9 (NAT9), mRNA [NM_015654] |
| NM_004914 | RAB36 | Homo sapiens RAB36, member RAS oncogene family (RAB36), mRNA [NM_004914] |
| NM_015335 | THRAP2 | Homo sapiens thyroid hormone receptor associated protein 2 (THRAP2), mRNA [NM_015335] |
| NM_012147 | DUX2 | Homo sapiens double homeobox, 2 (DUX2), mRNA [NM_012147] |
| NM_000587 | C7 | Homo sapiens complement component 7 (C7), mRNA [NM_000587] |
| AK127966 | AK127966 | Homo sapiens cDNA FLJ46080 fis, clone TESTI2004971. [AK127966] |
| NM_014501 | UBE2S | Homo sapiens ubiquitin-conjugating enzyme E2S (UBE2S), mRNA [NM_014501] |
| THC2670603 | THC2670603 | BQ690425 AGENCOURT_8176614 NIH_MGC_110 Homo sapiens cDNA clone IMAGE: 6252524 5', mRNA sequence [BQ690425] |
| NM_001277 | CHKA | Homo sapiens choline kinase alpha (CHKA), transcript variant 1, mRNA [NM_001277] |
| ENST00000323800 | ENST00000323800 | CDNA FLJ25155 fis, clone CBR07976. [Source: Uniprot/SPTREMBL; Acc: Q96LR6] [ENST00000323800] |
| BQ018742 | BQ018742 | BQ018742 UI-H-DH1-awu-d-06-0-UI.s1 NCI_CGAP_DH1 Homo sapiens cDNA clone IMAGE: 5823701 3', mRNA sequence [BQ018742] |
| AK057576 | AK057576 | Homo sapiens cDNA FLJ33014 fis, clone THYMU1000382. [AK057576] |
| THC2737361 | THC2737361 | Q2IMJ3_ANADE (Q2IMJ3) LigA, partial (5%) [THC2737361] |
| XM_209227 | LOC653464 | PREDICTED: Homo sapiens similar to SLIT-ROBO Rho GTPase-activating protein 2 (srGAP2) (Formin-binding protein 2) (LOC653464), mRNA [XM_209227] |
| THC2755576 | THC2755576 | ALU1_HUMAN (P39188) Alu subfamily J sequence contamination warning entry, partial (13%) [THC2755576] |
| NM_020061 | OPN1LW | Homo sapiens opsin 1 (cone pigments), long-wave-sensitive (color blindness, protan) (OPN1LW), mRNA [NM_020061] |
| AK128592 | DNHD2 | Homo sapiens cDNA FLJ46751 fis, clone TRACH3022960, weakly similar to Dynein beta chain, ciliary. [AK128592] |
| NM_006889 | CD86 | Homo sapiens CD86 molecule (CD86), transcript variant 2, mRNA [NM_006889] |
| THC2528011 | THC2528011 | O46172_NEPCL (O46172) Dragline silk protein spidroin 1 (Fragment), partial (7%) [THC2528011] |
| A_23_P206568 | A_23_P206568 | Unknown |
| A_24_P383934 | A_24_P383934 | Unknown |
| NM_015341 | NCAPH | Homo sapiens non-SMC condensin I complex, subunit H (NCAPH), mRNA [NM_015341] |
| AK092875 | AK092875 | Homo sapiens cDNA FLJ35556 fis, clone SPLEN2004844. [AK092875] |
| THC2712687 | THC2712687 | Unknown |
| NM_005357 | LIPE | Homo sapiens lipase, hormone-sensitive (LIPE), mRNA [NM_005357] |
| NM_198253 | TERT | Homo sapiens telomerase reverse transcriptase (TERT), transcript variant 1, mRNA [NM_198253] |
| THC2520542 | THC2520542 | Q9XDH2_MYCTU (Q9XDH2) Proline-rich mucin homolog, partial (3%) [THC2520542] |
| NM_144670 | A2ML1 | Homo sapiens alpha-2-macroglobulin-like 1 (A2ML1), mRNA [NM_144670] |
| A_24_P638608 | A_24_P638608 | Unknown |
| THC2725746 | THC2725746 | Unknown |

TABLE 14-continued

Gene list generated at the inclusion criteria of p ≤ 0.05 and the log-median-ratio being at least "0.585" or above.

| GenBank Accession | Gene Name | Description |
|---|---|---|
| AK129982 | AK129982 | *Homo sapiens* cDNA FLJ26472 fis, clone KDN04506. [AK129982] |
| NM_198253 | TERT | *Homo sapiens* telomerase reverse transcriptase (TERT), transcript variant 1, mRNA [NM_198253] |
| NM_002102 | GYPE | *Homo sapiens* glycophorin E (GYPE), transcript variant 1, mRNA [NM_002102] |
| THC2732966 | THC2732966 | Unknown |
| BC040619 | LOC346887 | *Homo sapiens* similar to solute carrier family 16 (monocarboxylic acid transporters), member 14, mRNA (cDNA clone IMAGE: 5726657). [BC040619] |
| NM_198253 | TERT | *Homo sapiens* telomerase reverse transcriptase (TERT), transcript variant 1, mRNA [NM_198253] |
| NM_178831 | GATS | *Homo sapiens* opposite strand transcription unit to STAG3 (GATS), mRNA [NM_178831] |
| NM_018125 | ARHGEF10L | *Homo sapiens* Rho guanine nucleotide exchange factor (GEF) 10-like (ARHGEF10L), transcript variant 1, mRNA [NM_018125] |
| XM_001133211 | LOC729003 | PREDICTED: *Homo sapiens* hypothetical protein LOC729003 (LOC729003), mRNA [XM_001133211] |
| NM_016379 | VCX3A | *Homo sapiens* variable charge, X-linked 3A (VCX3A), mRNA [NM_016379] |
| NM_198253 | TERT | *Homo sapiens* telomerase reverse transcriptase (TERT), transcript variant 1, mRNA [NM_198253] |
| ENST00000359466 | ENST00000359466 | chromosome X open reading frame 18 (CXorf18), misc RNA [Source: RefSeq_dna; Acc: XR_018001] [ENST00000359466] |
| NM_033059 | KRTAP4-14 | *Homo sapiens* keratin associated protein 4-14 (KRTAP4-14), mRNA [NM_033059] |
| NM_016423 | ZNF219 | *Homo sapiens* zinc finger protein 219 (ZNF219), mRNA [NM_016423] |
| A_24_P940079 | A_24_P940079 | Unknown |
| AF116718 | HDLBP | *Homo sapiens* PRO2900 mRNA, complete cds. [AF116718] |
| NM_198253 | TERT | *Homo sapiens* telomerase reverse transcriptase (TERT), transcript variant 1, mRNA [NM_198253] |
| AL512711 | HDAC10 | *Homo sapiens* mRNA; cDNA DKFZp761B039 (from clone DKFZp761B039). [AL512711] |
| AK056449 | AK056449 | *Homo sapiens* cDNA FLJ31887 fis, clone NT2RP7003050. [AK056449] |
| NM_001008661 | CCBL2 | *Homo sapiens* cysteine conjugate-beta lyase 2 (CCBL2), transcript variant 1, mRNA [NM_001008661] |
| NM_020932 | MAGEE1 | *Homo sapiens* melanoma antigen family E, 1 (MAGEE1), mRNA [NM_020932] |
| NM_018402 | IL26 | *Homo sapiens* interleukin 26 (IL26), mRNA [NM_018402] |
| ENST00000357697 | ENST00000357697 | Unknown |
| A_24_P843921 | A_24_P843921 | Unknown |
| NM_198253 | TERT | *Homo sapiens* telomerase reverse transcriptase (TERT), transcript variant 1, mRNA [NM_198253] |
| NM_198253 | TERT | *Homo sapiens* telomerase reverse transcriptase (TERT), transcript variant 1, mRNA [NM_198253] |
| NM_130766 | SKIP | *Homo sapiens* skeletal muscle and kidney enriched inositol phosphatase (SKIP), transcript variant 2, mRNA [NM_130766] |
| NM_002617 | PEX10 | *Homo sapiens* peroxisome biogenesis factor 10 (PEX10), transcript variant 2, mRNA [NM_002617] |
| NM_173833 | SCARA5 | *Homo sapiens* scavenger receptor class A, member 5 (putative) (SCARA5), mRNA [NM_173833] |
| NM_152339 | SPATA2L | *Homo sapiens* spermatogenesis associated 2-like (SPATA2L), mRNA [NM_152339] |
| NM_007185 | TNRC4 | *Homo sapiens* trinucleotide repeat containing 4 (TNRC4), mRNA [NM_007185] |
| NM_182688 | UBE2G2 | *Homo sapiens* ubiquitin-conjugating enzyme E2G 2 (UBC7 homolog, yeast) (UBE2G2), transcript variant 2, mRNA [NM_182688] |
| A_24_P636974 | A_24_P636974 | Unknown |
| NM_015901 | NUDT13 | *Homo sapiens* nudix (nucleoside diphosphate linked moiety X)-type motif 13 (NUDT13), mRNA [NM_015901] |
| NM_002141 | HOXA4 | *Homo sapiens* homeobox A4 (HOXA4), mRNA [NM_002141] |
| NM_001837 | CCR3 | *Homo sapiens* chemokine (C-C motif) receptor 3 (CCR3), transcript variant 1, mRNA [NM_001837] |
| NM_201999 | ELF2 | *Homo sapiens* E74-like factor 2 (ets domain transcription factor) (ELF2), transcript variant 1, mRNA [NM_201999] |
| AK000420 | AK000420 | *Homo sapiens* cDNA FLJ20413 fis, clone KAT02170. [AK000420] |
| NM_024812 | BAALC | *Homo sapiens* brain and acute leukemia, cytoplasmic (BAALC), transcript variant 1, mRNA [NM_024812] |
| A_23_P129405 | A_23_P129405 | Unknown |
| NM_000539 | RHO | *Homo sapiens* rhodopsin (opsin 2, rod pigment) (retinitis pigmentosa 4, autosomal dominant) (RHO), mRNA [NM_000539] |

TABLE 14-continued

Gene list generated at the inclusion criteria of p ≤ 0.05 and the
log-median-ratio being at least "0.585" or above.

| GenBank Accession | Gene Name | Description |
|---|---|---|
| NM_198253 | TERT | *Homo sapiens* telomerase reverse transcriptase (TERT), transcript variant 1, mRNA [NM_198253] |
| XM_372498 | LOC390427 | PREDICTED: *Homo sapiens* similar to TBP-associated factor 15 isoform 1 (LOC390427), mRNA [XM_372498] |
| THC2726959 | THC2726959 | Unknown |
| THC2760960 | THC2760960 | Unknown |
| THC2718728 | THC2718728 | Unknown |
| NM_173728 | ARHGEF15 | *Homo sapiens* Rho guanine nucleotide exchange factor (GEF) 15 (ARHGEF15), mRNA [NM_173728] |
| NM_198253 | TERT | *Homo sapiens* telomerase reverse transcriptase (TERT), transcript variant 1, mRNA [NM_198253] |
| THC2667666 | THC2667666 | Unknown |
| A_24_P636834 | A_24_P636834 | Unknown |
| NM_173078 | SLITRK4 | *Homo sapiens* SLIT and NTRK-like family, member 4 (SLITRK4), mRNA [NM_173078] |
| NM_002307 | LGALS7 | *Homo sapiens* lectin, galactoside-binding, soluble, 7 (galectin 7) (LGALS7), mRNA [NM_002307] |
| ENST00000248668 | LRFN1 | Leucine-rich repeat and fibronectin type III domain-containing protein 1 (Fragment). [Source: Uniprot/SPTREMBL; Acc: Q9P244] [ENST00000248668] |
| THC2532155 | THC2532155 | Q8K2W0_MOUSE (Q8K2W0) Procollagen, type IX, alpha 2, partial (3%) [THC2532155] |
| ENST00000325151 | ENST00000325151 | Small inducible cytokine A27 precursor (CCL27) (CC chemokine ILC) (IL-11 R-alpha-locus chemokine) (Skinkine) (ESkine) (Cutaneous T-cell-attracting chemokine) (CTACK). [Source: Uniprot/SWISSPROT; Acc: Q9Y4X3] [ENST00000325151] |
| NM_006266 | RALGDS | *Homo sapiens* ral guanine nucleotide dissociation stimulator (RALGDS), transcript variant 1, mRNA [NM_006266] |
| NM_198253 | TERT | *Homo sapiens* telomerase reverse transcriptase (TERT), transcript variant 1, mRNA [NM_198253] |
| NM_004703 | RABEP1 | *Homo sapiens* rabaptin, RAB GTPase binding effector protein 1 (RABEP1), transcript variant 1, mRNA [NM_004703] |
| NM_001138 | AGRP | *Homo sapiens* agouti related protein homolog (mouse) (AGRP), transcript variant 1, mRNA [NM_001138] |
| XM_001133403 | LOC732417 | PREDICTED: *Homo sapiens* hypothetical protein LOC732417 (LOC732417), mRNA [XM_001133403] |
| NM_207377 | UNQ9438 | *Homo sapiens* TIMM9 (UNQ9438), mRNA [NM_207377] |
| NM_002307 | LGALS7 | *Homo sapiens* lectin, galactoside-binding, soluble, 7 (galectin 7) (LGALS7), mRNA [NM_002307] |
| BI262095 | BI262095 | BI262095 602953519T1 NIH_MGC_99 *Homo sapiens* cDNA clone IMAGE: 5087621 3', mRNA sequence [BI262095] |
| NM_145234 | CHRDL1 | *Homo sapiens* chordin-like 1 (CHRDL1), mRNA [NM_145234] |
| NM_016219 | MAN1B1 | *Homo sapiens* mannosidase, alpha, class 1B, member 1 (MAN1B1), mRNA [NM_016219] |
| NM_018670 | MESP1 | *Homo sapiens* mesoderm posterior 1 homolog (mouse) (MESP1), mRNA [NM_018670] |
| NM_004819 | SYMPK | *Homo sapiens* symplekin (SYMPK), mRNA [NM_004819] |
| BU561469 | BU561469 | AGENCOURT_10278709 NIH_MGC_82 *Homo sapiens* cDNA clone IMAGE: 6592525 5', mRNA sequence [BU561469] |
| NM_015088 | TNRC6B | *Homo sapiens* trinucleotide repeat containing 6B (TNRC6B), transcript variant 1, mRNA [NM_015088] |
| ENST00000299974 | ENST00000299974 | ATP/GTP binding protein-like 1 [Source: RefSeq_peptide; Acc: NP_689549] [ENST00000299974] |
| NM_175734 | C17orf74 | *Homo sapiens* chromosome 17 open reading frame 74 (C17orf74), mRNA [NM_175734] |
| NM_152384 | BBS5 | *Homo sapiens* Bardet-Biedl syndrome 5 (BBS5), mRNA [NM_152384] |
| J03651 | J03651 | Human DF3 breast carcinoma-associated antigen mRNA, partial cds. [J03651] |
| A_23_P46070 | A_23_P46070 | Unknown |
| NM_004750 | CRLF1 | *Homo sapiens* cytokine receptor-like factor 1 (CRLF1), mRNA [NM_004750] |
| NM_003508 | FZD9 | *Homo sapiens* frizzled homolog 9 (*Drosophila*) (FZD9), mRNA [NM_003508] |
| AL566332 | AL566332 | AL566332 AL566332 *Homo sapiens* FETAL BRAIN *Homo sapiens* cDNA clone CS0DF015YB18 3-PRIME, mRNA sequence [AL566332] |
| A_24_P144625 | A_24_P144625 | Unknown |
| AA418814 | AA418814 | AA418814 zw01a02.s1 Soares_NhHMPu_S1 *Homo sapiens* cDNA clone IMAGE: 767978 3', mRNA sequence [AA418814] |
| A_32_P186382 | A_32_P186382 | Unknown |
| NM_203374 | ZNF784 | *Homo sapiens* zinc finger protein 784 (ZNF784), mRNA [NM_203374] |

TABLE 14-continued

Gene list generated at the inclusion criteria of p ≤ 0.05 and the log-median-ratio being at least "0.585" or above.

| GenBank Accession | Gene Name | Description |
| --- | --- | --- |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | *Homo sapiens* forkhead box D3 (FOXD3), mRNA [NM_012183] |
| ENST00000328043 | ENST00000328043 | LRP11 protein (Fragment). [Source: Uniprot/SPTREMBL; Acc: Q96AT3] [ENST00000328043] |
| NM_019105 | TNXB | *Homo sapiens* tenascin XB (TNXB), transcript variant XB, mRNA [NM_019105] |
| ENST00000325371 | ENST00000325371 | *Homo sapiens* cDNA clone IMAGE: 4819956. [BC018035] |
| THC2504037 | THC2504037 | ALU1_HUMAN (P39188) Alu subfamily J sequence contamination warning entry, partial (7%) [THC2504037] |
| NM_174903 | RNF151 | *Homo sapiens* ring finger protein 151 (RNF151), mRNA [NM_174903] |
| NM_022555 | HLA-DRB3 | *Homo sapiens* major histocompatibility complex, class II, DR beta 3 (HLA-DRB3), mRNA [NM_022555] |
| ENST00000360514 | ENST00000360514 | *Homo sapiens* hypothetical LOC339483, mRNA (cDNA clone MGC: 52427 IMAGE: 4872239), complete cds. [BC041632] |
| THC2694242 | THC2694242 | Unknown |
| NM_138763 | BAX | *Homo sapiens* BCL2-associated X protein (BAX), transcript variant delta, mRNA [NM_138763] |
| NM_002691 | POLD1 | *Homo sapiens* polymerase (DNA directed), delta 1, catalytic subunit 125 kDa (POLD1), mRNA [NM_002691] |
| ENST00000331849 | FLJ20581 | CDNA FLJ20581 fis, clone REC00491. [Source: Uniprot/SPTREMBL; Acc: Q9NWV3] [ENST00000331849] |
| XR_018717 | FDPSL4 | PREDICTED: *Homo sapiens* similar to farnesyl diphosphate synthase (LOC390580), mRNA [XR_018717] |
| NM_152418 | WDR21C | *Homo sapiens* WD repeat domain 21C (WDR21C), mRNA [NM_152418] |
| NM_203304 | RKHD1 | *Homo sapiens* ring finger and KH domain containing 1 (RKHD1), mRNA [NM_203304] |
| NM_018490 | LGR4 | *Homo sapiens* leucine-rich repeat-containing G protein-coupled receptor 4 (LGR4), mRNA [NM_018490] |
| NM_001611 | ACP5 | *Homo sapiens* acid phosphatase 5, tartrate resistant (ACP5), mRNA [NM_001611] |
| NM_174976 | ZDHHC22 | *Homo sapiens* zinc finger, DHHC-type containing 22 (ZDHHC22), mRNA [NM_174976] |
| CV575560 | CV575560 | oe37f10.y1 Human keratoconus cornea, unamplified, (od [CV575560] |

TABLE 15

Gene list generated at the inclusion criteria of p ≤ 0.05 and the log-median-ratio being at least "1" or above.

| GenBank Accession | Gene Name | Description |
| --- | --- | --- |
| A_24_P843921 | A_24_P843921 | Unknown |
| NM_198253 | TERT | *Homo sapiens* telomerase reverse transcriptase (TERT), transcript variant 1, mRNA [NM_198253] |
| NM_198253 | TERT | *Homo sapiens* telomerase reverse transcriptase (TERT), transcript variant 1, mRNA [NM_198253] |
| NM_130766 | SKIP | *Homo sapiens* skeletal muscle and kidney enriched inositol phosphatase (SKIP), transcript variant 2, mRNA [NM_130766] |
| NM_002617 | PEX10 | *Homo sapiens* peroxisome biogenesis factor 10 (PEX10), transcript variant 2, mRNA [NM_002617] |
| NM_173833 | SCARA5 | *Homo sapiens* scavenger receptor class A, member 5 (putative) (SCARA5), mRNA [NM_173833] |
| NM_152339 | SPATA2L | *Homo sapiens* spermatogenesis associated 2-like (SPATA2L), mRNA [NM_152339] |
| NM_007185 | TNRC4 | *Homo sapiens* trinucleotide repeat containing 4 (TNRC4), mRNA [NM_007185] |
| NM_182688 | UBE2G2 | *Homo sapiens* ubiquitin-conjugating enzyme E2G 2 (UBC7 homolog, yeast) (UBE2G2), transcript variant 2, mRNA [NM_182688] |
| A_24_P636974 | A_24_P636974 | Unknown |
| NM_015901 | NUDT13 | *Homo sapiens* nudix (nucleoside diphosphate linked moiety X)-type motif 13 (NUDT13), mRNA [NM_015901] |

TABLE 15-continued

Gene list generated at the inclusion criteria of p ≤ 0.05 and
the log-median-ratio being at least "1" or above.

| GenBank Accession | Gene Name | Description |
|---|---|---|
| NM_002141 | HOXA4 | *Homo sapiens* homeobox A4 (HOXA4), mRNA [NM_002141] |
| NM_001837 | CCR3 | *Homo sapiens* chemokine (C-C motif) receptor 3 (CCR3), transcript variant 1, mRNA [NM_001837] |
| NM_201999 | ELF2 | *Homo sapiens* E74-like factor 2 (ets domain transcription factor) (ELF2), transcript variant 1, mRNA [NM_201999] |
| AK000420 | AK000420 | *Homo sapiens* cDNA FLJ20413 fis, clone KAT02170. [AK000420] |
| NM_024812 | BAALC | *Homo sapiens* brain and acute leukemia, cytoplasmic (BAALC), transcript variant 1, mRNA [NM_024812] |
| A_23_P129405 | A_23_P129405 | Unknown |
| NM_000539 | RHO | *Homo sapiens* rhodopsin (opsin 2, rod pigment) (retinitis pigmentosa 4, autosomal dominant) (RHO), mRNA [NM_000539] |
| NM_198253 | TERT | *Homo sapiens* telomerase reverse transcriptase (TERT), transcript variant 1, mRNA [NM_198253] |
| XM_372498 | LOC390427 | PREDICTED: *Homo sapiens* similar to TBP-associated factor 15 isoform 1 (LOC390427), mRNA [XM_372498] |
| THC2726959 | THC2726959 | Unknown |
| THC2760960 | THC2760960 | Unknown |
| THC2718728 | THC2718728 | Unknown |
| NM_173728 | ARHGEF15 | *Homo sapiens* Rho guanine nucleotide exchange factor (GEF) 15 (ARHGEF15), mRNA [NM_173728] |
| NM_198253 | TERT | *Homo sapiens* telomerase reverse transcriptase (TERT), transcript variant 1, mRNA [NM_198253] |
| THC2667666 | THC2667666 | Unknown |
| A_24_P636834 | A_24_P636834 | Unknown |
| NM_173078 | SLITRK4 | *Homo sapiens* SLIT and NTRK-like family, member 4 (SLITRK4), mRNA [NM_173078] |
| NM_002307 | LGALS7 | *Homo sapiens* lectin, galactoside-binding, soluble, 7 (galectin 7) (LGALS7), mRNA [NM_002307] |
| ENST00000248668 | LRFN1 | Leucine-rich repeat and fibronectin type III domain-containing protein 1 (Fragment). [Source: Uniprot/SPTREMBL; Acc: Q9P244] [ENST00000248668] |
| THC2532155 | THC2532155 | Q8K2W0_MOUSE (Q8K2W0) Procollagen, type IX, alpha 2, partial (3%) [THC2532155] |
| ENST00000325151 | ENST00000325151 | Small inducible cytokine A27 precursor (CCL27) (CC chemokine ILC) (IL- 11 R-alpha-locus chemokine) (Skinkine) (ESkine) (Cutaneous T-cell- attracting chemokine) (CTACK). [Source: Uniprot/SWISSPROT; Acc: Q9Y4X3] [ENST00000325151] |
| NM_006266 | RALGDS | *Homo sapiens* ral guanine nucleotide dissociation stimulator (RALGDS), transcript variant 1, mRNA [NM_006266] |
| NM_198253 | TERT | *Homo sapiens* telomerase reverse transcriptase (TERT), transcript variant 1, mRNA [NM_198253] |
| NM_004703 | RABEP1 | *Homo sapiens* rabaptin, RAB GTPase binding effector protein 1 (RABEP1), transcript variant 1, mRNA [NM_004703] |
| NM_001138 | AGRP | *Homo sapiens* agouti related protein homolog (mouse) (AGRP), transcript variant 1, mRNA [NM_001138] |
| XM_001133403 | LOC732417 | PREDICTED: *Homo sapiens* hypothetical protein LOC732417 (LOC732417), mRNA [XM_001133403] |
| NM_207377 | UNQ9438 | *Homo sapiens* TIMM9 (UNQ9438), mRNA [NM_207377] |
| NM_002307 | LGALS7 | *Homo sapiens* lectin, galactoside-binding, soluble, 7 (galectin 7) (LGALS7), mRNA [NM_002307] |
| BI262095 | BI262095 | BI262095 602953519T1 NIH_MGC_99 *Homo sapiens* cDNA clone IMAGE: 5087621 3', mRNA sequence [BI262095] |
| NM_145234 | CHRDL1 | *Homo sapiens* chordin-like 1 (CHRDL1), mRNA [NM_145234] |
| NM_016219 | MAN1B1 | *Homo sapiens* mannosidase, alpha, class 1B, member 1 (MAN1B1), mRNA [NM_016219] |
| NM_018670 | MESP1 | *Homo sapiens* mesoderm posterior 1 homolog (mouse) (MESP1), mRNA [NM_018670] |
| NM_004819 | SYMPK | *Homo sapiens* symplekin (SYMPK), mRNA [NM_004819] |
| BU561469 | BU561469 | AGENCOURT_10278709 NIH_MGC_82 *Homo sapiens* cDNA clone IMAGE: 6592525 5', mRNA sequence [BU561469] |
| NM_015088 | TNRC6B | *Homo sapiens* trinucleotide repeat containing 6B (TNRC6B), transcript variant 1, mRNA [NM_015088] |
| ENST00000299974 | ENST00000299974 | ATP/GTP binding protein-like 1 [Source: RefSeq_peptide; Acc: NP_689549] [ENST00000299974] |
| NM_175734 | C17orf74 | *Homo sapiens* chromosome 17 open reading frame 74 (C17orf74), mRNA [NM_175734] |
| NM_152384 | BBS5 | *Homo sapiens* Bardet-Biedl syndrome 5 (BBS5), mRNA [NM_152384] |
| J03651 | J03651 | Human DF3 breast carcinoma-associated antigen mRNA, partial cds. [J03651] |
| A_23_P46070 | A_23_P46070 | Unknown |
| NM_004750 | CRLF1 | *Homo sapiens* cytokine receptor-like factor 1 (CRLF1), mRNA [NM_004750] |

TABLE 15-continued

Gene list generated at the inclusion criteria of p ≤ 0.05 and
the log-median-ratio being at least "1" or above.

| GenBank Accession | Gene Name | Description |
|---|---|---|
| NM_003508 | FZD9 | *Homo sapiens* frizzled homolog 9 (*Drosophila*) (FLD9), mRNA [NM_003508] |
| AL566332 | AL566332 | AL566332 AL566332 *Homo sapiens* FETAL BRAIN *Homo sapiens* cDNA clone CS0DF015YB18 3-PRIME, mRNA sequence [AL566332] |
| A_24_P144625 | A_24_P144625 | Unknown |
| AA418814 | AA418814 | AA418814 zw01a02.s1 Soares_NhHMPu_S1 *Homo sapiens* cDNA clone IMAGE: 767978 3', mRNA sequence [AA418814] |
| A_32_P186382 | A_32_P186382 | Unknown |
| NM_203374 | ZNF784 | *Homo sapiens* zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | *Homo sapiens* forkhead box D3 (FOXD3), mRNA [NM_012183] |
| ENST00000328043 | ENST00000328043 | LRP11 protein (Fragment). [Source: Uniprot/SPTREMBL; Acc: Q96AT3] [ENST00000328043] |
| NM_019105 | TNXB | *Homo sapiens* tenascin XB (TNXB), transcript variant XB, mRNA [NM_019105] |
| ENST00000325371 | ENST00000325371 | *Homo sapiens* cDNA clone IMAGE: 4819956. [BC018035] |
| THC2504037 | THC2504037 | ALU1_HUMAN (P39188) Alu subfamily J sequence contamination warning entry, partial (7%) [THC2504037] |
| NM_174903 | RNF151 | *Homo sapiens* ring finger protein 151 (RNF151), mRNA [NM_174903] |
| NM_022555 | HLA-DRB3 | *Homo sapiens* major histocompatibility complex, class II, DR beta 3 (HLA-DRB3), mRNA [NM_022555] |
| ENST00000360514 | ENST00000360514 | *Homo sapiens* hypothetical LOC339483, mRNA (cDNA clone MGC: 52427 IMAGE: 4872239), complete cds. [BC041632] |
| THC2694242 | THC2694242 | Unknown |
| NM_138763 | BAX | *Homo sapiens* BCL2-associated X protein (BAX), transcript variant delta, mRNA [NM_138763] |
| NM_002691 | POLD1 | *Homo sapiens* polymerase (DNA directed), delta 1, catalytic subunit 125 kDa (POLD1), mRNA [NM_002691] |
| ENST00000331849 | FLJ20581 | CDNA FLJ20581 fis, clone KEC00491. [Source: Uniprot/SPTREMBL; Acc: Q9NWV3] [ENST00000331849] |
| XR_018717 | FDPSL4 | PREDICTED: *Homo sapiens* similar to farnesyl diphosphate synthase (LOC390580), mRNA [XR_018717] |
| NM_152418 | WDR21C | *Homo sapiens* WD repeat domain 21C (WDR21C), mRNA [NM_152418] |
| NM_203304 | RKHD1 | *Homo sapiens* ring finger and KH domain containing 1 (RKHD1), mRNA [NM_203304] |
| NM_018490 | LGR4 | *Homo sapiens* leucine-rich repeat-containing G protein-coupled receptor 4 (LGR4), mRNA [NM_018490] |
| NM_001611 | ACP5 | *Homo sapiens* acid phosphatase 5, tartrate resistant (ACP5), mRNA [NM_001611] |
| NM_174976 | ZDHHC22 | *Homo sapiens* zinc finger, DHHC-type containing 22 (ZDHHC22), mRNA [NM_174976] |
| CV575560 | CV575560 | oe37f10.y1 Human keratoconus cornea, unamplified, (od [CV575560] |

TABLE 16

Gene list generated at the inclusion criteria of p ≤ 0.001.

| GenBank Accession | GeneName | Description |
|---|---|---|
| NM_006709 | EHMT2 | *Homo sapiens* euchromatic histone-lysine N-methyltransferase 2 (EHMT2), transcript variant NG36/G9a, mRNA [NM_006709] |
| NM_000978 | RPL23 | *Homo sapiens* ribosomal protein L23 (RPL23), mRNA [NM_000978] |
| NM_001017 | RPS13 | *Homo sapiens* ribosomal protein S13 (RPS13), mRNA [NM_001017] |
| A_24_P50489 | A_24_P50489 | Unknown |
| NM_139280 | ORMDL3 | *Homo sapiens* ORM1-like 3 (*S. cerevisiae*) (ORMDL3), mRNA [NM_139280] |
| NM_000979 | RPL18 | *Homo sapiens* ribosomal protein L18 (RPL18), mRNA [NM_000979] |

TABLE 16-continued

Gene list generated at the inclusion criteria of p ≤ 0.001.

| GenBank Accession | GeneName | Description |
|---|---|---|
| A_32_P230059 | A_32_P230059 | Unknown |
| XR_019168 | LOC391847 | PREDICTED: *Homo sapiens* similar to ribosomal protein L19 (LOC391847), mRNA [XR_019168] |
| BC065737 | BC065737 | *Homo sapiens* cDNA clone IMAGE: 30404477, partial cds. [BC065737] |
| M55405 | MUC3A | *Homo sapiens* mucin (MUC-3) mRNA, partial cds. [M55405] |
| AF335478 | KLK3 | *Homo sapiens* prostate-specific antigen variant 2 mRNA, complete cds, alternatively spliced. [AF335478] |
| NM_018090 | NECAP2 | *Homo sapiens* NECAP endocytosis associated 2 (NECAP2), mRNA [NM_018090] |
| NM_001080484 | KIAA1751 | *Homo sapiens* KIAA1751 (KIAA1751), mRNA [NM_001080484] |
| A_24_P144163 | A_24_P144163 | Unknown |
| NM_013328 | PYCR2 | *Homo sapiens* pyrroline-5-carboxylate reductase family, member 2 (PYCR2), mRNA [NM_013328] |
| NM_052854 | CREB3L1 | *Homo sapiens* cAMP responsive element binding protein 3-like 1 (CREB3L1), mRNA [NM_052854] |
| A_32_P128781 | A_32_P128781 | Unknown |
| NM_000610 | CD44 | *Homo sapiens* CD44 molecule (Indian blood group) (CD44), transcript variant 1, mRNA [NM_000610] |
| THC2718728 | THC2718728 | Unknown |
| NM_002085 | GPX4 | *Homo sapiens* glutathione peroxidase 4 (phospholipid hydroperoxidase) (GPX4), transcript variant 1, mRNA [NM_002085] |
| NM_004657 | SDPR | *Homo sapiens* serum deprivation response (phosphatidylserine binding protein) (SDPR), mRNA [NM_004657] |
| NM_000996 | RPL35A | *Homo sapiens* ribosomal protein L35a (RPL35A), mRNA [NM_000996] |
| NM_005601 | NKG7 | *Homo sapiens* natural killer cell group 7 sequence (NKG7), mRNA [NM_005601] |
| NM_175744 | RHOC | *Homo sapiens* ras homolog gene family, member C (RHOC), transcript variant 1, mRNA [NM_175744] |
| ENST00000333650 | ENST00000333650 | PREDICTED: *Homo sapiens* similar to 60S ribosomal protein L14 (CAG-ISL 7) (LOC730747), mRNA [XR_015398] |
| THC2527647 | THC2527647 | Q59GY2_HUMAN (Q59GY2) Ribosomal protein L4 variant (Fragment), partial (51%) [THC2527647] |
| CR594528 | CR594528 | full-length cDNA clone CS0DM002YC17 of Fetal liver of *Homo sapiens* (human) [CR594528] |
| NM_006013 | RPL10 | *Homo sapiens* ribosomal protein L10 (RPL10), mRNA [NM_006013] |
| A_32_P11425 | A_32_P11425 | Unknown |
| NM_001028 | RPS25 | *Homo sapiens* ribosomal protein S25 (RPS25), mRNA [NM_001028] |
| NM_006482 | DYRK2 | *Homo sapiens* dual-specificity tyrosine-(Y)-phosphorylation regulated kinase 2 (DYRK2), transcript variant 2, mRNA [NM_006482] |
| NM_025004 | CCDC15 | *Homo sapiens* coiled-coil domain containing 15 (CCDC15), mRNA [NM_025004] |
| A_24_P333112 | A_24_P333112 | Unknown |
| NM_015894 | STMN3 | *Homo sapiens* stathmin-like 3 (STMN3), mRNA [NM_015894] |
| NM_001803 | CD52 | *Homo sapiens* CD52 molecule (CD52), mRNA [NM_001803] |
| NM_000984 | RPL23A | *Homo sapiens* ribosomal protein L23a (RPL23A), mRNA [NM_000984] |
| NM_000486 | AQP2 | *Homo sapiens* aquaporin 2 (collecting duct) (AQP2), mRNA [NM_000486] |
| NM_001000 | RPL39 | *Homo sapiens* ribosomal protein L39 (RPL39), mRNA [NM_001000] |
| NM_001568 | EIF3S6 | *Homo sapiens* eukaryotic translation initiation factor 3, subunit 6 48 kDa (EIF3S6), mRNA [NM_001568] |
| NM_001032 | RPS29 | *Homo sapiens* ribosomal protein S29 (RPS29), transcript variant 1, mRNA [NM_001032] |
| NM_005553 | KRTAP5-9 | *Homo sapiens* keratin associated protein 5-9 (KRTAP5-9), mRNA [NM_005553] |
| NM_006280 | SSR4 | *Homo sapiens* signal sequence receptor, delta (translocon-associated protein delta) (SSR4), mRNA [NM_006280] |
| A_24_P212605 | A_24_P212605 | Unknown |
| XR_018868 | LOC645000 | PREDICTED: *Homo sapiens* similar to 40S ribosomal protein S3 (LOC645000), mRNA [XR_018868] |
| A_24_P392661 | A_24_P392661 | Unknown |
| NM_018127 | ELAC2 | *Homo sapiens* elaC homolog 2 (*E. coli*) (ELAC2), mRNA [NM_018127] |
| NM_175863 | ARID1B | *Homo sapiens* AT rich interactive domain 1B (SWI1-like) (ARID1B), transcript variant 3, mRNA [NM_175863] |
| NM_030915 | LBH | *Homo sapiens* limb bud and heart development homolog (mouse) (LBH), mRNA [NM_030915] |

TABLE 16-continued

Gene list generated at the inclusion criteria of p ≤ 0.001.

| GenBank Accession | GeneName | Description |
|---|---|---|
| NM_000968 | RPL4 | *Homo sapiens* ribosomal protein L4 (RPL4), mRNA [NM_000968] |
| NM_001014 | RPS10 | *Homo sapiens* ribosomal protein S10 (RPS10), mRNA [NM_001014] |
| A_24_P160920 | A_24_P160920 | Unknown |
| NM_014183 | DYNLRB1 | *Homo sapiens* dynein, light chain, roadblock-type 1 (DYNLRB1), mRNA [NM_014183] |
| ENST00000312528 | ENST00000312528 | Unknown |
| BC104478 | RPL21 | *Homo sapiens* ribosomal protein L21, mRNA (cDNA clone IMAGE: 6605832), complete cds. [BC104478] |
| THC2481836 | THC2481836 | Q412F2_KINRA (Q412F2) MOSC, partial (10%) [THC2481836] |
| NM_015088 | TNRC6B | *Homo sapiens* trinucleotide repeat containing 6B (TNRC6B), transcript variant 1, mRNA [NM_015088] |
| NM_015414 | RPL36 | *Homo sapiens* ribosomal protein L36 (RPL36), transcript variant 2, mRNA [NM_015414] |
| CR933606 | C20orf80 | *Homo sapiens* mRNA; cDNA DKFZp686M08106 (from clone DKFZp686M08106). [CR933606] |
| A_24_P332441 | A_24_P332441 | Unknown |
| BC052613 | LOC728131 | *Homo sapiens* cDNA clone MGC: 59872 IMAGE: 6301163, complete cds. [BC052613] |
| NM_020939 | CPNE5 | *Homo sapiens* copine V (CPNE5), mRNA [NM_020939] |
| NM_003973 | RPL14 | *Homo sapiens* ribosomal protein L14 (RPL14), transcript variant 2, mRNA [NM_003973] |
| NM_032378 | EEF1D | *Homo sapiens* eukaryotic translation elongation factor 1 delta (guanine nucleotide exchange protein) (EEF1D), transcript variant 1, mRNA [NM_032378] |
| NM_001014 | RPS10 | *Homo sapiens* ribosomal protein S10 (RPS10), mRNA [NM_001014] |
| A_24_P853410 | A_24_P853410 | Unknown |
| XR_019052 | LOC391738 | PREDICTED: *Homo sapiens* similar to 60S ribosomal protein L29 (Cell surface heparin-binding protein HIP) (LOC391738), mRNA [XR_019052] |
| NM_032351 | MRPL45 | *Homo sapiens* mitochondrial ribosomal protein L45 (MRPL45), nuclear gene encoding mitochondrial protein, mRNA [NM_032351] |
| XM_379885 | hCG_2023776 | PREDICTED: *Homo sapiens* similar to Heterogeneous nuclear ribonucleoprotein A1 (Helix-destabilizing protein) (Single-strand binding protein) (hnRNP core protein A1) (HDP-1) (Topoisomerase-inhibitor suppressed) (LOC402562), mRNA [XM_379885] |
| AA279208 | AA279208 | AA279208 zs83e07.s1 NCI_CGAP_GCB1 *Homo sapiens* cDNA clone IMAGE: 704100 3', mRNA sequence [AA279208] |
| NM_203477 | MGC70863 | *Homo sapiens* similar to RPL23AP7 protein (MGC70863), transcript variant 1, mRNA [NM_203477] |
| NM_032476 | MRPS6 | *Homo sapiens* mitochondrial ribosomal protein S6 (MRPS6), nuclear gene encoding mitochondrial protein, mRNA [NM_032476] |
| NM_001005472 | LOC388524 | *Homo sapiens* similar to Laminin receptor 1 (LOC388524), mRNA [NM_001005472] |
| THC2717131 | THC2717131 | Q7NI46_GLOVI (Q7NI46) Cytochrome c550, partial (8%) [THC2717131] |
| XR_018975 | LOC389644 | PREDICTED: *Homo sapiens* similar to ribosomal protein L5 (LOC389644), mRNA [XR_018975] |
| A_24_P306968 | A_24_P306968 | Unknown |
| NM_194302 | CCDC108 | *Homo sapiens* coiled-coil domain containing 108 (CCDC108), transcript variant 1, mRNA [NM_194302] |
| NM_173680 | ZNF775 | *Homo sapiens* zinc finger protein 775 (ZNF775), mRNA [NM_173680] |
| NM_001344 | DAD1 | *Homo sapiens* defender against cell death 1 (DAD1), mRNA [NM_001344] |
| NM_016085 | C2orf28 | *Homo sapiens* chromosome 2 open reading frame 28 (C2orf28), transcript variant 1, mRNA [NM_016085] |
| NM_031901 | MRPS21 | *Homo sapiens* mitochondrial ribosomal protein S21 (MRPS21), nuclear gene encoding mitochondrial protein, transcript variant 1, mRNA [NM_031901] |
| NM_000999 | RPL38 | *Homo sapiens* ribosomal protein L38 (RPL38), transcript variant 1, mRNA [NM_000999] |
| NM_001988 | EVPL | *Homo sapiens* envoplakin (EVPL), mRNA [NM_001988] |
| NM_203374 | ZNF784 | *Homo sapiens* zinc finger protein 784 (ZNF784), mRNA [NM_203374] |
| NR_000029 | RPL23AP7 | *Homo sapiens* ribosomal protein L23a pseudogene 7 (RPL23AP7) on chromosome 2 [NR_000029] |
| THC2537928 | THC2537928 | HUMRPL4X ribosomal protein L4 {*Homo sapiens*} (exp = −1; wgp = 0; cg = 0), partial (34%) [THC2600839] |
| NM_001001 | RPL36AL | *Homo sapiens* ribosomal protein L36a-like (RPL36AL), mRNA [NM_001001] |

TABLE 16-continued

Gene list generated at the inclusion criteria of p ≤ 0.001.

| GenBank Accession | GeneName | Description |
|---|---|---|
| AK024389 | FLJ14327 | *Homo sapiens* cDNA FLJ14327 fis, clone PLACE4000250. [AK024389] |
| NM_007104 | RPL10A | *Homo sapiens* ribosomal protein L10a (RPL10A), mRNA [NM_007104] |
| NM_001018 | RPS15 | *Homo sapiens* ribosomal protein S15 (RPS15), mRNA [NM_001018] |
| NM_003752 | EIF3S8 | *Homo sapiens* eukaryotic translation initiation factor 3, subunit 8, 110 kDa (EIF3S8), transcript variant 1, mRNA [NM_003752] |
| A_24_P161459 | A_24_P161459 | Unknown |
| NM_178449 | TIP39 | *Homo sapiens* tuberoinfundibular 39 residue protein precursor (TIP39), mRNA [NM_178449] |
| XR_018430 | LOC391102 | PREDICTED: *Homo sapiens* similar to 60S acidic ribosomal protein P0 (L10E) (LOC391102), mRNA [XR_018430] |
| NM_002490 | NDUFA6 | *Homo sapiens* NADH dehydrogenase (ubiquinone) 1 alpha subcomplex, 6, 14 kDa (NDUFA6), nuclear gene encoding mitochondrial protein, mRNA [NM_002490] |
| A_24_P358578 | A_24_P358578 | Unknown |
| NM_000989 | RPL30 | *Homo sapiens* ribosomal protein L30 (RPL30), mRNA [NM_000989] |
| BC014606 | BC014606 | *Homo sapiens* cDNA clone IMAGE: 4826808. [BC014606] |
| XR_015710 | LOC731048 | PREDICTED: *Homo sapiens* similar to 60S ribosomal protein L17 (L23) (LOC731048), mRNA [XR_015710] |
| XM_928198 | LOC645161 | PREDICTED: *Homo sapiens* similar to 60S ribosomal protein L12 (LOC645161), mRNA [XM_928198] |
| XR_017813 | RPLP0-like | PREDICTED: *Homo sapiens* similar to ribosomal protein P0 (RPLP0-like), misc RNA [XR_017813] |
| NM_001011724 | RP11-78J21.1 | *Homo sapiens* heterogeneous nuclear ribonucleoprotein A1-like (LOC144983), transcript variant 1, mRNA [NM_001011724] |
| NM_024600 | C16orf30 | *Homo sapiens* chromosome 16 open reading frame 30 (C16orf30), mRNA [NM_024600] |
| NM_000761 | CYP1A2 | *Homo sapiens* cytochrome P450, family 1, subfamily A, polypeptide 2 (CYP1A2), mRNA [NM_000761] |
| NM_002568 | PABPC1 | *Homo sapiens* poly(A) binding protein, cytoplasmic 1 (PABPC1), mRNA [NM_002568] |
| BC030568 | LOC376693 | *Homo sapiens* hypothetical LOC376693, mRNA (cDNA clone MGC: 45392 IMAGE: 5526694), complete cds. [BC030568] |
| NM_198053 | CD247 | *Homo sapiens* CD247 molecule (CD247), transcript variant 1, mRNA [NM_198053] |
| NM_080425 | GNAS | *Homo sapiens* GNAS complex locus (GNAS), transcript variant 2, mRNA [NM_080425] |
| XM_087499 | LOC152663 | PREDICTED: *Homo sapiens* similar to 60S ribosomal protein L7a (LOC152663), mRNA [XM_087499] |
| A_24_P650893 | A_24_P650893 | Unknown |
| NM_012329 | MMD | *Homo sapiens* monocyte to macrophage differentiation-associated (MMD), mRNA [NM_012329] |
| XR_019277 | LOC391719 | PREDICTED: *Homo sapiens* similar to ribosomal protein L19 (LOC391719), mRNA [XR_019277] |
| A_24_P238426 | A_24_P238426 | Unknown |
| NM_003576 | STK24 | *Homo sapiens* serine/threonine kinase 24 (STE20 homolog, yeast) (STK24), transcript variant 1, mRNA [NM_003576] |
| NM_153719 | NUP62 | *Homo sapiens* nucleoporin 62 kDa (NUP62), transcript variant 1, mRNA [NM_153719] |
| NM_002539 | ODC1 | *Homo sapiens* ornithine decarboxylase 1 (ODC1), mRNA [NM_002539] |
| NM_001005472 | LOC388524 | *Homo sapiens* similar to Laminin receptor 1 (LOC388524), mRNA [NM_001005472] |
| NM_000454 | SOD1 | *Homo sapiens* superoxide dismutase 1, soluble (amyotrophic lateral sclerosis 1 (adult)) (SOD1), mRNA [NM_000454] |
| NM_005594 | NACA | *Homo sapiens* nascent-polypeptide-associated complex alpha polypeptide (NACA), mRNA [NM_005594] |
| NM_052871 | MGC4677 | *Homo sapiens* hypothetical protein MGC4677 (MGC4677), mRNA [NM_052871] |
| NM_006826 | YWHAQ | *Homo sapiens* tyrosine 3-monooxygenase/tryptophan 5-monooxygenase activation protein, theta polypeptide (YWHAQ), mRNA [NM_006826] |
| ENST00000310391 | ENST00000310391 | Unknown |
| NM_000398 | CYB5R3 | *Homo sapiens* cytochrome b5 reductase 3 (CYB5R3), transcript variant M, mRNA [NM_000398] |
| NM_032932 | RAB11FIP4 | *Homo sapiens* RAB11 family interacting protein 4 (class II) (RAB11FIP4), mRNA [NM_032932] |
| XR_018048 | LOC646161 | PREDICTED: *Homo sapiens* similar to 60S ribosomal protein L26 (LOC646161), mRNA [XR_018048] |
| BC006438 | BC006438 | *Homo sapiens* cDNA clone MGC: 13162 IMAGE: 3010103, complete cds. [BC006438] |

TABLE 16-continued

Gene list generated at the inclusion criteria of p ≤ 0.001.

| GenBank Accession | GeneName | Description |
|---|---|---|
| NM_002121 | HLA-DPB1 | *Homo sapiens* major histocompatibility complex, class II, DP beta 1 (HLA-DPB1), mRNA [NM_002121] |
| NM_013939 | OR10H2 | *Homo sapiens* olfactory receptor, family 10, subfamily H, member 2 (OR10H2), mRNA [NM_013939] |
| NM_001030 | RPS27 | *Homo sapiens* ribosomal protein S27 (metallopanstimulin 1) (RPS27), mRNA [NM_001030] |
| ENST00000340005 | LOC731959 | similar to 60S ribosomal protein L12 (LOC644202), mRNA [Source: RefSeq_dna; Acc: XR_016588] [ENST00000340005] |
| NM_015444 | TMEM158 | *Homo sapiens* transmembrane protein 158 (TMEM158), mRNA [NM_015444] |
| NM_005340 | HINT1 | *Homo sapiens* histidine triad nucleotide binding protein 1 (HINT1), mRNA [NM_005340] |
| NM_001032 | RPS29 | *Homo sapiens* ribosomal protein S29 (RPS29), transcript variant 1, mRNA [NM_001032] |
| AF147412 | AF147412 | *Homo sapiens* full length insert cDNA clone YP59C02. [AF147412] |
| NM_000732 | CD3D | *Homo sapiens* CD3d molecule, delta (CD3-TCR complex) (CD3D), transcript variant 1, mRNA [NM_000732] |
| THC2586367 | THC2586367 | Q9D7P1_MOUSE (Q9D7P1) Adult male tongue cDNA, RIKEN full-length enriched library, clone: 2300009C10 product: ribosomal protein S24, full insert sequence, partial (95%) [THC2586367] |
| BX427435 | BX427435 | BX427435 *Homo sapiens* FETAL LIVER *Homo sapiens* cDNA clone CS0DM010YK16 3-PRIME, mRNA sequence [BX427435] |
| NM_006266 | RALGDS | *Homo sapiens* ral guanine nucleotide dissociation stimulator (RALGDS), transcript variant 1, mRNA [NM_006266] |
| NM_000978 | RPL23 | *Homo sapiens* ribosomal protein L23 (RPL23), mRNA [NM_000978] |
| A_24_P195257 | A_24_P195257 | Unknown |
| NM_021103 | TMSB10 | *Homo sapiens* thymosin, beta 10 (TMSB10), mRNA [NM_021103] |
| XR_018222 | RPL31P4 | PREDICTED: *Homo sapiens* ribosomal protein L31 pseudogene 4 (RPL31P4), mRNA [XR_018222] |
| ENST00000360514 | ENST00000360514 | *Homo sapiens* hypothetical LOC339483, mRNA (cDNA clone MGC: 52427 IMAGE: 4872239), complete cds. [BC041632] |
| NM_006098 | GNB2L1 | *Homo sapiens* guanine nucleotide binding protein (G protein), beta polypeptide 2-like 1 (GNB2L1), mRNA [NM_006098] |
| A_32_P167577 | A_32_P167577 | Unknown |
| U19144 | GAGE3 | Human GAGE-3 protein mRNA, complete cds. [U19144] |
| NM_003973 | RPL14 | *Homo sapiens* ribosomal protein L14 (RPL14), transcript variant 2, mRNA [NM_003973] |
| NM_005950 | MT1G | *Homo sapiens* metallothionein 1G (MT1G), mRNA [NM_005950] |
| NM_000967 | RPL3 | *Homo sapiens* ribosomal protein L3 (RPL3), transcript variant 1, mRNA [NM_000967] |
| NM_033251 | RPL13 | *Homo sapiens* ribosomal protein L13 (RPL13), transcript variant 2, mRNA [NM_033251] |
| A_24_P578641 | A_24_P578641 | Unknown |
| XM_001131279 | LOC343851 | PREDICTED: *Homo sapiens* similar to 40S ribosomal protein S10 (LOC343851), mRNA [XM_001131279] |
| A_32_P233211 | A_32_P233211 | Unknown |
| NM_178352 | LCE1D | *Homo sapiens* late cornified envelope 1D (LCE1D), mRNA [NM_178352] |
| NM_003932 | ST13 | *Homo sapiens* suppression of tumorigenicity 13 (colon carcinoma) (Hsp70 interacting protein) (ST13), mRNA [NM_003932] |
| NM_003295 | TPT1 | *Homo sapiens* tumor protein, translationally-controlled 1 (TPT1), mRNA [NM_003295] |
| NM_001018 | RPS15 | *Homo sapiens* ribosomal protein S15 (RPS15), mRNA [NM_001018] |
| NM_001618 | PARP1 | *Homo sapiens* poly (ADP-ribose) polymerase family, member 1 (PARP1), mRNA [NM_001618] |
| A_24_P307255 | A_24_P307255 | Unknown |
| NM_000661 | RPL9 | *Homo sapiens* ribosomal protein L9 (RPL9), transcript variant 1, mRNA [NM_000661] |
| NM_206833 | CTXN1 | *Homo sapiens* cortexin 1 (CTXN1), mRNA [NM_206833] |
| NM_005694 | COX17 | *Homo sapiens* COX17 cytochrome c oxidase assembly homolog (*S. cerevisiae*) (COX17), nuclear gene encoding mitochondrial protein, mRNA [NM_005694] |
| NM_001080403 | FLJ22184 | *Homo sapiens* hypothetical protein FLJ22184 (FLJ22184), mRNA [NM_001080403] |
| M36647 | UQCRH | *Homo sapiens* mitochondrial hinge protein precursor, mRNA, complete cds. [M36647] |
| NM_001007074 | RPL32 | *Homo sapiens* ribosomal protein L32 (RPL32), transcript variant 3, mRNA [NM_001007074] |
| A_24_P84408 | A_24_P84408 | Unknown |
| NM_001003845 | SP5 | *Homo sapiens* Sp5 transcription factor (SP5), mRNA [NM_001003845] |

TABLE 16-continued

Gene list generated at the inclusion criteria of p ≤ 0.001.

| GenBank Accession | GeneName | Description |
|---|---|---|
| ENST00000303979 | ENST00000303979 | Unknown |
| NM_014765 | TOMM20 | *Homo sapiens* translocase of outer mitochondrial membrane 20 homolog (yeast) (TOMM20), mRNA [NM_014765] |
| XR_018138 | LOC392497 | PREDICTED: *Homo sapiens* similar to 40S ribosomal protein S6 (LOC392497), mRNA [XR_018138] |
| NM_004048 | B2M | *Homo sapiens* beta-2-microglobulin (B2M), mRNA [NM_004048] |
| NM_014328 | RUSC1 | *Homo sapiens* RUN and SH3 domain containing 1 (RUSC1), mRNA [NM_014328] |
| AK090444 | AYTL2 | *Homo sapiens* mRNA for FLJ00365 protein. [AK090444] |
| A_24_P93452 | A_24_P93452 | Unknown |
| NM_005594 | NACA | *Homo sapiens* nascent-polypeptide-associated complex alpha polypeptide (NACA), mRNA [NM_005594] |
| NM_002985 | CCL5 | *Homo sapiens* chemokine (C-C motif) ligand 5 (CCL5), mRNA [NM_002985] |
| NM_000998 | RPL37A | *Homo sapiens* ribosomal protein L37a (RPL37A), mRNA [NM_000998] |
| NM_000983 | RPL22 | *Homo sapiens* ribosomal protein L22 (RPL22), mRNA [NM_000983] |
| NM_003746 | DYNLL1 | *Homo sapiens* dynein, light chain, LC8-type 1 (DYNLL1), transcript variant 3, mRNA [NM_003746] |
| XR_016879 | LOC388401 | PREDICTED: *Homo sapiens* similar to 60S ribosomal protein L7 (LOC388401), mRNA [XR_016879] |
| NM_012322 | LSM5 | *Homo sapiens* LSM5 homolog, U6 small nuclear RNA associated (*S. cerevisiae*) (LSM5), mRNA [NM_012322] |
| NM_001404 | EEF1G | *Homo sapiens* eukaryotic translation elongation factor 1 gamma (EEF1G), mRNA [NM_001404] |
| NM_001105 | ACVR1 | *Homo sapiens* activin A receptor, type I (ACVR1), mRNA [NM_001105] |
| A_32_P20040 | A_32_P20040 | Unknown |
| BF931515 | BF931515 | BF931515 IL2-NT0202-141200-308-H03 NT0202 *Homo sapiens* cDNA, mRNA sequence [BF931515] |
| XR_019504 | LOC391126 | PREDICTED: *Homo sapiens* similar to 60S ribosomal protein L26 (Silica-induced gene 20 protein) (SIG-20) (LOC391126), mRNA [XR_019504] |
| NM_001021 | RPS17 | *Homo sapiens* ribosomal protein S17 (RPS17), mRNA [NM_001021] |
| NM_006013 | RPL10 | *Homo sapiens* ribosomal protein L10 (RPL10), mRNA [NM_006013] |
| NM_001028 | RPS25 | *Homo sapiens* ribosomal protein S25 (RPS25), mRNA [NM_001028] |
| NM_021631 | FKSG2 | *Homo sapiens* apoptosis inhibitor (FKSG2), mRNA [NM_021631] |
| NM_203477 | MGC70863 | *Homo sapiens* similar to RPL23AP7 protein (MGC70863), transcript variant 1, mRNA [NM_203477] |
| NM_000986 | RPL24 | *Homo sapiens* ribosomal protein L24 (RPL24), mRNA [NM_000986] |
| A_24_P881608 | A_24_P881608 | Unknown |
| NM_001022 | RPS19 | *Homo sapiens* ribosomal protein S19 (RPS19), mRNA [NM_001022] |
| A_32_P49392 | A_32_P49392 | Unknown |
| XR_018970 | LOC391140 | PREDICTED: *Homo sapiens* similar to ribosomal protein L13 (LOC391140), mRNA [XR_018970] |
| NM_000987 | RPL26 | *Homo sapiens* ribosomal protein L26 (RPL26), mRNA [NM_000987] |
| A_24_P936393 | A_24_P936393 | Unknown |
| AK074778 | LOC388152 | *Homo sapiens* cDNA FLJ90297 fis, clone NT2RP2000447, moderately similar to GOLGIN-95. [AK074778] |
| A_32_P95502 | A_32_P95502 | Unknown |
| NM_001040437 | C6orf48 | *Homo sapiens* chromosome 6 open reading frame 48 (C6orf48), transcript variant 1, mRNA [NM_001040437] |
| NM_014849 | SV2A | *Homo sapiens* synaptic vesicle glycoprotein 2A (SV2A), mRNA [NM_014849] |
| AL049447 | AL049447 | *Homo sapiens* mRNA; cDNA DKFZp586A0722 (from clone DKFZp586A0722). [AL049447] |
| NM_024670 | SUV39H2 | *Homo sapiens* suppressor of variegation 3-9 homolog 2 (*Drosophila*) (SUV39H2), mRNA [NM_024670] |
| XM_001128309 | LOC730663 | PREDICTED: *Homo sapiens* similar to 60S ribosomal protein L23a (LOC730663), mRNA [XM_001128309] |
| A_32_P194182 | A_32_P194182 | Unknown |
| NM_021148 | ZNF273 | *Homo sapiens* zinc finger protein 273 (ZNF273), transcript variant 1, mRNA [NM_021148] |
| NM_017971 | MRPL20 | *Homo sapiens* mitochondrial ribosomal protein L20 (MRPL20), nuclear gene encoding mitochondrial protein, mRNA [NM_017971] |

TABLE 16-continued

Gene list generated at the inclusion criteria of p ≤ 0.001.

| GenBank Accession | GeneName | Description |
|---|---|---|
| NM_004048 | B2M | *Homo sapiens* beta-2-microglobulin (B2M), mRNA [NM_004048] |
| BM979607 | BM979607 | BM979607 UI-CF-DU1-adt-k-11-0-UI.s1 UI-CF-DU1 *Homo sapiens* cDNA clone UI-CF-DU1-adt-k-11-0-UI 3', mRNA sequence [BM979607] |
| A_24_P417922 | A_24_P417922 | Unknown |
| NM_000997 | RPL37 | *Homo sapiens* ribosomal protein L37 (RPL37), mRNA [NM_000997] |
| THC2755576 | THC2755576 | ALU1_HUMAN (P39188) Alu subfamily J sequence contamination warning entry, partial (13%) [THC2755576] |
| NM_152789 | FAM133B | *Homo sapiens* hypothetical protein MGC40405 (MGC40405), transcript variant 1, mRNA [NM_152789] |
| NM_000336 | SCNN1B | *Homo sapiens* sodium channel, nonvoltage-gated 1, beta (Liddle syndrome) (SCNN1B), mRNA [NM_000336] |
| NM_000986 | RPL24 | *Homo sapiens* ribosomal protein L24 (RPL24), mRNA [NM_000986] |
| NM_000633 | BCL2 | *Homo sapiens* B-cell CLL/lymphoma 2 (BCL2), nuclear gene encoding mitochondrial protein, transcript variant alpha, mRNA [NM_000633] |
| THC2679528 | THC2679528 | Unknown |
| BX090181 | BX090181 | BX090181 NCI_CGAP_Lu5 *Homo sapiens* cDNA clone IMAGp998M204062; IMAGE: 1602235, mRNA sequence [BX090181] |
| NM_001214 | C16orf3 | *Homo sapiens* chromosome 16 open reading frame 3 (C16orf3), mRNA [NM_001214] |
| AF113008 | AF113008 | *Homo sapiens* clone FLB0708 mRNA sequence. [AF113008] |
| NM_014625 | NPHS2 | *Homo sapiens* nephrosis 2, idiopathic, steroid-resistant (podocin) (NPHS2), mRNA [NM_014625] |
| A_24_P366457 | A_24_P366457 | Unknown |
| NM_014189 | ADD1 | *Homo sapiens* adducin 1 (alpha) (ADD1), transcript variant 2, mRNA [NM_014189] |
| AK092748 | RP3-377H14.5 | *Homo sapiens* cDNA FLJ35429 fis, clone SMINT2002126. [AK092748] |
| NM_021046 | KRTAP5-8 | *Homo sapiens* keratin associated protein 5-8 (KRTAP5-8), mRNA [NM_021046] |
| NM_145019 | FAM124A | *Homo sapiens* family with sequence similarity 124A (FAM124A), mRNA [NM_145019] |
| NM_033318 | C22orf32 | *Homo sapiens* chromosome 22 open reading frame 32 (C22orf32), mRNA [NM_033318] |
| A_24_P144275 | A_24_P144275 | Unknown |
| NM_002490 | NDUFA6 | *Homo sapiens* NADH dehydrogenase (ubiquinone) 1 alpha subcomplex, 6, 14 kDa (NDUFA6), nuclear gene encoding mitochondrial protein, mRNA [NM_002490] |
| AK090412 | LOC375010 | *Homo sapiens* mRNA for FLJ00310 protein. [AK090412] |
| AK124946 | DPF3 | *Homo sapiens* cDNA FLJ42956 fis, clone BRSTN2009899. [AK124946] |
| ENST00000337102 | ENST00000337102 | 40S ribosomal protein S21. [Source: Uniprot/SWISSPROT; Acc: P63220] [ENST00000337102] |
| NM_001861 | COX4I1 | *Homo sapiens* cytochrome c oxidase subunit IV isoform 1 (COX4I1), mRNA [NM_001861] |
| NM_207121 | FAM110A | *Homo sapiens* family with sequence similarity 110, member A (FAM110A), transcript variant 2, mRNA [NM_207121] |
| NM_145308 | C11orf76 | *Homo sapiens* chromosome 11 open reading frame 76 (C11orf76), mRNA [NM_145308] |
| NM_014417 | BBC3 | *Homo sapiens* BCL2 binding component 3 (BBC3), mRNA [NM_014417] |
| NM_001012 | RPS8 | *Homo sapiens* ribosomal protein S8 (RPS8), mRNA [NM_001012] |
| NM_181698 | CCNY | *Homo sapiens* cyclin Y (CCNY), transcript variant 2, mRNA [NM_181698] |
| A_24_P629163 | A_24_P629163 | Unknown |
| AL137354 | AL137354 | *Homo sapiens* mRNA; cDNA DKFZp434A0326 (from clone DKFZp434A0326). [AL137354] |
| NM_001011 | RPS7 | *Homo sapiens* ribosomal protein S7 (RPS7), mRNA [NM_001011] |
| ENST00000341376 | NFYA | Nuclear transcription factor Y subunit alpha (Nuclear transcription factor Y subunit A) (NF-YA) (CAAT-box DNA-binding protein subunit A). [Source: Uniprot/SWISSPROT; Acc: P23511] [ENST00000341376] |
| NM_001025295 | IFITM5 | *Homo sapiens* interferon induced transmembrane protein 5 (IFITM5), mRNA [NM_001025295] |
| A_24_P730256 | A_24_P730256 | Unknown |
| NM_021640 | C12orf10 | *Homo sapiens* chromosome 12 open reading frame 10 (C12orf10), mRNA [NM_021640] |
| NM_199249 | C19orf48 | *Homo sapiens* chromosome 19 open reading frame 48 (C19orf48), mRNA [NM_199249] |
| XR_018695 | RPL31P10 | PREDICTED: *Homo sapiens* similar to ribosomal protein L31 (LOC390283), mRNA [XR_018695] |

TABLE 16-continued

Gene list generated at the inclusion criteria of p ≤ 0.001.

| GenBank Accession | GeneName | Description |
| --- | --- | --- |
| A_24_P118874 | A_24_P118874 | Unknown |
| XR_017377 | LOC647094 | PREDICTED: *Homo sapiens* similar to acidic ribosomal phosphoprotein P0 (LOC647094), mRNA [XR_017377] |
| NM_001778 | CD48 | *Homo sapiens* CD48 molecule (CD48), mRNA [NM_001778] |
| NM_000967 | RPL3 | *Homo sapiens* ribosomal protein L3 (RPL3), transcript variant 1, mRNA [NM_000967] |
| NM_000610 | CD44 | *Homo sapiens* CD44 molecule (Indian blood group) (CD44), transcript variant 1, mRNA [NM_000610] |
| NM_001006 | RPS3A | *Homo sapiens* ribosomal protein S3A (RPS3A), mRNA [NM_001006] |
| NM_178428 | LCE2A | *Homo sapiens* late cornified envelope 2A (LCE2A), mRNA [NM_178428] |
| NM_144601 | CMTM3 | *Homo sapiens* CKLF-like MARVEL transmembrane domain containing 3 (CMTM3), transcript variant 1, mRNA [NM_144601] |
| NM_198969 | AES | *Homo sapiens* amino-terminal enhancer of split (AES), transcript variant 1, mRNA [NM_198969] |
| NM_016404 | HSPC152 | *Homo sapiens* hypothetical protein HSPC152 (HSPC152), mRNA [NM_016404] |
| NM_021978 | ST14 | *Homo sapiens* suppression of tumorigenicity 14 (colon carcinoma) (ST14), mRNA [NM_021978] |
| A_24_P921980 | A_24_P921980 | Unknown |
| ENST00000310218 | ENST00000310218 | PREDICTED: *Homo sapiens* similar to large subunit ribosomal protein L36a (LOC729621), mRNA [XM_001133900] |
| NM_001082575 | HRNBP3 | *Homo sapiens* hypothetical protein LOC146713 (HRNBP3), mRNA [NM_001082575] |
| XR_018803 | LOC649915 | PREDICTED: *Homo sapiens* similar to Glyceraldehyde-3-phosphate dehydrogenase (GAPDH) (LOC649915), mRNA [XR_018803] |
| NM_001019 | RPS15A | *Homo sapiens* ribosomal protein S15a (RPS15A), transcript variant 2, mRNA [NM_001019] |
| NM_016091 | EIF3S6IP | *Homo sapiens* eukaryotic translation initiation factor 3, subunit 6 interacting protein (EIF3S6IP), mRNA [NM_016091] |
| NM_080614 | WFDC3 | *Homo sapiens* WAP four-disulfide core domain 3 (WFDC3), mRNA [NM_080614] |
| NM_001989 | EVX1 | *Homo sapiens* even-skipped homeobox 1 (EVX1), mRNA [NM_001989] |
| BC039555 | SNHG8 | *Homo sapiens* cDNA clone IMAGE: 4184613, partial cds. [BC039555] |
| NM_032378 | EEF1D | *Homo sapiens* eukaryotic translation elongation factor 1 delta (guanine nucleotide exchange protein) (EEF1D), transcript variant 1, mRNA [NM_032378] |
| NM_025207 | FLAD1 | *Homo sapiens* FAD1 flavin adenine dinucleotide synthetase homolog (*S. cerevisiae*) (FLAD1), transcript variant 1, mRNA [NM_025207] |
| NR_001564 | XIST | *Homo sapiens* X (inactive)-specific transcript (XIST) on chromosome X [NR_001564] |
| NM_001031 | RPS28 | *Homo sapiens* ribosomal protein S28 (RPS28), mRNA [NM_001031] |
| XR_016930 | LOC645412 | PREDICTED: *Homo sapiens* similar to 40S ribosomal protein S16 (LOC645412), mRNA [XR_016930] |
| BC107865 | LOC204010 | *Homo sapiens* similar to 40S ribosomal protein SA (P40) (34/67 kDa laminin receptor) (Colon carcinoma laminin-binding protein) (NEM/1CHD4) (Multidrug resistance-associated protein MGr1-Ag), mRNA (cDNA clone MGC: 104447 IMAGE: 4095371), complete cds . . . |
| A_32_P235293 | A_32_P235293 | Unknown |
| BC040156 | LOC284570 | *Homo sapiens*, clone IMAGE: 4941949, mRNA. [BC040156] |
| A_24_P204454 | A_24_P204454 | Unknown |
| NM_014507 | MCAT | *Homo sapiens* malonyl CoA:ACP acyltransferase (mitochondrial) (MCAT), nuclear gene encoding mitochondrial protein, transcript variant 2, mRNA [NM_014507] |
| XR_015767 | LOC731224 | PREDICTED: *Homo sapiens* similar to 60S ribosomal protein L9 (LOC731224), mRNA [XR_015767] |
| A_32_P760762 | A_32_P760762 | Unknown |
| NM_012266 | DNAJB5 | *Homo sapiens* DnaJ (Hsp40) homolog, subfamily B, member 5 (DNAJB5), mRNA [NM_012266] |
| NM_001088 | AANAT | *Homo sapiens* arylalkylamine N-acetyltransferase (AANAT), mRNA [NM_001088] |
| A_24_P229438 | A_24_P229438 | Unknown |
| NM_000980 | RPL18A | *Homo sapiens* ribosomal protein L18a (RPL18A), mRNA [NM_000980] |
| A_24_P533990 | A_24_P533990 | Unknown |
| BX648200 | BX648200 | *Homo sapiens* mRNA; cDNA DKFZp779C0742 (from clone DKFZp779C0742). [BX648200] |

TABLE 16-continued

Gene list generated at the inclusion criteria of p ≤ 0.001.

| GenBank Accession | GeneName | Description |
|---|---|---|
| XR_018411 | LOC390993 | PREDICTED: *Homo sapiens* similar to 60S ribosomal protein L7a (LOC390993), mRNA [XR_018411] |
| NM_001402 | EEF1A1 | *Homo sapiens* eukaryotic translation elongation factor 1 alpha 1 (EEF1A1), mRNA [NM_001402] |
| A_24_P375932 | A_24_P375932 | Unknown |
| ENST00000247761 | ENST00000247761 | Unknown |
| NM_054023 | SCGB3A2 | *Homo sapiens* secretoglobin, family 3A, member 2 (SCGB3A2), mRNA [NM_054023] |
| NM_001078171 | FAM127A | *Homo sapiens* family with sequence similarity 127, member A (FAM127A), mRNA [NM_001078171] |
| NM_182513 | SPC24 | *Homo sapiens* SPC24, NDC80 kinetochore complex component, homolog (*S. cerevisiae*) (SPC24), mRNA [NM_182513] |
| NM_024407 | NDUFS7 | *Homo sapiens* NADH dehydrogenase (ubiquinone) Fe—S protein 7, 20 kDa (NADH-coenzyme Q reductase) (NDUFS7), mRNA [NM_024407] |
| BC009038 | BC009038 | *Homo sapiens*, clone IMAGE: 4179482, mRNA. [BC009038] |
| ENST00000240349 | NACA3P | PREDICTED: *Homo sapiens* similar to nascent polypeptide-associated complex alpha polypeptide (LOC389240), mRNA [XM_371715] |
| THC2518594 | THC2518594 | Q6PJD4_HUMAN (Q6PJD4) LOC389906 protein (Fragment), partial (10%) [THC2518594] |
| NM_007286 | SYNPO | *Homo sapiens* synaptopodin (SYNPO), mRNA [NM_007286] |
| NM_203477 | MGC70863 | *Homo sapiens* similar to RPL23AP7 protein (MGC70863), transcript variant 1, mRNA [NM_203477] |
| NM_173502 | PRSS36 | *Homo sapiens* protease, serine, 36 (PRSS36), mRNA [NM_173502] |
| NM_053274 | GLMN | *Homo sapiens* glomulin, FKBP associated protein (GLMN), mRNA [NM_053274] |
| NM_203495 | COMMD6 | *Homo sapiens* COMM domain containing 6 (COMMD6), transcript variant 2, mRNA [NM_203495] |
| BC047708 | BC047708 | *Homo sapiens*, clone IMAGE: 5750141, mRNA. [BC047708] |
| NM_003202 | TCF7 | *Homo sapiens* transcription factor 7 (T-cell specific, HMG-box) (TCF7), transcript variant 1, mRNA [NM_003202] |
| NM_001688 | ATP5F1 | *Homo sapiens* ATP synthase, H+ transporting, mitochondrial F0 complex, subunit B1 (ATP5F1), nuclear gene encoding mitochondrial protein, mRNA [NM_001688] |
| NM_194248 | OTOF | *Homo sapiens* otoferlin (OTOF), transcript variant 1, mRNA [NM_194248] |
| A_23_P210285 | A_23_P210285 | Unknown |
| NM_000610 | CD44 | *Homo sapiens* CD44 molecule (Indian blood group) (CD44), transcript variant 1, mRNA [NM_000610] |
| A_24_P136011 | A_24_P136011 | Unknown |
| L10123 | SPAR | *Homo sapiens* surfactant protein A mRNA, complete cds. [L10123] |
| BC028232 | BC028232 | *Homo sapiens*, clone IMAGE: 5221276, mRNA, partial cds. [BC028232] |
| NM_007311 | TSPO | *Homo sapiens* translocator protein (18 kDa) (TSPO), transcript variant PBR-S, mRNA [NM_007311] |
| NM_001020 | RPS16 | *Homo sapiens* ribosomal protein S16 (RPS16), mRNA [NM_001020] |
| A_24_P93052 | A_24_P93052 | Unknown |
| NM_014567 | BCAR1 | *Homo sapiens* breast cancer anti-estrogen resistance 1 (BCAR1), mRNA [NM_014567] |
| NM_014272 | ADAMTS7 | *Homo sapiens* ADAM metallopeptidase with thrombospondin type 1 motif, 7 (ADAMTS7), mRNA [NM_014272] |
| XR_018303 | LOC648378 | PREDICTED: *Homo sapiens* similar to ribosomal protein S14 (LOC648378), mRNA [XR_018303] |
| NM_175738 | RAB37 | *Homo sapiens* RAB37, member RAS oncogene family (RAB37), transcript variant 3, mRNA [NM_175738] |
| NM_001005472 | LOC388524 | *Homo sapiens* similar to Laminin receptor 1 (LOC388524), mRNA [NM_001005472] |
| A_24_P145787 | A_24_P145787 | Unknown |
| BC035978 | ATP6V1B1 | *Homo sapiens* ATPase, H+ transporting, lysosomal 56/58 kDa, V1 subunit B1 (Renal tubular acidosis with deafness), mRNA (cDNA clone MGC: 32642 IMAGE: 4594171), complete cds. [BC035978] |
| A_24_P135771 | A_24_P135771 | Unknown |
| NM_002954 | RPS27A | *Homo sapiens* ribosomal protein S27a (RPS27A), mRNA [NM_002954] |
| NM_001045548 | LOC441743 | *Homo sapiens* similar to C367G8.3 (novel protein similar to RPL23A (60S ribosomal protein L23A)) (LOC441743), mRNA [NM_001045548] |
| NM_013279 | C11orf9 | *Homo sapiens* chromosome 11 open reading frame 9 (C11orf9), mRNA [NM_013279] |
| A_24_P7785 | A_24_P7785 | Unknown |
| BC067830 | LOC653391 | *Homo sapiens* similar to hypothetical protein LOC153561, mRNA (cDNA clone MGC: 87375 IMAGE: 5299741), complete cds. [BC067830] |

TABLE 16-continued

Gene list generated at the inclusion criteria of p ≤ 0.001.

| GenBank Accession | GeneName | Description |
|---|---|---|
| NM_000980 | RPL18A | *Homo sapiens* ribosomal protein L18a (RPL18A), mRNA [NM_000980] |
| BC041959 | BC041959 | *Homo sapiens* cDNA clone IMAGE: 5302136. [BC041959] |
| NM_022731 | NUCKS1 | *Homo sapiens* nuclear casein kinase and cyclin-dependent kinase substrate 1 (NUCKS1), mRNA [NM_022731] |
| A_24_P724106 | A_24_P724106 | Unknown |
| NM_001023 | RPS20 | *Homo sapiens* ribosomal protein S20 (RPS20), mRNA [NM_001023] |
| A_24_P229848 | A_24_P229848 | Unknown |
| NM_012320 | LYPLA3 | *Homo sapiens* lysophospholipase 3 (lysosomal phospholipase A2) (LYPLA3), mRNA [NM_012320] |
| NM_001039567 | RPS4Y2 | *Homo sapiens* ribosomal protein S4, Y-linked 2 (RPS4Y2), mRNA [NM_001039567] |
| A_24_P178784 | A_24_P178784 | Unknown |
| AK091931 | AK091931 | *Homo sapiens* cDNA FLJ34612 fis, clone KIDNE2014170, highly similar to 40S RIBOSOMAL PROTEIN S4, X ISOFORM. [AK091931] |
| BC007394 | MGC16291 | *Homo sapiens* hypothetical protein MGC16291, mRNA (cDNA clone MGC: 16291 IMAGE: 3834089), complete cds. [BC007394] |
| NM_003973 | RPL14 | *Homo sapiens* ribosomal protein L14 (RPL14), transcript variant 2, mRNA [NM_003973] |
| NM_030913 | SEMA6C | *Homo sapiens* sema domain, transmembrane domain (TM), and cytoplasmic domain, (semaphorin) 6C (SEMA6C), mRNA [NM_030913] |
| XM_497657 | LOC441876 | PREDICTED: *Homo sapiens* similar to 40S ribosomal protein S16, transcript variant 1 (LOC441876), mRNA [XM_497657] |
| BF149382 | BF149382 | BF149382 28_15 Human Epidermal Keratinocyte Subtraction Library- Upregulated Transcripts *Homo sapiens* cDNA similar to thiosulfate sulfurtransferase (TST), mRNA sequence [BF149382] |
| NM_170683 | P2RX2 | *Homo sapiens* purinergic receptor P2X, ligand-gated ion channel, 2 (P2RX2), transcript variant 4, mRNA [NM_170683] |
| NM_025228 | TRAF3IP3 | *Homo sapiens* TRAF3 interacting protein 3 (TRAF3IP3), mRNA [NM_025228] |
| AK124741 | AK124741 | *Homo sapiens* cDNA FLJ42751 fis, clone BRAWH3000491, moderately similar to 40S ribosomal protein S12. [AK124741] |
| NM_020212 | LOC56964 | *Homo sapiens* hypothetical protein from EUROIMAGE 384293 (LOC56964), mRNA [NM_020212] |
| NM_000940 | PON3 | *Homo sapiens* paraoxonase 3 (PON3), mRNA [NM_000940] |
| NM_004386 | NCAN | *Homo sapiens* neurocan (NCAN), mRNA [NM_004386] |
| NM_001010853 | ACY1L2 | *Homo sapiens* aminoacylase 1-like 2 (ACY1L2), mRNA [NM_001010853] |
| AK095213 | AK095213 | *Homo sapiens* cDNA FLJ37894 fis, clone BRTHA2004639. [AK095213] |
| NM_000985 | RPL17 | *Homo sapiens* ribosomal protein L17 (RPL17), transcript variant 1, mRNA [NM_000985] |
| THC2666258 | THC2666258 | P13985_HUMAN (P13985) P25 protein, partial (97%) [THC2666258] |
| BC033528 | BC033528 | *Homo sapiens* cDNA clone IMAGE: 4822684. [BC033528] |
| NM_003724 | JRK | *Homo sapiens* jerky homolog (mouse) (JRK), transcript variant 1, mRNA [NM_003724] |
| THC2679528 | THC2679528 | Unknown |
| ENST00000336505 | ENST00000336505 | Uncharacterized protein C9orf126. [Source: Uniprot/SWISSPROT; Acc: Q8N9R8] [ENST00000336505] |
| NM_000455 | STK11 | *Homo sapiens* serine/threonine kinase 11 (STK11), mRNA [NM_000455] |
| ENST00000335083 | LOC728449 | annexin A8 [Source: RefSeq_peptide; Acc: NP_001621] [ENST00000335083] |
| A_24_P298835 | A_24_P298835 | Unknown |
| NM_001006 | RPS3A | *Homo sapiens* ribosomal protein S3A (RPS3A), mRNA [NM_001006] |
| NM_019059 | TOMM7 | *Homo sapiens* translocase of outer mitochondrial membrane 7 homolog (yeast) (TOMM7), mRNA [NM_019059] |
| NM_025228 | TRAF3IP3 | *Homo sapiens* TRAF3 interacting protein 3 (TRAF3IP3), mRNA [NM_025228] |
| A_24_P685729 | A_24_P685729 | Unknown |
| XR_018231 | LOC648027 | PREDICTED: *Homo sapiens* similar to Elongation factor 1-gamma (EF-1-gamma) (eEF-1B gamma) (LOC648027), mRNA [XR_018231] |
| AK096498 | AK096498 | *Homo sapiens* cDNA FLJ39179 fis, clone OCBBF2004147. [AK096498] |
| XR_017130 | LOC158345 | PREDICTED: *Homo sapiens* similar to ribosomal protein L4 (LOC158345), mRNA [XR_017130] |
| NM_014276 | RBPJL | *Homo sapiens* recombination signal binding protein for immunoglobulin kappa J region-like (RBPJL), mRNA [NM_014276] |

TABLE 16-continued

Gene list generated at the inclusion criteria of p ≤ 0.001.

| GenBank Accession | GeneName | Description |
|---|---|---|
| NM_003950 | F2RL3 | *Homo sapiens* coagulation factor II (thrombin) receptor-like 3 (F2RL3), mRNA [NM_003950] |
| NM_001907 | CTRL | *Homo sapiens* chymotrypsin-like (CTRL), mRNA [NM_001907] |
| NM_001618 | PARP1 | *Homo sapiens* poly (ADP-ribose) polymerase family, member 1 (PARP1), mRNA [NM_001618] |
| A_24_P24724 | A_24_P24724 | Unknown |
| ENST00000321214 | C16orf81 | Uncharacterized protein C16orf81. [Source: Uniprot/SPTREMBL; Acc: Q8N9R0] [ENST00000321214] |
| NM_198253 | TERT | *Homo sapiens* telomerase reverse transcriptase (TERT), transcript variant 1, mRNA [NM_198253] |
| NM_153338 | GGT6 | *Homo sapiens* gamma-glutamyltransferase 6 homolog (rat) (GGT6), mRNA [NM_153338] |
| NM_182924 | MICALL2 | *Homo sapiens* MICAL-like 2 (MICALL2), transcript variant 1, mRNA [NM_182924] |
| NM_174918 | C19orf59 | *Homo sapiens* chromosome 19 open reading frame 59 (C19orf59), mRNA [NM_174918] |
| NR_002182 | NACAP1 | *Homo sapiens* nascent-polypeptide-associated complex alpha polypeptide pseudogene 1 (NACAP1) on chromosome 8 [NR_002182] |
| XR_016196 | LOC642652 | PREDICTED: *Homo sapiens* hypothetical LOC642652 (LOC642652), mRNA [XR_016196] |
| AA807824 | AA807824 | AA807824 nu96g07.s1 NCI_CGAP_Pr22 *Homo sapiens* cDNA clone IMAGE: 1218588 3', mRNA sequence [AA807824] |
| NM_053275 | RPLP0 | *Homo sapiens* ribosomal protein, large, P0 (RPLP0), transcript variant 2, mRNA [NM_053275] |
| XM_372331 | NKX1-2 | PREDICTED: *Homo sapiens* NK1 transcription factor related, locus 2 (*Drosophila*) (NKX1-2), mRNA [XM_372331] |
| XR_019454 | LOC130865 | PREDICTED: *Homo sapiens* similar to 60S ribosomal protein L26 (Silica-induced gene 20 protein) (SIG-20) (LOC130865), mRNA [XR_019454] |
| THC2504576 | THC2504576 | RL26_BOVIN (P61257) 60S ribosomal protein L26, complete [THC2504576] |
| A_24_P101694 | A_24_P101694 | Unknown |
| THC2668710 | THC2668710 | Q8NI81_HUMAN (Q8NI81) OK/SW-CL.41, partial (21%) [THC2668710] |
| NM_001432 | EREG | *Homo sapiens* epiregulin (EREG), mRNA [NM_001432] |
| NM_005568 | LHX1 | *Homo sapiens* LIM homeobox 1 (LHX1), mRNA [NM_005568] |
| NM_001153 | ANXA4 | *Homo sapiens* annexin A4 (ANXA4), mRNA [NM_001153] |
| A_24_P135242 | A_24_P135242 | Unknown |
| NM_014351 | SULT4A1 | *Homo sapiens* sulfotransferase family 4A, member 1 (SULT4A1), mRNA [NM_014351] |
| NM_019064 | SDK2 | *Homo sapiens* sidekick homolog 2 (chicken) (SDK2), mRNA [NM_019064] |
| NM_032219 | MFSD7 | *Homo sapiens* major facilitator superfamily domain containing 7 (MFSD7), mRNA [NM_032219] |
| NM_033625 | RPL34 | *Homo sapiens* ribosomal protein L34 (RPL34), transcript variant 2, mRNA [NM_033625] |
| ENST00000321566 | ENST00000321566 | PREDICTED: *Homo sapiens* similar to 60S ribosomal protein L7a, transcript variant 3 (LOC388474), mRNA [XM_938181] |
| XM_060535 | hCG_1641703 | PREDICTED: *Homo sapiens* similar to ribosomal protein L18a (LOC127545), mRNA [XM_060535] |
| ENST00000297544 | hCG_1818237 | PREDICTED: *Homo sapiens* similar to 60S acidic ribosomal protein P1 (LOC133609), mRNA [XM_068430] |
| NR_002797 | LOC255783 | *Homo sapiens* hypothetical protein LOC255783 (LOC255783) on chromosome 19 [NR_002797] |
| NM_014501 | UBE2S | *Homo sapiens* ubiquitin-conjugating enzyme E2S (UBE2S), mRNA [NM_014501] |
| NM_145015 | MRGPRF | *Homo sapiens* MAS-related GPR, member F (MRGPRF), mRNA [NM_145015] |
| XR_019248 | LOC130728 | PREDICTED: *Homo sapiens* similar to 60S ribosomal protein L7 (LOC130728), mRNA [XR_019248] |
| ENST00000356196 | hCG_26523 | PREDICTED: *Homo sapiens* similar to 60S ribosomal protein L26 (LOC646161), mRNA [XR_018048] |
| NM_000955 | PTGER1 | *Homo sapiens* prostaglandin E receptor 1 (subtype EP1), 42 kDa (PTGER1), mRNA [NM_000955] |
| ENST00000273844 | ENST00000273844 | PREDICTED: *Homo sapiens* similar to ribosomal protein S15a (LOC391656), mRNA [XM_373027] |
| NM_032087 | PCDHGA7 | *Homo sapiens* protocadherin gamma subfamily A, 7 (PCDHGA7), transcript variant 2, mRNA [NM_032087] |
| AK092739 | MCF2L | *Homo sapiens* cDNA FLJ35420 fis, clone SMINT2001183. [AK092739] |
| NM_021008 | DEAF1 | *Homo sapiens* deformed epidermal autoregulatory factor 1 (*Drosophila*) (DEAF1), mRNA [NM_021008] |
| NM_004420 | DUSP8 | *Homo sapiens* dual specificity phosphatase 8 (DUSP8), mRNA [NM_004420] |

TABLE 16-continued

Gene list generated at the inclusion criteria of p ≤ 0.001.

| GenBank Accession | GeneName | Description |
|---|---|---|
| ENST00000237840 | hCG_1642354 | PREDICTED: *Homo sapiens* similar to 60S ribosomal protein L23a (LOC341511), mRNA [XM_292109] |
| THC2722749 | THC2722749 | Q4RTW1_TETNG (Q4RTW1) Chromosome 12 SCAF14996, whole genome shotgun sequence. (Fragment), partial (77%) [THC2722749] |
| NM_005987 | SPRR1A | *Homo sapiens* small proline-rich protein 1A (SPRR1A), mRNA [NM_005987] |
| AK096241 | AK096241 | *Homo sapiens* cDNA FLJ38922 fis, clone NT2NE2011691. [AK096241] |
| NM_006506 | RASA2 | *Homo sapiens* RAS p21 protein activator 2 (RASA2), mRNA [NM_006506] |
| THC2612025 | THC2612025 | Q883S2_PSESM (Q883S2) Universal stress protein family, partial (9%) [THC2612025] |
| A_24_P340886 | A_24_P340886 | Unknown |
| THC2533242 | THC2533242 | FRG1_HUMAN (Q14331) FRG1 protein (FSHD region gene 1 protein), partial (21%) [THC2533242] |
| A_24_P367063 | A_24_P367063 | Unknown |
| A_24_P464798 | A_24_P464798 | Unknown |
| NM_173828 | C5orf16 | *Homo sapiens* chromosome 5 open reading frame 16 (C5orf16), mRNA [NM_173828] |
| NM_016274 | PLEKHO1 | *Homo sapiens* pleckstrin homology domain containing, family O member 1 (PLEKHO1), mRNA [NM_016274] |
| AK000420 | AK000420 | *Homo sapiens* cDNA FLJ20413 fis, clone KAT02170. [AK000420] |
| A_32_P78164 | A_32_P78164 | Unknown |
| XM_070233 | LOC137107 | PREDICTED: *Homo sapiens* similar to ribosomal protein L10a (LOC137107), mRNA [XM_070233] |
| NM_000998 | RPL37A | *Homo sapiens* ribosomal protein L37a (RPL37A), mRNA [NM_000998] |
| A_24_P169493 | A_24_P169493 | Unknown |
| NM_007209 | RPL35 | *Homo sapiens* ribosomal protein L35 (RPL35), mRNA [NM_007209] |
| NM_030966 | KRTAP1-3 | *Homo sapiens* keratin associated protein 1-3 (KRTAP1-3), mRNA [NM_030966] |
| AA418814 | AA418814 | AA418814 zw01a02.s1 Soares_NhHMPu_S1 *Homo sapiens* cDNA clone IMAGE: 767978 3', mRNA sequence [AA418814] |
| ENST00000361461 | LOC387867 | *Homo sapiens* cDNA clone IMAGE: 30318308, partial cds. [BC070327] |
| BG036557 | BG036557 | 602326332F1 NIH_MGC_91 *Homo sapiens* cDNA clone IMAGE: 4428126 5', mRNA sequence [BG036557] |
| BC080624 | BC080624 | *Homo sapiens* cDNA clone MGC: 99790 IMAGE: 6304510, complete cds. [BC080624] |
| AK024362 | LOC147650 | *Homo sapiens* cDNA FLJ14300 fis, clone PLACE1011891. [AK024362] |
| XM_928025 | LOC644937 | PREDICTED: *Homo sapiens* similar to 60S ribosomal protein L10 (QM protein) (Tumor suppressor QM) (Laminin receptor homolog) (LOC644937), mRNA [XM_928025] |
| NM_006032 | CPNE6 | *Homo sapiens* copine VI (neuronal) (CPNE6), mRNA [NM_006032] |
| XR_015402 | LOC731170 | PREDICTED: *Homo sapiens* similar to eukaryotic translation elongation factor 1 alpha 2 (LOC731170), mRNA [XR_015402] |
| NM_002512 | NME2 | *Homo sapiens* non-metastatic cells 2, protein (NM23B) expressed in (NME2), transcript variant 1, mRNA [NM_002512] |
| AK074447 | FLJ23867 | *Homo sapiens* cDNA FLJ23867 fis, clone LNG09729. [AK074447] |
| NM_138693 | KLF14 | *Homo sapiens* Kruppel-like factor 14 (KLF14), mRNA [NM_138693] |
| NM_033347 | KCNK7 | *Homo sapiens* potassium channel, subfamily K, member 7 (KCNK7), transcript variant A, mRNA [NM_033347] |
| BG209258 | LOC728315 | RST28773 Athersys RAGE Library *Homo sapiens* cDNA, mRNA sequence [BG209258] |
| AF111848 | AF111848 | *Homo sapiens* PRO0529 mRNA, complete cds. [AF111848] |
| XM_372498 | LOC390427 | PREDICTED: *Homo sapiens* similar to TBP-associated factor 15 isoform 1 (LOC390427), mRNA [XM_372498] |
| AK025430 | AK025430 | *Homo sapiens* cDNA: FLJ21777 fis, clone HEP00173. [AK025430] |
| NM_153266 | TMEM151 | *Homo sapiens* transmembrane protein 151 (TMEM151), mRNA [NM_153266] |
| A_24_P315654 | A_24_P315654 | Unknown |
| THC2649348 | THC2649348 | AY491776 alpha 1A adrenoceptor isoform 2c {*Homo sapiens*} (exp = −1; wgp = 0; cg = 0), partial (11%) [THC2649348] |
| NM_005617 | RPS14 | *Homo sapiens* ribosomal protein S14 (RPS14), transcript variant 3, mRNA [NM_005617] |
| NM_012183 | FOXD3 | *Homo sapiens* forkhead box D3 (FOXD3), mRNA [NM_012183] |
| ENST00000273794 | LOC90113 | *Homo sapiens* mRNA; cDNA DKFZp761K032 (from clone DKFZp761K032). [AL834499] |
| NM_007209 | RPL35 | *Homo sapiens* ribosomal protein L35 (RPL35), mRNA [NM_007209] |

TABLE 16-continued

Gene list generated at the inclusion criteria of p ≤ 0.001.

| GenBank Accession | GeneName | Description |
|---|---|---|
| A_24_P307466 | A_24_P307466 | Unknown |
| THC2541331 | THC2541331 | HSU02032 ribosomal protein L23a {Homo sapiens} (exp = −1; wgp = 0; cg = 0), partial (71%) [THC2541331] |
| A_24_P32207 | A_24_P32207 | Unknown |
| A_24_P118382 | A_24_P118382 | Unknown |
| NM_017805 | RASIP1 | Homo sapiens Ras interacting protein 1 (RASIP1), mRNA [NM_017805] |
| THC2545510 | THC2545510 | ALU1_HUMAN (P39188) Alu subfamily J sequence contamination warning entry, partial (13%) [THC2545510] |
| AK131261 | TMPRSS9 | Homo sapiens cDNA FLJ16193 fis, clone BRTHA2018011, weakly similar to EPITHIN (EC 3.4.21.—). [AK131261] |
| NM_002823 | PTMA | Homo sapiens prothymosin, alpha (gene sequence 28) (PTMA), mRNA [NM_002823] |
| BX115782 | BX115782 | BX115782 Soares_testis_NHT Homo sapiens cDNA clone IMAGp998E224413, mRNA sequence [BX115782] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| AW269579 | AW269579 | xv43d08.x1 Soares_NFL_T_GBC_S1 Homo sapiens cDNA clone IMAGE: 2815887 3' similar to gb: Z23090 HEAT SHOCK 27 KD PROTEIN (HUMAN);, mRNA sequence [AW269579] |
| ENST00000323057 | ENST00000323057 | Uncharacterized protein C1orf46 (Skin-specific protein xp33) (Fragment). [Source: Uniprot/SPTREMBL; Acc: O14635] [ENST00000323057] |
| THC2655508 | THC2655508 | Q4SPR8_TETNG (Q4SPR8) Chromosome 16 SCAF14537, whole genome shotgun sequence. (Fragment), partial (16%) [THC2655508] |
| NM_001014 | RPS10 | Homo sapiens ribosomal protein S10 (RPS10), mRNA [NM_001014] |
| NM_003560 | PLA2G6 | Homo sapiens phospholipase A2, group VI (cytosolic, calcium-independent) (PLA2G6), transcript variant 1, mRNA [NM_003560] |
| THC2704973 | THC2704973 | Unknown |
| NM_000984 | RPL23A | Homo sapiens ribosomal protein L23a (RPL23A), mRNA [NM_000984] |
| NM_003107 | SOX4 | Homo sapiens SRY (sex determining region Y)-box 4 (SOX4), mRNA [NM_003107] |
| AL080233 | AL080233 | Homo sapiens mRNA; cDNA DKFZp586L111 (from clone DKFZp586L111). [AL080233] |
| NM_006302 | GCS1 | Homo sapiens glucosidase I (GCS1), mRNA [NM_006302] |
| A_24_P358390 | A_24_P358390 | Unknown |
| NM_020433 | JPH2 | Homo sapiens junctophilin 2 (JPH2), transcript variant 1, mRNA [NM_020433] |
| NM_006597 | HSPA8 | Homo sapiens heat shock 70 kDa protein 8 (HSPA8), transcript variant 1, mRNA [NM_006597] |
| NM_032792 | ZBTB45 | Homo sapiens zinc finger and BTB domain containing 45 (ZBTB45), mRNA [NM_032792] |
| XR_019376 | LOC285260 | PREDICTED: Homo sapiens similar to ribosomal protein L31 (LOC285260), mRNA [XR_019376] |
| A_24_P587803 | A_24_P587803 | Unknown |
| NM_006235 | POU2AF1 | Homo sapiens POU domain, class 2, associating factor 1 (POU2AF1), mRNA [NM_006235] |
| AK095945 | AK095945 | Homo sapiens cDNA FLJ38626 fis, clone HEART2009599. [AK095945] |
| A_24_P221375 | A_24_P221375 | Unknown |
| A_24_P341386 | A_24_P341386 | Unknown |
| NM_032378 | EEF1D | Homo sapiens eukaryotic translation elongation factor 1 delta (guanine nucleotide exchange protein) (EEF1D), transcript variant 1, mRNA [NM_032378] |
| A_24_P358205 | A_24_P358205 | Unknown |
| NM_194278 | C14orf43 | Homo sapiens chromosome 14 open reading frame 43 (C14orf43), transcript variant 1, mRNA [NM_194278] |
| AF136171 | RPL22 | Homo sapiens heparin-binding protein HBp15 mRNA, complete cds. [AF136171] |
| NM_033625 | RPL34 | Homo sapiens ribosomal protein L34 (RPL34), transcript variant 2, mRNA [NM_033625] |
| NM_003202 | TCF7 | Homo sapiens transcription factor 7 (T-cell specific, HMG-box) (TCF7), transcript variant 1, mRNA [NM_003202] |
| NM_178013 | PRIMA1 | Homo sapiens proline rich membrane anchor 1 (PRIMA1), mRNA [NM_178013] |
| A_24_P878388 | A_24_P878388 | Unknown |
| NM_021025 | TLX3 | Homo sapiens T-cell leukemia homeobox 3 (TLX3), mRNA [NM_021025] |

TABLE 16-continued

Gene list generated at the inclusion criteria of p ≤ 0.001.

| GenBank Accession | GeneName | Description |
|---|---|---|
| A_24_P349489 | A_24_P349489 | Unknown |
| NM_033260 | FOXQ1 | *Homo sapiens* forkhead box Q1 (FOXQ1), mRNA [NM_033260] |
| NM_025187 | C16orf70 | *Homo sapiens* chromosome 16 open reading frame 70 (C16orf70), mRNA [NM_025187] |
| NM_018490 | LGR4 | *Homo sapiens* leucine-rich repeat-containing G protein-coupled receptor 4 (LGR4), mRNA [NM_018490] |
| XR_018554 | LOC402219 | PREDICTED: *Homo sapiens* similar to ribosomal protein L5 (LOC402219), mRNA [XR_018554] |
| XR_018010 | LOC641727 | PREDICTED: *Homo sapiens* similar to 60S ribosomal protein L7a (LOC641727), mRNA [XR_018010] |
| NM_002723 | PRB4 | *Homo sapiens* proline-rich protein BstNI subfamily 4 (PRB4), mRNA [NM_002723] |
| NM_019095 | CRLS1 | *Homo sapiens* cardiolipin synthase 1 (CRLS1), mRNA [NM_019095] |
| NM_022558 | GH2 | *Homo sapiens* growth hormone 2 (GH2), transcript variant 3, mRNA [NM_022558] |
| XR_018786 | LOC649303 | PREDICTED: *Homo sapiens* similar to ribosomal protein S10 (LOC649303), mRNA [XR_018786] |
| NM_005356 | LCK | *Homo sapiens* lymphocyte-specific protein tyrosine kinase (LCK), transcript variant 2, mRNA [NM_005356] |
| NM_001006 | RPS3A | *Homo sapiens* ribosomal protein S3A (RPS3A), mRNA [NM_001006] |
| NM_020932 | MAGEE1 | *Homo sapiens* melanoma antigen family E, 1 (MAGEE1), mRNA [NM_020932] |
| NM_024099 | C11orf48 | *Homo sapiens* chromosome 11 open reading frame 48 (C11orf48), mRNA [NM_024099] |
| THC2540532 | THC2540532 | Unknown |
| ENST00000372073 | TMEM164 | Transmembrane protein 164. [Source: Uniprot/SWISSPROT; Acc: Q5U3C3] [ENST00000372073] |
| NM_153813 | ZFPM1 | *Homo sapiens* zinc finger protein, multitype 1 (ZFPM1), mRNA [NM_153813] |
| NM_006270 | RRAS | *Homo sapiens* related RAS viral (r-ras) oncogene homolog (RRAS), mRNA [NM_006270] |
| NM_001006 | RPS3A | *Homo sapiens* ribosomal protein S3A (RPS3A), mRNA [NM_001006] |
| NM_021044 | DHH | *Homo sapiens* desert hedgehog homolog (*Drosophila*) (DHH), mRNA [NM_021044] |
| BC006438 | BC006438 | *Homo sapiens* cDNA clone MGC: 13162 IMAGE: 3010103, complete cds. [BC006438] |
| NM_001012361 | WDR31 | *Homo sapiens* WD repeat domain 31 (WDR31), transcript variant 1, mRNA [NM_001012361] |
| A_24_P32836 | A_24_P32836 | Unknown |
| A_24_P862251 | A_24_P862251 | Unknown |
| NM_002823 | PTMA | *Homo sapiens* prothymosin, alpha (gene sequence 28) (PTMA), mRNA [NM_002823] |
| NM_022036 | GPRC5C | *Homo sapiens* G protein-coupled receptor, family C, group 5, member C (GPRC5C), transcript variant 1, mRNA [NM_022036] |
| NM_133328 | DEDD2 | *Homo sapiens* death effector domain containing 2 (DEDD2), mRNA [NM_133328] |
| NM_005632 | SOLH | *Homo sapiens* small optic lobes homolog (*Drosophila*) (SOLH), mRNA [NM_005632] |
| ENST00000359659 | ENST00000359659 | Q8BT90_MOUSE (Q8BT90) 10, 11 days embryo whole body cDNA, RIKEN full-length enriched library, clone: 2810021H19 product: ribosomal protein S17, full insert sequence. (Fragment), partial (98%) [THC2555910] |
| A_32_P25809 | A_32_P25809 | Unknown |
| NM_000041 | APOE | *Homo sapiens* apolipoprotein E (APOE), mRNA [NM_000041] |
| AK057177 | L3MBTL2 | *Homo sapiens* cDNA FLJ32615 fis, clone STOMA2000148. [AK057177] |
| NM_152571 | C9orf163 | *Homo sapiens* chromosome 9 open reading frame 163 (C9orf163), mRNA [NM_152571] |
| NM_024901 | DENND2D | *Homo sapiens* DENN/MADD domain containing 2D (DENND2D), mRNA [NM_024901] |
| NM_001021 | RPS17 | *Homo sapiens* ribosomal protein S17 (RPS17), mRNA [NM_001021] |
| NM_005284 | GPR6 | *Homo sapiens* G protein-coupled receptor 6 (GPR6), mRNA [NM_005284] |
| NM_001042535 | CENTG3 | *Homo sapiens* centaurin, gamma 3 (CENTG3), transcript variant 2, mRNA [NM_001042535] |
| NM_152243 | CDC42EP1 | *Homo sapiens* CDC42 effector protein (Rho GTPase binding) 1 (CDC42EP1), transcript variant 1, mRNA [NM_152243] |
| NM_001009 | RPS5 | *Homo sapiens* ribosomal protein S5 (RPS5), mRNA [NM_001009] |
| NM_002801 | PSMB10 | *Homo sapiens* proteasome (prosome, macropain) subunit, beta type, 10 (PSMB10), mRNA [NM_002801] |

TABLE 16-continued

Gene list generated at the inclusion criteria of p ≤ 0.001.

| GenBank Accession | GeneName | Description |
|---|---|---|
| AK025353 | AK025353 | *Homo sapiens* cDNA: FLJ21700 fis, clone COL09849, highly similar to HSU14972 Human ribosomal protein S10 mRNA. [AK025353] |
| AB019568 | AB019568 | *Homo sapiens* mRNA expressed only in placental villi, clone SMAP83. [AB019568] |
| NM_006476 | ATP5L | *Homo sapiens* ATP synthase, H+ transporting, mitochondrial F0 complex, subunit G (ATP5L), nuclear gene encoding mitochondrial protein, mRNA [NM_006476] |
| NM_005586 | MDFI | *Homo sapiens* MyoD family inhibitor (MDFI), mRNA [NM_005586] |
| AI537201 | AI537201 | AI537201 tp06e06.x1 NCI_CGAP_Gas4 *Homo sapiens* cDNA clone IMAGE: 2187010 3', mRNA sequence [AI537201] |
| NM_021136 | RTN1 | *Homo sapiens* reticulon 1 (RTN1), transcript variant 1, mRNA [NM_021136] |
| NM_001959 | EEF1B2 | *Homo sapiens* eukaryotic translation elongation factor 1 beta 2 (EEF1B2), transcript variant 1, mRNA [NM_001959] |
| ENST00000359449 | ENST00000359449 | Sequence 237 from Patent WO0220754. [AX721277] |
| A_24_P745960 | A_24_P745960 | Unknown |
| A_24_P247493 | A_24_P247493 | Unknown |
| NM_016579 | CD320 | *Homo sapiens* CD320 molecule (CD320), mRNA [NM_016579] |
| NM_024933 | ANKRD53 | *Homo sapiens* ankyrin repeat domain 53 (ANKRD53), mRNA [NM_024933] |
| XM_926013 | LOC642398 | PREDICTED: *Homo sapiens* hypothetical LOC642398, transcript variant 1 (LOC642398), mRNA [XM_926013] |
| AI971459 | AI971459 | AI971459 wq86e07.x1 NCI_CGAP_GC6 *Homo sapiens* cDNA clone IMAGE: 2478948 3', mRNA sequence [AI971459] |
| A_24_P752279 | A_24_P752279 | Unknown |
| NM_001522 | GUCY2F | *Homo sapiens* guanylate cyclase 2F, retinal (GUCY2F), mRNA [NM_001522] |
| NM_052952 | DIRC1 | *Homo sapiens* disrupted in renal carcinoma 1 (DIRC1), mRNA [NM_052952] |
| NM_003202 | TCF7 | *Homo sapiens* transcription factor 7 (T-cell specific, HMG-box) (TCF7), transcript variant 1, mRNA [NM_003202] |
| NM_052940 | LRRC42 | *Homo sapiens* leucine rich repeat containing 42 (LRRC42), mRNA [NM_052940] |
| NM_004265 | FADS2 | *Homo sapiens* fatty acid desaturase 2 (FADS2), mRNA [NM_004265] |
| BC071734 | BC071734 | *Homo sapiens* cDNA clone MGC: 88072 IMAGE: 5549882, complete cds. [BC071734] |
| NM_002466 | MYBL2 | *Homo sapiens* v-myb myeloblastosis viral oncogene homolog (avian)-like 2 (MYBL2), mRNA [NM_002466] |
| NM_017645 | FAM29A | *Homo sapiens* family with sequence similarity 29, member A (FAM29A), mRNA [NM_017645] |
| NM_145273 | CD300LG | *Homo sapiens* CD300 molecule-like family member g (CD300LG), mRNA [NM_145273] |
| A_32_P71864 | A_32_P71864 | Unknown |
| NM_015417 | C20orf28 | *Homo sapiens* chromosome 20 open reading frame 28 (C20orf28), mRNA [NM_015417] |
| NM_002446 | MAP3K10 | *Homo sapiens* mitogen-activated protein kinase kinase kinase 10 (MAP3K10), mRNA [NM_002446] |
| A_24_P341176 | A_24_P341176 | Unknown |
| XR_019059 | LOC654170 | PREDICTED: *Homo sapiens* similar to 40S ribosomal protein S16 (LOC654170), mRNA [XR_019059] |
| NM_001022 | RPS19 | *Homo sapiens* ribosomal protein S19 (RPS19), mRNA [NM_001022] |
| NM_001632 | ALPP | *Homo sapiens* alkaline phosphatase, placental (Regan isozyme) (ALPP), mRNA [NM_001632] |
| NM_014343 | CLDN15 | *Homo sapiens* claudin 15 (CLDN15), transcript variant 1, mRNA [NM_014343] |
| A_24_P272735 | A_24_P272735 | Unknown |
| NM_004977 | KCNC3 | *Homo sapiens* potassium voltage-gated channel, Shaw-related subfamily, member 3 (KCNC3), mRNA [NM_004977] |
| AK074960 | AK074960 | *Homo sapiens* cDNA FLJ90479 fis, clone NT2RP3002836, highly similar to Plexin A2. [AK074960] |
| NM_002081 | GPC1 | *Homo sapiens* glypican 1 (GPC1), mRNA [NM_002081] |
| AF086468 | AF086468 | *Homo sapiens* full length insert cDNA clone ZD86H05. [AF086468] |
| XR_015398 | LOC730747 | PREDICTED: *Homo sapiens* similar to 60S ribosomal protein L14 (CAG-ISL 7) (LOC730747), mRNA [XR_015398] |
| ENST00000332804 | ENST00000332804 | PREDICTED: *Homo sapiens* similar to 60S ribosomal protein L22 (Heparin-binding protein HBp15) (LOC727747), mRNA [XR_015114] |
| XM_935576 | LOC641827 | PREDICTED: *Homo sapiens* similar to eukaryotic translation elongation factor 1 beta 2 (LOC641827), mRNA [XM_935576] |

TABLE 16-continued

Gene list generated at the inclusion criteria of p ≤ 0.001.

| GenBank Accession | GeneName | Description |
|---|---|---|
| NM_054114 | TAGAP | *Homo sapiens* T-cell activation GTPase activating protein (TAGAP), transcript variant 2, mRNA [NM_054114] |
| NM_012423 | RPL13A | *Homo sapiens* ribosomal protein L13a (RPL13A), mRNA [NM_012423] |
| A_23_P58072 | A_23_P58072 | Unknown |
| BC034005 | LOC388494 | *Homo sapiens* hypothetical gene supported by AL365406; BC034005, mRNA (cDNA clone IMAGE: 5276795). [BC034005] |
| NM_000982 | RPL21 | *Homo sapiens* ribosomal protein L21 (RPL21), mRNA [NM_000982] |
| THC2611974 | THC2611974 | AY250221 nogo receptor-like 3 {*Homo sapiens*} (exp = −1; wgp = 0; cg = 0), partial (12%) [THC2611974] |
| NM_002124 | HLA-DRB1 | *Homo sapiens* major histocompatibility complex, class II, DR beta 1 (HLA-DRB1), mRNA [NM_002124] |
| NM_153236 | GIMAP7 | *Homo sapiens* GTPase, IMAP family member 7 (GIMAP7), mRNA [NM_153236] |
| AK096674 | AK096674 | *Homo sapiens* cDNA FLJ39355 fis, clone PEBLM2003426. [AK096674] |
| NM_024345 | WDR32 | *Homo sapiens* WD repeat domain 32 (WDR32), mRNA [NM_024345] |
| A_24_P384469 | A_24_P384469 | Unknown |
| NM_058219 | EXOSC6 | *Homo sapiens* exosome component 6 (EXOSC6), mRNA [NM_058219] |
| NM_032810 | ATAD1 | *Homo sapiens* ATPase family, AAA domain containing 1 (ATAD1), mRNA [NM_032810] |
| NM_003202 | TCF7 | *Homo sapiens* transcription factor 7 (T-cell specific, HMG-box) (TCF7), transcript variant 1, mRNA [NM_003202] |
| NM_006690 | MMP24 | *Homo sapiens* matrix metallopeptidase 24 (membrane-inserted) (MMP24), mRNA [NM_006690] |
| NM_006360 | PCID1 | *Homo sapiens* PCI domain containing 1 (herpesvirus entry mediator) (PCID1), mRNA [NM_006360] |
| NM_138573 | NRG4 | *Homo sapiens* neuregulin 4 (NRG4), mRNA [NM_138573] |
| AK056421 | TNRC6C | *Homo sapiens* cDNA FLJ31859 fis, clone NT2RP7001231. [AK056421] |
| NM_000164 | GIPR | *Homo sapiens* gastric inhibitory polypeptide receptor (GIPR), mRNA [NM_000164] |
| XR_015445 | LOC730773 | PREDICTED: *Homo sapiens* similar to 60S ribosomal protein L7a (Surfeit locus protein 3) (LOC730773), mRNA [XR_015445] |
| NM_000587 | C7 | *Homo sapiens* complement component 7 (C7), mRNA [NM_000587] |
| A_24_P383934 | A_24_P383934 | Unknown |
| NM_001042413 | GLIS3 | *Homo sapiens* GLIS family zinc finger 3 (GLIS3), transcript variant 1, mRNA [NM_001042413] |
| XM_931016 | LOC388076 | PREDICTED: *Homo sapiens* similar to ribosomal protein S8, transcript variant 2 (LOC388076), mRNA [XM_931016] |
| NM_001007176 | C8orf22 | *Homo sapiens* chromosome 8 open reading frame 22 (C8orf22), mRNA [NM_001007176] |
| A_24_P238996 | A_24_P238996 | Unknown |
| NM_005338 | HIP1 | *Homo sapiens* huntingtin interacting protein 1 (HIP1), mRNA [NM_005338] |
| NM_014395 | DAPP1 | *Homo sapiens* dual adaptor of phosphotyrosine and 3-phosphoinositides (DAPP1), mRNA [NM_014395] |
| NM_018231 | FLJ10815 | *Homo sapiens* amino acid transporter (FLJ10815), mRNA [NM_018231] |
| XR_019444 | LOC122589 | PREDICTED: *Homo sapiens* similar to 60S acidic ribosomal protein P0 (L10E) (LOC122589), mRNA [XR_019444] |
| NM_001747 | CAPG | *Homo sapiens* capping protein (actin filament), gelsolin-like (CAPG), mRNA [NM_001747] |
| BC011940 | BC011940 | *Homo sapiens* cDNA clone IMAGE: 4329532, partial cds. [BC011940] |
| NM_001798 | CDK2 | *Homo sapiens* cyclin-dependent kinase 2 (CDK2), transcript variant 1, mRNA [NM_001798] |
| A_24_P551530 | A_24_P551530 | Unknown |
| NM_000607 | ORM1 | *Homo sapiens* orosomucoid 1 (ORM1), mRNA [NM_000607] |
| NM_021130 | PPIA | *Homo sapiens* peptidylprolyl isomerase A (cyclophilin A) (PPIA), mRNA [NM_021130] |
| XR_018155 | LOC643013 | PREDICTED: *Homo sapiens* similar to laminin receptor 1 (ribosomal protein SA) (LOC643013), mRNA [XR_018155] |
| NM_002973 | ATXN2 | *Homo sapiens* ataxin 2 (ATXN2), mRNA [NM_002973] |
| NM_012272 | PRPF40B | *Homo sapiens* PRP40 pre-mRNA processing factor 40 homolog B (*S. cerevisiae*) (PRPF40B), transcript variant 2, mRNA [NM_012272] |
| NM_003456 | ZNF205 | *Homo sapiens* zinc finger protein 205 (ZNF205), transcript variant 1, mRNA [NM_003456] |

TABLE 16-continued

Gene list generated at the inclusion criteria of p ≤ 0.001.

| GenBank Accession | GeneName | Description |
| --- | --- | --- |
| BC025734 | BC025734 | *Homo sapiens*, clone IMAGE: 5204729, mRNA. [BC025734] |
| NM_020240 | CDC42SE2 | *Homo sapiens* CDC42 small effector 2 (CDC42SE2), transcript variant 1, mRNA [NM_020240] |
| AB011149 | AB011149 | *Homo sapiens* mRNA for KIAA0577 protein, partial cds. [AB011149] |
| NM_005828 | WDR68 | *Homo sapiens* WD repeat domain 68 (WDR68), mRNA [NM_005828] |
| NM_004137 | KCNMB1 | *Homo sapiens* potassium large conductance calcium-activated channel, subfamily M, beta member 1 (KCNMB1), mRNA [NM_004137] |
| NM_016263 | FZR1 | *Homo sapiens* fizzy/cell division cycle 20 related 1 (*Drosophila*) (FZR1), mRNA [NM_016263] |
| ENST00000383061 | ENST00000383061 | PREDICTED: *Homo sapiens* similar to myosin regulatory light chain-like (LOC442204), mRNA [XM_498088] |
| DQ786228 | DQ786228 | *Homo sapiens* clone HLS_IMAGE_1699118 mRNA sequence. [DQ786228] |
| XM_941195 | LOC388621 | PREDICTED: *Homo sapiens* similar to ribosomal protein L21 (LOC388621), mRNA [XM_941195] |
| NM_002824 | PTMS | *Homo sapiens* parathymosin (PTMS), mRNA [NM_002824] |
| AA725389 | AA725389 | ai17f05.s1 Soares_parathyroid_tumor_NbHPA *Homo sapiens* cDNA clone 1343073 3' similar to TR: P79324 P79324 RIBOSOMAL PROTEIN L15;, mRNA sequence [AA725389] |
| DW451363 | DW451363 | HHAGE004093 Human liver regeneration after partial hepatectomy *Homo sapiens* cDNA, mRNA sequence [DW451363] |
| NM_057088 | KRT3 | *Homo sapiens* keratin 3 (KRT3), mRNA [NM_057088] |
| NM_174910 | TCTE3 | *Homo sapiens* t-complex-associated-testis-expressed 3 (TCTE3), mRNA [NM_174910] |
| BE551270 | BE551270 | BE551270 7b62a07.x1 NCI_CGAP_Lu24 *Homo sapiens* cDNA clone IMAGE: 3232788 3', mRNA sequence [BE551270] |
| NM_002948 | RPL15 | *Homo sapiens* ribosomal protein L15 (RPL15), mRNA [NM_002948] |
| NM_000610 | CD44 | *Homo sapiens* CD44 molecule (Indian blood group) (CD44), transcript variant 1, mRNA [NM_000610] |
| A_24_P919283 | A_24_P919283 | Unknown |
| CD174733 | CD174733 | CD174733 AGENCOURT_13961604 NIH_MGC_172 *Homo sapiens* cDNA 5', mRNA sequence [CD174733] |
| NM_002341 | LTB | *Homo sapiens* lymphotoxin beta (TNF superfamily, member 3) (LTB), transcript variant 1, mRNA [NM_002341] |
| NM_005356 | LCK | *Homo sapiens* lymphocyte-specific protein tyrosine kinase (LCK), transcript variant 2, mRNA [NM_005356] |
| A_32_P22679 | A_32_P22679 | Unknown |
| NM_005309 | GPT | *Homo sapiens* glutamic-pyruvate transaminase (alanine aminotransferase) (GPT), mRNA [NM_005309] |
| NM_198904 | GABRG2 | *Homo sapiens* gamma-aminobutyric acid (GABA) A receptor, gamma 2 (GABRG2), transcript variant 1, mRNA [NM_198904] |
| NM_015335 | THRAP2 | *Homo sapiens* thyroid hormone receptor associated protein 2 (THRAP2), mRNA [NM_015335] |
| AK096229 | AK096229 | *Homo sapiens* cDNA FLJ38910 fis, clone NT2NE2006813, weakly similar to CELL SURFACE GLYCOPROTEIN 1 PRECURSOR. [AK096229] |
| NM_013373 | ZDHHC8 | *Homo sapiens* zinc finger, DHHC-type containing 8 (ZDHHC8), mRNA [NM_013373] |
| XR_018405 | LOC391655 | PREDICTED: *Homo sapiens* similar to 60S ribosomal protein L17 (L23) (LOC391655), mRNA [XR_018405] |
| A_24_P916759 | A_24_P916759 | Unknown |
| BC016140 | MVK | *Homo sapiens* mevalonate kinase (mevalonic aciduria), mRNA (cDNA clone MGC: 9001 IMAGE: 3921543), complete cds. [BC016140] |
| BC105992 | SYNGR2 | *Homo sapiens* synaptogyrin 2, mRNA (cDNA clone MGC: 102914 IMAGE: 4746277), complete cds. [BC105992] |
| NM_001077710 | FAM110C | *Homo sapiens* family with sequence similarity 110, member C (FAM110C), mRNA [NM_001077710] |
| BC018140 | RPS21 | *Homo sapiens* ribosomal protein S21, mRNA (cDNA clone MGC: 9438 IMAGE: 3903320), complete cds. [BC018140] |
| AA627135 | AA627135 | nq71a04.s1 NCI_CGAP_Pr22 *Homo sapiens* cDNA clone IMAGE: 1157742 3' similar to SW: R13A_HUMAN P40429 60S RIBOSOMAL PROTEIN L13A;, mRNA sequence [AA627135] |
| NM_000661 | RPL9 | *Homo sapiens* ribosomal protein L9 (RPL9), transcript variant 1, mRNA [NM_000661] |
| AB075859 | ZNF525 | *Homo sapiens* mRNA for KIAA1979 protein. [AB075859] |
| NM_003052 | SLC34A1 | *Homo sapiens* solute carrier family 34 (sodium phosphate), member 1 (SLC34A1), mRNA [NM_003052] |
| XR_018720 | LOC392206 | PREDICTED: *Homo sapiens* similar to ribosomal protein L10a (LOC392206), mRNA [XR_018720] |

TABLE 16-continued

Gene list generated at the inclusion criteria of p ≤ 0.001.

| GenBank Accession | GeneName | Description |
|---|---|---|
| NM_138763 | BAX | *Homo sapiens* BCL2-associated X protein (BAX), transcript variant delta, mRNA [NM_138763] |
| NM_001410 | MEGF8 | *Homo sapiens* multiple EGF-like-domains 8 (MEGF8), mRNA [NM_001410] |
| NM_014807 | TMEM24 | *Homo sapiens* transmembrane protein 24 (TMEM24), mRNA [NM_014807] |
| NM_001014980 | FAM132A | *Homo sapiens* C1q domain containing 2 (C1QDC2), mRNA [NM_001014980] |
| NM_001356 | DDX3X | *Homo sapiens* DEAD (Asp-Glu-Ala-Asp) box polypeptide 3, X-linked (DDX3X), mRNA [NM_001356] |
| NM_198149 | TMEM58 | *Homo sapiens* transmembrane protein 58 (TMEM58), mRNA [NM_198149] |
| A_24_P127442 | A_24_P127442 | Unknown |
| NM_016155 | MMP17 | *Homo sapiens* matrix metallopeptidase 17 (membrane-inserted) (MMP17), mRNA [NM_016155] |
| U79275 | HSU79275 | Human clone 23947 mRNA, partial cds. [U79275] |
| NM_021569 | GRIN1 | *Homo sapiens* glutamate receptor, ionotropic, N-methyl D-aspartate 1 (GRIN1), transcript variant NR1-2, mRNA [NM_021569] |
| THC2567891 | THC2567891 | Q6NXR8_HUMAN (Q6NXR8) Ribosomal protein S3a, partial (91%) [THC2567891] |
| NM_003295 | TPT1 | *Homo sapiens* tumor protein, translationally-controlled 1 (TPT1), mRNA [NM_003295] |
| NM_016428 | ABI3 | *Homo sapiens* ABI gene family, member 3 (ABI3), mRNA [NM_016428] |
| AK091355 | LOC284926 | *Homo sapiens* cDNA FLJ34036 fis, clone FCBBF2005069. [AK091355] |
| NM_001823 | CKB | *Homo sapiens* creatine kinase, brain (CKB), mRNA [NM_001823] |
| THC2655417 | THC2655417 | Q5TDX9_HUMAN (Q5TDX9) OTTHUMP00000030619 (Fragment), complete [THC2655417] |
| ENST00000302096 | ENST00000302096 | bA299N6.3 (LOC198437), mRNA [Source: RefSeq_dna; Acc: NM_001007125] [ENST00000302096] |
| NM_001958 | EEF1A2 | *Homo sapiens* eukaryotic translation elongation factor 1 alpha 2 (EEF1A2), mRNA [NM_001958] |
| NM_000610 | CD44 | *Homo sapiens* CD44 molecule (Indian blood group) (CD44), transcript variant 1, mRNA [NM_000610] |
| ENST00000338509 | ENST00000338509 | PREDICTED: *Homo sapiens* similar to 60S ribosomal protein L7a (LOC641727), mRNA [XR_018010] |
| BC060766 | SLC2A14 | *Homo sapiens* solute carrier family 2 (facilitated glucose transporter), member 14, mRNA (cDNA clone MGC: 71510 IMAGE: 5297510), complete cds. [BC060766] |
| NM_005634 | SOX3 | *Homo sapiens* SRY (sex determining region Y)-box 3 (SOX3), mRNA [NM_005634] |
| A_24_P384411 | A_24_P384411 | Unknown |
| NM_000982 | RPL21 | *Homo sapiens* ribosomal protein L21 (RPL21), mRNA [NM_000982] |
| THC2506377 | THC2506377 | HSU02032 ribosomal protein L23a {*Homo sapiens*} (exp = -1; wgp = 0; cg = 0), partial (92%) [THC2506377] |
| NM_001080544 | LOC653314 | *Homo sapiens* similar to ribosomal protein L19 (LOC653314), mRNA [NM_001080544] |
| NM_003809 | TNFSF12 | *Homo sapiens* tumor necrosis factor (ligand) superfamily, member 12 (TNFSF12), mRNA [NM_003809] |
| NM_053275 | RPLP0 | *Homo sapiens* ribosomal protein, large, P0 (RPLP0), transcript variant 2, mRNA [NM_053275] |
| XR_019597 | LOC401863 | PREDICTED: *Homo sapiens* similar to ribosomal protein L10a (LOC401863), mRNA [XR_019597] |
| NM_080862 | SPSB4 | *Homo sapiens* splA/ryanodine receptor domain and SOCS box containing 4 (SPSB4), mRNA [NM_080862] |
| NM_024324 | CRELD2 | *Homo sapiens* cysteine-rich with EGF-like domains 2 (CRELD2), mRNA [NM_024324] |
| AA282192 | AA282192 | AA282192 zs89b10.r1 NCI_CGAP_GCB1 *Homo sapiens* cDNA clone IMAGE: 704635 5', mRNA sequence [AA282192] |
| NM_182688 | UBE2G2 | *Homo sapiens* ubiquitin-conjugating enzyme E2G 2 (UBC7 homolog, yeast) (UBE2G2), transcript variant 2, mRNA [NM_182688] |
| NM_001395 | DUSP9 | *Homo sapiens* dual specificity phosphatase 9 (DUSP9), mRNA [NM_001395] |
| A_24_P547010 | A_24_P547010 | Unknown |
| ENST00000259289 | ENST00000259289 | Unknown |
| BC067080 | FCRLB | *Homo sapiens* Fc receptor-like B, mRNA (cDNA clone MGC: 71141 IMAGE: 3529386), complete cds. [BC067080] |
| NM_004689 | MTA1 | *Homo sapiens* metastasis associated 1 (MTA1), mRNA [NM_004689] |
| NM_005250 | FOXL1 | *Homo sapiens* forkhead box L1 (FOXL1), mRNA [NM_005250] |
| ENST00000355748 | ENST00000355748 | Endogenous retrovirus H D1 leader region/integrase-derived ORF1, ORF2, and putative envelope protein (Endogenous retrovirus H |

TABLE 16-continued

Gene list generated at the inclusion criteria of p ≤ 0.001.

| GenBank Accession | GeneName | Description |
|---|---|---|
| | | protease/integrase-derived ORF1, ORF2, and putative envelope protein). [Source: Uniprot/SPTREMBL; Acc: O00627] [ENST00000355748] |
| AK130207 | LOC442325 | Homo sapiens cDNA FLJ26697 fis, clone PCD00618. [AK130207] |
| NM_138778 | WDR85 | Homo sapiens WD repeat domain 85 (WDR85), mRNA [NM_138778] |
| A_24_P714316 | A_24_P714316 | Unknown |
| NM_003021 | SGTA | Homo sapiens small glutamine-rich tetratricopeptide repeat (TPR)-containing, alpha (SGTA), mRNA [NM_003021] |
| NM_002333 | LRP3 | Homo sapiens low density lipoprotein receptor-related protein 3 (LRP3), mRNA [NM_002333] |
| NM_001997 | FAU | Homo sapiens Finkel-Biskis-Reilly murine sarcoma virus (FBR-MuSV) ubiquitously expressed (fox derived); ribosomal protein S30 (FAU), mRNA [NM_001997] |
| NM_020150 | SAR1A | Homo sapiens SAR1 gene homolog A (S. cerevisiae) (SAR1A), mRNA [NM_020150] |
| A_32_P79515 | A_32_P79515 | Unknown |
| XR_018574 | LOC402214 | PREDICTED: Homo sapiens hypothetical LOC402214 (LOC402214), mRNA [XR_018574] |
| NM_178354 | LCE1F | Homo sapiens late cornified envelope 1F (LCE1F), mRNA [NM_178354] |
| THC2618720 | THC2618720 | Unknown |
| NM_001728 | BSG | Homo sapiens basigin (Ok blood group) (BSG), transcript variant 1, mRNA [NM_001728] |
| NM_024742 | ARMC5 | Homo sapiens armadillo repeat containing 5 (ARMC5), mRNA [NM_024742] |
| NM_053275 | RPLP0 | Homo sapiens ribosomal protein, large, P0 (RPLP0), transcript variant 2, mRNA [NM_053275] |
| NM_021104 | RPL41 | Homo_sapiens ribosomal protein L41 (RPL41), transcript variant 1, mRNA [NM_021104] |
| XR_019574 | LOC400064 | PREDICTED: Homo sapiens hypothetical LOC400064 (LOC400064), mRNA [XR_019574] |
| AL834350 | PPP2R5C | Homo sapiens mRNA; cDNA DKFZp761H0317 (from clone DKFZp761H0317). [AL834350] |
| BC040412 | BC040412 | Homo sapiens, clone IMAGE: 5184855, mRNA. [BC040412] |
| NM_170746 | C11orf31 | Homo sapiens chromosome 11 open reading frame 31 (C11orf31), mRNA [NM_170746] |
| BC028083 | TRBV5-4 | Homo sapiens T cell receptor beta variable 5-4, mRNA (cDNA clone MGC: 40031 IMAGE: 5217067), complete cds. [BC028083] |
| NM_000454 | SOD1 | Homo sapiens superoxide dismutase 1, soluble (amyotrophic lateral sclerosis 1 (adult)) (SOD1), mRNA [NM_000454] |
| AA484677 | AA484677 | AA484677 ne64a07.s1 NCI_CGAP_Alv1 Homo sapiens cDNA clone IMAGE: 909012, mRNA sequence [AA484677] |
| NM_001004321 | FLJ45445 | Homo sapiens FLJ45445 protein (FLJ45445), mRNA [NM_001004321] |
| NM_153002 | GPR156 | Homo sapiens G protein-coupled receptor 156 (GPR156), mRNA [NM_153002] |
| NM_019105 | TNXB | Homo sapiens tenascin XB (TNXB), transcript variant XB, mRNA [NM_019105] |
| AK026367 | AK026367 | Homo sapiens cDNA: FLJ22714 fis, clone HSI13646. [AK026367] |
| NM_000989 | RPL30 | Homo sapiens ribosomal protein L30 (RPL30), mRNA [NM_000989] |
| ENST00000332696 | ENST00000332696 | similar to 60S ribosomal protein L23a (LOC644384), mRNA [Source: RefSeq_dna; Acc: XR_017413] [ENST00000332696] |
| XR_015944 | LOC731681 | PREDICTED: Homo sapiens similar to 60S ribosomal protein L9 (LOC731681), mRNA [XR_015944] |
| NM_030649 | CENTB5 | Homo sapiens centaurin, beta 5 (CENTB5), mRNA [NM_030649] |
| NM_001138 | AGRP | Homo sapiens agouti related protein homolog (mouse) (AGRP), transcript variant 1, mRNA [NM_001138] |
| NM_000991 | RPL28 | Homo sapiens ribosomal protein L28 (RPL28), mRNA [NM_000991] |
| NM_016423 | ZNF219 | Homo sapiens zinc finger protein 219 (ZNF219), mRNA [NM_016423] |
| A_32_P234913 | A_32_P234913 | Unknown |
| NM_144779 | FXYD5 | Homo sapiens FXYD domain containing ion transport regulator 5 (FXYD5), transcript variant 1, mRNA [NM_144779] |
| XR_019544 | LOC652890 | PREDICTED: Homo sapiens similar to 60S ribosomal protein L7 (LOC652890), mRNA [XR_019544] |
| NM_001000 | RPL39 | Homo sapiens ribosomal protein L39 (RPL39), mRNA [NM_001000] |
| NM_152901 | PYDC1 | Homo sapiens PYD (pyrin domain) containing 1 (PYDC1), mRNA [NM_152901] |
| NM_002823 | PTMA | Homo sapiens prothymosin, alpha (gene sequence 28) (PTMA), mRNA [NM_002823] |

TABLE 16-continued

Gene list generated at the inclusion criteria of p ≤ 0.001.

| GenBank Accession | GeneName | Description |
|---|---|---|
| NM_001006 | RPS3A | *Homo sapiens* ribosomal protein S3A (RPS3A), mRNA [NM_001006] |
| ENST00000361800 | ENST00000361800 | Unknown |
| N47494 | N47494 | N47494 yy90a12.s1 Soares_multiple_sclerosis_2NbHMSP *Homo sapiens* cDNA clone IMAGE: 280798 3' similar to gb: M23115 CALCIUM-TRANSPORTING ATPASE SARCOPLASMIC RETICULUM TYPE, SLOW (HUMAN);, mRNA sequence [N47494] |
| NM_016564 | CEND1 | *Homo sapiens* cell cycle exit and neuronal differentiation 1 (CEND1), mRNA [NM_016564] |
| NM_001077238 | SPPL2B | *Homo sapiens* signal peptide peptidase-like 2B (SPPL2B), transcript variant 3, mRNA [NM_001077238] |
| XR_018553 | LOC648294 | PREDICTED: *Homo sapiens* hypothetical LOC648294 (LOC648294), mRNA [XR_018553] |
| AK096778 | AK096778 | *Homo sapiens* cDNA FLJ39459 fis, clone PROST2011439. [AK096778] |
| A_24_P911837 | A_24_P911837 | Unknown |
| BQ018742 | BQ018742 | BQ018742 UI-H-DH1-awu-d-06-0-UI.s1 NCI_CGAP_DH1 *Homo sapiens* cDNA clone IMAGE: 5823701 3', mRNA sequence [BQ018742] |
| NM_020764 | CASKIN1 | *Homo sapiens* CASK interacting protein 1 (CASKIN1), mRNA [NM_020764] |
| THC2550272 | THC2550272 | Unknown |
| NM_032848 | C12orf52 | *Homo sapiens* chromosome 12 open reading frame 52 (C12orf52), mRNA [NM_032848] |
| ENST00000302932 | ENST00000302932 | Uncharacterized protein C20orf181 (Fragment). [Source: Uniprot/SPTREMBL; Acc: Q92884] [ENST00000302932] |
| A_24_P912856 | A_24_P912856 | Unknown |
| THC2700213 | THC2700213 | Q5VZP2_HUMAN (Q5VZP2) HERV-H LTR-associating 3, partial (21%) [THC2700213] |
| NM_053275 | RPLP0 | *Homo sapiens* ribosomal protein, large, P0 (RPLP0), transcript variant 2, mRNA [NM_053275] |
| CN304251 | CN304251 | 17000532640995 GRN_ES *Homo sapiens* cDNA 5', mRNA sequence [CN304251] |
| NM_000545 | TCF1 | *Homo sapiens* transcription factor 1, hepatic; LF-B1, hepatic nuclear factor (HNF1), albumin proximal factor (TCF1), mRNA [NM_000545] |
| XM_929928 | LOC646960 | PREDICTED: *Homo sapiens* similar to transmembrane protease, serine 9 (LOC646960), mRNA [XM_929928] |
| AW204925 | AW204925 | UI-H-BI1-aer-a-07-0-UI.s1 NCI_CGAP_Sub3 *Homo sapiens* cDNA clone IMAGE: 2720149 3', mRNA sequence [AW204925] |
| NM_002258 | KLRB1 | *Homo sapiens* killer cell lectin-like receptor subfamily B, member 1 (KLRB1), mRNA [NM_002258] |
| NM_031313 | ALPPL2 | *Homo sapiens* alkaline phosphatase, placental-like 2 (ALPPL2), mRNA [NM_031313] |
| AK090467 | LOC284542 | *Homo sapiens* mRNA for FLJ00388 protein. [AK090467] |
| NM_031478 | FAM57B | *Homo sapiens* family with sequence similarity 57, member B (FAM57B), mRNA [NM_031478] |
| A_24_P238427 | A_24_P238427 | Unknown |
| NM_022465 | IKZF4 | *Homo sapiens* IKAROS family zinc finger 4 (Eos) (IKZF4), mRNA [NM_022465] |
| NM_001416 | EIF4A1 | *Homo sapiens* eukaryotic translation initiation factor 4A, isoform 1 (EIF4A1), mRNA [NM_001416] |
| NM_000971 | RPL7 | *Homo sapiens* ribosomal protein L7 (RPL7), mRNA [NM_000971] |
| NR_002797 | LOC255783 | *Homo sapiens* hypothetical protein LOC255783 (LOC255783) on chromosome 19 [NR_002797] |
| NM_001078172 | FAM127B | *Homo sapiens* family with sequence similarity 127, member B (FAM127B), mRNA [NM_001078172] |
| BM680083 | BM680083 | BM680083 UI-E-EO1-aix-j-14-0-UI.s1 UI-E-EO1 *Homo sapiens* cDNA clone UI-E-EO1-aix-j-14-0-UI 3', mRNA sequence [BM680083] |
| ENST00000357697 | ENST00000357697 | Unknown |
| NM_021149 | COTL1 | *Homo sapiens* coactosin-like 1 (*Dictyostelium*) (COTL1), mRNA [NM_021149] |
| A_24_P689119 | A_24_P689119 | Unknown |
| NM_007104 | RPL10A | *Homo sapiens* ribosomal protein L10a (RPL10A), mRNA [NM_007104] |
| CA455253 | LOC341412 | AGENCOURT_10640955 NIH_MGC_126 *Homo sapiens* cDNA clone IMAGE: 6723568 5', mRNA sequence [CA455253] |
| NM_000972 | RPL7A | *Homo sapiens* ribosomal protein L7a (RPL7A), mRNA [NM_000972] |
| XR_018444 | LOC643981 | PREDICTED: *Homo sapiens* similar to 40S ribosomal protein S3a (V-fos transformation effector protein) (LOC643981), mRNA [XR_018444] |

TABLE 16-continued

Gene list generated at the inclusion criteria of p ≤ 0.001.

| GenBank Accession | GeneName | Description |
|---|---|---|
| XR_015583 | LOC731731 | PREDICTED: *Homo sapiens* similar to Nucleosome assembly protein 1-like 1 (NAP-1-related protein) (hNRP) (LOC731731), mRNA [XR_015583] |
| XR_018808 | LOC441641 | PREDICTED: *Homo sapiens* similar to ribosomal protein L13A (LOC441641), mRNA [XR_018808] |
| NM_015853 | LOC51035 | *Homo sapiens* SAPK substrate protein 1 (LOC51035), mRNA [NM_015853] |
| ENST00000330598 | ENST00000330598 | *Homo sapiens* HSPC088 mRNA, partial cds. [AF161351] |
| BC036762 | MGC46336 | *Homo sapiens* hypothetical protein MGC46336, mRNA (cDNA clone MGC: 46336 IMAGE: 5588928), complete cds. [BC036762] |
| NM_006640 | 09-Sep | *Homo sapiens* septin 9 (SEPT9), mRNA [NM_006640] |
| NM_001748 | CAPN2 | *Homo sapiens* calpain 2, (m/II) large subunit (CAPN2), mRNA [NM_001748] |
| NM_017622 | C17orf59 | *Homo sapiens* chromosome 17 open reading frame 59 (C17orf59), mRNA [NM_017622] |
| NM_017489 | TERF1 | *Homo sapiens* telomeric repeat binding factor (NIMA-interacting) 1 (TERF1), transcript variant 1, mRNA [NM_017489] |
| NM_001025 | RPS23 | *Homo sapiens* ribosomal protein S23 (RPS23), mRNA [NM_001025] |
| ENST00000295549 | LOC375295 | *Homo sapiens* hypothetical gene supported by BC013438, mRNA (cDNA clone IMAGE: 3899073), partial cds. [BC013438] |
| NM_053275 | RPLP0 | *Homo sapiens* ribosomal protein, large, P0 (RPLP0), transcript variant 2, mRNA [NM_053275] |
| NM_015284 | KIAA0467 | *Homo sapiens* KIAA0467 (KIAA0467), mRNA [NM_015284] |
| NM_003202 | TCF7 | *Homo sapiens* transcription factor 7 (T-cell specific, HMG-box) (TCF7), transcript variant 1, mRNA [NM_003202] |
| NM_013271 | PCSK1N | *Homo sapiens* proprotein convertase subtilisin/kexin type 1 inhibitor (PCSK1N), mRNA [NM_013271] |
| NM_024963 | FBXL18 | *Homo sapiens* F-box and leucine-rich repeat protein 18 (FBXL18), mRNA [NM_024963] |
| NR_002603 | LOC440353 | *Homo sapiens* nuclear pore complex interacting protein pseudogene (LOC440353) on chromosome 16 [NR_002603] |
| XR_019476 | LOC391845 | PREDICTED: *Homo sapiens* similar to 40S ribosomal protein S15 (RIG protein) (LOC391845), mRNA [XR_019476] |
| NM_033060 | KRTAP4-10 | *Homo sapiens* keratin associated protein 4-10 (KRTAP4-10), mRNA [NM_033060] |
| XR_018303 | LOC648378 | PREDICTED: *Homo sapiens* similar to ribosomal protein S14 (LOC648378), mRNA [XR_018303] |
| NM_005617 | RPS14 | *Homo sapiens* ribosomal protein S14 (RPS14), transcript variant 3, mRNA [NM_005617] |
| NM_199185 | NPM1 | *Homo sapiens* nucleophosmin (nucleolar phosphoprotein B23, numatrin) (NPM1), transcript variant 2, mRNA [NM_199185] |
| AA451906 | AA451906 | AA451906 zx16h04.s1 Soares_total_fetus_Nb2HF8_9w *Homo sapiens* cDNA clone IMAGE: 786679 3', mRNA sequence [AA451906] |
| BX096698 | BX096698 | BX096698 Soares breast 2NbHBst *Homo sapiens* cDNA clone IMAGp998E11242, mRNA sequence [BX096698] |
| NM_033025 | SYDE1 | *Homo sapiens* synapse defective 1, Rho GTPase, homolog 1 (*C. elegans*) (SYDE1), mRNA [NM_033025] |
| NM_033625 | RPL34 | *Homo sapiens* ribosomal protein L34 (RPL34), transcript variant 2, mRNA [NM_033625] |
| AK093171 | AK093171 | *Homo sapiens* cDNA FLJ35852 fis, clone TESTI2007074. [AK093171] |
| XM_929084 | LOC646119 | PREDICTED: *Homo sapiens* similar to ribosomal protein S8 (LOC646119), mRNA [XM_929084] |
| THC2658813 | THC2658813 | Unknown |
| AK128457 | AK128457 | *Homo sapiens* cDNA FLJ46600 fis, clone THYMU3047144. [AK128457] |
| NM_032378 | EEF1D | *Homo sapiens* eukaryotic translation elongation factor 1 delta (guanine nucleotide exchange protein) (EEF1D), transcript variant 1, mRNA [NM_032378] |
| ENST00000331096 | ENST00000331096 | Unknown |
| NM_021170 | HES4 | *Homo sapiens* hairy and enhancer of split 4 (*Drosophila*) (HES4), mRNA [NM_021170] |
| BC037255 | LOC389634 | *Homo sapiens* hypothetical LOC389634, mRNA (cDNA clone IMAGE: 4157715). [BC037255] |
| NM_003018 | SFTPC | *Homo sapiens* surfactant, pulmonary-associated protein C (SFTPC), mRNA [NM_003018] |
| XR_019634 | LOC402069 | PREDICTED: *Homo sapiens* similar to 40S ribosomal protein S16 (LOC402069), mRNA [XR_019634] |
| CV575560 | CV575560 | oe37f10.y1 Human keratoconus cornea, unamplified, (od [CV575560] |
| XR_018510 | LOC650650 | PREDICTED: *Homo sapiens* similar to ribosomal protein S5 (LOC650650), mRNA [XR_018510] |

TABLE 16-continued

Gene list generated at the inclusion criteria of p ≤ 0.001.

| GenBank Accession | GeneName | Description |
| --- | --- | --- |
| BF822111 | BF822111 | BF822111 CM3-RT0011-051200-531-f10 RT0011 *Homo sapiens* cDNA, mRNA sequence [BF822111] |
| NM_022139 | GFRA4 | *Homo sapiens* GDNF family receptor alpha 4 (GFRA4), transcript variant 1, mRNA [NM_022139] |
| NM_003689 | AKR7A2 | *Homo sapiens* aldo-keto reductase family 7, member A2 (aflatoxin aldehyde reductase) (AKR7A2), mRNA [NM_003689] |
| NM_002823 | PTMA | *Homo sapiens* prothymosin, alpha (gene sequence 28) (PTMA), mRNA [NM_002823] |
| NM_004964 | HDAC1 | *Homo sapiens* histone deacetylase 1 (HDAC1), mRNA [NM_004964] |
| NM_053275 | RPLP0 | *Homo sapiens* ribosomal protein, large, P0 (RPLP0), transcript variant 2, mRNA [NM_053275] |
| AL133632 | AL133632 | PREDICTED: *Homo sapiens* hypothetical LOC648245 (LOC648245), mRNA [XM_001127731] |
| NM_004907 | IER2 | *Homo sapiens* immediate early response 2 (IER2), mRNA [NM_004907] |
| BC018086 | MGC13017 | *Homo sapiens* similar to RIKEN cDNA A430101B06 gene, mRNA (cDNA clone MGC: 27045 IMAGE: 4793897), complete cds. [BC018086] |
| NM_006985 | NPIP | *Homo sapiens* nuclear pore complex interacting protein (NPIP), mRNA [NM_006985] |
| ENST00000248668 | LRFN1 | Leucine-rich repeat and fibronectin type III domain-containing protein 1 (Fragment). [Source: Uniprot/SPTREMBL; Acc: Q9P244] [ENST00000248668] |
| NM_178128 | FADS6 | *Homo sapiens* fatty acid desaturase domain family, member 6 (FADS6), mRNA [NM_178128] |
| A_24_P170147 | A_24_P170147 | Unknown |
| NM_152219 | GJC1 | *Homo sapiens* gap junction protein, chi 1, 31.9 kDa (GJC1), mRNA [NM_152219] |
| NM_000982 | RPL21 | *Homo sapiens* ribosomal protein L21 (RPL21), mRNA [NM_000982] |
| A_24_P264549 | A_24_P264549 | Unknown |
| NM_006013 | RPL10 | *Homo sapiens* ribosomal protein L10 (RPL10), mRNA [NM_006013] |
| NM_000985 | RPL17 | *Homo sapiens* ribosomal protein L17 (RPL17), transcript variant 1, mRNA [NM_000985] |
| A_24_P789842 | A_24_P789842 | Unknown |
| NM_003726 | SKAP1 | *Homo sapiens* src kinase associated phosphoprotein 1 (SKAP1), transcript variant 1, mRNA [NM_003726] |
| NM_003961 | RHBDL1 | *Homo sapiens* rhomboid, veinlet-like 1 (*Drosophila*) (RHBDL1), mRNA [NM_003961] |
| XR_019079 | LOC651591 | PREDICTED: *Homo sapiens* similar to 60S ribosomal protein L7a (LOC651591), mRNA [XR_019079] |
| AK055960 | AK055960 | *Homo sapiens* cDNA FLJ31398 fis, clone NT2NE1000175. [AK055960] |
| XR_015663 | LOC731113 | PREDICTED: *Homo sapiens* hypothetical protein LOC731113 (LOC731113), mRNA [XR_015663] |
| NM_005356 | LCK | *Homo sapiens* lymphocyte-specific protein tyrosine kinase (LCK), transcript variant 2, mRNA [NM_005356] |
| NM_001011 | RPS7 | *Homo sapiens* ribosomal protein S7 (RPS7), mRNA [NM_001011] |
| XR_019361 | LOC442260 | PREDICTED: *Homo sapiens* similar to 60S ribosomal protein L23a (LOC442260), mRNA [XR_019361] |
| AK027315 | AK027315 | *Homo sapiens* cDNA FLJ14409 fis, clone HEMBA1004408, moderately similar to PEPTIDYL-PROLYL CIS-TRANS ISOMERASE 10 (EC 5.2.1.8). [AK027315] |
| XR_017247 | LOC401975 | PREDICTED: *Homo sapiens* similar to ribosomal protein S3a (LOC401975), mRNA [XR_017247] |
| AK130118 | AK130118 | *Homo sapiens* cDNA FLJ26608 fis, clone LVR00914. [AK130118] |
| NM_145808 | MTPN | *Homo sapiens* myotrophin (MTPN), mRNA [NM_145808] |
| NM_003295 | TPT1 | *Homo sapiens* tumor protein, translationally-controlled 1 (TPT1), mRNA [NM_003295] |
| NM_000972 | RPL7A | *Homo sapiens* ribosomal protein L7a (RPL7A), mRNA [NM_000972] |
| A_32_P15169 | A_32_P15169 | Unknown |
| ENST00000308989 | ENST00000308989 | PREDICTED: *Homo sapiens* similar to ribosomal protein L31 (LOC729005), mRNA [XM_001133428] |
| NM_015023 | WDTC1 | *Homo sapiens* WD and tetratricopeptide repeats 1 (WDTC1), mRNA [NM_015023] |
| NM_203451 | LOC400120 | *Homo sapiens* hypothetical LOC400120 (LOC400120), mRNA [NM_203451] |
| THC2672892 | THC2672892 | Q2TXF9_ASPOR (Q2TXF9) Predicted protein, partial (5%) [THC2672892] |
| XR_019472 | LOC652328 | PREDICTED: *Homo sapiens* similar to ribosomal protein L21 (LOC652328), mRNA [XR_019472] |

TABLE 16-continued

Gene list generated at the inclusion criteria of p ≤ 0.001.

| GenBank Accession | GeneName | Description |
| --- | --- | --- |
| NM_006263 | PSME1 | *Homo sapiens* proteasome (prosome, macropain) activator subunit 1 (PA28 alpha) (PSME1), transcript variant 1, mRNA [NM_006263] |
| NM_001014 | RPS10 | *Homo sapiens* ribosomal protein S10 (RPS10), mRNA [NM_001014] |
| A_24_P186764 | A_24_P186764 | Unknown |
| XR_015936 | LOC731457 | PREDICTED: *Homo sapiens* similar to ribosomal protein S27a (LOC731457), mRNA [XR_015936] |
| NM_003202 | TCF7 | *Homo sapiens* transcription factor 7 (T-cell specific, HMG-box) (TCF7), transcript variant 1, mRNA [NM_003202] |
| ENST00000354668 | ENST00000354668 | myelin-associated oligodendrocyte basic protein [Source: RefSeq_peptide; Acc: NP_891980] [ENST00000354668] |
| NM_005247 | FGF3 | *Homo sapiens* fibroblast growth factor 3 (murine mammary tumor virus integration site (v-int-2) oncogene homolog) (FGF3), mRNA [NM_005247] |
| BC002470 | BC002470 | *Homo sapiens* mRNA similar to protein kinase, cAMP dependent regulatory, type I beta (cDNA clone IMAGE: 3349336). [BC002470] |
| NM_001025200 | CTRB2 | *Homo sapiens* chymotrypsinogen B2 (CTRB2), mRNA [NM_001025200] |
| NM_001152 | SLC25A5 | *Homo sapiens* solute carrier family 25 (mitochondrial carrier; adenine nucleotide translocator), member 5 (SLC25A5), mRNA [NM_001152] |
| NR_002578 | GAS5 | *Homo sapiens* growth arrest-specific 5 (GAS5) on chromosome 1 [NR_002578] |
| XR_019529 | LOC391595 | PREDICTED: *Homo sapiens* similar to 60S ribosomal protein L32 (LOC391595), mRNA [XR_019529] |
| NM_003775 | EDG6 | *Homo sapiens* endothelial differentiation, lysophosphatidic acid G-protein-coupled receptor, 6 (EDG6), mRNA [NM_003775] |
| NM_004382 | CRHR1 | *Homo sapiens* corticotropin releasing hormone receptor 1 (CRHR1), mRNA [NM_004382] |
| ENST00000323800 | ENST00000323800 | CDNA FLJ25155 fis, clone CBR07976. [Source: Uniprot/SPTREMBL; Acc: Q96LR6] [ENST00000323800] |
| NM_004578 | RAB4A | *Homo sapiens* RAB4A, member RAS oncogene family (RAB4A), mRNA [NM_004578] |
| NM_006985 | NPIP | *Homo sapiens* nuclear pore complex interacting protein (NPIP), mRNA [NM_006985] |
| NM_001666 | ARHGAP4 | *Homo sapiens* Rho GTPase activating protein 4 (ARHGAP4), mRNA [NM_001666] |
| A_24_P524519 | A_24_P524519 | Unknown |
| NM_002300 | LDHB | *Homo sapiens* lactate dehydrogenase B (LDHB), mRNA [NM_002300] |
| NM_000984 | RPL23A | *Homo sapiens* ribosomal protein L23a (RPL23A), mRNA [NM_000984] |
| NM_053275 | RPLP0 | *Homo sapiens* ribosomal protein, large, P0 (RPLP0), transcript variant 2, mRNA [NM_053275] |
| BC033110 | HSD17B1 | *Homo sapiens*, clone IMAGE: 5443970, mRNA, partial cds. [BC033110] |
| NM_014501 | UBE2S | *Homo sapiens* ubiquitin-conjugating enzyme E2S (UBE2S), mRNA [NM_014501] |
| NM_152600 | ZNF579 | *Homo sapiens* zinc finger protein 579 (ZNF579), mRNA [NM_152600] |
| NM_032378 | EEF1D | *Homo sapiens* eukaryotic translation elongation factor 1 delta (guanine nucleotide exchange protein) (EEF1D), transcript variant 1, mRNA [NM_032378] |
| A_24_P933372 | A_24_P933372 | Unknown |
| THC2718728 | THC2718728 | Unknown |
| AK000028 | FLJ20021 | *Homo sapiens* cDNA FLJ20021 fis, clone ADSE01233. [AK000028] |
| NM_130759 | GIMAP1 | *Homo sapiens* GTPase, IMAP family member 1 (GIMAP1), mRNA [NM_130759] |
| AK074191 | ZNF414 | *Homo sapiens* cDNA FLJ23611 fis, clone ADKA02380. [AK074191] |
| NM_004107 | FCGRT | *Homo sapiens* Fc fragment of IgG, receptor, transporter, alpha (FCGRT), mRNA [NM_004107] |
| XR_015600 | LOC730902 | PREDICTED: *Homo sapiens* similar to 60S ribosomal protein L7 (LOC730902), mRNA [XR_015600] |
| XR_019536 | LOC401725 | PREDICTED: *Homo sapiens* similar to 60S ribosomal protein L6 (TAX-responsive enhancer element-binding protein 107) (TAXREB107) (Neoplasm-related protein C140) (LOC401725), mRNA [XR_019536] |
| ENST00000307437 | ENST00000307437 | PREDICTED: *Homo sapiens* similar to ribosomal protein S12 (LOC727997), mRNA [XM_001127053] |
| XR_017289 | LOC643932 | PREDICTED: *Homo sapiens* similar to 40S ribosomal protein S3a (V-fos transformation effector protein) (LOC643932), mRNA [XR_017289] |

TABLE 16-continued

Gene list generated at the inclusion criteria of p ≤ 0.001.

| GenBank Accession | GeneName | Description |
| --- | --- | --- |
| XR_018091 | LOC646672 | PREDICTED: Homo sapiens similar to ribosomal protein L15 (LOC646672), mRNA [XR_018091] |
| BC002431 | B4GALT2 | Homo sapiens cDNA clone IMAGE: 3347310, containing frame-shift errors. [BC002431] |
| NM_033405 | PRIC285 | Homo sapiens peroxisomal proliferator-activated receptor A interacting complex 285 (PRIC285), transcript variant 2, mRNA [NM_033405] |
| NM_014267 | C11orf58 | Homo sapiens chromosome 11 open reading frame 58 (C11orf58), mRNA [NM_014267] |
| NM_003756 | EIF3S3 | Homo sapiens eukaryotic translation initiation factor 3, subunit 3 gamma, 40 kDa (EIF3S3), mRNA [NM_003756] |
| NM_000454 | SOD1 | Homo sapiens superoxide dismutase 1, soluble (amyotrophic lateral sclerosis 1 (adult)) (SOD1), mRNA [NM_000454] |
| BC063531 | SIN3B | Homo sapiens SIN3 homolog B, transcription regulator (yeast), mRNA (cDNA clone IMAGE: 4417458), complete cds. [BC063531] |
| NM_006122 | MAN2A2 | Homo sapiens mannosidase, alpha, class 2A, member 2 (MAN2A2), mRNA [NM_006122] |
| NM_000454 | SOD1 | Homo sapiens superoxide dismutase 1, soluble (amyotrophic lateral sclerosis 1 (adult)) (SOD1), mRNA [NM_000454] |
| NM_000983 | RPL22 | Homo sapiens ribosomal protein L22 (RPL22), mRNA [NM_000983] |
| NM_024104 | C19orf42 | Homo sapiens chromosome 19 open reading frame 42 (C19orf42), mRNA [NM_024104] |
| NM_003038 | SLC1A4 | Homo sapiens solute carrier family 1 (glutamate/neutral amino acid transporter), member 4 (SLC1A4), mRNA [NM_003038] |
| NM_006923 | SDF2 | Homo sapiens stromal cell-derived factor 2 (SDF2), mRNA [NM_006923] |
| NM_022370 | ROBO3 | Homo sapiens roundabout, axon guidance receptor, homolog 3 (Drosophila) (ROBO3), mRNA [NM_022370] |
| AK023286 | FLJ13224 | Homo sapiens cDNA FLJ13224 fis, clone OVARC1000008. [AK023286] |
| NM_152636 | METT5D1 | Homo sapiens methyltransferase 5 domain containing 1 (METT5D1), mRNA [NM_152636] |
| NM_015481 | ZNF385 | Homo sapiens zinc finger protein 385 (ZNF385), mRNA [NM_015481] |
| AY090769 | AY090769 | Homo sapiens ribosomal protein S18/S6-like mRNA, complete sequence. [AY090769] |
| NM_001697 | ATP5O | Homo sapiens ATP synthase, H+ transporting, mitochondrial F1 complex, O subunit (oligomycin sensitivity conferring protein) (ATP5O), nuclear gene encoding mitochondrial protein, mRNA [NM_001697] |
| NM_147129 | ALS2CL | Homo sapiens ALS2 C-terminal like (ALS2CL), transcript variant 1, mRNA [NM_147129] |
| NM_001402 | EEF1A1 | Homo sapiens eukaryotic translation elongation factor 1 alpha 1 (EEF1A1), mRNA [NM_001402] |
| NM_000982 | RPL21 | Homo sapiens ribosomal protein L21 (RPL21), mRNA [NM_000982] |
| NM_002984 | CCL4 | Homo sapiens chemokine (C-C motif) ligand 4 (CCL4), transcript variant 1, mRNA [NM_002984] |
| NM_182796 | MAT2B | Homo sapiens methionine adenosyltransferase II, beta (MAT2B), transcript variant 2, mRNA [NM_182796] |
| ENST00000359466 | ENST00000359466 | chromosome X open reading frame 18 (CXorf18), misc RNA [Source: RefSeq_dna; Acc: XR_018001] [ENST00000359466] |
| NM_001152 | SLC25A5 | Homo sapiens solute carrier family 25 (mitochondrial carrier; adenine nucleotide translocator), member 5 (SLC25A5), mRNA [NM_001152] |
| NM_022551 | RPS18 | Homo sapiens ribosomal protein S18 (RPS18), mRNA [NM_022551] |
| N75427 | N75427 | za82f07.s1 Soares_fetal_lung_NbHL19W Homo sapiens cDNA clone IMAGE: 299077 3' similar to gb: X69654 40S RIBOSOMAL PROTEIN S26 (HUMAN);, mRNA sequence [N75427] |
| NM_001867 | COX7C | Homo sapiens cytochrome c oxidase subunit VIIc (COX7C), nuclear gene encoding mitochondrial protein, mRNA [NM_001867] |
| NM_172138 | IL28A | Homo sapiens interleukin 28A (interferon, lambda 2) (IL28A), mRNA [NM_172138] |
| NM_053004 | GNB1L | Homo sapiens guanine nucleotide binding protein (G protein), beta polypeptide 1-like (GNB1L), mRNA [NM_053004] |
| BC034005 | LOC388494 | Homo sapiens hypothetical gene supported by AL365406; BC034005, mRNA (cDNA clone IMAGE: 5276795). [BC034005] |
| NM_138418 | C16orf14 | Homo sapiens chromosome 16 open reading frame 14 (C16orf14), mRNA [NM_138418] |

TABLE 16-continued

Gene list generated at the inclusion criteria of p ≤ 0.001.

| GenBank Accession | GeneName | Description |
|---|---|---|
| XM_927514 | LOC644357 | PREDICTED: *Homo sapiens* similar to Elongation factor 1-delta (EF-1-delta) (Antigen NY-CO-4) (LOC644357), mRNA [XM_927514] |
| AF007190 | AF007190 | *Homo sapiens* SIB 227C intestinal mucin (MUC3) mRNA, partial cds. [AF007190] |
| NM_001030 | RPS27 | *Homo sapiens* ribosomal protein S27 (metallopanstimulin 1) (RPS27), mRNA [NM_001030] |
| NM_000970 | RPL6 | *Homo sapiens* ribosomal protein L6 (RPL6), transcript variant 2, mRNA [NM_000970] |
| NM_002818 | PSME2 | *Homo sapiens* proteasome (prosome, macropain) activator subunit 2 (PA28 beta) (PSME2), mRNA [NM_002818] |
| NM_000992 | RPL29 | *Homo sapiens* ribosomal protein L29 (RPL29), mRNA [NM_000992] |
| AK074162 | AK074162 | *Homo sapiens* mRNA for FLJ00235 protein. [AK074162] |
| NM_176812 | CHMP4B | *Homo sapiens* chromatin modifying protein 4B (CHMP4B), mRNA [NM_176812] |
| A_24_P298238 | A_24_P298238 | Unknown |
| NM_003202 | TCF7 | *Homo sapiens* transcription factor 7 (T-cell specific, HMG-box) (TCF7), transcript variant 1, mRNA [NM_003202] |
| M74509 | M74509 | Human endogenous retrovirus type C oncovirus sequence. [M74509] |
| NM_139286 | CDC26 | *Homo sapiens* cell division cycle 26 homolog (*S. cerevisiae*) (CDC26), mRNA [NM_139286] |
| NM_053025 | MYLK | *Homo sapiens* myosin, light chain kinase (MYLK), transcript variant 1, mRNA [NM_053025] |
| A_24_P126902 | A_24_P126902 | Unknown |
| NM_002808 | PSMD2 | *Homo sapiens* proteasome (prosome, macropain) 26S subunit, non-ATPase, 2 (PSMD2), mRNA [NM_002808] |
| A_24_P212654 | A_24_P212654 | Unknown |
| A_24_P341376 | A_24_P341376 | Unknown |
| THC2579654 | THC2579654 | Q6P9U5_RAT (Q6P9U5) Ribosomal protein L9, partial (74%) [THC2579654] |
| NM_145113 | MAX | *Homo sapiens* MYC associated factor X (MAX), transcript variant 3, mRNA [NM_145113] |
| NM_001016 | RPS12 | *Homo sapiens* ribosomal protein S12 (RPS12), mRNA [NM_001016] |
| ENST00000389400 | ENST00000389400 | similar to 40S ribosomal protein S3a (V-fos transformation effector protein) (LOC391706), mRNA [Source: RefSeq_dna; Acc: XR_017186] [ENST00000389400] |
| XR_018903 | LOC390612 | PREDICTED: *Homo sapiens* similar to ribosomal protein L18 (LOC390612), mRNA [XR_018903] |
| XR_019233 | LOC644029 | PREDICTED: *Homo sapiens* similar to 60S ribosomal protein L7a (LOC644029), mRNA [XR_019233] |
| A_24_P392436 | A_24_P392436 | Unknown |
| NM_052896 | CSMD2 | *Homo sapiens* CUB and Sushi multiple domains 2 (CSMD2), mRNA [NM_052896] |
| NM_145808 | MTPN | *Homo sapiens* myotrophin (MTPN), mRNA [NM_145808] |
| NM_000982 | RPL21 | *Homo sapiens* ribosomal protein L21 (RPL21), mRNA [NM_000982] |
| NM_007224 | NXPH4 | *Homo sapiens* neurexophilin 4 (NXPH4), mRNA [NM_007224] |
| NM_001959 | EEF1B2 | *Homo sapiens* eukaryotic translation elongation factor 1 beta 2 (EEF1B2), transcript variant 1, mRNA [NM_001959] |
| XR_018292 | LOC392522 | PREDICTED: *Homo sapiens* similar to ribosomal protein L18a (LOC392522), mRNA [XR_018292] |
| XM_940966 | ASCL5 | PREDICTED: *Homo sapiens* similar to Achaete-scute homolog 3 (bHLH transcriptional regulator Sgn-1) (Mash-3) (LOC647219), mRNA [XM_940966] |
| NM_000997 | RPL37 | *Homo sapiens* ribosomal protein L37 (RPL37), mRNA [NM_000997] |
| XR_018339 | LOC648448 | PREDICTED: *Homo sapiens* similar to Keratin, type I cytoskeletal 18 (Cytokeratin-18) (CK-18) (Keratin-18) (K18) (LOC648448), mRNA [XR_018339] |
| BC037281 | LOC439951 | *Homo sapiens* hypothetical LOC439951, mRNA (cDNA clone MGC: 33041 IMAGE: 4838780), complete cds. [BC037281] |
| NM_080621 | SAMD10 | *Homo sapiens* sterile alpha motif domain containing 10 (SAMD10), mRNA [NM_080621] |
| NM_033251 | RPL13 | *Homo sapiens* ribosomal protein L13 (RPL13), transcript variant 2, mRNA [NM_033251] |
| A_24_P350008 | A_24_P350008 | Unknown |
| A_24_P745670 | A_24_P745670 | Unknown |
| NM_000982 | RPL21 | *Homo sapiens* ribosomal protein L21 (RPL21), mRNA [NM_000982] |
| NM_005626 | SFRS4 | *Homo sapiens* splicing factor, arginine/serine-rich 4 (SFRS4), mRNA [NM_005626] |

TABLE 16-continued

Gene list generated at the inclusion criteria of p ≤ 0.001.

| GenBank Accession | GeneName | Description |
|---|---|---|
| NR_002229 | RPL23AP13 | *Homo sapiens* ribosomal protein L23a pseudogene 13 (RPL23AP13) on chromosome 2 [NR_002229] |
| NM_002954 | RPS27A | *Homo sapiens* ribosomal protein S27a (RPS27A), mRNA [NM_002954] |
| NM_033625 | RPL34 | *Homo sapiens* ribosomal protein L34 (RPL34), transcript variant 2, mRNA [NM_033625] |
| NM_021248 | CDH22 | *Homo sapiens* cadherin-like 22 (CDH22), mRNA [NM_021248] |
| ENST00000367058 | CR2 | Complement receptor type 2 precursor (Cr2) (Complement C3d receptor) (Epstein-Barr virus receptor) (EBV receptor) (CD21 antigen). [Source: Uniprot/SWISSPROT; Acc: P20023] [ENST00000367058] |
| A_24_P33213 | A_24_P33213 | Unknown |
| NM_001767 | CD2 | *Homo sapiens* CD2 molecule (CD2), mRNA [NM_001767] |
| NM_001014373 | C19orf31 | *Homo sapiens* chromosome 19 open reading frame 31 (C19orf31), mRNA [NM_001014373] |
| NM_001039842 | LOC339229 | *Homo sapiens* hypothetical protein LOC339229 (LOC339229), mRNA [NM_001039842] |
| NM_012423 | RPL13A | *Homo sapiens* ribosomal protein L13a (RPL13A), mRNA [NM_012423] |
| XM_496446 | LOC440737 | PREDICTED: *Homo sapiens* similar to 60S ribosomal protein L35 (LOC440737), mRNA [XM_496446] |
| NM_015654 | NAT9 | *Homo sapiens* N-acetyltransferase 9 (NAT9), mRNA [NM_015654] |
| A_24_P127621 | A_24_P127621 | Unknown |
| NM_025247 | ACAD10 | *Homo sapiens* acyl-Coenzyme A dehydrogenase family, member 10 (ACAD10), mRNA [NM_025247] |
| A_23_P329062 | A_23_P329062 | Unknown |
| A_24_P845649 | A_24_P845649 | Unknown |
| NM_006370 | VTI1B | *Homo sapiens* vesicle transport through interaction with t-SNAREs homolog 1B (yeast) (VTI1B), mRNA [NM_006370] |
| A_24_P480722 | A_24_P480722 | Unknown |
| NM_012086 | GTF3C3 | *Homo sapiens* general transcription factor IIIC, polypeptide 3, 102 kDa (GTF3C3), mRNA [NM_012086] |
| NM_199427 | ZFP64 | *Homo sapiens* zinc finger protein 64 homolog (mouse) (ZFP64), transcript variant 4, mRNA [NM_199427] |
| AL117481 | DKFZP434B061 | *Homo sapiens* mRNA; cDNA DKFZp434B061 (from clone DKFZp434B061); partial cds. [AL117481] |
| NR_001435 | HLA-DPB2 | *Homo sapiens* major histocompatibility complex, class II, DP beta 2 (pseudogene) (HLA-DPB2) on chromosome 6 [NR_001435] |
| NM_018462 | C3orf10 | *Homo sapiens* chromosome 3 open reading frame 10 (C3orf10), mRNA [NM_018462] |
| THC2494410 | THC2494410 | 2113200F ribosomal protein S9. {*Homo sapiens*} (exp = -1; wgp = -1; cg = -1), complete [THC2494410] |
| NM_005581 | BCAM | *Homo sapiens* basal cell adhesion molecule (Lutheran blood group) (BCAM), transcript variant 1, mRNA [NM_005581] |
| XR_018133 | LOC389404 | PREDICTED: *Homo sapiens* similar to 60S ribosomal protein L9 (LOC389404), mRNA [XR_018133] |
| NM_001005862 | ERBB2 | *Homo sapiens* v-erb-b2 erythroblastic leukemia viral oncogene homolog 2, neuro/glioblastoma derived oncogene homolog (avian) (ERBB2), transcript variant 2, mRNA [NM_001005862] |
| AK025669 | AK025669 | *Homo sapiens* cDNA: FLJ22016 fis, clone HEP07422. [AK025669] |
| NM_138499 | PWWP2 | *Homo sapiens* PWWP domain containing 2 (PWWP2), mRNA [NM_138499] |
| NM_001003 | RPLP1 | *Homo sapiens* ribosomal protein, large, P1 (RPLP1), transcript variant 1, mRNA [NM_001003] |
| NM_015893 | PRLH | *Homo sapiens* prolactin releasing hormone (PRLH), mRNA [NM_015893] |
| XM_001133211 | LOC729003 | PREDICTED: *Homo sapiens* hypothetical protein LOC729003 (LOC729003), mRNA [XM_001133211] |
| A_24_P932253 | A_24_P932253 | Unknown |
| NM_000975 | RPL11 | *Homo sapiens* ribosomal protein L11 (RPL11), mRNA [NM_000975] |
| A_32_P92922 | A_32_P92922 | Unknown |
| NM_201286 | USP51 | *Homo sapiens* ubiquitin specific peptidase 51 (USP51), mRNA [NM_201286] |
| NM_002760 | PRKY | *Homo sapiens* protein kinase, Y-linked (PRKY), mRNA [NM_002760] |
| XR_018135 | LOC390306 | PREDICTED: *Homo sapiens* hypothetical LOC390306 (LOC390306), mRNA [XR_018135] |
| NM_006695 | RPIP8 | *Homo sapiens* RaP2 interacting protein 8 (RPIP8), mRNA [NM_006695] |
| NM_006354 | TADA3L | *Homo sapiens* transcriptional adaptor 3 (NGG1 homolog, yeast)-like (TADA3L), transcript variant 1, mRNA [NM_006354] |
| NM_000993 | RPL31 | *Homo sapiens* ribosomal protein L31 (RPL31), mRNA [NM_000993] |

TABLE 16-continued

Gene list generated at the inclusion criteria of p ≤ 0.001.

| GenBank Accession | GeneName | Description |
|---|---|---|
| NM_206839 | MORF4L1 | Homo sapiens mortality factor 4 like 1 (MORF4L1), transcript variant 2, mRNA [NM_206839] |
| ENST00000270031 | ENST00000270031 | interferon induced transmembrane protein 3 (1-8U) (IFITM3), mRNA [Source: RefSeq_dna; Acc: NM_021034] [ENST00000270031] |
| NM_003202 | TCF7 | Homo sapiens transcription factor 7 (T-cell specific, HMG-box) (TCF7), transcript variant 1, mRNA [NM_003202] |
| XR_019386 | LOC652558 | PREDICTED: Homo sapiens similar to 60S ribosomal protein L7 (LOC652558), mRNA [XR_019386] |
| A_24_P807445 | A_24_P807445 | Unknown |
| A_24_P213073 | A_24_P213073 | Unknown |
| NM_014222 | NDUFA8 | Homo sapiens NADH dehydrogenase (ubiquinone) 1 alpha subcomplex, 8, 19 kDa (NDUFA8), nuclear gene encoding mitochondrial protein, mRNA [NM_014222] |
| NM_002124 | HILA-DRB1 | Homo sapiens major histocompatibility complex, class II, DR beta 1 (HLA-DRB1), mRNA [NM_002124] |
| THC2510656 | THC2510656 | ALU6_HUMAN (P39193) Alu subfamily SP sequence contamination warning entry, partial (13%) [THC2510656] |
| NM_175734 | C17orf74 | Homo sapiens chromosome 17 open reading frame 74 (C17orf74), mRNA [NM_175734] |
| NM_002273 | KRT8 | Homo sapiens keratin 8 (KRT8), mRNA [NM_002273] |
| NM_021173 | POLD4 | Homo sapiens polymerase (DNA-directed), delta 4 (POLD4), mRNA [NM_021173] |
| A_32_P185089 | A_32_P185089 | Unknown |
| NM_001005862 | ERBB2 | Homo sapiens v-erb-b2 erythroblastic leukemia viral oncogene homolog 2, neuro/glioblastoma derived oncogene homolog (avian) (ERBB2), transcript variant 2, mRNA [NM_001005862] |
| A_24_P392195 | A_24_P392195 | Unknown |
| THC2782843 | THC2782843 | RL18A_HUMAN (Q02543) 60S ribosomal protein L18a, partial (89%) [THC2782843] |
| NM_152889 | CHST13 | Homo sapiens carbohydrate (chondroitin 4) sulfotransferase 13 (CHST13), mRNA [NM_152889] |
| NM_002855 | PVRL1 | Homo sapiens poliovirus receptor-related 1 (herpesvirus entry mediator C; nectin) (PVRL1), transcript variant 1, mRNA [NM_002855] |
| NM_004852 | ONECUT2 | Homo sapiens one cut domain, family member 2 (ONECUT2), mRNA [NM_004852] |
| NM_003753 | EIF3S7 | Homo sapiens eukaryotic translation initiation factor 3, subunit 7 zeta, 66/67 kDa (EIF3S7), mRNA [NM_003753] |
| NM_003636 | KCNAB2 | Homo sapiens potassium voltage-gated channel, shaker-related subfamily, beta member 2 (KCNAB2), transcript variant 1, mRNA [NM_003636] |
| NM_001017 | RPS13 | Homo sapiens ribosomal protein S13 (RPS13), mRNA [NM_001017] |
| NM_005946 | MT1A | Homo sapiens metallothionein 1A (MT1A), mRNA [NM_005946] |
| XR_015591 | LOC730861 | PREDICTED: Homo sapiens similar to 40S ribosomal protein S3a (V-fos transformation effector protein) (LOC730861), mRNA [XR_015591] |
| THC2725746 | THC2725746 | Unknown |
| NM_014786 | ARHGEF17 | Homo sapiens Rho guanine nucleotide exchange factor (GEF) 17 (ARHGEF17), mRNA [NM_014786] |
| NM_001005 | RPS3 | Homo sapiens ribosomal protein S3 (RPS3), mRNA [NM_001005] |
| NM_001003 | RPLP1 | Homo sapiens ribosomal protein, large, P1 (RPLP1), transcript variant 1, mRNA [NM_001003] |
| NM_000985 | RPL17 | Homo sapiens ribosomal protein L17 (RPL17), transcript variant 1, mRNA [NM_000985] |
| NM_053275 | RPLP0 | Homo sapiens ribosomal protein, large, P0 (RPLP0), transcript variant 2, mRNA [NM_053275] |
| NM_017458 | MVP | Homo sapiens major vault protein (MVP), transcript variant 1, mRNA [NM_017458] |
| NM_019111 | HLA-DRA | Homo sapiens major histocompatibility complex, class II, DR alpha (HLA-DRA), mRNA [NM_019111] |
| NM_002948 | RPL15 | Homo sapiens ribosomal protein L15 (RPL15), mRNA [NM_002948] |
| THC2515524 | THC2515524 | Unknown |
| NM_001006 | RPS3A | Homo sapiens ribosomal protein S3A (RPS3A), mRNA [NM_001006] |
| NM_003290 | TPM4 | Homo sapiens tropomyosin 4 (TPM4), mRNA [NM_003290] |
| BC043547 | BC043547 | Homo sapiens, clone IMAGE: 5171873, mRNA. [BC043547] |
| THC2737361 | THC2737361 | Q2IMJ3_ANADE (Q2IMJ3) LigA, partial (5%) [THC2737361] |
| XR_018509 | LOC391701 | PREDICTED: Homo sapiens similar to ribosomal protein S23 (LOC391701), mRNA [XR_018509] |
| NM_002462 | MX1 | Homo sapiens myxovirus (influenza virus) resistance 1, interferon-inducible protein p78 (mouse) (MX1), mRNA [NM_002462] |

TABLE 16-continued

Gene list generated at the inclusion criteria of p ≤ 0.001.

| GenBank Accession | GeneName | Description |
| --- | --- | --- |
| NP1252191 | NP1252191 | GB|AACC02000041.1|EAL24419.1 similar to 60S ribosomal protein L32 [*Homo sapiens*] [NP1252191] |
| A_24_P118422 | A_24_P118422 | Unknown |
| NM_001080414 | KIAA1509 | *Homo sapiens* KIAA1509 (KIAA1509), mRNA [NM_001080414] |
| A_24_P41979 | A_24_P41979 | Unknown |
| NM_033626 | CCDC120 | *Homo sapiens* coiled-coil domain containing 120 (CCDC120), mRNA [NM_033626] |
| NM_033546 | MRLC2 | *Homo sapiens* myosin regulatory light chain MRLC2 (MRLC2), mRNA [NM_033546] |
| NM_213602 | CD33L3 | *Homo sapiens* CD33 molecule-like 3 (CD33L3), mRNA [NM_213602] |
| AW302767 | LOC641784 | xr55h07.x1 NCI_CGAP_Ov26 *Homo sapiens* cDNA clone IMAGE: 2764093 3' similar to gb: X69181 60S RIBOSOMAL PROTEIN L31 (HUMAN);, mRNA sequence [AW302767] |
| NM_153822 | PSMD4 | *Homo sapiens* proteasome (prosome, macropain) 26S subunit, non-ATPase, 4 (PSMD4), transcript variant 2, mRNA [NM_153822] |
| THC2615996 | THC2615996 | Unknown |
| NM_080660 | ZC3HAV1L | *Homo sapiens* zinc finger CCCH-type, antiviral 1-like (ZC3HAV1L), mRNA [NM_080660] |
| XR_018524 | LOC391560 | PREDICTED: *Homo sapiens* similar to 60S ribosomal protein L32 (LOC391560), mRNA [XR_018524] |
| NM_203477 | MGC70863 | *Homo sapiens* similar to RPL23AP7 protein (MGC70863), transcript variant 1, mRNA [NM_203477] |
| NM_000906 | NPR1 | *Homo sapiens* natriuretic peptide receptor A/guanylate cyclase A (atrionatriuretic peptide receptor A) (NPR1), mRNA [NM_000906] |
| NM_004396 | DDX5 | *Homo sapiens* DEAD (Asp-Glu-Ala-Asp) box polypeptide 5 (DDX5), mRNA [NM_004396] |
| NM_203305 | FAM102A | *Homo sapiens* family with sequence similarity 102, member A (FAM102A), transcript variant 2, mRNA [NM_203305] |
| NM_020210 | SEMA4B | *Homo sapiens* sema domain, immunoglobulin domain (Ig), transmembrane domain (TM) and short cytoplasmic domain, (semaphorin) 4B (SEMA4B), transcript variant 1, mRNA [NM_020210] |
| NM_025182 | KIAA1539 | *Homo sapiens* KIAA1539 (KIAA1539), mRNA [NM_025182] |
| NM_005617 | RPS14 | *Homo sapiens* ribosomal protein S14 (RPS14), transcript variant 3, mRNA [NM_005617] |
| NM_206908 | GUSBL2 | *Homo sapiens* glucuronidase, beta-like 2 (GUSBL2), mRNA [NM_206908] |
| A_24_P41250 | A_24_P41250 | Unknown |
| ENST00000078131 | ENST00000078131 | OTTHUMP00000016594. [Source: Uniprot/SPTREMBL; Acc: Q9NU98] [ENST00000078131] |
| NM_030792 | GDPD5 | *Homo sapiens* glycerophosphodiester phosphodiesterase domain containing 5 (GDPD5), mRNA [NM_030792] |
| XM_930195 | hCG_18290 | PREDICTED: *Homo sapiens* similar to 60S ribosomal protein L32 (LOC644907), mRNA [XM_930195] |
| A_24_P280953 | A_24_P280953 | Unknown |
| XR_018994 | LOC391181 | PREDICTED: *Homo sapiens* similar to 60S ribosomal protein L6 (TAX-responsive enhancer element-binding protein 107) (TAXREB107) (Neoplasm-related protein C140) (LOC391181), mRNA [XR_018994] |
| THC2619175 | THC2619175 | Q4B270_9BURK (Q4B270) Amidohydrolase 2, partial (6%) [THC2619175] |
| BF969441 | BF969441 | 602271732F1 NIH_MGC_84 *Homo sapiens* cDNA clone IMAGE: 4360158 5', mRNA sequence [BF969441] |
| NM_016269 | LEF1 | *Homo sapiens* lymphoid enhancer-binding factor 1 (LEF1), mRNA [NM_016269] |
| ENST00000246872 | hCG_1983332 | PREDICTED: *Homo sapiens* similar to 60S ribosomal protein L35, transcript variant 1 (LOC441246), mRNA [XM_496890] |
| BC054347 | RP5-860F19.3 | *Homo sapiens* KIAA1442 protein, mRNA (cDNA clone IMAGE: 5502800), complete cds. [BC054347] |
| NM_000987 | RPL26 | *Homo sapiens* ribosomal protein L26 (RPL26), mRNA [NM_000987] |
| XM_926898 | LOC643594 | PREDICTED: *Homo sapiens* similar to CG13731-PA (LOC643594), mRNA [XM_926898] |
| THC2578835 | THC2578835 | Unknown |
| NM_001238 | CCNE1 | *Homo sapiens* cyclin E1 (CCNE1), transcript variant 1, mRNA [NM_001238] |
| BF803942 | BF803942 | BF803942 CM2-C10135-021100-477-g08 CI0135 *Homo sapiens* cDNA, mRNA sequence [BF803942] |
| AK094477 | AK094477 | *Homo sapiens* cDNA FLJ37158 fis, clone BRACE2026293. [AK094477] |
| NM_005772 | RCL1 | *Homo sapiens* RNA terminal phosphate cyclase-like 1 (RCL1), mRNA [NM_005772] |
| NM_013284 | POLM | *Homo sapiens* polymerase (DNA directed), mu (POLM), mRNA [NM_013284] |

TABLE 16-continued

Gene list generated at the inclusion criteria of p ≤ 0.001.

| GenBank Accession | GeneName | Description |
|---|---|---|
| XR_018944 | LOC442171 | PREDICTED: *Homo sapiens* similar to ribosomal protein L10 (LOC442171), mRNA [XR_018944] |
| BC011266 | C3orf50 | *Homo sapiens* cDNA clone IMAGE: 4156795. [BC011266] |
| NM_138425 | C12orf57 | *Homo sapiens* chromosome 12 open reading frame 57 (C12orf57), mRNA [NM_138425] |
| ENST00000310344 | LOC730647 | PREDICTED: *Homo sapiens* similar to Histidine triad nucleotide-binding protein 1 (Adenosine 5-monophosphoramidase) (Protein kinase C inhibitor 1) (Protein kinase C-interacting protein 1) (PKCI-1) (LOC730647), mRNA [XM_001126674] |
| NM_148887 | MRPL10 | *Homo sapiens* mitochondrial ribosomal protein L10 (MRPL10), nuclear gene encoding mitochondrial protein, transcript variant 2, mRNA [NM_148887] |
| NM_199290 | NACA2 | *Homo sapiens* nascent-polypeptide-associated complex alpha polypeptide-like (NACAL), mRNA [NM_199290] |
| NM_002568 | PABPC1 | *Homo sapiens* poly(A) binding protein, cytoplasmic 1 (PABPC1), mRNA [NM_002568] |
| NM_153183 | NUDT10 | *Homo sapiens* nudix (nucleoside diphosphate linked moiety X)-type motif 10 (NUDT10), mRNA [NM_153183] |
| ENST00000369248 | KIAA1600 | KIAA1600 (KIAA1600), mRNA [Source: RefSeq_dna; Acc: NM_020940] [ENST00000369248] |
| NM_021147 | CCNU | *Homo sapiens* cyclin U (CCNU), mRNA [NM_021147] |
| NM_024587 | TMEM53 | *Homo sapiens* transmembrane protein 53 (TMEM53), mRNA [NM_024587] |
| AK098605 | AK098605 | *Homo sapiens* cDNA FLJ25739 fis, clone TST05834. [AK098605] |
| BC085019 | GDF5OS | *Homo sapiens* hypothetical LOC554250, mRNA (cDNA clone MGC: 99835 IMAGE: 6650156), complete cds. [BC085019] |
| L79986 | SP100 | *Homo sapiens* nuclear autoantigen mRNA, partial cds; alternatively spliced. [L79986] |
| NM_004458 | ACSL4 | *Homo sapiens* acyl-CoA synthetase long-chain family member 4 (ACSL4), transcript variant 1, mRNA [NM_004458] |
| ENST00000334683 | ENST00000334683 | PREDICTED: *Homo sapiens* similar to 60S ribosomal protein L17 (L23) (LOC650848), mRNA [XR_019013] |
| THC2714530 | THC2714530 | Unknown |
| THC2544911 | THC2544911 | MUSEFTU elongation factor Tu {*Mus musculus*} (exp = −1; wgp = 0; cg = 0), partial (37%) [THC2544911] |
| THC2553216 | THC2553216 | HUMRRL3A ribosomal protein L3 {*Homo sapiens*} (exp = −1; wgp = 0; cg = 0), partial (24%) [THC2553216] |
| BC063671 | LOC92659 | *Homo sapiens* hypothetical protein BC009233, mRNA (cDNA clone IMAGE: 3924188), partial cds. [BC063671] |
| NM_053275 | RPLP0 | *Homo sapiens* ribosomal protein, large, P0 (RPLP0), transcript variant 2, mRNA [NM_053275] |
| NM_001404 | EEF1G | *Homo sapiens* eukaryotic translation elongation factor 1 gamma (EEF1G), mRNA [NM_001404] |
| NM_014931 | SAPS1 | *Homo sapiens* SAPS domain family, member 1 (SAPS1), mRNA [NM_014931] |
| NM_005356 | LCK | *Homo sapiens* lymphocyte-specific protein tyrosine kinase (LCK), transcript variant 2, mRNA [NM_005356] |
| NM_005271 | GLUD1 | *Homo sapiens* glutamate dehydrogenase 1 (GLUD1), mRNA [NM_005271] |
| XM_001125895 | LOC730452 | PREDICTED: *Homo sapiens* similar to 60S ribosomal protein L7 (LOC730452), mRNA [XM_001125895] |
| NM_000454 | SOD1 | *Homo sapiens* superoxide dismutase 1, soluble (amyotrophic lateral sclerosis 1 (adult)) (SOD1), mRNA [NM_000454] |
| NM_133499 | SYN1 | *Homo sapiens* synapsin I (SYN1), transcript variant Ib, mRNA [NM_133499] |
| AK021957 | COL27A1 | *Homo sapiens* cDNA FLJ11895 fis, clone HEMBA1007301, weakly similar to COLLAGEN ALPHA 1(III) CHAIN. [AK021957] |
| XR_016376 | LOC441073 | PREDICTED: *Homo sapiens* similar to 60S ribosomal protein L26 (Silica-induced gene 20 protein) (SIG-20) (LOC441073), mRNA [XR_016376] |
| XR_018530 | LOC649178 | PREDICTED: *Homo sapiens* similar to Preli (LOC649178), mRNA [XR_018530] |
| NM_006291 | TNFAIP2 | *Homo sapiens* tumor necrosis factor, alpha-induced protein 2 (TNFAIP2), mRNA [NM_006291] |
| THC2654039 | THC2654039 | ALU2_HUMAN (P39189) Alu subfamily SB sequence contamination warning entry, partial (4%) [THC2654039] |
| THC2736130 | THC2736130 | Q921R2_MOUSE (Q921R2) Rps13 protein, partial (51%) [THC2736130] |
| NM_001024 | RPS21 | *Homo sapiens* ribosomal protein S21 (RPS21), mRNA [NM_001024] |
| A_24_P755505 | A_24_P755505 | Unknown |
| THC2683228 | THC2683228 | O61351_DROME (O61351) CG12794-PA (La costa), partial (10%) [THC2683228] |

TABLE 16-continued

Gene list generated at the inclusion criteria of p ≤ 0.001.

| GenBank Accession | GeneName | Description |
|---|---|---|
| NM_006597 | HSPA8 | *Homo sapiens* heat shock 70 kDa protein 8 (HSPA8), transcript variant 1, mRNA [NM_006597] |
| NM_020358 | TRIM49 | *Homo sapiens* tripartite motif-containing 49 (TRIM49), mRNA [NM_020358] |
| THC2694215 | THC2694215 | Q3W9Q7_9ACTO (Q3W9Q7) Pyridoxamine 5′-phosphate oxidase, partial (3%) [THC2694215] |
| NM_003184 | TAF2 | *Homo sapiens* TAF2 RNA polymerase II, TATA box binding protein (TBP)-associated factor, 150 kDa (TAF2), mRNA [NM_003184] |
| BM351936 | BM351936 | BM351936 ig84d05.x1 HR85 islet *Homo sapiens* cDNA 3′, mRNA sequence [BM351936] |
| NM_138794 | LYPLAL1 | *Homo sapiens* lysophospholipase-like 1 (LYPLAL1), mRNA [NM_138794] |
| NM_021959 | PPP1R11 | *Homo sapiens* protein phosphatase 1, regulatory (inhibitor) subunit 11 (PPP1R11), mRNA [NM_021959] |
| NM_006522 | WNT6 | *Homo sapiens* wingless-type MMTV integration site family, member 6 (WNT6), mRNA [NM_006522] |
| XR_019443 | LOC442270 | PREDICTED: *Homo sapiens* similar to 40S ribosomal protein S12 (LOC442270), mRNA [XR_019443] |
| A_32_P208856 | A_32_P208856 | Unknown |
| A_24_P213375 | A_24_P213375 | Unknown |
| NM_003222 | TFAP2C | *Homo sapiens* transcription factor AP-2 gamma (activating enhancer binding protein 2 gamma) (TFAP2C), mRNA [NM_003222] |
| NM_021029 | RPL36A | *Homo sapiens* ribosomal protein L36a (RPL36A), mRNA [NM_021029] |
| NM_173833 | SCARA5 | *Homo sapiens* scavenger receptor class A, member 5 (putative) (SCARA5), mRNA [NM_173833] |
| THC2565422 | THC2565422 | ALU1_HUMAN (P39188) Alu subfamily J sequence contamination warning entry, partial (3%) [THC2565422] |
| NM_152680 | TMEM154 | *Homo sapiens* transmembrane protein 154 (TMEM154), mRNA [NM_152680] |
| NM_024067 | C7orf26 | *Homo sapiens* chromosome 7 open reading frame 26 (C7orf26), mRNA [NM_024067] |
| NM_005340 | HINT1 | *Homo sapiens* histidine triad nucleotide binding protein 1 (HINT1), mRNA [NM_005340] |
| NM_177458 | LYNX1 | *Homo sapiens* Ly6/neurotoxin 1 (LYNX1), transcript variant SLURP2, mRNA [NM_177458] |
| ENST00000325151 | ENST00000325151 | Small inducible cytokine A27 precursor (CCL27) (CC chemokine ILC) (IL-11 R-alpha-locus chemokine) (Skinkine) (ESkine) (Cutaneous T-cell-attracting chemokine) (CTACK). [Source: Uniprot/SWISSPROT; Acc: Q9Y4X3] [ENST00000325151] |
| NM_024958 | NRSN2 | *Homo sapiens* neurensin 2 (NRSN2), mRNA [NM_024958] |
| NM_144569 | SPOCD1 | *Homo sapiens* SPOC domain containing 1 (SPOCD1), mRNA [NM_144569] |
| NM_001017395 | TMCC1 | *Homo sapiens* transmembrane and coiled-coil domain family 1 (TMCC1), transcript variant 1, mRNA [NM_001017395] |
| NM_178519 | C17orf55 | *Homo sapiens* chromosome 17 open reading frame 55 (C17orf55), mRNA [NM_178519] |
| THC2650296 | THC2650296 | RL18A_MOUSE (P62717) 60S ribosomal protein L18a, complete [THC2650296] |
| NM_001013 | RPS9 | *Homo sapiens* ribosomal protein S9 (RPS9), mRNA [NM_001013] |
| AA436686 | AA436686 | AA436686 zv59a12.s1 Soares_testis_NHT *Homo sapiens* cDNA clone IMAGE: 757918 3′ similar to contains Alu repetitive element;, mRNA sequence [AA436686] |
| NM_138732 | NRXN2 | *Homo sapiens* neurexin 2 (NRXN2), transcript variant alpha-2, mRNA [NM_138732] |
| NM_173473 | C10orf104 | *Homo sapiens* chromosome 10 open reading frame 104 (C10orf104), mRNA [NM_173473] |
| BC093850 | C18orf23 | *Homo sapiens* chromosome 18 open reading frame 23, mRNA (cDNA clone MGC: 120885 IMAGE: 7939695), complete cds. [BC093850] |
| NM_005157 | ABL1 | *Homo sapiens* v-abl Abelson murine leukemia viral oncogene homolog 1 (ABL1), transcript variant a, mRNA [NM_005157] |
| NM_018166 | C1orf78 | *Homo sapiens* chromosome 1 open reading frame 78 (C1orf78), mRNA [NM_018166] |
| NM_001011724 | RP11-78J21.1 | *Homo sapiens* heterogeneous nuclear ribonucleoprotein A1-like (LOC144983), transcript variant 1, mRNA [NM_001011724] |
| NM_080746 | RPL10L | *Homo sapiens* ribosomal protein L10-like (RPL10L), mRNA [NM_080746] |
| NM_207377 | UNQ9438 | *Homo sapiens* TIMM9 (UNQ9438), mRNA [NM_207377] |
| A_24_P641673 | A_24_P641673 | Unknown |
| ENST00000330370 | LOC649839 | PREDICTED: *Homo sapiens* similar to large subunit ribosomal protein L36a (LOC649839), mRNA [XM_001129410] |

TABLE 16-continued

Gene list generated at the inclusion criteria of p ≤ 0.001.

| GenBank Accession | GeneName | Description |
|---|---|---|
| A_24_P698376 | A_24_P698376 | Unknown |
| NM_033625 | RPL34 | *Homo sapiens* ribosomal protein L34 (RPL34), transcript variant 2, mRNA [NM_033625] |
| NM_001005862 | ERBB2 | *Homo sapiens* v-erb-b2 erythroblastic leukemia viral oncogene homolog 2, neuro/glioblastoma derived oncogene homolog (avian) (ERBB2), transcript variant 2, mRNA [NM_001005862] |
| ENST00000313620 | LOC342994 | PREDICTED: *Homo sapiens* similar to ribosomal protein L34 (LOC342994), mRNA [XM_938484] |
| NM_015710 | GLTSCR2 | *Homo sapiens* glioma tumor suppressor candidate region gene 2 (GLTSCR2), mRNA [NM_015710] |
| NM_001416 | EIF4A1 | *Homo sapiens* eukaryotic translation initiation factor 4A, isoform 1 (EIF4A1), mRNA [NM_001416] |
| BX641027 | BX641027 | *Homo sapiens* mRNA; cDNA DKFZp686O10247 (from clone DKFZp686O10247). [BX641027] |
| NM_003078 | SMARCD3 | *Homo sapiens* SWI/SNF related, matrix associated, actin dependent regulator of chromatin, subfamily d, member 3 (SMARCD3), transcript variant 2, mRNA [NM_003078] |
| NM_004450 | ERH | *Homo sapiens* enhancer of rudimentary homolog (*Drosophila*) (ERH), mRNA [NM_004450] |
| NM_001005291 | SREBF1 | *Homo sapiens* sterol regulatory element binding transcription factor 1 (SREBF1), transcript variant 1, mRNA [NM_001005291] |
| A_24_P194954 | A_24_P194954 | Unknown |
| NM_014362 | HIBCH | *Homo sapiens* 3-hydroxyisobutyryl-Coenzyme A hydrolase (HIBCH), transcript variant 1, mRNA [NM_014362] |
| XR_018187 | LOC647722 | PREDICTED: *Homo sapiens* similar to ribosomal protein L3 isoform a (LOC647722), mRNA [XR_018187] |
| NM_001018051 | POLR3H | *Homo sapiens* polymerase (RNA) III (DNA directed) polypeptide H (22.9 kD) (POLR3H), transcript variant 4, mRNA [NM_001018051] |
| NM_145245 | EVI5L | *Homo sapiens* ecotropic viral integration site 5-like (EVI5L), mRNA [NM_145245] |
| NM_016337 | EVL | *Homo sapiens* Enah/Vasp-like (EVL), mRNA [NM_016337] |
| A_24_P736617 | A_24_P736617 | Unknown |
| NM_032152 | PRAM1 | *Homo sapiens* PML-RARA regulated adaptor molecule 1 (PRAM1), mRNA [NM_032152] |
| NM_003202 | TCF7 | *Homo sapiens* transcription factor 7 (T-cell specific, HMG-box) (TCF7), transcript variant 1, mRNA [NM_003202] |
| A_24_P587938 | A_24_P587938 | Unknown |
| NM_203298 | CHCHD1 | *Homo sapiens* coiled-coil-helix-coiled-coil-helix domain containing 1 (CHCHD1), mRNA [NM_203298] |
| THC2560098 | THC2560098 | S35960 C-terminal {*Homo sapiens*} (exp = −1; wgp = 0; cg = 0), partial (64%) [THC2560098] |
| NM_000948 | PRL | *Homo sapiens* prolactin (PRL), mRNA [NM_000948] |
| A_24_P273074 | A_24_P273074 | Unknown |
| NM_014367 | C3orf28 | *Homo sapiens* chromosome 3 open reading frame 28 (C3orf28), mRNA [NM_014367] |
| AY168775 | CXorf52 | *Homo sapiens* SPCX mRNA, complete cds. [AY168775] |
| NM_025073 | SIKE | *Homo sapiens* suppressor of IKK epsilon (SIKE), mRNA [NM_025073] |
| AI291464 | AI291464 | AI291464 qm73h06.x1 Soares_placenta_8to9weeks_2NbHP8to9W *Homo sapiens* cDNA clone IMAGE: 1894427 3', mRNA sequence [AI291464] |
| NM_012225 | NUBP2 | *Homo sapiens* nucleotide binding protein 2 (MinD homolog, *E. coli*) (NUBP2), mRNA [NM_012225] |
| NM_080825 | C20orf144 | *Homo sapiens* chromosome 20 open reading frame 144 (C20orf144), mRNA [NM_080825] |
| NM_002229 | JUNB | *Homo sapiens* jun B proto-oncogene (JUNB), mRNA [NM_002229] |
| NM_203304 | RKHD1 | *Homo sapiens* ring finger and KH domain containing 1 (RKHD1), mRNA [NM_203304] |
| ENST00000356196 | hCG_26523 | PREDICTED: *Homo sapiens* similar to 60S ribosomal protein L26 (Silica-induced gene 20 protein) (SIG-20) (LOC400055), mRNA [XM_374987] |
| ENST00000311218 | LOC401911 | similar to 60S ribosomal protein L29 (Cell surface heparin-binding protein HIP) (LOC401911), mRNA [Source: RefSeq_dna; Acc: XR_016465] [ENST00000311218] |
| NM_012317 | LDOC1 | *Homo sapiens* leucine zipper, down-regulated in cancer 1 (LDOC1), mRNA [NM_012317] |
| NM_015710 | GLTSCR2 | *Homo sapiens* glioma tumor suppressor candidate region gene 2 (GLTSCR2), mRNA [NM_015710] |
| XR_015536 | LOC731599 | PREDICTED: *Homo sapiens* hypothetical protein LOC731599 (LOC731599), mRNA [XR_015536] |
| AX721252 | AX721252 | Sequence 212 from Patent WO0220754. [AX721252] |
| NM_001009 | RPS5 | *Homo sapiens* ribosomal protein S5 (RPS5), mRNA [NM_001009] |
| NM_000972 | RPL7A | *Homo sapiens* ribosomal protein L7a (RPL7A), mRNA [NM_000972] |

TABLE 16-continued

Gene list generated at the inclusion criteria of p ≤ 0.001.

| GenBank Accession | GeneName | Description |
| --- | --- | --- |
| NM_006013 | RPL10 | *Homo sapiens* ribosomal protein L10 (RPL10), mRNA [NM_006013] |
| NM_003202 | TCF7 | *Homo sapiens* transcription factor 7 (T-cell specific, HMG-box) (TCF7), transcript variant 1, mRNA [NM_003202] |
| A_24_P101271 | A_24_P101271 | Unknown |
| NM_033199 | UCN2 | *Homo sapiens* urocortin 2 (UCN2), mRNA [NM_033199] |
| NM_003246 | THBS1 | *Homo sapiens* thrombospondin 1 (THBS1), mRNA [NM_003246] |
| XR_019375 | LOC645326 | PREDICTED: *Homo sapiens* similar to laminin receptor 1 (ribosomal protein SA) (LOC645326), mRNA [XR_019375] |
| A_24_P929974 | A_24_P929974 | Unknown |
| NM_002624 | PFDN5 | *Homo sapiens* prefoldin subunit 5 (PFDN5), transcript variant 1, mRNA [NM_002624] |
| NM_005911 | MAT2A | *Homo sapiens* methionine adenosyltransferase II, alpha (MAT2A), mRNA [NM_005911] |
| NM_206819 | MYBPC1 | *Homo sapiens* myosin binding protein C, slow type (MYBPC1), transcript variant 2, mRNA [NM_206819] |
| A_24_P332292 | A_24_P332292 | Unknown |
| NM_000972 | RPL7A | *Homo sapiens* ribosomal protein L7a (RPL7A), mRNA [NM_000972] |
| NM_001402 | EEF1A1 | *Homo sapiens* eukaryotic translation elongation factor 1 alpha 1 (EEF1A1), mRNA [NM_001402] |
| NM_033184 | KRTAP2-4 | *Homo sapiens* keratin associated protein 2-4 (KRTAP2-4), mRNA [NM_033184] |
| A_24_P169645 | A_24_P169645 | Unknown |
| A_32_P77759 | A_32_P77759 | Unknown |
| THC2584902 | THC2584902 | Q5M9L9_MOUSE (Q5M9L9) Ribosomal protein S8, partial (73%) [THC2584902] |
| NM_030981 | RAB1B | *Homo sapiens* RAB1B, member RAS oncogene family (RAB1B), mRNA [NM_030981] |
| NM_000981 | RPL19 | *Homo sapiens* ribosomal protein L19 (RPL19), mRNA [NM_000981] |
| NM_152525 | ALS2CR11 | *Homo sapiens* amyotrophic lateral sclerosis 2 (juvenile) chromosome region, candidate 11 (ALS2CR11), mRNA [NM_152525] |
| NM_000661 | RPL9 | *Homo sapiens* ribosomal protein L9 (RPL9), transcript variant 1, mRNA [NM_000661] |
| NM_016480 | PAIP2 | *Homo sapiens* poly(A) binding protein interacting protein 2 (PAIP2), transcript variant 2, mRNA [NM_016480] |
| NM_004750 | CRLF1 | *Homo sapiens* cytokine receptor-like factor 1 (CRLF1), mRNA [NM_004750] |
| NM_006471 | MRCL3 | *Homo sapiens* myosin regulatory light chain MRCL3 (MRCL3), mRNA [NM_006471] |
| NM_033625 | RPL34 | *Homo sapiens* ribosomal protein L34 (RPL34), transcript variant 2, mRNA [NM_033625] |
| NM_032378 | EEF1D | *Homo sapiens* eukaryotic translation elongation factor 1 delta (guanine nucleotide exchange protein) (EEF1D), transcript variant 1, mRNA [NM_032378] |
| CA503163 | CA503163 | UI-CF-FN0-afp-1-04-0-UI.s1 UI-CF-FN0 *Homo sapiens* cDNA clone UI-CF-FN0-afp-1-04-0-UI 3', mRNA sequence [CA503163] |
| NR_003110 | CCT6AP1 | *Homo sapiens* chaperonin containing TCP1, subunit 6A (zeta 1) pseudogene 1 (CCT6AP1) on chromosome 7 [NR_003110] |
| NM_175065 | HIST2H2AB | *Homo sapiens* histone cluster 2, H2ab (HIST2H2AB), mRNA [NM_175065] |
| NM_004714 | DYRK1B | *Homo sapiens* dual-specificity tyrosine-(Y)-phosphorylation regulated kinase 1B (DYRK1B), transcript variant a, mRNA [NM_004714] |
| X78926 | ZNF268 | *H. sapiens* HZF3 mRNA for zinc finger protein. [X78926] |
| NM_021038 | MBNL1 | *Homo sapiens* muscleblind-like (*Drosophila*) (MBNL1), transcript variant 1, mRNA [NM_021038] |
| A_32_P231880 | A_32_P231880 | Unknown |
| NM_015355 | SUZ12 | *Homo sapiens* suppressor of zeste 12 homolog (*Drosophila*) (SUZ12), mRNA [NM_015355] |
| NM_002124 | HLA-DRB1 | *Homo sapiens* major histocompatibility complex, class II, DR beta 1 (HLA-DRB1), mRNA [NM_002124] |
| BC014023 | BC014023 | *Homo sapiens* cDNA clone IMAGE: 4309177, **** WARNING: chimeric clone ****. [BC014023] |
| A_24_P170103 | A_24_P170103 | Unknown |
| A_32_P25838 | A_32_P25838 | Unknown |
| ENST00000332289 | ENST00000332289 | PREDICTED: *Homo sapiens* similar to 40S ribosomal protein SA (p40) (34 [XR_019580] |
| NM_013271 | PCSK1N | *Homo sapiens* proprotein convertase subtilisin/kexin type 1 inhibitor (PCSK1N), mRNA [NM_013271] |
| AY037153 | CAMTA1 | *Homo sapiens* hypothetical protein SB141 mRNA, complete cds. [AY037153] |

TABLE 16-continued

Gene list generated at the inclusion criteria of p ≤ 0.001.

| GenBank Accession | GeneName | Description |
|---|---|---|
| CR627135 | CR627135 | *Homo sapiens* mRNA; cDNA DKFZp779J0122 (from clone DKFZp779J0122). [CR627135] |
| AK026675 | AK026675 | *Homo sapiens* cDNA: FLJ23022 fis, clone LNG01117. [AK026675] |
| XR_018545 | LOC649228 | PREDICTED: *Homo sapiens* similar to 60S ribosomal protein L11 (LOC649228), mRNA [XR_018545] |
| NM_014851 | KLHL21 | *Homo sapiens* kelch-like 21 (*Drosophila*) (KLHL21), mRNA [NM_014851] |
| XR_018063 | LOC392030 | PREDICTED: *Homo sapiens* hypothetical LOC392030 (LOC392030), mRNA [XR_018063] |
| NM_017545 | HAO1 | *Homo sapiens* hydroxyacid oxidase (glycolate oxidase) 1 (HAO1), mRNA [NM_017545] |
| A_32_P101195 | A_32_P101195 | Unknown |
| NM_000969 | RPL5 | *Homo sapiens* ribosomal protein L5 (RPL5), mRNA [NM_000969] |
| THC2646356 | THC2646356 | Q2US65_ASPOR (Q2US65) Cytochrome P450 CYP3/CYP5/CYP6/CYP9 subfamilies, partial (4%) [THC2646356] |
| NM_033184 | KRTAP2-4 | *Homo sapiens* keratin associated protein 2-4 (KRTAP2-4), mRNA [NM_033184] |
| A_24_P366445 | A_24_P366445 | Unknown |
| NM_024012 | HTR5A | *Homo sapiens* 5-hydroxytryptamine (serotonin) receptor 5A (HTR5A), mRNA [NM_024012] |
| XR_018963 | LOC442237 | PREDICTED: *Homo sapiens* similar to 40S ribosomal protein S7 (S8) (LOC442237), mRNA [XR_018963] |
| A_24_P410070 | A_24_P410070 | Unknown |
| NM_005646 | TARBP1 | *Homo sapiens* Tar (HIV-1) RNA binding protein 1 (TARBP1), mRNA [NM_005646] |
| XM_374010 | LOC389033 | PREDICTED: *Homo sapiens* hypothetical LOC389033 (LOC389033), mRNA [XM_374010] |
| NM_033251 | RPL13 | *Homo sapiens* ribosomal protein L13 (RPL13), transcript variant 2, mRNA [NM_033251] |
| NM_000454 | SOD1 | *Homo sapiens* superoxide dismutase 1, soluble (amyotrophic lateral sclerosis 1 (adult)) (SOD1), mRNA [NM_000454] |
| XR_015548 | LOC729449 | PREDICTED: *Homo sapiens* similar to 60S ribosomal protein L7 (LOC729449), mRNA [XR_015548] |
| THC2693842 | THC2693842 | Unknown |
| A_24_P75399 | A_24_P75399 | Unknown |
| NM_184041 | ALDOA | *Homo sapiens* aldolase A, fructose-bisphosphate (ALDOA), transcript variant 2, mRNA [NM_184041] |
| NM_001031 | RPS28 | *Homo sapiens* ribosomal protein S28 (RPS28), mRNA [NM_001031] |
| THC2533996 | THC2533996 | HSU09954 ribosomal protein L9 {*Homo sapiens*} (exp = −1; wgp = 0; cg = 0), partial (42%) [THC2533996] |
| NM_015937 | PIGT | *Homo sapiens* phosphatidylinositol glycan anchor biosynthesis, class T (PIGT), mRNA [NM_015937] |
| NM_006294 | UQCRB | *Homo sapiens* ubiquinol-cytochrome c reductase binding protein (UQCRB), mRNA [NM_006294] |
| NM_019059 | TOMM7 | *Homo sapiens* translocase of outer mitochondrial membrane 7 homolog (yeast) (TOMM7), mRNA [NM_019059] |
| NM_001778 | CD48 | *Homo sapiens* CD48 molecule (CD48), mRNA [NM_001778] |
| NM_032789 | PARP10 | *Homo sapiens* poly (ADP-ribose) polymerase family, member 10 (PARP10), mRNA [NM_032789] |
| NR_002778 | RPL29P2 | *Homo sapiens* ribosomal protein L29 pseudogene 2 (RPL29P2) on chromosome 17 [NR_002778] |
| THC2689192 | THC2689192 | Q7XC69_ORYSA (Q7XC69) Expressed protein, partial (6%) [THC2689192] |
| NM_000993 | RPL31 | *Homo sapiens* ribosomal protein L31 (RPL31), mRNA [NM_000993] |
| NM_000610 | CD44 | *Homo sapiens* CD44 molecule (Indian blood group) (CD44), transcript variant 1, mRNA [NM_000610] |
| NM_005538 | INHBC | *Homo sapiens* inhibin, beta C (INHBC), mRNA [NM_005538] |
| NM_030928 | CDT1 | *Homo sapiens* chromatin licensing and DNA replication factor 1 (CDT1), mRNA [NM_030928] |
| BE843546 | BE843546 | BE843546 CM3-TN0066-080800-269-g03 TN0066 *Homo sapiens* cDNA, mRNA sequence [BE843546] |
| A_24_P714750 | A_24_P714750 | Unknown |
| XR_018189 | LOC401717 | PREDICTED: *Homo sapiens* similar to eukaryotic translation elongation factor 1 alpha 2 (LOC401717), mRNA [XR_018189] |
| NM_003614 | GALR3 | *Homo sapiens* galanin receptor 3 (GALR3), mRNA [NM_003614] |
| NM_007262 | PARK7 | *Homo sapiens* Parkinson disease (autosomal recessive, early onset) 7 (PARK7), mRNA [NM_007262] |
| NM_006738 | AKAP13 | *Homo sapiens* A kinase (PRKA) anchor protein 13 (AKAP13), transcript variant 1, mRNA [NM_006738] |
| NM_017801 | CMTM6 | *Homo sapiens* CKLF-like MARVEL transmembrane domain containing 6 (CMTM6), mRNA [NM_017801] |

TABLE 16-continued

Gene list generated at the inclusion criteria of p ≤ 0.001.

| GenBank Accession | GeneName | Description |
|---|---|---|
| ENST00000332500 | PTP4A2 | Protein tyrosine phosphatase type IVA protein 2 (EC 3.1.3.48) (Protein-tyrosine phosphatase 4a2) (Protein-tyrosine phosphatase of regenerating liver 2) (PRL-2) (PTP(CAAXII)) (HU-PP-1) (OV-1). [Source: Uniprot/SWISSPROT; Acc: Q12974] [ENST00000332500] |
| NM_002421 | MMP1 | *Homo sapiens* matrix metallopeptidase 1 (interstitial collagenase) (MMP1), mRNA [NM_002421] |
| NM_016270 | KLF2 | *Homo sapiens* Kruppel-like factor 2 (lung) (KLF2), mRNA [NM_016270] |
| NM_017881 | C9orf95 | *Homo sapiens* chromosome 9 open reading frame 95 (C9orf95), mRNA [NM_017881] |
| NM_000428 | LTBP2 | *Homo sapiens* latent transforming growth factor beta binding protein 2 (LTBP2), mRNA [NM_000428] |
| XR_017260 | LOC646710 | PREDICTED: *Homo sapiens* hypothetical LOC646710 (LOC646710), mRNA [XR_017260] |
| NM_024812 | BAALC | *Homo sapiens* brain and acute leukemia, cytoplasmic (BAALC), transcript variant 1, mRNA [NM_024812] |
| NM_030979 | PABPC3 | *Homo sapiens* poly(A) binding protein, cytoplasmic 3 (PABPC3), mRNA [NM_030979] |
| XR_018341 | LOC390413 | PREDICTED: *Homo sapiens* similar to 60S ribosomal protein L7 (LOC390413), mRNA [XR_018341] |
| NM_000970 | RPL6 | *Homo sapiens* ribosomal protein L6 (RPL6), transcript variant 2, mRNA [NM_000970] |
| BC048265 | LOC439990 | *Homo sapiens* hypothetical gene supported by BC009626; BC048265, mRNA (cDNA clone IMAGE: 4400050). [BC048265] |
| NM_001042646 | TRAK1 | *Homo sapiens* trafficking protein, kinesin binding 1 (TRAK1), transcript variant 1, mRNA [NM_001042646] |
| XR_016779 | LOC440311 | PREDICTED: *Homo sapiens* similar to Glioma tumor suppressor candidate region gene 2 protein (p60) (LOC440311), mRNA [XR_016779] |
| NM_001080418 | DLGAP3 | *Homo sapiens* discs, large (*Drosophila*) homolog-associated protein 3 (DLGAP3), mRNA [NM_001080418] |
| BC018095 | BC018095 | *Homo sapiens* cDNA clone IMAGE: 4793786. [BC018095] |
| NM_003508 | FZD9 | *Homo sapiens* frizzled homolog 9 (*Drosophila*) (FZD9), mRNA [NM_003508] |
| NM_000453 | SLC5A5 | *Homo sapiens* solute carrier family 5 (sodium iodide symporter), member 5 (SLC5A5), mRNA [NM_000453] |
| NM_016104 | RWDD1 | *Homo sapiens* RWD domain containing 1 (RWDD1), transcript variant 2, mRNA [NM_016104] |
| NM_207322 | NLF1 | *Homo sapiens* nuclear localized factor 1 (NLF1), mRNA [NM_207322] |
| BC103878 | MOGAT2 | *Homo sapiens* monoacylglycerol O-acyltransferase 2, mRNA (cDNA clone MGC: 119185 IMAGE: 40004283), complete cds. [BC103878] |
| A_24_P572229 | A_24_P572229 | Unknown |
| NM_022356 | LEPRE1 | *Homo sapiens* leucine proline-enriched proteoglycan (leprecan) 1 (LEPRE1), mRNA [NM_022356] |
| NM_080392 | PTP4A2 | *Homo sapiens* protein tyrosine phosphatase type IVA, member 2 (PTP4A2), transcript variant 2, mRNA [NM_080392] |
| NM_002307 | LGALS7 | *Homo sapiens* lectin, galactoside-binding, soluble, 7 (galectin 7) (LGALS7), mRNA [NM_002307] |
| NM_001042519 | MGC13057 | *Homo sapiens* hypothetical protein MGC13057 (MGC13057), transcript variant 1, mRNA [NM_001042519] |
| NM_023078 | PYCRL | *Homo sapiens* pyrroline-5-carboxylate reductase-like (PYCRL), mRNA [NM_023078] |
| XR_018052 | LOC442288 | PREDICTED: *Homo sapiens* similar to 60S ribosomal protein L7a (LOC442288), mRNA [XR_018052] |
| NM_000979 | RPL18 | *Homo sapiens* ribosomal protein L18 (RPL18), mRNA [NM_000979] |
| NM_013354 | CNOT7 | *Homo sapiens* CCR4-NOT transcription complex, subunit 7 (CNOT7), transcript variant 1, mRNA [NM_013354] |
| XR_018054 | LOC392878 | PREDICTED: *Homo sapiens* hypothetical LOC392878 (LOC392878), mRNA [XR_018054] |
| AF100640 | AF100640 | *Homo sapiens* metastasis related protein (MB2) mRNA, partial cds. [AF100640] |
| NM_014248 | RBX1 | *Homo sapiens* ring-box 1 (RBX1), mRNA [NM_014248] |
| NM_001005472 | LOC388524 | *Homo sapiens* similar to Laminin receptor 1 (LOC388524), mRNA [NM_001005472] |
| ENST00000381140 | ENST00000381140 | Transcription factor IIIA (Factor A) (TFIIIA). [Source: Uniprot/SWISSPROT; Acc: Q92664] [ENST00000381140] |
| NM_018326 | GIMAP4 | *Homo sapiens* GTPase, IMAP family member 4 (GIMAP4), mRNA [NM_018326] |
| NM_013234 | EIF3S12 | *Homo sapiens* eukaryotic translation initiation factor 3, subunit 12 (EIF3S12), mRNA [NM_013234] |
| NM_172006 | WFDC10B | *Homo sapiens* WAP four-disulfide core domain 10B (WFDC10B), transcript variant 1, mRNA [NM_172006] |

TABLE 16-continued

Gene list generated at the inclusion criteria of p ≤ 0.001.

| GenBank Accession | GeneName | Description |
|---|---|---|
| BC024303 | FLJ35390 | *Homo sapiens* hypothetical protein FLJ35390, mRNA (cDNA clone IMAGE: 4328569), with apparent retained intron. [BC024303] |
| NM_000982 | RPL21 | *Homo sapiens* ribosomal protein L21 (RPL21), mRNA [NM_000982] |
| NM_000454 | SOD1 | *Homo sapiens* superoxide dismutase 1, soluble (amyotrophic lateral sclerosis 1 (adult)) (SOD1), mRNA [NM_000454] |
| NM_024676 | C1orf113 | *Homo sapiens* chromosome 1 open reading frame 113 (C1orf113), mRNA [NM_024676] |
| A_24_P850187 | A_24_P850187 | Unknown |
| THC2513403 | THC2513403 | HUMBCAA Br-cadherin {*Homo sapiens*} (exp = −1; wgp = 0; cg = 0), partial (13%) [THC2513403] |
| NM_006285 | TESK1 | *Homo sapiens* testis-specific kinase 1 (TESK1), mRNA [NM_006285] |
| NM_000988 | RPL27 | *Homo sapiens* ribosomal protein L27 (RPL27), mRNA [NM_000988] |
| NM_020836 | KIAA1446 | *Homo sapiens* likely ortholog of rat brain-enriched guanylate kinase-associated protein (KIAA1446), mRNA [NM_020836] |
| NM_032611 | PTP4A3 | *Homo sapiens* protein tyrosine phosphatase type IVA, member 3 (PTP4A3), transcript variant 1, mRNA [NM_032611] |
| AI751518 | AI751518 | AI751518 cn10d09.y1 Normal Human Trabecular Bone Cells *Homo sapiens* cDNA clone NHTBC_cn10d09 random, mRNA sequence [AI751518] |
| NM_001465 | FYB | *Homo sapiens* FYN binding protein (FYB-120/130) (FYB), transcript variant 1, mRNA [NM_001465] |
| BC018681 | NDST2 | *Homo sapiens* N-deacetylase/N-sulfotransferase (heparan glucosaminyl) 2, mRNA (cDNA clone IMAGE: 4665687), partial cds. [BC018681] |
| A_24_P67308 | A_24_P67308 | Unknown |
| ENST00000329784 | ENST00000329784 | PREDICTED: *Homo sapiens* similar to large subunit ribosomal protein L36a (LOC284230), mRNA [XM_208185] |
| NM_001004 | RPLP2 | *Homo sapiens* ribosomal protein, large, P2 (RPLP2), mRNA [NM_001004] |
| A_24_P298320 | A_24_P298320 | Unknown |
| NM_016055 | MRPL48 | *Homo sapiens* mitochondrial ribosomal protein L48 (MRPL48), nuclear gene encoding mitochondrial protein, mRNA [NM_016055] |
| BC064430 | LOC205251 | *Homo sapiens* cDNA clone IMAGE: 5763979. [BC064430] |
| BC069765 | C15orf5 | *Homo sapiens* chromosome 15 open reading frame 5, mRNA (cDNA clone MGC: 97283 IMAGE: 7262532), complete cds. [BC069765] |
| THC2719015 | THC2719015 | Unknown |
| THC2675117 | THC2675117 | D90774 RecT protein (P33). {*Escherichia coli*} (exp = −1; wgp = 0; cg = 0), partial (5%) [THC2675117] |
| NM_001404 | EEF1G | *Homo sapiens* eukaryotic translation elongation factor 1 gamma (EEF1G), mRNA [NM_001404] |
| NM_001293 | CLNS1A | *Homo sapiens* chloride channel, nucleotide-sensitive, 1A (CLNS1A), mRNA [NM_001293] |
| NM_002945 | RPA1 | *Homo sapiens* replication protein A1, 70 kDa (RPA1), mRNA [NM_002945] |
| NM_006830 | UQCR | *Homo sapiens* ubiquinol-cytochrome c reductase, 6.4 kDa subunit (UQCR), mRNA [NM_006830] |
| AF318380 | AF318380 | *Homo sapiens* pp9943 mRNA, complete cds. [AF318380] |
| NM_001039211 | ATAD3C | *Homo sapiens* ATPase family, AAA domain containing 3C (ATAD3C), mRNA [NM_001039211] |
| NM_003145 | SSR2 | *Homo sapiens* signal sequence receptor, beta (translocon-associated protein beta) (SSR2), mRNA [NM_003145] |
| NM_001967 | EIF4A2 | *Homo sapiens* eukaryotic translation initiation factor 4A, isoform 2 (EIF4A2), mRNA [NM_001967] |
| NM_001011 | RPS7 | *Homo sapiens* ribosomal protein S7 (RPS7), mRNA [NM_001011] |
| NM_001007 | RPS4X | *Homo sapiens* ribosomal protein S4, X-linked (RPS4X), mRNA [NM_001007] |
| NM_173571 | RP6-166C19.11 | *Homo sapiens* cancer/testis CT47 family, member 11 (CT47.11), mRNA [NM_173571] |
| NM_004907 | IER2 | *Homo sapiens* immediate early response 2 (IER2), mRNA [NM_004907] |
| ENST00000333351 | ENST00000333351 | PREDICTED: *Homo sapiens* hypothetical LOC391504 (LOC391504), mRNA [XR_018627] |
| NM_001122 | ADFP | *Homo sapiens* adipose differentiation-related protein (ADFP), mRNA [NM_001122] |
| NM_152540 | SCFD2 | *Homo sapiens* sec1 family domain containing 2 (SCFD2), mRNA [NM_152540] |
| A_24_P204474 | A_24_P204474 | Unknown |
| BC004968 | MGC2664 | *Homo sapiens*, clone IMAGE: 3543963, mRNA. [BC004968] |
| NM_001028 | RPS25 | *Homo sapiens* ribosomal protein S25 (RPS25), mRNA [NM_001028] |

TABLE 16-continued

Gene list generated at the inclusion criteria of p ≤ 0.001.

| GenBank Accession | GeneName | Description |
|---|---|---|
| NM_001861 | COX4I1 | *Homo sapiens* cytochrome c oxidase subunit IV isoform 1 (COX4I1), mRNA [NM_001861] |
| NM_178230 | PPIAL4 | *Homo sapiens* peptidylprolyl isomerase A (cyclophilin A)-like 4 (PPIAL4), mRNA [NM_178230] |
| ENST00000256969 | C12orf39 | Uncharacterized protein C12orf39 precursor [Contains: Putative amidated peptide NWTPQAMLYLKGAQ]. [Source: Uniprot/SWISSPROT; Acc: Q9BT56] [ENST00000256969] |
| A_24_P196024 | A_24_P196024 | Unknown |
| NM_006671 | SLC1A7 | *Homo sapiens* solute carrier family 1 (glutamate transporter), member 7 (SLC1A7), mRNA [NM_006671] |
| NM_002118 | HLA-DMB | *Homo sapiens* major histocompatibility complex, class II, DM beta (HLA-DMB), mRNA [NM_002118] |
| BU956542 | BU956542 | BU956542 AGENCOURT_10615527 NIH_MGC_107 *Homo sapiens* cDNA clone IMAGE: 6730153 5', mRNA sequence [BU956542] |
| AK057161 | MEF2B | *Homo sapiens* cDNA FLJ32599 fis, clone STOMA1000047. [AK057161] |
| NM_017549 | EPDR1 | *Homo sapiens* ependymin related protein 1 (zebrafish) (EPDR1), mRNA [NM_017549] |
| NM_033342 | TRIM7 | *Homo sapiens* tripartite motif-containing 7 (TRIM7), transcript variant 6, mRNA [NM_033342] |
| AL547890 | AL547890 | AL547890 AL547890 *Homo sapiens* PLACENTA COT 25-NORMALIZED *Homo sapiens* cDNA clone CS0DI033YB09 5-PRIME, mRNA sequence [AL547890] |
| THC2726954 | THC2726954 | Q5Y2C1_9STRA (Q5Y2C1) Silaffin, partial (4%) [THC2726954] |
| A_24_P392790 | A_24_P392790 | Unknown |
| NM_001537 | HSBP1 | *Homo sapiens* heat shock factor binding protein 1 (HSBP1), mRNA [NM_001537] |
| XR_017498 | LOC645693 | PREDICTED: *Homo sapiens* similar to eukaryotic translation elongation factor 1 alpha 2 (LOC645693), mRNA [XR_017498] |
| THC2745287 | THC2745287 | Q6C3B8_YARLI (Q6C3B8) Similarity, partial (10%) [THC2745287] |
| BC001697 | RPS15A | *Homo sapiens* ribosomal protein S15a, mRNA (cDNA clone MGC: 2466 IMAGE: 2967511), complete cds. [BC001697] |
| NM_003754 | EIF3S5 | *Homo sapiens* eukaryotic translation initiation factor 3, subunit 5 epsilon, 47 kDa (EIF3S5), mRNA [NM_003754] |
| NM_001008 | RPS4Y1 | *Homo sapiens* ribosomal protein S4, Y-linked 1 (RPS4Y1), mRNA [NM_001008] |
| NM_002405 | MFNG | *Homo sapiens* MFNG O-fucosylpeptide 3-beta-N-acetylglucosaminyltransferase (MFNG), mRNA [NM_002405] |
| A_24_P324224 | A_24_P324224 | Unknown |
| A_24_P714620 | A_24_P714620 | Unknown |
| NM_030912 | TRIM8 | *Homo sapiens* tripartite motif-containing 8 (TRIM8), mRNA [NM_030912] |
| NM_001017418 | SPRR2B | *Homo sapiens* small proline-rich protein 2B (SPRR2B), mRNA [NM_001017418] |
| THC2529969 | THC2529969 | Unknown |
| NM_015853 | LOC51035 | *Homo sapiens* SAPK substrate protein 1 (LOC51035), mRNA [NM_015853] |
| NM_020246 | SLC12A9 | *Homo sapiens* solute carrier family 12 (potassium/chloride transporters), member 9 (SLC12A9), mRNA [NM_020246] |
| NM_152429 | FGFBP3 | *Homo sapiens* fibroblast growth factor binding protein 3 (FGFBP3), mRNA [NM_152429] |
| A_24_P50567 | A_24_P50567 | Unknown |
| NM_018949 | UTS2R | *Homo sapiens* urotensin 2 receptor (UTS2R), mRNA [NM_018949] |
| NM_002397 | MEF2C | *Homo sapiens* MADS box transcription enhancer factor 2, polypeptide C (myocyte enhancer factor 2C) (MEF2C), mRNA [NM_002397] |
| NM_001005472 | LOC388524 | *Homo sapiens* similar to Laminin receptor 1 (LOC388524), mRNA [NM_001005472] |
| XR_019242 | LOC402149 | PREDICTED: *Homo sapiens* similar to ribosomal protein L28 (LOC402149), mRNA [XR_019242] |
| NM_198175 | NME1 | *Homo sapiens* non-metastatic cells 1, protein (NM23A) expressed in (NME1), transcript variant 1, mRNA [NM_198175] |
| NM_014335 | EID1 | *Homo sapiens* EP300 interacting inhibitor of differentiation 1 (EID1), mRNA [NM_014335] |
| AF147440 | AF147440 | *Homo sapiens* full length insert cDNA clone YP90G10. [AF147440] |
| A_24_P375435 | A_24_P375435 | Unknown |
| NM_007369 | GPR161 | *Homo sapiens* G protein-coupled receptor 161 (GPR161), transcript variant 1, mRNA [NM_007369] |
| S76980 | HEXA | HEXA {HEXA4bpDeltaA mutation, exon 11} [human, Tay-Sachs disease patient, mRNA Partial Mutant, 78 nt]. [S76980] |
| NM_000967 | RPL3 | *Homo sapiens* ribosomal protein L3 (RPL3), transcript variant 1, mRNA [NM_000967] |

TABLE 16-continued

Gene list generated at the inclusion criteria of p ≤ 0.001.

| GenBank Accession | GeneName | Description |
|---|---|---|
| NM_001568 | EIF3S6 | Homo sapiens eukaryotic translation initiation factor 3, subunit 6 48 kDa (EIF3S6), mRNA [NM_001568] |
| NM_015646 | RAP1B | Homo sapiens RAP1B, member of RAS oncogene family (RAP1B), transcript variant 1, mRNA [NM_015646] |
| NM_001436 | FBL | Homo sapiens fibrillarin (FBL), mRNA [NM_001436] |
| NM_005356 | LCK | Homo sapiens lymphocyte-specific protein tyrosine kinase (LCK), transcript variant 2, mRNA [NM_005356] |
| NM_002350 | LYN | Homo sapiens v-yes-1 Yamaguchi sarcoma viral related oncogene homolog (LYN), mRNA [NM_002350] |
| A_24_P212726 | A_24_P212726 | Unknown |
| A_24_P367139 | A_24_P367139 | Unknown |
| NM_006682 | FGL2 | Homo sapiens fibrinogen-like 2 (FGL2), mRNA [NM_006682] |
| A_24_P332326 | A_24_P332326 | Unknown |
| NM_033251 | RPL13 | Homo sapiens ribosomal protein L13 (RPL13), transcript variant 2, mRNA [NM_033251] |
| A_24_P144383 | A_24_P144383 | Unknown |
| NM_001010938 | TNK2 | Homo sapiens tyrosine kinase, non-receptor, 2 (TNK2), transcript variant 2, mRNA [NM_001010938] |
| AK026078 | AK026078 | Homo sapiens cDNA: FLJ22425 fis, clone HRC08686. [AK026078] |
| THC2529614 | THC2529614 | Q3VHI9_9SPHN (Q3VHI9) Manganese and iron superoxide dismutase precursor, partial (8%) [THC2529614] |
| NM_145690 | YWHAZ | Homo sapiens tyrosine 3-monooxygenase/tryptophan 5-monooxygenase activation protein, zeta polypeptide (YWHAZ), transcript variant 2, mRNA [NM_145690] |
| NM_001014 | RPS10 | Homo sapiens ribosomal protein S10 (RPS10), mRNA [NM_001014] |
| A_24_P290114 | A_24_P290114 | Unknown |
| XR_017294 | LOC646949 | PREDICTED: Homo sapiens similar to ribosomal protein L23 (LOC646949), mRNA [XR_017294] |
| E01979 | E01979 | CD671824 fg07f07.x1 Human Iris cDNA (Normalized): fg Homo sapiens cDNA clone fg07f07 3', mRNA sequence [CD671824] |
| NM_013232 | PDCD6 | Homo sapiens programmed cell death 6 (PDCD6), mRNA [NM_013232] |
| NM_001212 | C1QBP | Homo sapiens complement component 1, q subcomponent binding protein (C1QBP), nuclear gene encoding mitochondrial protein, mRNA [NM_001212] |
| XR_018025 | LOC641790 | PREDICTED: Homo sapiens similar to ribosomal protein L31 (LOC641790), mRNA [XR_018025] |
| NM_019839 | LTB4R2 | Homo sapiens leukotriene B4 receptor 2 (LTB4R2), mRNA [NM_019839] |
| NM_001019 | RPS15A | Homo sapiens ribosomal protein S15a (RPS15A), transcript variant 2, mRNA [NM_001019] |
| NM_004810 | GRAP2 | Homo sapiens GRB2-related adaptor protein 2 (GRAP2), mRNA [NM_004810] |
| NM_182623 | FAM131C | Homo sapiens family with sequence similarity 131, member C (FAM131C), mRNA [NM_182623] |
| NM_001961 | EEF2 | Homo sapiens eukaryotic translation elongation factor 2 (EEF2), mRNA [NM_001961] |
| A_24_P289884 | A_24_P289884 | Unknown |
| A_23_P200955 | A_23_P200955 | Unknown |
| NM_016824 | ADD3 | Homo sapiens adducin 3 (gamma) (ADD3), transcript variant 1, mRNA [NM_016824] |
| ENST00000239730 | ENST00000239730 | Novel protein. [Source: Uniprot/SPTREMBL; Acc: Q5W161] [ENST00000239730] |
| NR_001577 | NME2P1 | Homo sapiens non-metastatic cells 2, protein (NM23B) expressed in, pseudogene 1 (NME2P1) on chromosome 12 [NR_001577] |
| NM_021198 | CTDSP1 | Homo sapiens CTD (carboxy-terminal domain, RNA polymerase II, polypeptide A) small phosphatase 1 (CTDSP1), transcript variant 1, mRNA [NM_021198] |
| NM_006597 | HSPA8 | Homo sapiens heat shock 70 kDa protein 8 (HSPA8), transcript variant 1, mRNA [NM_006597] |
| BC005008 | CEACAM6 | Homo sapiens carcinoembryonic antigen-related cell adhesion molecule 6 (non-specific cross reacting antigen), mRNA (cDNA clone MGC: 10467 IMAGE: 3640231), complete cds. [BC005008] |
| NM_003757 | EIF3S2 | Homo sapiens eukaryotic translation initiation factor 3, subunit 2 beta, 36 kDa (EIF3S2), mRNA [NM_003757] |
| THC2647276 | THC2647276 | Unknown |
| A_24_P255252 | A_24_P255252 | Unknown |
| NM_001402 | EEF1A1 | Homo sapiens eukaryotic translation elongation factor 1 alpha 1 (EEF1A1), mRNA [NM_001402] |
| XR_018386 | LOC392358 | PREDICTED: Homo sapiens similar to 40S ribosomal protein S6 (LOC392358), mRNA [XR_018386] |
| NM_001005472 | LOC388524 | Homo sapiens similar to Laminin receptor 1 (LOC388524), mRNA [NM_001005472] |

TABLE 16-continued

Gene list generated at the inclusion criteria of p ≤ 0.001.

| GenBank Accession | GeneName | Description |
|---|---|---|
| BC067891 | LOC645683 | *Homo sapiens* cDNA clone MGC: 87657 IMAGE: 5271409, complete cds. [BC067891] |
| NM_021130 | PPIA | *Homo sapiens* peptidylprolyl isomerase A (cyclophilin A) (PPIA), mRNA [NM_021130] |
| NM_002037 | FYN | *Homo sapiens* FYN oncogene related to SRC, FGR, YES (FYN), transcript variant 1, mRNA [NM_002037] |
| A_24_P505981 | A_24_P505981 | Unknown |
| NM_005401 | PTPN14 | *Homo sapiens* protein tyrosine phosphatase, non-receptor type 14 (PTPN14), mRNA [NM_005401] |
| NM_031918 | KLF16 | *Homo sapiens* Kruppel-like factor 16 (KLF16), mRNA [NM_031918] |
| NM_000454 | SOD1 | *Homo sapiens* superoxide dismutase 1, soluble (amyotrophic lateral sclerosis 1 (adult)) (SOD1), mRNA [NM_000454] |
| NR_003246 | FLJ40113 | *Homo sapiens* golgi autoantigen, golgin subfamily a-like pseudogene (FLJ40113) on chromosome 15 [NR_003246] |
| XR_015785 | LOC402643 | PREDICTED: *Homo sapiens* tropomyosin 3-like (LOC402643), misc RNA [XR_015785] |
| NM_001010 | RPS6 | *Homo sapiens* ribosomal protein S6 (RPS6), mRNA [NM_001010] |

TABLE 17

Gene list generated at the inclusion criteria of $p \leq 5 \times 10^{-2}$ and the log-median-ratio being at least "1" or above or being at least "−1" or below. The p-values were corrected using Benjamin and Hochberg method.

| Genbank Accession | Gene Name | Description |
|---|---|---|
| NM_001039567 | RPS4Y2 | *Homo sapiens* ribosomal protein S4, Y-linked 2 (RPS4Y2), mRNA [NM_001039567] |
| NM_183049 | TMSL3 | *Homo sapiens* thymosin-like 3 (TMSL3), mRNA [NM_183049] |
| NM_001008 | RPS4Y1 | *Homo sapiens* ribosomal protein S4, Y-linked 1 (RPS4Y1), mRNA [NM_001008] |
| NM_004126 | GNG11 | *Homo sapiens* guanine nucleotide binding protein (G protein), gamma 11 (GNG11), mRNA [NM_004126] |
| NM_002985 | CCL5 | *Homo sapiens* chemokine (C-C motif) ligand 5 (CCL5), mRNA [NM_002985] |
| A_24_P530977 | A_24_P530977 | Unknown |
| NM_004048 | B2M | *Homo sapiens* beta-2-microglobulin (B2M), mRNA [NM_004048] |
| NM_004907 | IER2 | *Homo sapiens* immediate early response 2 (IER2), mRNA [NM_004907] |
| NM_001005339 | RGS10 | *Homo sapiens* regulator of G-protein signalling 10 (RGS10), transcript variant 1, mRNA [NM_001005339] |
| NM_201397 | GPX1 | *Homo sapiens* glutathione peroxidase 1 (GPX1), transcript variant 2, mRNA [NM_201397] |
| NM_015646 | RAP1B | *Homo sapiens* RAP1B, member of RAS oncogene family (RAP1B), transcript variant 1, mRNA [NM_015646] |
| AL049447 | AL049447 | *Homo sapiens* mRNA; cDNA DKFZp586A0722 (from clone DKFZp586A0722). [AL049447] |
| NM_031286 | SH3BGRL3 | *Homo sapiens* SH3 domain binding glutamic acid-rich protein like 3 (SH3BGRL3), mRNA [NM_031286] |
| NM_012329 | MMD | *Homo sapiens* monocyte to macrophage differentiation-associated (MMD), mRNA [NM_012329] |
| NM_002620 | PF4V1 | *Homo sapiens* platelet factor 4 variant 1 (PF4V1), mRNA [NM_002620] |
| NM_001004 | RPLP2 | *Homo sapiens* ribosomal protein, large, P2 (RPLP2), mRNA [NM_001004] |
| NM_033251 | RPL13 | *Homo sapiens* ribosomal protein L13 (RPL13), transcript variant 2, mRNA [NM_033251] |
| ENST00000383061 | ENST00000383061 | PREDICTED: *Homo sapiens* similar to myosin regulatory light chain-like (LOC442204), mRNA [XM_498088] |
| NM_004907 | IER2 | *Homo sapiens* immediate early response 2 (IER2), mRNA [NM_004907] |
| NM_001803 | CD52 | Homo sapiens CD52 molecule (CD52), mRNA [NM_001803] |
| NM_145113 | MAX | *Homo sapiens* MYC associated factor X (MAX), transcript variant 3, mRNA [NM_145113] |
| NM_002954 | RPS27A | *Homo sapiens* ribosomal protein S27a (RPS27A), mRNA [NM_002954] |
| NM_006471 | MRCL3 | *Homo sapiens* myosin regulatory light chain MRCL3 (MRCL3), mRNA [NM_006471] |
| NM_006597 | HSPA8 | *Homo sapiens* heat shock 70 kDa protein 8 (HSPA8), transcript variant 1, mRNA [NM_006597] |

TABLE 17-continued

Gene list generated at the inclusion criteria of $p \leq 5 \times 10^{-2}$ and the log-median-ratio being at least "1" or above or being at least "−1" or below. The p-values were corrected using Benjamin and Hochberg method.

| Genbank Accession | Gene Name | Description |
|---|---|---|
| NM_001030 | RPS27 | Homo sapiens ribosomal protein S27 (metallopanstimulin 1) (RPS27), mRNA [NM_001030] |
| NM_080425 | GNAS | Homo sapiens GNAS complex locus (GNAS), transcript variant 2, mRNA [NM_0804251 |
| NM_001032 | RPS29 | Homo sapiens ribosomal protein S29 (RPS29), transcript variant 1, mRNA [NM_0010321 |
| NM_001012 | RPS8 | Homo sapiens ribosomal protein S8 (RPS8), mRNA [NM_001012] |
| XR_017498 | LOC645693 | PREDICTED: Homo sapiens similar to eukaryotic translation elongation factor 1 alpha 2 (LOC645693), mRNA [XR_017498] |
| NM_006597 | HSPA8 | Homo sapiens heat shock 70 kDa protein 8 (HSPA8), transcript variant 1, mRNA [NM_006597] |
| NM_001030 | RPS27 | Homo sapiens ribosomal protein S27 (metallopanstimulin 1) (RPS27), mRNA [NM_001030] |
| A_24_P229756 | A_24_P229756 | Unknown |
| THC2544911 | THC2544911 | MUSEFTU elongation factor Tu {Mus musculus} (exp = −1; wgp = 0; cg = 0), partial (37%) [THC2544911] |
| NM_021104 | RPL41 | Homo sapiens ribosomal protein L41 (RPL41), transcript variant 1, mRNA [NM_021104] |
| NM_000981 | RPL19 | Homo sapiens ribosomal protein L19 (RPL19), mRNA [NM_0009811 |
| A_24_P929974 | A_24_P929974 | Unknown |
| NM_002300 | LDHB | Homo sapiens lactate dehydrogenase B (LDHB), mRNA [NM_002300] |
| NM_001031 | RPS28 | Homo sapiens ribosomal protein S28 (RPS28), mRNA [NM_001031] |
| NM_000978 | RPL23 | Homo sapiens ribosomal protein L23 (RPL23), mRNA [NM_000978] |
| NM_033251 | RPL13 | Homo sapiens ribosomal protein L13 (RPL13), transcript variant 2, mRNA [NM_033251] |
| NM_001003 | RPLP1 | Homo sapiens ribosomal protein, large, P1 (RPLP1), transcript variant 1, mRNA [NM_001003] |
| NM_001028 | RPS25 | Homo sapiens ribosomal protein S25 (RPS25), mRNA [NM_001028] |
| NM_001032 | RPS29 | Homo sapiens ribosomal protein S29 (RPS29), transcript variant 1, mRNA [NM_001032] |
| A_24_P238426 | A_24_P238426 | Unknown |
| NM_018447 | TMEM111 | Homo sapiens transmembrane protein 111 (TMEM111), mRNA [NM_018447] |
| BX096698 | BX096698 | BX096698 Soares breast 2NbHBst Homo sapiens cDNA clone IMAGp998E11242, mRNA sequence [BX096698] |
| NM_001003 | RPLP1 | Homo sapiens ribosomal protein, large, P1 (RPLP1), transcript variant 1, mRNA [NM_001003] |
| NM_002823 | PTMA | Homo sapiens prothymosin, alpha (gene sequence 28) (PTMA), mRNA [NM_002823] |
| NM_033251 | RPL13 | Homo sapiens ribosomal protein L13 (RPL13), transcript variant 2, mRNA [NM_033251] |
| XR_017294 | LOC646949 | PREDICTED: Homo sapiens similar to ribosomal protein L23 (LOC646949), mRNA [XR_017294] |
| NM_000993 | RPL31 | Homo sapiens ribosomal protein L31 (RPL31), mRNA [NM_000993] |
| XR_015548 | LOC729449 | PREDICTED: Homo sapiens similar to 60S ribosomal protein L7 (LOC729449), mRNA [XR_015548] |
| BC052613 | LOC728131 | Homo sapiens cDNA clone MGC: 59872 IMAGE: 6301163, complete cds. [BC052613] |
| A_24_P306968 | A_24_P306968 | Unknown |
| XM_497657 | LOC441876 | PREDICTED: Homo sapiens similar to 40S ribosomal protein S16, transcript variant 1 (LOC441876), mRNA [XM_497657] |
| NM_001025 | RPS23 | Homo sapiens ribosomal protein S23 (RPS23), mRNA [NM_001025] |
| BU956542 | BU956542 | BU956542 AGENCOURT_10615527 NIH_MGC_107 Homo sapiens cDNA clone IMAGE: 6730153 5', mRNA sequence [BU956542] |
| NM_006597 | HSPA8 | Homo sapiens heat shock 70 kDa protein 8 (HSPA8), transcript variant 1, mRNA [NM_006597] |
| NM_001402 | EEF1A1 | Homo sapiens eukaryotic translation elongation factor 1 alpha 1 (EEF1A1), mRNA [NM_001402] |
| NM_000975 | RPL11 | Homo sapiens ribosomal protein L11 (RPL11), mRNA [NM_000975] |
| NR_003038 | SNHG5 | Homo sapiens small nucleolar RNA host gene (non-protein coding) 5 (SNHG5) on chromosome 6 [NR_003038] |
| NM_015710 | GLTSCR2 | Homo sapiens glioma tumor suppressor candidate region gene 2 (GLTSCR2), mRNA [NM_015710] |
| A_24_P332292 | A_24_P332292 | Unknown |
| NM_000989 | RPL30 | Homo sapiens ribosomal protein L30 (RPL30), mRNA [NM_000989] |
| NM_000989 | RPL30 | Homo sapiens ribosomal protein L30 (RPL30), mRNA [NM_000989] |
| CR620748 | LOC729329 | full-length cDNA clone CS0DK011Y114 of HeLa cells |

TABLE 17-continued

Gene list generated at the inclusion criteria of $p \leq 5 \times 10^{-2}$ and the log-median-ratio being at least "1" or above or being at least "−1" or below. The p-values were corrected using Benjamin and Hochberg method.

| Genbank Accession | Gene Name | Description |
|---|---|---|
| ENST00000337102 | ENST00000337102 | Cot 25-normalized of *Homo sapiens* (human) [CR620748] 40S ribosomal protein S21. [Source: Uniprot/SWISSPROT; Acc: P63220] [ENST00000337102] |
| XR_018138 | LOC392497 | PREDICTED: *Homo sapiens* similar to 40S ribosomal protein S6 (LOC392497), mRNA [XR_018138] |
| NM_002341 | LTB | *Homo sapiens* lymphotoxin beta (TNF superfamily, member 3) (LTB), transcript variant 1, mRNA [NM_002341] |
| NM_000967 | RPL3 | *Homo sapiens* ribosomal protein L3 (RPL3), transcript variant 1, mRNA [NM_000967] |
| A_24_P84408 | A_24_P84408 | Unknown |
| NM_000661 | RPL9 | *Homo sapiens* ribosomal protein L9 (RPL9), transcript variant 1, mRNA [NM_000661] |
| NM_000991 | RPL28 | *Homo sapiens* ribosomal protein L28 (RPL28), mRNA [NM_000991] |
| NM_000661 | RPL9 | *Homo sapiens* ribosomal protein L9 (RPL9), transcript variant 1, mRNA [NM_000661] |
| A_24_P50567 | A_24_P50567 | Unknown |
| A_24_P298238 | A_24_P298238 | Unknown |
| NM_003295 | TPT1 | *Homo sapiens* tumor protein, translationally-controlled 1 (TPT1), mRNA [NM_003295] |
| BC018140 | RPS21 | *Homo sapiens* ribosomal protein S21, mRNA (cDNA clone MGC: 9438 IMAGE: 3903320), complete cds. [9C018140] |
| BC067891 | LOC645683 | *Homo sapiens* cDNA clone MGC: 87657 IMAGE: 5271409, complete cds. [BC067891] |
| NM_001028 | RPS25 | *Homo sapiens* ribosomal protein S25 (RPS25), mRNA [NM_001028] |
| THC2567891 | THC2567891 | Q6NXR8_HUMAN (Q6NXR8) Ribosomal protein S3a, partial (91%) [THC2567891] |
| NM_000988 | RPL27 | *Homo sapiens* ribosomal protein L27 (RPL27), mRNA [NM_000988] |
| NM_000978 | RPL23 | *Homo sapiens* ribosomal protein L23 (RPL23), mRNA [NM_000978] |
| BC001697 | RPS15A | *Homo sapiens* ribosomal protein S15a, mRNA (cDNA clone MGC: 2466 IMAGE: 2967511), complete cds. [BC001697] |
| A_24_P862524 | A_24_P862524 | Unknown |
| NM_001007074 | RPL32 | *Homo sapiens* ribosomal protein L32 (RPL32), transcript variant 3, mRNA [NM_001007074] |
| A_24_P41979 | A_24_P41979 | Unknown |
| A_23_P210285 | A_23_P210285 | Unknown |
| NM_003973 | RPL14 | *Homo sapiens* ribosomal protein L14 (RPL14), transcript variant 2, mRNA [NM_003973] |
| A_24_P255252 | A_24_P255252 | Unknown |
| NM_002954 | RPS27A | *Homo sapiens* ribosomal protein S27a (RPS27A), mRNA [NM_002954] |
| NM_000984 | RPL23A | *Homo sapiens* ribosomal protein L23a (RPL23A), mRNA [NM_000984] |
| NM_001016 | RPS12 | *Homo sapiens* ribosomal protein S12 (RPS12), mRNA [NM_001016] |
| NM_003295 | TPT1 | *Homo sapiens* tumor protein, translationally-controlled 1 (TPT1), mRNA [NM_0032951 |
| NM_033625 | RPL34 | *Homo sapiens* ribosomal protein L34 (RPL34), transcript variant 2, mRNA [NM_033625] |
| XR_015936 | LOC731457 | PREDICTED: *Homo sapiens* similar to ribosomal protein S27a (LOC731457), mRNA [XR_015936] |
| XR_018222 | RPL31P4 | PREDICTED: *Homo sapiens* ribosomal protein L31 pseudogene 4 (RPL31P4), mRNA [XR_018222] |
| A_24_P367063 | A_24_P367063 | Unknown |
| NM_001010 | RPS6 | *Homo sapiens* ribosomal protein S6 (RPS6), mRNA [NM_001010] |
| NM_033625 | RPL34 | *Homo sapiens* ribosomal protein L34 (RPL34), transcript variant 2, mRNA [NM_033625] |
| NM_022551 | RPS18 | *Homo sapiens* ribosomal protein S18 (RPS18), mRNA [NM_022551] |
| NM_001028 | RPS25 | *Homo sapiens* ribosomal protein S25 (RPS25), mRNA [NM_001028] |
| XR_018695 | RPL31P10 | PREDICTED: *Homo sapiens* similar to ribosomal protein L31 (LOC390283), [XR_018695] |
| ENST00000356196 | hCG_26523 | PREDICTED: *Homo sapiens* similar to 60S ribosomal protein L26 (LOC646161), mRNA [XR_018048] |
| ENST00000356196 | hCG_26523 | PREDICTED: *Homo sapiens* similar to 60S ribosomal protein L26 (Silica-induced gene 20 protein) (SIG-20) (LOC400055), mRNA [XM_374987] |
| NM_005617 | RPS14 | *Homo sapiens* ribosomal protein S14 (RPS14), transcript variant 3, mRNA [NM_005617] |
| XR_018048 | LOC646161 | PREDICTED: *Homo sapiens* similar to 60S ribosomal protein L26 (LOC646161), mRNA [XR_018048] |
| NM_003295 | TPT1 | *Homo sapiens* tumor protein, translationally-controlled 1 (TPT1), mRNA [NM_003295] |
| NM_000986 | RPL24 | *Homo sapiens* ribosomal protein L24 (RP124), mRNA [NM_000986] |
| ENST00000313620 | LOC342994 | PREDICTED: *Homo sapiens* similar to ribosomal protein L34 (LOC342994), mRNA [XM_938484] |

TABLE 17-continued

Gene list generated at the inclusion criteria of $p \leq 5 \times 10^{-2}$ and the log-median-ratio being at least "1" or above or being at least "−1" or below. The p-values were corrected using Benjamin and Hochberg method.

| Genbank Accession | Gene Name | Description |
| --- | --- | --- |
| THC2506377 | THC2506377 | HSU02032 ribosomal protein L23a {Homo sapiens} (exp = −1; wgp = 0; cg = 0), partial (92%) [THC2506377] |
| NM_002568 | PABPC1 | Homo sapiens poly(A) binding protein, cytoplasmic 1 (PABPC1), mRNA [NM_002568] |
| NM_000997 | RPL37 | Homo sapiens ribosomal protein L37 (RPL37), mRNA [NM_000997] |
| XR_018303 | LOC648378 | PREDICTED: Homo sapiens similar to ribosomal protein S14 (LOC648378), mRNA [XR_018303] |
| NM_005617 | RPS14 | Homo sapiens ribosomal protein S14 (RPS14), transcript variant 3, mRNA [NM_005617] |
| NM_001023 | RPS20 | Homo sapiens ribosomal protein S20 (RPS20), mRNA [NM_001023] |
| NM_003973 | RPL14 | Homo sapiens ribosomal protein L14 (RPL14), transcript variant 2, mRNA [NM_003973] |
| NM_001006 | RPS3A | Homo sapiens ribosomal protein S3A (RPS3A), mRNA (NM_001006] |
| NM_001024 | RPS21 | Homo sapiens ribosomal protein S21 (RPS21), mRNA [NM_001024] |
| NM_001021 | RPS17 | Homo sapiens ribosomal protein S17 (RPS17), mRNA [NM_001021] |
| NM_002823 | PTMA | Homo sapiens prothymosin, alpha (gene sequence 28) (PTMA), mRNA [NM_002823] |
| ENST00000357697 | ENST00000357697 | Unknown |
| XM_372498 | LOC390427 | PREDICTED: Homo sapiens similar to TBP-associated factor 15 isoform 1 (LOC390427), mRNA [XM_372498] |
| NM_173078 | SLITRK4 | Homo sapiens SLIT and NTRK-like family, member 4 (SLITRK4), mRNA [NM_173078] |
| NM_002307 | LGALS7 | Homo sapiens lectin, galactoside-binding, soluble, 7 (galectin 7) (LGALS7), mRNA [NM_002307] |
| ENST00000325151 | ENST00000325151 | Small inducible cytokine A27 precursor (CCL27) (CC chemokine ILC) (IL-11 R-alpha-locus chemokine) (Skinkine) (ESkine) (Cutaneous T-cell-attracting chemokine) (CTACK). [Source: Uniprot/SWISSPROT; Acc: Q9Y4X3] [ENST00000325151] |
| NM_006266 | RALGDS | Homo sapiens ral guanine nucleotide dissociation stimulator (RALGDS), transcript variant 1, mRNA [NM 006266] |
| NM_018670 | MESP1 | Homo sapiens mesoderm posterior 1 homolog (mouse) (MESP1), mRNA [NM_018670] |
| NM_004819 | SYMPK | Homo sapiens symplekin (SYMPK), mRNA [NM_004819] |
| NM_175734 | C17orf74 | Homo sapiens chromosome 17 open reading frame 74 (C17orf74), mRNA [NM_175734] |
| J03651 | J03651 | Human DF3 breast carcinoma-associated antigen mRNA, partial cds. [J03651] |
| NM_003508 | FZD9 | Homo sapiens frizzled homolog 9 (Drosophila) (FZD9), mRNA [NM_003508] |
| AL566332 | AL566332 | AL566332 AL566332 Homo sapiens FETAL BRAIN Homo sapiens cDNA clone CS0DF015YB18 3-PRIME, mRNA sequence [AL566332] |
| NM_203374 | ZNF784 | Homo sapiens zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | Homo sapiens forkhead box D3 (FOXD3), mRNA [NM_012183] |
| ENST00000325371 | ENST00000325371 | Homo sapiens cDNA clone IMAGE:4819956. [BC018035] |
| THC2504037 | THC2504037 | ALU1_HUMAN (P39188) Alu subfamily J sequence contamination warning entry, partial (7%) [THC2504037] |
| NM_174903 | RNF151 | Homo sapiens ring finger protein 151 (RNF151), mRNA [NM_174903] |
| ENST00000360514 | ENST00000360514 | Homo sapiens hypothetical LOC339483, mRNA (cDNA clone MGC: 52427 IMAGE: 4872239), complete cds. [BC041632] |
| NM_138763 | BAX | Homo sapiens BCL2-associated X protein (BAX), transcript variant delta, mRNA [NM_138763] |
| NM_002691 | POLD1 | Homo sapiens polymerase (DNA directed), delta 1, catalytic subunit 125 kDa (POLD1), mRNA [NM_002691] |
| NM_203304 | RKHD1 | Homo sapiens ring finger and KH domain containing 1 (RKHD1), mRNA [NM_203304] |
| NM_018490 | LGR4 | Homo sapiens leucine-rich repeat-containing G protein-coupled receptor 4 (LGR4), mRNA [NM_018490] |
| CV575560 | CV575560 | oe37f10.y1 Human keratoconus cornea, unamplified, (od [CV575560] |

TABLE 18

Gene list generated at the inclusion criteria of $p \leq 5 \times 10^{-2}$ and the log-median-ratio being at least "1" or above or being at least "−1.5" or below. The p-values were corrected using Benjamin and Hochberg method.

| GenBank Accession | Gene Name | Description |
|---|---|---|
| NM_183049 | TMSL3 | Homo sapiens thymosin-like 3 (TMSL3), mRNA [NM_183049] |
| NM_004126 | GNG11 | Homo sapiens guanine nucleotide binding protein (G protein), gamma 11 (GNG11), mRNA [NM_004126] |
| A_24_P530977 | A_24_P530977 | Unknown |
| NM_004048 | B2M | Homo sapiens beta-2-microglobulin (B2M), mRNA [NM_004048] |
| NM_001005339 | RGS10 | Homo sapiens regulator of G-protein signalling 10 (RGS10), transcript variant 1, mRNA [NM_001005339] |
| NM_201397 | GPX1 | Homo sapiens glutathione peroxidase 1 (GPX1), transcript variant 2, mRNA [NM_201397] |
| NM_001032 | RPS29 | Homo sapiens ribosomal protein S29 (RPS29), transcript variant 1, mRNA [NM_001032] |
| ENST00000357697 | ENST00000357697 | Unknown |
| XM_372498 | LOC390427 | PREDICTED: Homo sapiens similar to TBP-associated factor 15 isoform 1 (LOC390427), mRNA [XM_372498] |
| NM_173078 | SLITRK4 | Homo sapiens SLIT and NTRK-like family, member 4 (SLITRK4), mRNA [NM_173078] |
| NM_002307 | LGALS7 | Homo sapiens lectin, galactoside-binding, soluble, 7 (galectin 7) (LGALS7), mRNA [NM_002307] |
| ENST00000325151 | ENST00000325151 | Small inducible cytokine A27 precursor (CCL27) (CC chemokine ILC) (IL-11 R-alpha-locus chemokine) (Skinkine) (ESkine) (Cutaneous T-cell- attracting chemokine) (CTACK). [Source: Uniprot/SWISSPROT; Acc: Q9Y4X3] [ENST00000325151] |
| NM_006266 | RALGDS | Homo sapiens ral guanine nucleotide dissociation stimulator (RALGDS), transcript variant 1, mRNA [NM_006266] |
| NM_018670 | MESP1 | Homo sapiens mesoderm posterior 1 homolog (mouse) (MESP1), mRNA [NM_018670] |
| NM_004819 | SYMPK | Homo sapiens symplekin (SYMPK), mRNA [NM_004819] |
| NM_175734 | C17orf74 | Homo sapiens chromosome 17 open reading frame 74 (C17orf74), mRNA [NM_175734] |
| J03651 | J03651 | Human DF3 breast carcinoma-associated antigen mRNA, partial cds. [J03651] |
| NM_003508 | FZD9 | Homo sapiens frizzled homolog 9 (Drosophila) (FZD9), mRNA [NM_003508] |
| AL566332 | AL566332 | AL566332 AL566332 Homo sapiens FETAL BRAIN Homo sapiens cDNA clone CS0DF015Y818 3-PRIME, mRNA sequence [AL566332] |
| NM_203374 | ZNF784 | Homo sapiens zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | Homo sapiens forkhead box D3 (FOXD3), mRNA [NM_012183] |
| ENST00000325371 | ENST00000325371 | Homo sapiens cDNA clone IMAGE: 4819956. [BC018035] |
| THC2504037 | THC2504037 | ALU1_HUMAN (P39188) Alu subfamily J sequence contamination warning entry, partial (7%) [THC2504037] |
| NM_174903 | RNF151 | Homo sapiens ring finger protein 151 (RNF151), mRNA [NM_174903] |
| ENST00000360514 | ENST00000360514 | Homo sapiens hypothetical LOC339483, mRNA (cDNA clone MGC: 52427 IMAGE: 4872239), complete cds. [BC041632] |
| NM_138763 | BAX | Homo sapiens BCL2-associated X protein (BAX), transcript variant delta, mRNA [NM_138763] |
| NM_002691 | POLD1 | Homo sapiens polymerase (DNA directed), delta 1, catalytic subunit 125 kDa (POLD1), mRNA [NM_002691] |
| NM_203304 | RKHD1 | Homo sapiens ring finger and KH domain containing 1 (RKHD1), mRNA [NM_203304] |
| NM_018490 | LGR4 | Homo sapiens leucine-rich repeat-containing G protein-coupled receptor 4 (LGR4), mRNA [NM_018490] |
| CV575560 | CV575560 | oe37f10.y1 Human keratoconus cornea, unamplified, (od [CV575560] |

TABLE 19

Gene list generated at the inclusion criteria of $p \leq 5 \times 10^{-2}$ and the log-median-ratio being at least "1" or above. The p-values were corrected using Benjamin and Hochberg method.

| GenBank Accession | Gene Name | Description |
|---|---|---|
| ENST00000357697 | ENST00000357697 | Unknown |
| XM_372498 | LOC390427 | PREDICTED: Homo sapiens similar to TBP-associated factor 15 isoform 1 (LOC390427), mRNA [XM_372498] |
| NM_173078 | SLITRK4 | Homo sapiens SLIT and NTRK-like family, member 4 (SLITRK4), mRNA [NM_173078] |

TABLE 19-continued

Gene list generated at the inclusion criteria of $p \leq 5 \times 10^{-2}$ and the log-median-ratio being at least "1" or above. The p-values were corrected using Benjamin and Hochberg method.

| GenBank Accession | Gene Name | Description |
|---|---|---|
| NM_002307 | LGALS7 | Homo sapiens lectin, galactoside-binding, soluble, 7 (galectin 7) (LGALS7), mRNA [NM_002307] |
| ENST00000325151 | ENST00000325151 | Small inducible cytokine A27 precursor (CCL27) (CC chemokine ILC) (IL- 11 R-alpha-locus chemokine) (Skinkine) (ESkine) (Cutaneous T-cell- attracting chemokine) (CTACK). [Source: Uniprot/SWISSPROT; Acc: Q9Y4X3] [ENST00000325151] |
| NM_006266 | RALGDS | Homo sapiens ral guanine nucleotide dissociation stimulator (RALGDS), transcript variant 1, mRNA [NM_006266] |
| NM_018670 | MESP1 | Homo sapiens mesoderm posterior 1 homolog (mouse) (MESP1), mRNA [NM_018670] |
| NM_004819 | SYMPK | Homo sapiens symplekin (SYMPK), mRNA [NM_004819] |
| NM_175734 | C17orf74 | Homo sapiens chromosome 17 open reading frame 74 (C17orf74), mRNA [NM_175734] |
| J03651 | J03651 | Human DF3 breast carcinoma-associated antigen mRNA, partial cds. [J03651] |
| NM_003508 | FZD9 | Homo sapiens frizzled homolog 9 (Drosophila) (FZD9), mRNA [NM_003508] |
| AL566332 | AL566332 | AL566332 Homo sapiens FETAL BRAIN Homo sapiens cDNA clone CS0DF015YB18 3-PRIME, mRNA sequence [AL566332] |
| NM_203374 | ZNF784 | Homo sapiens zinc finger protein 784 (ZNF784), mRNA [NM_203374] |
| ENST00000380739 | SERPINB1 | Leukocyte elastase inhibitor (LEI) (Serpin B1) (Monocyte/neutrophil elastase inhibitor) (M/NEI) (EI). [Source: Uniprot/SWISSPROT; Acc: P30740] [ENST00000380739] |
| NM_012183 | FOXD3 | Homo sapiens forkhead box D3 (FOXD3), mRNA [NM_012183] |
| ENST00000325371 | ENST00000325371 | Homo sapiens cDNA clone IMAGE: 4819956. [BC018035] |
| THC2504037 | THC2504037 | ALU1_HUMAN (P39188) Alu subfamily J sequence contamination warning entry, partial (7%) [THC2504037] |
| NM_174903 | RNF151 | Homo sapiens ring finger protein 151 (RNF151), mRNA [NM_174903] |
| ENST00000360514 | ENST00000360514 | Homo sapiens hypothetical LOC339483, mRNA (cDNA clone MGC: 52427 IMAGE: 4872239), complete cds. [BC041632] |
| NM_138763 | BAX | Homo sapiens BCL2- associated X protein (BAX), transcript variant delta, mRNA [NM_138763] |
| NM_002691 | POLD1 | Homo sapiens polymerase (DNA directed), delta 1, catalytic subunit 125 kDa (POLD1), mRNA [NM_002691] |
| NM_203304 | RKHD1 | Homo sapiens ring finger and KH domain containing 1 (RKHD1), mRNA [NM_203304] |
| NM_018490 | LGR4 | Homo sapiens leucine-rich repeat-containing G protein-coupled receptor 4 (LGR4), mRNA [NM_018490] |
| CV575560 | CV575560 | oe37f10.y1 Human keratoconus cornea, unamplified, od [CV575560] |

TABLE 20

Gene list generated at the inclusion criteria of $p \leq 5 \times 10^{-2}$ and the log-median-ratio being at least "−1.5" or below. The p-values were corrected using Benjamin and Hochberg method.

| GenBank Accession | Gene Name | Description |
|---|---|---|
| NM_001039567 | RPS4Y2 | Homo sapiens ribosomal protein S4, Y-linked 2 (RPS4Y2), mRNA [NM_001039567] |
| NM_183049 | TMSL3 | Homo sapiens thymosin-like 3 (TMSL3), mRNA [NM_183049] |
| NM_001008 | RPS4Y1 | Homo sapiens ribosomal protein S4, Y-linked 1 (RPS4Y1), mRNA [NM_001008] |
| NM_004126 | GNG11 | Homo sapiens guanine nucleotide binding protein (G protein), gamma 11 (GNG11), mRNA [NM_004126] |
| NM_002985 | CCL5 | Homo sapiens chemokine (C-C motif) ligand 5 (CCL5), mRNA [NM_002985] |
| A_24_P530977 | A_24_P530977 | Unknown |
| NM_004048 | B2M | Homo sapiens beta-2-microglobulin (B2M), mRNA [NM_004048] |
| NM_004907 | IER2 | Homo sapiens immediate early response 2 (IER2), mRNA [NM_004907] |
| NM_001005339 | RGS10 | Homo sapiens regulator of G-protein signalling 10 (RGS10), transcript variant 1, mRNA [NM_001005339] |
| NM_201397 | GPX1 | Homo sapiens glutathione peroxidase 1 (GPX1), transcript variant 2, mRNA [NM_201397] |
| NM_015646 | RAP1B | Homo sapiens RAP1B, member of RAS oncogene family (RAP1B), transcript variant 1, mRNA [NM_015646] |
| AL049447 | AL049447 | Homo sapiens mRNA; cDNA DKFZp586A0722 (from |

TABLE 20-continued

Gene list generated at the inclusion criteria of $p \leq 5 \times 10^{-2}$ and the log-median-ratio being at least "−1.5" or below. The p-values were corrected using Benjamin and Hochberg method.

| GenBank Accession | Gene Name | Description |
|---|---|---|
| NM_031286 | SH3BGRL3 | clone DKFZp586A0722). [AL049447]. *Homo sapiens* SH3 domain binding glutamic acid-rich protein like 3 (SH3BGRL3), mRNA [NM_031286] |
| NM_012329 | MMD | *Homo sapiens* monocyte to macrophage differentiation-associated (MMD), mRNA [NM_012329] |
| NM_002620 | PF4V1 | *Homo sapiens* platelet factor 4 variant 1 (PF4V1), mRNA [NM_002620] |
| NM_001004 | RPLP2 | *Homo sapiens* ribosomal protein, large, P2 (RPLP2), mRNA [NM_001004] |
| NM_033251 | RPL13 | *Homo sapiens* ribosomal protein L13 (RPL13), transcript variant 2, mRNA [NM_033251] |
| ENST00000383061 | ENST00000383061 | PREDICTED: *Homo sapiens* similar to myosin regulatory light chain-like (LOC442204), mRNA [XM_498088] |
| NM_004907 | IER2 | *Homo sapiens* immediate early response 2 (IER2), mRNA [NM_004907] |
| NM_001803 | CD52 | *Homo sapiens* CD52 molecule (CD52), mRNA [NM_001803] |
| NM_145113 | MAX | *Homo sapiens* MYC associated factor X (MAX), transcript variant 3, mRNA [NM_145113] |
| NM_002954 | RPS27A | *Homo sapiens* ribosomal protein S27a (RPS27A), mRNA [NM_002954] |
| NM_006471 | MRCL3 | *Homo sapiens* myosin regulatory light chain MRCL3 (MRCL3), mRNA [NM_006471] |
| NM_006597 | HSPA8 | *Homo sapiens* heat shock 70 kDa protein 8 (HSPA8), transcript variant 1, mRNA [NM_006597] |
| NM_001030 | RPS27 | *Homo sapiens* ribosomal protein S27 (metallopanstimulin 1) (RPS27), mRNA NM_001030] |
| NM_080425 | GNAS | *Homo sapiens* GNAS complex locus (GNAS), transcript variant 2, mRNA [NM_080425] |
| NM_001032 | RPS29 | *Homo sapiens* ribosomal protein S29 (RPS29), transcript variant 1, mRNA [NM_0010321 |
| NM_001012 | RPS8 | *Homo sapiens* ribosomal protein S8 (RPS8), mRNA [NM_001012] |
| XR_017498 | LOC645693 | PREDICTED: *Homo sapiens* similar to eukaryotic translation elongation factor 1 alpha 2 (LOC645693), mRNA [XR_017498] |
| NM_006597 | HSPA8 | *Homo sapiens* heat shock 70 kDa protein 8 (HSPA8), transcript variant 1, mRNA [NM_006597] |
| NM_001030 | RPS27 | *Homo sapiens* ribosomal protein S27 (metallopanstinnulin 1) (R13527), mRNA [NM_001030] |
| A_24_P229756 THC2544911 | A_24_P229756 THC2544911 | Unknown MUSEFTU elongation factor Tu {*Mus musculus*} (exp = −1; wgp = 0; cg = 0), partial (37%) [THC2544911] |
| NM_021104 | RPL41 | *Homo sapiens* ribosomal protein L41 (RPL41), transcript variant 1, mRNA [NM_021104] |
| NM_000981 | RPL19 | *Homo sapiens* ribosomal protein L19 (RPL19), mRNA [NM_000981] |
| A_24_P929974 | A_24_P929974 | Unknown |
| NM_002300 | LDHB | *Homo sapiens* lactate dehydrogenase B (LDHB), mRNA [NM_002300] |
| NM_001031 | RPS28 | *Homo sapiens* ribosomal protein S28 (RPS28), mRNA [NM_001031] |
| NM_000978 | RPL23 | *Homo sapiens* ribosomal protein L23 (RPL23), mRNA [NM_000978] |
| NM_033251 | RPL13 | *Homo sapiens* ribosomal protein L13 (RPL13), transcript variant 2, mRNA [NM_033251] |
| NM_001003 | RPLP1 | *Homo sapiens* ribosomal protein, large, P1 (RPLP1), transcript variant 1, mRNA [NM_0010031 |
| NM_001028 | RPS25 | *Homo sapiens* ribosomal protein S25 (RPS25), mRNA [NM_001028] |
| NM_001032 | RPS29 | *Homo sapiens* ribosomal protein S29 (RPS29), transcript variant 1, mRNA [NM_001032] |
| A_24_P238426 | A_24_P238426 | Unknown |
| NM_018447 | TMEM111 | *Homo sapiens* transmembrane protein 111 (TMEM111), mRNA [NM_018447] |
| BX096698 | BX096698 | BX096698 Soares breast 2NbHBst *Homo sapiens* cDNA clone IMAGp998E11242, mRNA sequence [BX096698] |
| NM_001003 | RPLP1 | *Homo sapiens* ribosomal protein, large, P1 (RPLP1), transcript variant 1, mRNA [NM_001003] |
| NM_002823 | PTMA | *Homo sapiens* prothymosin, alpha (gene sequence 28) (PTMA), mRNA [NM_002823] |
| NM_033251 | RPL13 | *Homo sapiens* ribosomal protein L13 (RPL13), transcript variant 2, mRNA [NM_033251] |
| XR_017294 | LOC646949 | PREDICTED: *Homo sapiens* similar to ribosomal protein L23 (LOC646949), mRNA [XR_017294] |
| NM_000993 | RPL31 | *Homo sapiens* ribosomal protein L31 (RPL31), mRNA [NM_000993] |
| XR_015548 | LOC729449 | PREDICTED: *Homo sapiens* similar to 60S ribosomal protein L7 (LOC729449), mRNA [XR_015548] |

TABLE 20-continued

Gene list generated at the inclusion criteria of $p \leq 5 \times 10^{-2}$ and the log-median-ratio being at least "−1.5" or below. The p-values were corrected using Benjamin and Hochberg method.

| GenBank Accession | Gene Name | Description |
|---|---|---|
| BC052613 | LOC728131 | *Homo sapiens* cDNA clone MGC: 59872 IMAGE: 6301163, complete cds. [BC052613] |
| A_24_P306968 | A_24_P306968 | Unknown |
| XM_497657 | LOC441876 | PREDICTED: *Homo sapiens* similar to 40S ribosomal protein S16, transcript variant 1 (LOC441876), mRNA [XM_497657] |
| NM_001025 | RPS23 | *Homo sapiens* ribosomal protein S23 (RPS23), mRNA [NM_001025] |
| BU956542 | BU956542 | BU956542 AGENCOURT_10615527 NIH_MGC_107 *Homo sapiens* cDNA clone IMAGE: 6730153 5', mRNA sequence [BU956542] |
| NM_006597 | HSPA8 | *Homo sapiens* heat shock 70 kDa protein 8 (HSPA8), transcript variant 1, mRNA [NM_006597] |
| NM_001402 | EEF1A1 | *Homo sapiens* eukaryotic translation elongation factor 1 alpha 1 (EEF1A1), mRNA [NM_001402] |
| NM_000975 | RPL11 | *Homo sapiens* ribosomal protein L11 (RPL11), mRNA [NM_000975] |
| NR_003038 | SNHG5 | *Homo sapiens* small nucleolar RNA host gene (non-protein coding) 5 (SNHG5) on chromosome 6 [NR_003038] |
| NM_015710 | GLTSCR2 | *Homo sapiens* glioma tumor suppressor candidate region gene 2 (GLTSCR2), mRNA [NM_015710] |
| A_24_P332292 | A_24_P332292 | Unknown |
| NM_000989 | RPL30 | *Homo sapiens* ribosomal protein L30 (RPL30), mRNA [NM_000989] |
| NM_000989 | RPL30 | *Homo sapiens* ribosomal protein L30 (RPL30), mRNA [NM_000989] |
| CR620748 | LOC729329 | full-length cDNA clone CS0DK011Y114 of HeLa cells Cot 25-normalized of *Homo sapiens* (human) [CR620748] |
| ENST00000337102 | ENST00000337102 | 40S ribosomal protein S21. [Source: Uniprot/SWISSPROT; Acc: P63220] [ENST00000337102] |
| XR_018138 | LOC392497 | PREDICTED: *Homo sapiens* similar to 40S ribosomal protein S6 (LOC392497), mRNA [XR_018138] |
| NM_002341 | LTB | *Homo sapiens* lymphotoxin beta (TNF superfamily, member 3) (LTB), transcript variant 1, mRNA [NM_002341] |
| NM_000967 | RPL3 | *Homo sapiens* ribosomal protein L3 (RPL3), transcript variant 1, mRNA [NM_000967] |
| A_24_P84408 | A_24_1384408 | Unknown |
| NM_000661 | RPL9 | *Homo sapiens* ribosomal protein L9 (RPL9), transcript variant 1, mRNA [NM_000661] |
| NM_000991 | RPL28 | *Homo sapiens* ribosomal protein L28 (RPL28), mRNA [NM_000991] |
| NM_000661 | RPL9 | *Homo sapiens* ribosomal protein L9 (RPL9), transcript variant 1, mRNA [NM_000661] |
| A_24_P50567 | A_24_P50567 | Unknown |
| A_24_P298238 | A_24_P298238 | Unknown |
| NM_003295 | TPT1 | *Homo sapiens* tumor protein, translationally-controlled 1 (TPT1), mRNA [NM_003295] |
| BC018140 | RPS21 | *Homo sapiens* ribosomal protein S21, mRNA (cDNA clone MGC: 9438 IMAGE: 3903320), complete cds. [BC018140] |
| BC067891 | LOC645683 | *Homo sapiens* cDNA clone MGC: 87657 IMAGE: 5271409, complete cds. [BC067891] |
| NM_001028 | RPS25 | *Homo sapiens* ribosomal protein S25 (RPS25), mRNA [NM_001028] |
| THC2567891 | THC2567891 | Q6NXR8_HUMAN (Q6NXR8) Ribosomal protein S3a, partial (91%) [THC2567891] |
| NM_000988 | RPL27 | *Homo sapiens* ribosomal protein L27 (RPL27), mRNA [NM_000988] |
| NM_000978 | RPL23 | *Homo sapiens* ribosomal protein L23 (RPL23), mRNA [NM_000978] |
| BC001697 | RPS15A | *Homo sapiens* ribosomal protein S15a, mRNA (cDNA clone MGC: 2466 IMAGE: 2967511), complete cds. [BC001697] |
| A_24_P862524 | A_24_P862524 | Unknown |
| NM_001007074 | RPL32 | *Homo sapiens* ribosomal protein L32 (RPL32), transcript variant 3, mRNA [NM_001007074] |
| A_24_P41979 | A_24_P41979 | Unknown |
| A_23_P210285 | A_23_P210285 | Unknown |
| NM_003973 | RPL14 | *Homo sapiens* ribosomal protein L14 (RPL14), transcript variant 2, mRNA [NM_003973] |
| A_24_P255252 | A_24_P255252 | Unknown |
| NM_002954 | RPS27A | *Homo sapiens* ribosomal protein S27a (RPS27A), mRNA [NM_002954] |
| NM_000984 | RPL23A | *Homo sapiens* ribosomal protein L23a (RPL23A), mRNA [NM_000984] |
| NM_001016 | RPS12 | *Homo sapiens* ribosomal protein S12 (RPS12), mRNA [NM_001016] |
| NM_003295 | TPT1 | *Homo sapiens* tumor protein, translationally-controlled 1 (TPT1), mRNA [NM_003295] |
| NM_033625 | RPL34 | *Homo sapiens* ribosomal protein L34 (RPL34), transcript variant 2, mRNA [NM_033625] |
| XR_015936 | LOC731457 | PREDICTED: *Homo sapiens* similar to ribosomal protein S27a (LOC731457), mRNA [XR_015936] |

TABLE 20-continued

Gene list generated at the inclusion criteria of p ≤ 5 × 10$^{-2}$ and the log-median-ratio being at least "−1.5" or below. The p-values were corrected using Benjamin and Hochberg method.

| GenBank Accession | Gene Name | Description |
|---|---|---|
| XR_018222 | RPL31P4 | PREDICTED: *Homo sapiens* ribosomal protein L31 pseudogene 4 (RPL31P4), mRNA [XR_018222] |
| A_24_P367063 | A_24_P367063 | Unknown |
| NM_001010 | RPS6 | *Homo sapiens* ribosomal protein S6 (RPS6), mRNA [NM_001010] |
| NM_033625 | RPL34 | *Homo sapiens* ribosomal protein L34 (RPL34), transcript variant 2, mRNA [NM_033625] |
| NM_022551 | RPS18 | *Homo sapiens* ribosomal protein S18 (RPS18), mRNA [NM_022551] |
| NM_001028 | RPS25 | *Homo sapiens* ribosomal protein S25 (RPS25), mRNA [NM_0010281] |
| XR_018695 | RPL31P10 | PREDICTED: *Homo sapiens* similar to ribosomal protein L31 (LOC390283), mRNA [XR_018695] |
| ENST00000356196 | hCG_26523 | PREDICTED: *Homo sapiens* similar to 60S ribosomal protein L26 (100646161), mRNA [X14_018048] |
| ENST00000356196 | hCG_26523 | PREDICTED: *Homo sapiens* similar to 60S ribosomal protein L26 (Silica-induced gene 20 protein) (SIG-20) (LOC400055), mRNA [XM_374987] |
| NM_005617 | RPS14 | *Homo sapiens* ribosomal protein S14 (RPS14), transcript variant 3, mRNA [NM_005617] |
| XR_018048 | LOC646161 | PREDICTED: *Homo sapiens* similar to 60S ribosomal protein L26 (LOC646161), mRNA [XR_018048] |
| NM_003295 | TPT1 | *Homo sapiens* tumor protein, translationally-controlled 1 (TPT1), mRNA [NM_003295] |
| NM_000986 | RP124 | *Homo sapiens* ribosomal protein L24 (RP124), mRNA [NM_000986] |
| ENST00000313620 | LOC342994 | PREDICTED: *Homo sapiens* similar to ribosomal protein L34 (LOC342994), mRNA [XM_938484] |
| THC2506377 | THC2506377 | HSU02032 ribosomal protein L23a {*Homo sapiens*} (exp = −1; wgp = 0; cg = 0), partial (92%) [THC2506377] |
| NM_002568 | PABPC1 | *Homo sapiens* poly(A) binding protein, cytoplasmic 1 (PABPC1), mRNA [NM_002568] |
| NM_000997 | RP137 | *Homo sapiens* ribosomal protein L37 (RPL37), mRNA [NM_000997] |
| XR_018303 | LOC648378 | PREDICTED: *Homo sapiens* similar to ribosomal protein S14 (LOC648378), mRNA [XR_018303] |
| NM_005617 | RPS14 | *Homo sapiens* ribosomal protein S14 (RPS14), transcript variant 3, mRNA [NM_005617] |
| NM_001023 | RPS20 | *Homo sapiens* ribosomal protein S20 (RPS20), mRNA [NM_001023] |
| NM_003973 | RPL14 | *Homo sapiens* ribosomal protein L14 (RPL14), transcript variant 2, mRNA [NM_003973] |
| NM_001006 | RPS3A | *Homo sapiens* ribosomal protein S3A (RPS3A), mRNA [NM_001006] |
| NM_001024 | RPS21 | *Homo sapiens* ribosomal protein S21 (RPS21), mRNA [NM_001024] |
| NM_001021 | RPS17 | *Homo sapiens* ribosomal protein S17 (RPS17), mRNA [NM_001021] |
| NM_002823 | PTMA | *Homo sapiens* prothymosin, alpha (gene sequence 28) (PTMA), mRNA [NM_002823] |

What is claimed is:

1. A method of treating glioblastoma in a subject, comprising:
   a. extracting RNA transcripts from at least one microvesicle isolated from a biological sample from the subject;
   b. measuring the expression level of the genes consisting of the genes recited in Table 16 in the extracted RNA transcripts;
   c. creating a genetic profile of the subject based on the measured expression level of each gene;
   d. comparing the genetic profile to a reference profile using clustering analysis or principle component analysis; and
   e. treating glioblastoma in the subject having a statistically significant difference in the genetic profile compared to the reference profile.

2. The method of claim 1, wherein the biological sample is selected from the group consisting of blood, serum, plasma and urine.

3. The method of claim 1, wherein measuring expression comprises determination of the presence or absence of the RNA transcribed from the gene, determination of the quantitative level of the RNA transcribed, or a combination thereof.

4. The method of claim 1, wherein measuring expression level is by microarray analysis, reverse transcription PCR, quantitative PCR, or a combination thereof.

5. The method of claim 1, wherein the at least one microvesicle originates from a specific cell type.

6. The method of claim 1, wherein the subject is a human subject.

7. The method of claim 6, wherein the human subject is a glioblastoma patient.

* * * * *